United States Patent
Bhandari et al.

(10) Patent No.: US 11,111,272 B2
(45) Date of Patent: *Sep. 7, 2021

(54) α4α7 PEPTIDE MONOMER AND DIMER ANTAGONISTS

(71) Applicant: Protagonist Therapeutics, Inc., Newark, CA (US)

(72) Inventors: Ashok Bhandari, Pleasanton, CA (US); Dinesh V. Patel, Fremont, CA (US); Genet Zemede, San Jose, CA (US); Larry C. Mattheakis, Cupertino, CA (US); David Liu, Newark, CA (US)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,516

(22) Filed: Feb. 4, 2020

(65) Prior Publication Data
US 2020/0308229 A1    Oct. 1, 2020

Related U.S. Application Data

(63) Continuation of application No. 15/698,407, filed on Sep. 7, 2017, now abandoned, which is a continuation of application No. 14/872,975, filed on Oct. 1, 2015, now Pat. No. 9,809,623.

(60) Provisional application No. 62/058,506, filed on Oct. 1, 2014, provisional application No. 62/058,510, filed on Oct. 1, 2014, provisional application No. 62/149,257, filed on Apr. 17, 2015, provisional application No. 62/192,934, filed on Jul. 15, 2015.

(51) Int. Cl.
C07K 7/08     (2006.01)
C07K 14/725   (2006.01)
C07K 7/06     (2006.01)
A61K 38/00    (2006.01)

(52) U.S. Cl.
CPC ............. *C07K 7/08* (2013.01); *C07K 7/06* (2013.01); *C07K 14/7051* (2013.01); *A61K 38/00* (2013.01)

(58) Field of Classification Search
CPC . A61K 38/00; A61P 1/00; A61P 43/00; C07K 14/7051; C07K 7/06; C07K 7/08
See application file for complete search history.

(56) References Cited

U.S. PATENT DOCUMENTS

| | | | |
|---|---|---|---|
| 4,684,620 A | 8/1987 | Hruby et al. |
| 4,724,229 A | 2/1988 | Ali |
| 5,192,746 A | 3/1993 | Lobl et al. |
| 5,494,897 A | 2/1996 | Shikawa et al. |
| 5,990,084 A | 11/1999 | Lutz Richter et al. |
| 6,087,334 A | 7/2000 | Beeley et al. |
| 6,235,711 B1 | 5/2001 | Dutta |
| 6,818,617 B1 | 11/2004 | Niewiarowski |
| 7,534,764 B2 | 5/2009 | Ganz et al. |
| 8,313,950 B2 | 11/2012 | Rovin et al. |
| 8,435,941 B2 | 5/2013 | Ganz et al. |
| 8,536,140 B2 | 9/2013 | Clandinin et al. |
| 8,568,706 B2 | 10/2013 | Grabstein et al. |
| 8,796,418 B2 | 8/2014 | Walensky et al. |
| 8,946,150 B2 | 2/2015 | Gallagher et al. |
| 8,999,935 B2 | 4/2015 | Huang |
| 9,169,292 B2 | 10/2015 | Gallagher et al. |
| 9,273,093 B2 | 3/2016 | Bhandari et al. |
| 9,518,091 B2 | 12/2016 | Bhandari et al. |
| 9,624,268 B2 | 4/2017 | Bourne et al. |
| 9,714,270 B2 | 7/2017 | Bhandari et al. |
| 9,809,623 B2 | 11/2017 | Bhandari et al. |
| 9,822,157 B2 | 11/2017 | Smythe et al. |
| 10,023,614 B2 | 7/2018 | Bhandari et al. |
| 10,030,061 B2 | 7/2018 | Smythe et al. |
| 10,035,824 B2 | 7/2018 | Bhandari et al. |
| 10,059,744 B2 | 8/2018 | Bhandari et al. |
| 10,196,424 B2 | 2/2019 | Bourne et al. |
| 10,278,957 B2 | 5/2019 | Anandan et al. |
| 10,301,371 B2 | 5/2019 | Bhandari et al. |
| 10,407,468 B2 | 9/2019 | Bhandari et al. |
| 10,442,846 B2 | 10/2019 | Smythe et al. |
| 10,501,515 B2 | 12/2019 | Smythe et al. |
| 10,626,146 B2 | 4/2020 | Bhandari et al. |
| 10,787,490 B2 | 9/2020 | Bhandari et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0176293 A1 | 9/2004 | Peterson et al. |

(Continued)

FOREIGN PATENT DOCUMENTS

| | | |
|---|---|---|
| CN | 101307085 A | 11/2008 |
| CN | 101358201 A | 2/2009 |

(Continued)

OTHER PUBLICATIONS

Govind K. Makharia, Current and emerging therapy for celiac disease, Frontiers in Medicine, Mar. 2014, vol. 1, Article 6, pp. 1-11.*

(Continued)

*Primary Examiner* — James H Alstrum-Acevedo
*Assistant Examiner* — Erinne R Dabkowski
(74) *Attorney, Agent, or Firm* — Cooley LLP

(57) ABSTRACT

The invention relates to peptide dimer compounds and peptide monomer compounds that potently inhibit binding of α4β7 to the mucosal addressin cell adhesion molecule (MAdCAM) in vivo, possess high selectivity against α4β1 binding, and have high stability under gastrointestinal conditions.

14 Claims, 24 Drawing Sheets

Specification includes a Sequence Listing.

(56) References Cited

U.S. PATENT DOCUMENTS

| | | |
|---|---|---|
| 2006/0183884 A1 | 8/2006 | Blaschuk et al. |
| 2007/0032417 A1 | 2/2007 | Baell |
| 2007/0166308 A1 | 7/2007 | Pullen et al. |
| 2007/0197430 A1 | 8/2007 | Baell et al. |
| 2008/0019913 A1 | 1/2008 | Polt et al. |
| 2008/0213277 A1 | 9/2008 | Sasu et al. |
| 2008/0260820 A1 | 10/2008 | Borrelly et al. |
| 2008/0300180 A1 | 12/2008 | Schambye et al. |
| 2009/0053819 A1 | 2/2009 | Seymour et al. |
| 2009/0257952 A1 | 10/2009 | Cochran et al. |
| 2010/0151487 A1 | 6/2010 | Rovin et al. |
| 2010/0183617 A1 | 7/2010 | Herr et al. |
| 2010/0190710 A1 | 7/2010 | Chemtob et al. |
| 2010/0196441 A1 | 8/2010 | Sondermeijer et al. |
| 2010/0272731 A1 | 10/2010 | Presta et al. |
| 2010/0280098 A1 | 11/2010 | Juliano et al. |
| 2011/0059087 A1 | 3/2011 | Lewis et al. |
| 2011/0086024 A1 | 4/2011 | Arthos et al. |
| 2011/0118186 A1 | 5/2011 | Schteingart et al. |
| 2011/0282029 A1 | 11/2011 | Holmes et al. |
| 2012/0021975 A1 | 1/2012 | Hoffman et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2014/0005128 A1 | 1/2014 | Mo et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0118315 A1 | 4/2015 | Wilson |
| 2015/0157692 A1 | 6/2015 | Fu |
| 2015/0203555 A1 | 7/2015 | Gellman et al. |
| 2015/0284429 A1 | 10/2015 | Merutka |
| 2016/0031944 A1 | 2/2016 | Bhandari et al. |
| 2016/0039878 A1 | 2/2016 | Gallagher et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0199437 A1 | 7/2016 | Wilson |
| 2016/0222076 A1 | 8/2016 | Smythe et al. |
| 2016/0228491 A1 | 8/2016 | Wilson |
| 2016/0368966 A1 | 12/2016 | Bhandari et al. |
| 2017/0313754 A1 | 11/2017 | Bourne et al. |
| 2017/0327541 A1 | 11/2017 | Bhandari et al. |
| 2018/0022778 A1 | 1/2018 | Bourne et al. |
| 2018/0079782 A1 | 3/2018 | Bhandari et al. |
| 2018/0079783 A1 | 3/2018 | Bhandari et al. |
| 2018/0099995 A1 | 4/2018 | Bhandari et al. |
| 2018/0100004 A1 | 4/2018 | Smythe et al. |
| 2018/0105572 A1 | 4/2018 | Bhandari et al. |
| 2018/0148477 A1 | 5/2018 | Bhandari et al. |
| 2019/0002500 A1 | 1/2019 | Bhandari et al. |
| 2019/0002503 A1 | 1/2019 | Bourne et al. |
| 2019/0016756 A1 | 1/2019 | Bhandari et al. |
| 2019/0076400 A1 | 3/2019 | Anandan et al. |
| 2019/0185535 A1 | 6/2019 | Smythe et al. |
| 2019/0185536 A1 | 6/2019 | Smythe et al. |
| 2019/0231746 A1 | 8/2019 | Anandan et al. |
| 2019/0248870 A1 | 8/2019 | Bhandari et al. |
| 2019/0270786 A1 | 9/2019 | Bhandari et al. |
| 2019/0300590 A1 | 10/2019 | Bhandari et al. |
| 2019/0337983 A1 | 11/2019 | Bhandari et al. |
| 2020/0017549 A1 | 1/2020 | Bhandari et al. |
| 2020/0017566 A1 | 1/2020 | Bourne et al. |
| 2020/0040037 A1 | 2/2020 | Bhandari et al. |
| 2020/0064357 A1 | 2/2020 | Cheng et al. |
| 2020/0207822 A1 | 7/2020 | Bhandari et al. |
| 2020/0239523 A1 | 7/2020 | Bhandari et al. |
| 2020/0361992 A1 | 11/2020 | Bourne et al. |

FOREIGN PATENT DOCUMENTS

| | | |
|---|---|---|
| DE | 10107707 A1 | 8/2002 |
| JP | 2010-517529 A | 5/2010 |
| JP | 2010-536364 A | 12/2010 |
| JP | 2011-231085 A | 11/2011 |
| JP | 2012-525124 A | 10/2012 |
| JP | 2016-521257 A | 7/2016 |
| WO | WO 1992/017492 A1 | 10/1992 |
| WO | WO 1997/025351 A2 | 7/1997 |
| WO | WO 1998/008871 A1 | 3/1998 |
| WO | WO 2000/055184 A1 | 3/1998 |
| WO | WO 1999/002194 A1 | 1/1999 |
| WO | WO 1999/026615 A1 | 6/1999 |
| WO | WO 2000/006243 A2 | 2/2000 |
| WO | WO 2000/009560 A1 | 2/2000 |
| WO | WO 2000/018789 A1 | 4/2000 |
| WO | WO 2000/018790 A1 | 4/2000 |
| WO | WO 2000/023474 A1 | 4/2000 |
| WO | WO 2000/055119 A1 | 9/2000 |
| WO | WO 2000/061580 A1 | 10/2000 |
| WO | WO 2001/068586 A2 | 9/2001 |
| WO | WO 2003/066678 A1 | 8/2003 |
| WO | WO 2004/011650 A2 | 2/2004 |
| WO | WO 2004/092405 A2 | 10/2004 |
| WO | WO 2006/032104 A1 | 3/2006 |
| WO | WO 2007/138291 A2 | 12/2007 |
| WO | WO 2008/097461 A2 | 8/2008 |
| WO | WO 2008/134659 A2 | 11/2008 |
| WO | WO 2008/140602 A2 | 11/2008 |
| WO | WO 2009/002947 A2 | 12/2008 |
| WO | WO 2009/027752 A2 | 3/2009 |
| WO | WO 2010/065815 A2 | 6/2010 |
| WO | WO 2010/116752 A1 | 10/2010 |
| WO | WO 2010/124874 A1 | 11/2010 |
| WO | WO 2011/091357 A1 | 7/2011 |
| WO | WO 2011/149942 A2 | 12/2011 |
| WO | WO 2012/052205 A1 | 4/2012 |
| WO | WO 2013/086143 A1 | 6/2013 |
| WO | WO 2014/059213 A1 | 4/2014 |
| WO | WO 2014/127316 A2 | 8/2014 |
| WO | WO 2014/145561 A2 | 9/2014 |
| WO | WO 2014/165448 A1 | 10/2014 |
| WO | WO 2014/165449 A1 | 10/2014 |
| WO | WO 2014/210056 A1 | 12/2014 |
| WO | WO 2015/054500 A2 | 4/2015 |
| WO | WO 2015/157283 A1 | 10/2015 |
| WO | WO 2015/176035 A1 | 11/2015 |
| WO | WO 2015/183963 A2 | 12/2015 |
| WO | WO 2015/200916 A2 | 12/2015 |
| WO | WO 2016/004093 A2 | 1/2016 |
| WO | WO 2016/011208 A1 | 1/2016 |
| WO | WO 2016/054411 A1 | 4/2016 |
| WO | WO 2016/054445 A1 | 4/2016 |
| WO | WO 2016/109363 A1 | 7/2016 |
| WO | WO 2016/115168 A1 | 7/2016 |
| WO | WO 2016/195663 A1 | 12/2016 |
| WO | WO 2016/200364 A1 | 12/2016 |
| WO | WO 2017/011820 A2 | 1/2017 |
| WO | WO 2017/117411 A1 | 7/2017 |
| WO | WO 2018/022937 A1 | 2/2018 |
| WO | WO 2018/089693 A2 | 5/2018 |
| WO | WO 2018/136646 A1 | 7/2018 |
| WO | WO 2019/157268 A1 | 8/2019 |
| WO | WO 2019/246273 A1 | 12/2019 |
| WO | WO 2020/014646 A1 | 1/2020 |
| WO | WO 2021/007433 A1 | 1/2021 |

OTHER PUBLICATIONS

U.S. Appl. No. 16/113,072, filed Aug. 27, 2018, Bhandari, et al.
U.S. Appl. No. 16/282,920, filed Feb. 22, 2019, Bhandari, et al.
U.S. Appl. No. 16/319,958, filed Jan. 23, 2019, Bhandari, et al.
U.S. Appl. No. 16/376,565, filed Apr. 5, 2019, Bhandari, et al.
U.S. Appl. No. 16/382,783, filed Apr. 12, 2019, Bhandari, et al.
U.S. Appl. No. 16/478,733, filed Jul. 17, 2019, Bhandari, et al.
U.S. Appl. No. 16/553,486, filed Aug. 28, 2019, Smythe, et al.
U.S. Appl. No. 16/656,339, filed Oct. 17, 2019, Bhandari, et al.

(56) References Cited

OTHER PUBLICATIONS

U.S. Appl. No. 16/689,884, filed Nov. 20, 2019, Bhandari, et al.
U.S. Appl. No. 16/700,659, filed Dec. 2, 2019, Bhandari, et al.
U.S. Appl. No. 16/774,686, filed Jan. 28, 2020, Bhandari, et al.
U.S. Appl. No. 16/780,297, filed Feb. 3, 2020, Bhandari, et al.
U.S. Appl. No. 16/839,368, filed Apr. 3, 2020, Smythe, et al.
U.S. Appl. No. 16/856,521, filed Apr. 23, 2020, Bhandari, et al.
Adams and Macmillan, "Investigation of peptide thioester formation via N→Se acyl transfer." Journal of Peptide Science (2013); 19 (2): 65-73.
Andreu, et al., "Formation of Disulfide Bonds in Synthetic Peptides and Proteins" Ch. 7 in Synthetic Peptides and Proteins. In: Pennington M.W., Dunn B.M. (eds) Peptide Synthesis Protocols. Methods in Molecular Biology (1994); 35: 91-169.
Ashby, et al., "Plasma hepcidin levels are elevated but responsive to erythropoietin therapy in renal disease." Kidney International (2009); 75 (9): 976-981.
Balasubramanian and Kuppuswamy, "RGD-containing Peptides Activate S6K1 through $\beta_3$ Integrin in Adult Cardiac Muscle Cells", J Biol Chem. (Oct. 24, 2003); 278(43): 42214-42224. Epub Aug. 9, 2003.
Boer, J., et al., "Design and Synthesis of Potent and Selective $\alpha_4\beta_7$ Integrin Antagonists." J. Med. Chem. (2001); 44 (16): 2586-2592.
Bowie, et al., " Deciphering the Message in Protein Sequences: Tolerance to Amino Acid Substitutions." Science (1990); 247: 1306-1310.
Brayden, D.J., and Mrsny, R.J., "Oral peptide delivery: prioritizing the leading technologies". Therapeutic Delivery (2011); 2(12): 1567-1573.
Chatterjee, J. et al., "N-Methylation of Peptides: a New Perspective in Medicinal Chemistry", Accounts of Chemical Research, 41(10): 1331-1342 (2008).
Clark, et al., "Understanding the Structure/Activity Relationships of the Iron Regulatory Peptide Hepcidin." Chem Biol. (Mar. 2011); 18(3): 336-343.
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from U.S. Pat. No. 8,313,950.", XP002761650, retrieved from EBI accession No. USPOP:AGA36544 Database accession No. AGA36544, 1 page.
Davies, J.S., "The Cyclization of Peptides and Depsipeptides", J Pept Sci. (Aug. 2003); 9(8): 471-501.
De Mast, et al., "Increased serum hepcidin and alterations in blood iron parameters associated with asymptomatic P. falciparum and P. vivax malaria." Haematologica (2010); 95 (7): 1068-1074.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)—Mediated Cell Adhesion Based on the Ile-Leu-Asp-Val Tetrapeptide", J. Peptide Sci. (2000); 6: 321-341.

European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Extended European Search Report dated Feb. 17, 2017, 9 pages.
European Application No. 14780207.8, Partial Supplementary European Search Report dated Nov. 16, 2016, 6 pages.
European Application No. 15792950.6, Extended European Search Report dated May 2, 2018, 10 pages.
European Application No. 15812513.8, Extended European Search Report dated Apr. 12, 2018, 11 pages.
European Application No. 15821351.2, Extended European Search Report dated Jan. 3, 2018, 6 pages.
European Application No. 15846131.9, Extended European Search Report dated Jan. 25, 2018, 8 pages.
European Application No. 15846983.3, Extended European Search Report dated Jun. 19, 2018, 10 pages.
European Application No. 15846983.3, Partial European Search Report dated Mar. 2, 2018, 11 pages.
European Application No. 16825301.1, Extended European Search Report dated Jan. 21, 2019, 6 pages.
Ganz and Nemeth, "Hepcidin and iron homeostasis." Biochimica et Biophysica Acta (BBA)—Molecular Cell Research (Sep. 2012); 1823 (9): 1434-1443.
Gee et al. "Cyclic Peptides as Non-carboxyl-terminal Ligands of Syntrophin PDZ Domains," The Journal of Biological Chemistry, 273(34): 21980-21987 (1998).
Gentilucci, et al., "Chemical Modifications Designed to Improve Peptide Stability: Incorporation of Non-Natural Amino Acids, Pseudo-Peptide Bonds, and Cyclization". Curr Pharm Des. (2010); 16(28): 3185-3203.
Girelli, Domenico, et al. "Hepcidin in the diagnosis of iron disorders." Blood (2016); 127.23 : 2809-2813.
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al. "Hepcidin revisited, disulfide connectivity, dynamics, and structure." Journal of Biological Chemistry (2009); 284.36: 24155-24167.
Kelleman, A. et al., "Incorporation of thioether building blocks into an $\alpha_v\beta_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.
Kluskens, L.D. et al., "Angiotensin—(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Legge and Morieson, "On the prediction of partition coefficients and $R_F$ values of peptides." Aust. J. Biol. Sci. (1964); 17: 561-571.

(56) References Cited

OTHER PUBLICATIONS

Ley, Klaus, et al. "Integrin-based therapeutics: biological basis, clinical use and new drugs." Nature Reviews Drug Discovery (2016); 15.3: 173-183.

Li and Roller, "Cyclization Strategies in Peptide Derived Drug Design." Curr. Topics Med. Chem. (2002); 2: 325-341.

Liu, Shuang, "Radiolabeled Cyclic RGD Peptides as Integrin $\alpha_v\beta_3$-Targeted Radiotracers: Maximizing Binding Affinity via Bivalency." Bioconjugate Chem. (2009); 20 (12): 2199-2213.

Liu, Shuang, "Radiolabeled Multimeric Cyclic RGD Peptides as Integrin avB3 Targeted Radiotracers for Tumor Imaging", School of Health Science, Purdue University, Molecular Pharmaceuticals (2006); 3(5): 472-487.

Madsen, Kjeld, et al. "Structure—activity and protraction relationship of long-acting glucagon-like peptide-1 derivatives: importance of fatty acid length, polarity, and bulkiness." Journal of Medicinal Chemistry (2007); 50.24: 6126-6132.

Hruby and Bonner, "Design of Novel Synthetic Peptides Inlcuding Cyclic Conformationally and Topgraphically Constrained Analogs". Methods in Molecular Biology, Ch. 11, vol. 35 Peptide Synthesis Protocols, Edited by M.W Pennington and B. M. Dunn Copyright, 1994 Humana Press Inc, Totowa, NJ, pp. 201-241, 40 pages.

Munoz, Manuel, et al. "Disorders of iron metabolism. Part II: iron deficiency and iron overload." Journal of Clinical Pathology (2011); 64.4: 287-296.

Nemeth, Elizabeta, et al. "The N-terminus of hepcidin is essential for its interaction with ferroportin: structure-function study." Blood (2006); 107.1: 328-333.

Park, C.H., et al., "Hepcidin, a urinary antimicrobial peptide synthesized in the liver." J Biol Chem. (2001); 276(11): 7806-7810. Epub Dec. 11, 2000.

Parrow, et al., "Prospects for a hepcidin mimic to treat β-thalassemia and hemochromatosis." Expert Review of Hematology (2011); 4 (3): 233-235.

Pattarawarapan, "Selective Formation of Homo- and Heterobivalent Peptidomimetics." J. Med. Chem. (Aug. 2003); 46 (17): 3565-3567.

PCT/US2013/064439, International Preliminary Report on Patentability, dated Apr. 14, 2015, 8 pages.
PCT/US2013/064439, International Search Report and Written Opinion, dated Jan. 24, 2014, 15 pages.
PCT/US2014/030352, International Preliminary Report on Patentability, dated Sep. 15, 2015, 7 pages.
PCT/US2014/030352, International Search Report and Written Opinion, dated Nov. 28, 2014, 12 pages.
PCT/US2014/030352, Invitation to Pay Additional Fees, mailed Sep. 10, 2014, 2 pages.
PCT/US2014/032391, International Preliminary Report on Patentability, dated Oct. 6, 2015, 8 pages.
PCT/US2014/032391, International Search Report, dated Aug. 7, 2014, 5 pages.
PCT/US2014/032391, Written Opinion, dated Aug. 7, 2014, 7 pages.
PCT/US2014/032392, International Preliminary Report on Patentability, dated Oct. 6, 2015, 10 pages.
PCT/US2014/032392, International Search Report and Written Opinion, dated Sep. 15, 2014, 15 pages.
PCT/US2015/031243, International Preliminary Report on Patentability, dated Nov. 22, 2016, 8 pages.
PCT/US2015/031243, International Search Report and Written Opinion, dated Aug. 5, 2015, 14 pages.
PCT/US2015/038370, International Preliminary Report on Patentability, dated Dec. 27, 2016, 4 pages.
PCT/US2015/038370, International Search Report and Written Opinion, dated Sep. 14, 2015, 5 pages.
PCT/US2015/040658, International Preliminary Report on Patentability, dated Jan. 17, 2017, 5 pages.
PCT/US2015/040658, International Search Report and Written Opinion, dated Oct. 28, 2015, 12 pages.
PCT/US2015/053558, International Preliminary Report on Patentability, dated Apr. 4, 2017, 9 pages.
PCT/US2015/053558, International Search Report and Written Opinion, dated Feb. 19, 2016, 16 pages.
PCT/US2015/053558, Invitation to Pay Additional Fees, mailed Dec. 16, 2015, 3 pages.
PCT/US2015/053603, International Preliminary Report on Patentability, dated Apr. 4, 2017, 8 pages.
PCT/US2015/053603, International Search Report and Written Opinion, dated Feb. 12, 2016, 13 pages.
PCT/US2015/053603, Invitation to Pay Additional Fees, mailed Dec. 10, 2015, 3 pages.
PCT/US2016/042680, (2nd) International Search Report and Written Opinion, dated Apr. 17, 2017, 13 pages.
PCT/US2016/042680, International Search Report and Written Opinion, dated Jan. 13, 2017, 12 pages.
PCT/US2016/069255, International Search Report and Written Opinion dated Jun. 1, 2017, 11 pages.
PCT/US2016/069255, Invitation to Pay Additional Fees, mailed Mar. 30, 2017, 2 pages.
PCT/US2016/069255, International Preliminary Report on Patentability, dated Jul. 3, 2018, 7 pages.
PCT/US2017/044249, International Preliminary Report on Patentability, dated Jan. 29, 2019, 9 pages.
PCT/US2017/044249, International Search Report and Written Opinion, dated Nov. 21, 2017, 14 pages.
PCT/US2017/044249, Invitation to Pay Additional Fees, mailed Sep. 14, 2017, 3 pages.
PCT/US2018/014257, International Preliminary Report on Patentability, dated Jul. 23, 2019, 9 pages.
PCT/US2018/014257, International Search Report and Written Opinion, dated May 14, 2018, 13 pages.
PCT/US2018/014257, Invitation to Pay Additional Fees, mailed Mar. 22, 2018, 2 pages.
PCT/US2018/050480, International Preliminary Report on Patentability dated Mar. 17, 2020, 7 pages.
PCT/US2018/050480, International Search Report and Written Opinion, dated Jan. 29, 2019, 13 pages.
PCT/US2018/050480, Invitation to Pay Additional Fees, mailed Nov. 6, 2018, 3 pages.
PCT/US2019/017192, International Search Report and Written Opinion, dated Jun. 11, 2019, 13 pages.
PCT/US2019/017192, Invitation to Pay Additional Fees, mailed Apr. 16, 2019, 2 pages.
PCT/US2019/041665, Invitation to Pay Additional Fees, mailed Oct. 22, 2019, 3 pages.
PCT/US2019/041665, International Search Report and Written Opinion dated Dec. 19, 2019, 16 pages.

Pelton, J.T. et al., "Somatostatin Analogs with Affinity for Opiate Receptors in Rat Brain Binding Assay", Peptides, 6(Suppl 1): 159-163 (1985).

Preza, G., et al., "Minihepcidins are rationally designed small peptides that mimic hepcidin activity in mice and may be useful for the treatment of iron overload", J Clin Invest (2011); 121(12): 4880-4888.

Ramos, E., et al., "Minihepcidins prevent iron overload in a hepcidin-deficient mouse model of severe hemochromatosis." Blood (Nov. 2012); 120(18): 3829-3836. Epub Sep. 18, 2012.

Rivera, Seth, et al. "Synthetic hepcidin causes rapid dose-dependent hypoferremia and is concentrated in ferroportin-containing organs." Blood (2005); 106.6: 2196-2199.

Rostovtsev, et al., "A Stepwise Huisgen Cycloaddition Process: Copper(I)-Catalyzed Regioselective "Ligation" of Azides and Terminal Alkynes". Angewandte Chemie Int. Ed. (Jul. 2, 2002); 41(14): 2596-2599.

Sasaki, et al., "D-Arg2-dermorphin tetrapeptide analogs: a potent and long-lasting analgesic activity after subcutaneous administration." Biochem Biophys Res Commun. (1984); 120 (1): 214-218.

Search Report and Written Opinion in Singaporean Application No. 11201609614Q, dated Mar. 12, 2018, 9 pages.

Search Report and Written Opinion in Singaporean Application No. 11201610799W, dated May 31, 2018, 4 pages.

Search Report and Written Opinion in Singaporean Application No. 11201700327W, dated Mar. 16, 2018, 10 pages.

(56) References Cited

OTHER PUBLICATIONS

Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Speers, et al., "Activity-Based Protein Profiling in Vivo Using a Copper(I)-Catalyzed Azide-Alkyne [3+2] Cycloaddition". J. Am. Chem. Soc. (Mar. 28, 2003); 125(16): 4686-4687.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Tornøe, et al., "Peptidotriazoles on solid phase: [1,2,3]-triazoles by regiospecific copper(i)-catalyzed 1,3-dipolar cycloadditions of terminal alkynes to azides." J Org Chem. (May 3, 2002); 67(9): 3057-3064.
Tuvia, et al., "A Novel Suspension Formulation Enhances Intestinal Absorption of Macromolecules Via Transient and Reversible Transport Mechanisms". Pharm Res. (Feb. 21, 2014); 31(8): 2010-2021.
U.S. Appl. No. 14/050,349, Final Office Action dated Sep. 9, 2015, 17 pages.
U.S. Appl. No. 14/050,349, Non-Final Office Action dated Feb. 27, 2015, 14 pages.
U.S. Appl. No. 14/050,349, Notice of Allowance dated Jan. 12, 2016, 9 pages.
U.S. Appl. No. 14/229,784, Non-Final Office Action dated Aug. 13, 2015, 16 pages.
U.S. Appl. No. 14/229,784, Office Action dated Mar. 8, 2016, 6 pages.
U.S. Appl. No. 14/229,799, Non-Final Office Action dated Jul. 24, 2015, 19 pages.
U.S. Appl. No. 14/229,799, Office Action dated Mar. 4, 2016, 18 pages.
U.S. Appl. No. 14/714,198, Notice of Allowance dated Mar. 17, 2017, 3 pages.
U.S. Appl. No. 14/714,198, Office Action dated Nov. 7, 2016, 6 pages.
U.S. Appl. No. 14/775,469, Notice of Allowance dated Aug. 10, 2017, 11 pages.
U.S. Appl. No. 14/775,469, Notice of Allowance dated Sep. 5, 2017, 9 pages.
U.S. Appl. No. 14/775,469, Office Action dated Apr. 11, 2017, 22 pages.
U.S. Appl. No. 14/800,627, Notice of Allowance dated Feb. 15, 2017, 9 pages.
U.S. Appl. No. 14/800,627, Office Action dated Aug. 25, 2016, 11 pages.
U.S. Appl. No. 14/872,975, Notice of Allowance dated Aug. 16, 2017, 9 pages.
U.S. Appl. No. 14/872,975, Office Action dated Dec. 27, 2016, 14 pages.
U.S. Appl. No. 15/046,325, Office Action dated Aug. 1, 2016, 13 pages.
U.S. Appl. No. 15/442,229, Notice of Allowance dated Sep. 12, 2018, 9 pages.
U.S. Appl. No. 15/442,229, Office Action dated Apr. 20, 2018, 12 pages.
U.S. Appl. No. 15/514,983, Office Action dated Nov. 2, 2018, 8 pages.
U.S. Appl. No. 15/614,047, Notice of Allowance dated Jun. 7, 2018, 8 pages.
U.S. Appl. No. 15/698,407, Office Action dated Apr. 25, 2019, 15 pages.
U.S. Appl. No. 15/720,333, Office Action dated Aug. 28, 2018, 24 pages.
U.S. Appl. No. 15/828,214, Notice of Allowance dated Jun. 11, 2018, 9 pages.
U.S. Appl. No. 15/828,214, Office Action dated May 15, 2018, 12 pages.
U.S. Appl. No. 15/831,087, Notice of Allowance dated May 11, 2018, 8 pages.
U.S. Appl. No. 15/831,087, Office Action dated Apr. 12, 2018, 10 pages.
U.S. Appl. No. 15/831,100, Notice of Allowance dated May 8, 2018, 8 pages.
U.S. Appl. No. 15/831,100, Office Action dated Apr. 12, 2018, 11 pages.
U.S. Appl. No. 15/836,648, Office Action dated Nov. 6, 2018, 7 pages.
U.S. Appl. No. 15/514,983, Notice of Allowance dated Jan. 7, 2019, 6 pages.
U.S. Appl. No. 16/128,352, Notice of Allowability dated Feb. 21, 2019, 2 pages.
U.S. Appl. No. 16/128,352, Notice of Allowance dated Feb. 6, 2019, 5 pages.
U.S. Appl. No. 16/289,451, Office Action dated Mar. 21, 2019, 21 pages.
U.S. Appl. No. 16/037,982, Office Action dated Mar. 22, 2019, 29 pages.
U.S. Appl. No. 16/039,813, Office Action dated Apr. 19, 2019, 11 pages.
U.S. Appl. No. 15/698,407, Office Action dated Aug. 5, 2019, 10 pages.
U.S. Appl. No. 16/039,813, Office Action dated Aug. 22, 2019, 11 pages.
U.S. Appl. No. 16/039,813, Notice of Allowance dated Nov. 7, 2019, 10 pages.
U.S. Appl. No. 15/745,371, Office Action dated Dec. 19, 2019, 22 pages.
U.S. Appl. No. 16/039,813, Corrected Notice of Allowability dated Jan. 31, 2020, 5 pages.
U.S. Appl. No. 16/067,568, Office Action dated Apr. 2, 2020, 15 pages.
Waitemata District Health Board, "Crushing Guide for Oral Medication in Residential Aged Care", 2 pages (2011).
Wang, et al., "Bioconjugation by Copper(I)-Catalyzed Azide-Alkyne [3+2] Cycloaddition". J Am Chem Soc. (Mar. 19, 2003); 125(11): 3192-3193.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yampolsky and Stoltzfus, "The Exchangeability of Amino Acids in Proteins", Genetics (Aug. 2005); 170(4): 1459-1472. Epub Jun. 8 2005.
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
U.S. Appl. No. 14/050,349, filed Oct. 10, 2013, US 2014-0193465 A1, Jul. 10, 2014, U.S. Pat. No. 9,273,093, Mar. 1, 2016, Registered.
U.S. Appl. No. 14/229,784, filed Mar. 28, 2014, US 2014-0294901 A1, Oct. 2, 2014, Abandoned.
U.S. Appl. No. 14/229,799, filed Mar. 28, 2014, US 2014-0294902 A1, Oct. 2, 2014, Abandoned.
U.S. Appl. No. 14/714,198, filed May 15, 2015, US 2016-0031944 A1, Feb. 4, 2016, U.S. Pat. No. 9,714,270, Jul. 25, 2017, Registered.

(56) References Cited

OTHER PUBLICATIONS

U.S. Appl. No. 14/775,469, filed Mar. 17, 2014, US 2016-0222076 A1, Aug. 4, 2016, U.S. Pat. No. 9,822,157, Nov. 21, 2017, Registered.
U.S. Appl. No. 14/800,627, filed Jul. 15, 2015, US 2016-0145306 A1, May 26, 2016, U.S. Pat. No. 9,624,268, Apr. 18, 2017, Registered.
U.S. Appl. No. 14/872,975, filed Oct. 1, 2015, US 2016-0152664 A1, Jun. 2, 2016, U.S. Pat. No. 9,809,623, Nov. 7, 2017, Registered.
U.S. Appl. No. 15/000,923, filed Jan. 19, 2016, US 2016-0368966 A1, Dec. 22, 2016, Abandoned.
U.S. Appl. No. 15/046,325, filed Feb. 17, 2016, US 2016-0159862 A1, Jun. 9, 2016, U.S. Pat. No. 9,518,091, Dec. 13, 2016, Registered.
U.S. Appl. No. 15/255,750, filed Sep. 2, 2016, Abandoned.
U.S. Appl. No. 15/258,540, filed Sep. 7, 2016, Abandoned.
U.S. Appl. No. 15/321,124, filed Jun. 29, 2015, US 2017-0313754 A1, Nov. 2, 2017, Abandoned.
U.S. Appl. No. 15/442,229, filed Feb. 24, 2017, US 2018-0022778 A1, Jan. 25, 2018, U.S. Pat. No. 10,196,424, Feb. 5, 2019, Registered.
U.S. Appl. No. 15/467,810, filed Mar. 23, 2017, US 2017-0327541 A1, Nov. 16, 2017, U.S. Pat. No. 10,407,468, Sep. 10, 2019, Registered.
U.S. Appl. No. 15/486,684, filed Apr. 13, 2017, Abandoned.
U.S. Appl. No. 15/491,773, filed Apr. 19, 2017, Abandoned.
U.S. Appl. No. 15/493,471, filed Apr. 21, 2017, Abandoned.
U.S. Appl. No. 15/514,983, filed Oct. 1, 2015, US 2018-0105572 A1, Apr. 19, 2018, U.S. Pat. No. 10,301,371, May 28, 2019, Registered.
U.S. Appl. No. 15/614,047, filed Jun. 5, 2017, US 2018-0099995 A1, Apr. 12, 2018, U.S. Pat. No. 10,059,744, Aug. 28, 2018, Registered.
U.S. Appl. No. 15/698,407, filed Sep. 7, 2017, US 2018-0148477 A1, May 31, 2018, Abandoned.
U.S. Appl. No. 15/720,333, filed Sep. 29, 2017, US 2018-0100004 A1, Apr. 12, 2018, Abandoned.
U.S. Appl. No. 15/745,371, filed Jul. 15, 2016, US 2019-0300590 A1, Oct. 3, 2019, Allowed.
U.S. Appl. No. 15/828,214, filed Nov. 30, 2017, US 2018-0086811 A1, Mar. 29, 2018, U.S. Pat. No. 10,030,061, Jul. 24, 2018, Registered.
U.S. Appl. No. 15/831,087, filed Dec. 4, 2017, US 2018-0079782 A1, Mar. 22, 2018, U.S. Pat. No. 10,035,824, Jul. 31, 2018, Registered.
U.S. Appl. No. 15/831,099, filed Dec. 4, 2017, Abandoned.
U.S. Appl. No. 15/831,100, filed Dec. 4, 2017, US 2018-0079783 A1, Mar. 22, 2018, U.S. Pat. No. 10,023,614, Jul. 17, 2018, Registered.
U.S. Appl. No. 15/831,120, filed Dec. 4, 2017, Abandoned.
U.S. Appl. No. 15/836,648, filed Dec. 8, 2017, US 2019-0002500 A1, Jan. 3, 2019, Abandoned.
U.S. Appl. No. 16/032,400, filed Jul. 11, 2018, Abandoned.
U.S. Appl. No. 16/035,060, filed Jul. 13, 2018, Abandoned.
U.S. Appl. No. 16/037,982, filed Jul. 17, 2018, US 2019-0185535 A1, Jun. 20, 2019, U.S. Pat. No. 10,442,846, Oct. 15, 2019, Registered.
U.S. Appl. No. 16/039,813, filed Jul. 19, 2018, US 2019-0016756 A1, Jan. 17, 2019, U.S. Pat. No. 10,626,146, Apr. 21, 2020, Registered.
U.S. Appl. No. 16/067,568, filed Dec. 29, 2016, US2019-0002503 A1, Jan. 3, 2019, Pending.
U.S. Appl. No. 16/113,072, filed Aug. 27, 2018, Abandoned.
U.S. Appl. No. 16/128,352, filed Sep. 11, 2018, US 2019-0076400 A1, Mar. 14, 2019, U.S. Pat. No. 10,278,957, May 7, 2019, Registered.
U.S. Appl. No. 16/217,864, filed Dec. 12, 2018, US 2019-0337983 A1, Nov. 7, 2019, Pending.
U.S. Appl. No. 16/282,908, filed Feb. 22, 2019, US 2019-0248870 A1, Aug. 15, 2019, Abandoned.
U.S. Appl. No. 16/282,920, filed Feb. 22, 2019, US 2020-0017549 A1, Jan. 16, 2020, Pending.
U.S. Appl. No. 16/289,451, filed Feb. 28, 2019, US 2019-0185536 A1, Jun. 20, 2019, U.S. Pat. No. 10,501,515, Dec. 10, 2019, Registered.
U.S. Appl. No. 16/294,717, filed Mar. 6, 2019, US 2019-0231746 A1, Aug. 1, 2019, Allowed.
U.S. Appl. No. 16/319,958, filed Jul. 27, 2017, US 2019-0270786 A1, Sep. 5, 2019, Pending.
U.S. Appl. No. 16/319,959, filed Jul. 27, 2017, US 2019-0264197 A1, Aug. 29, 2019, Pending.
U.S. Appl. No. 16/348,293, filed Nov. 9, 2017, US 2020-0064357 A1, Feb. 27, 2020, Pending.
U.S. Appl. No. 16/376,565, filed Apr. 5, 2019, Abandoned.
U.S. Appl. No. 16/382,783, filed Apr. 12, 2019, Abandoned.
U.S. Appl. No. 16/417,075, filed May 20, 2019, Abandoned.
U.S. Appl. No. 16/439,435, filed Jun. 12, 2019, US 2020-0017566 A1, Jan. 16, 2020, Pending.
U.S. Appl. No. 16/478,733, filed Jan. 18, 2018, Pending.
U.S. Appl. No. 16/510,118, filed Jul. 12, 2019, US 2020-0040037 A1, Feb. 6, 2020, Pending.
U.S. Appl. No. 16/553,486, filed Aug. 28, 2019, Abandoned.
U.S. Appl. No. 16/656,339, filed Oct. 17, 2019, Pending.
U.S. Appl. No. 16/689,884, filed Nov. 20, 2019, Pending.
U.S. Appl. No. 16/700,659, filed Dec. 2, 2019, Pending.
U.S. Appl. No. 16/774,686, filed Jan. 28, 2020, Pending.
U.S. Appl. No. 16/780,297, filed Feb. 3, 2020, Pending.
U.S. Appl. No. 16/839,368, filed Apr. 3, 2020, Pending.
U.S. Appl. No. 16/856,521, filed Apr. 23, 2020, Pending.
U.S. Appl. No. 14/714,198, filed May 15, 2015, Bhandari, et al.
U.S. Appl. No. 14/775,469, filed Mar. 17, 2014, Smythe, et al.
U.S. Appl. No. 14/800,627, filed Jul. 15, 2015, Bourne, et al.
U.S. Appl. No. 14/872,975, filed Oct. 1, 2015, Bhandari, et al.
U.S. Appl. No. 15/000,923, filed Jan. 19, 2016, Bhandari, et al.
U.S. Appl. No. 15/046,325, filed Feb. 17, 2016, Bhandari, et al.
U.S. Appl. No. 15/255,750, filed Sep. 2, 2016, Bhandari, et al.
U.S. Appl. No. 15/258,540, filed Sep. 7, 2016, Bhandari, et al.
U.S. Appl. No. 15/321,124, filed Dec. 21, 2016, Bourne, et al.
U.S. Appl. No. 15/442,229, filed Feb. 24, 2017, Bourne, et al.
U.S. Appl. No. 15/467,810, filed Mar. 23, 2017, Bhandari, et al.
U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/514,983, filed Mar. 28, 2017, Bhandari, et al.
U.S. Appl. No. 15/614,047, filed Jun. 5, 2017, Bhandari, et al.
U.S. Appl. No. 15/698,407, filed Sep. 7, 2017, Bhandari, et al.
U.S. Appl. No. 15/720,333, filed Sep. 29, 2017, Smythe, et al.
U.S. Appl. No. 15/828,214, filed Nov. 30, 2017, Smythe, et al.
U.S. Appl. No. 15/831,087, filed Dec. 4, 2017, Bhandari, et al.
U.S. Appl. No. 15/831,099, filed Dec. 4, 2017, Bhandari, et al.
U.S. Appl. No. 15/831,100, filed Dec. 4, 2017, Bhandari, et al.
U.S. Appl. No. 15/831,120, filed Dec. 4, 2017, Bhandari, et al.
U.S. Appl. No. 15/836,648, filed Dec. 8, 2017, Bhandari, et al.
U.S. Appl. No. 15/745,371, filed Jan. 16, 2018, Bhandari, et al.
U.S. Appl. No. 16/035,060, filed Jul. 13, 2018, Bhandari, et al.
U.S. Appl. No. 16/037,982, filed Jul. 17, 2018, Smythe, et al.
U.S. Appl. No. 16/039,813, filed Jul. 19, 2018, Bhandari, et al.
U.S. Appl. No. 16/128,352, filed Sep. 11, 2018, Anandan, et al.
U.S. Appl. No. 16/217,864, filed Dec. 12, 2018, Bourne, et al.
U.S. Appl. No. 16/282,908, filed Feb. 22, 2019, Bhandari, et al.
U.S. Appl. No. 16/348,293, filed May 8, 2019, Cheng, et al.
U.S. Appl. No. 16/417,075, filed May 20, 2019, Bhandari, et al.
U.S. Appl. No. 16/439,435, filed Jun. 12, 2019, Bourne, et al.
U.S. Appl. No. 16/510,118, filed Jul. 12, 2019, Bhandari, et al.
U.S. Appl. No. 16/931,046, filed Jul. 16, 2020, Bhandari, et al.
U.S. Appl. No. 16/940,989, filed Jul. 28, 2020, Bhandari, et al.
U.S. Appl. No. 16/964,708, filed Jul. 24, 2020, Bourne, et al.
U.S. Appl. No. 17/001,428, filed Aug. 24, 2020, Bhandari, et al.
U.S. Appl. No. 17/011,844, filed Sep. 3, 2020, Liu,et al.
U.S. Appl. No. 17/061,336, filed Oct. 1, 2020, Bourne, et al.
U.S. Appl. No. 17/084,225, filed Oct. 29, 2020, Bourne, et al.
U.S. Appl. No. 17/099,308, filed Nov. 16, 2020, Smythe, et al.
U.S. Appl. No. 17/104,596, filed Nov. 25, 2020, Bhandari, et al.
U.S. Appl. No. 17/137,049, filed Dec. 29, 2020, Bhandari, et al.

(56) References Cited

OTHER PUBLICATIONS

U.S. Appl. No. 17/149,509, filed Jan. 14, 2021, Sun, et al.
U.S. Appl. No. 17/149,544, filed Jan. 14, 2021, Sun, et al.
U.S. Appl. No. 17/161,370, filed Jan. 28, 2021, Bhandari, et al.
Cherry, et al., "Vedolizumab: an α4β7 integrin antagonist for ulcerative colitis and Crohn's disease." Ther Adv Chronic Dis. (2015); 6(5): 224-233.
European Application No. 17771175.1, Partial Supplementary European Search Report dated Nov. 25, 2019, 15 pages.
Kuchař, et al., "Human interleukin-23 receptor antagonists derived from an albumin-binding domain scaffold inhibit IL-23-dependent ex vivo expansion of IL-17-producing T-cells". Proteins (Jun. 2014); 82(6): 975-989. Epub Nov. 23, 2013.
PCT/US2017/023859, Invitation to Pay Additional Fees, mailed May 25, 2017, 9 pages.
PCT/US2017/060944, International Preliminary Report on Patentability dated May 21, 2019, 8 pages.
PCT/US2017/060944, International Search Report and Written Opinion dated Feb. 2, 2020, 10 pages.
PCT/US2017/023859, International Preliminary Report on Patentability, dated Sep. 25, 2018, 9 pages.
PCT/US2017/023859, International Search Report and Written Opinion, dated Jul. 26, 2017, 14 pages.

\* cited by examiner

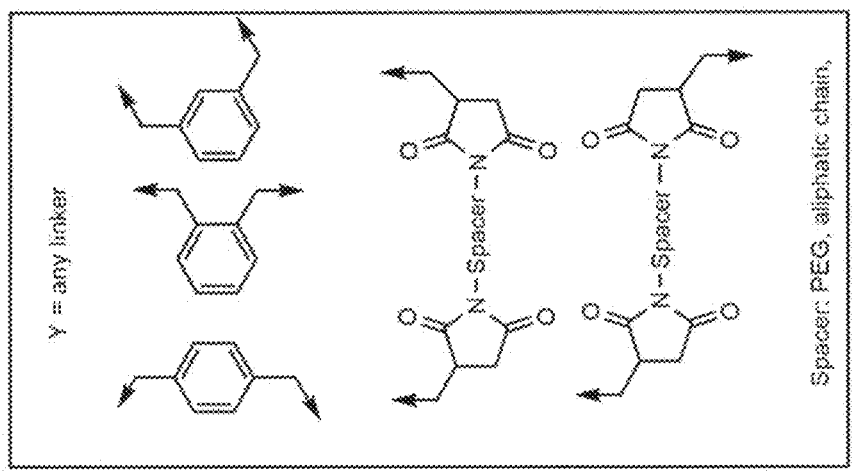
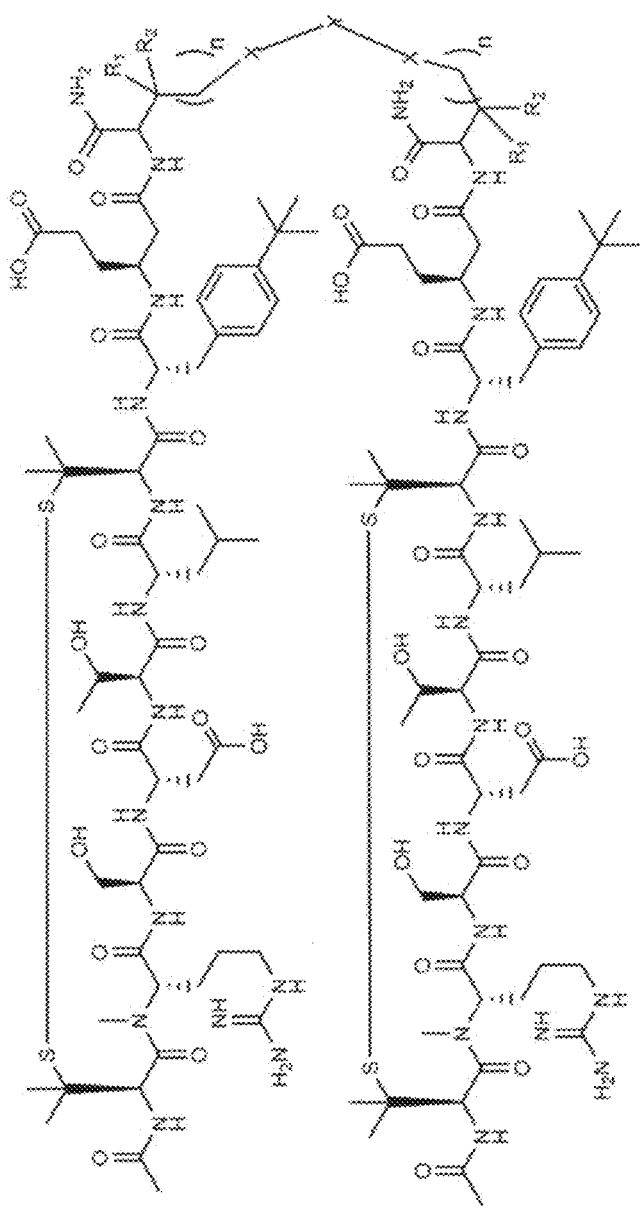
$R_1$ and $R_2$ are H OR ME
N is any integer from 2 to 10
X is $CH_2$, NHCO, CONH, S-S, C=O, CHOH, S, S=O, NH, or O
FIG. 3A

| Intestinal half-life | | | | | | Gastric half-life | Plasma half-life | Metabolism | |
|---|---|---|---|---|---|---|---|---|---|
| SIF | RIW | HIF | CW | IMH | CMH | SGF | Rat | Hu S9 | RL S9 |
| 1 h | >5 h | >24 h | >6 h | >6 h | >6 h | >5 h | >5 h | >6 h | >6 h |

SIF - simulated intestinal fluid (porcine)
RIW - rat intestinal wash
HIF - human intestinal fluid
CW - colonic wash (rat)
IMH - intestinal mucosal homogenate (rat)
CMG - colonic mucosal homogenate (rat)
SGF - simulated gastric fluid (porcine)
Hu S9 - human intestinal S9 fraction
RL S9 - rat liver S9

Microbiome stability of closely related peptides

- Stable after 48 hr. incubation in anaerobic cultures of C. difficile, B. fragilis, E. coli, B. bifidum, and L. acidophilus

- No evidence of antimicrobial activity against 19 different intestinal bacteria grown under anaerobic conditions.

*FIG. 5*

SEQUENCE LISTING

<160> NUMBER OF SEQ ID NOS: 349

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)

```
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Glu
<220> FEATURE:
<221> NAME/KEY: MOD_RES
<222> LOCATION: (10)..(10)
<223> OTHER INFORMATION: D-Lys

<400> SEQUENCE: 1

Xaa Arg Ser Asp Thr Leu Xaa Trp Glu Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 2

Xaa Arg Ser Asp Thr Leu Xaa Phe Glu Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

```
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-CF3)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 3

Xaa Arg Ser Asp Thr Leu Xaa Phe Glu Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (3)..(3)
<223> OTHER INFORMATION: N-Me-Arg
<220> FEATURE:
<221> NAME/KEY: MOD_RES
<222> LOCATION: (10)..(10)
<223> OTHER INFORMATION: D-Lys

<400> SEQUENCE: 4

Lys Cys Arg Ser Asp Thr Leu Cys Trp Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (3)..(3)
<223> OTHER INFORMATION: N-Me-Arg
<220> FEATURE:
<221> NAME/KEY: MOD_RES
<222> LOCATION: (10)..(10)
<223> OTHER INFORMATION: D-Lys

<400> SEQUENCE: 5

Lys Cys Arg Ser Asp Thr Leu Cys Trp Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (2)..(2)
<223> OTHER INFORMATION: N-Me-Arg

<400> SEQUENCE: 6

Cys Arg Ser Asp Thr Leu Cys Trp
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe

<400> SEQUENCE: 7

Xaa Arg Ser Asp Thr Leu Xaa Phe
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 8

Xaa Arg Ser Asp Thr Leu Xaa Xaa Glu Lys
1               5                   10
```

```
<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 9

Xaa Arg Ser Asp Thr Leu Xaa Xaa Glu Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-1-Nal
<220> FEATURE:
<221> NAME/KEY: MOD_RES
<222> LOCATION: (10)..(10)
<223> OTHER INFORMATION: D-Lys

<400> SEQUENCE: 10

Xaa Arg Ser Asp Thr Leu Xaa Xaa Glu Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-2-Nal
<220> FEATURE:
<221> NAME/KEY: MOD_RES
<222> LOCATION: (10)..(10)
<223> OTHER INFORMATION: D-Lys

<400> SEQUENCE: 11

Xaa Arg Ser Asp Thr Leu Xaa Xaa Glu Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: N-Me-D-Lys

<400> SEQUENCE: 12

Xaa Arg Ser Asp Thr Leu Xaa Xaa Glu Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
```

```
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: N-Me-D-Lys

<400> SEQUENCE: 13

Xaa Arg Ser Asp Thr Leu Xaa Xaa Glu Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: H-Phe
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 14

Xaa Arg Ser Asp Thr Leu Xaa Phe Glu Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
```

```
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-D-Lys

<400> SEQUENCE: 15

Xaa Arg Ser Asp Thr Leu Xaa Xaa Glu Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(2,4diCl)
<220> FEATURE:
<221> NAME/KEY: MOD_RES
<222> LOCATION: (10)..(10)
<223> OTHER INFORMATION: D-Lys

<400> SEQUENCE: 16

Xaa Arg Ser Asp Thr Leu Xaa Phe Glu Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(3,4diCl)
<220> FEATURE:
<221> NAME/KEY: MOD_RES
<222> LOCATION: (10)..(10)
<223> OTHER INFORMATION: D-Lys
```

```
<400> SEQUENCE: 17

Xaa Arg Ser Asp Thr Leu Xaa Phe Glu Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (10)..(10)
<223> OTHER INFORMATION: N-Me-D-Lys

<400> SEQUENCE: 18

Xaa Arg Ser Asp Thr Leu Xaa Xaa Glu Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: H-Phe
<220> FEATURE:
<221> NAME/KEY: MOD_RES
<222> LOCATION: (10)..(10)
<223> OTHER INFORMATION: D-Lys

<400> SEQUENCE: 19

Xaa Arg Ser Asp Thr Leu Xaa Phe Glu Lys
1               5                   10

<210> SEQ ID NO 20
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 20

Cys Arg Ser Asp Thr Leu Xaa Trp
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 21

Cys Arg Ser Asp Thr Leu Xaa Trp
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 22

Xaa Arg Ser Asp Thr Leu Xaa Tyr Glu Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: D-Lys

<400> SEQUENCE: 23

Xaa Arg Ser Asp Thr Leu Xaa Xaa Tyr Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (10)..(10)
<223> OTHER INFORMATION: D-Lys

<400> SEQUENCE: 24

Xaa Arg Ser Asp Thr Leu Xaa Xaa Glu Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (10)..(10)
<223> OTHER INFORMATION: D-Lys

<400> SEQUENCE: 25

Xaa Arg Ser Asp Thr Leu Xaa His Glu Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 26

Xaa Arg Ser Asp Thr Leu Xaa His Tyr Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Tyr
<220> FEATURE:
<221> NAME/KEY: MOD_RES
<222> LOCATION: (10)..(10)
<223> OTHER INFORMATION: D-Lys

<400> SEQUENCE: 27

Xaa Arg Ser Asp Thr Leu Xaa Xaa Tyr Lys
1               5                   10

<210> SEQ ID NO 28
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Trp
<220> FEATURE:
<221> NAME/KEY: MOD_RES
<222> LOCATION: (10)..(10)
<223> OTHER INFORMATION: D-Lys

<400> SEQUENCE: 28

Xaa Arg Ser Asp Thr Leu Xaa Trp Glu Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 29

Xaa Arg Ser Asp Thr Leu Xaa Xaa Glu Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (10)..(10)
<223> OTHER INFORMATION: D-Lys

<400> SEQUENCE: 30

Xaa Arg Ser Asp Thr Leu Xaa Phe Glu Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: N-Me-Glu
<220> FEATURE:
<221> NAME/KEY: MOD_RES
<222> LOCATION: (10)..(10)
<223> OTHER INFORMATION: D-Lys

<400> SEQUENCE: 31

Xaa Arg Ser Asp Thr Leu Xaa Trp Glu Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
```

```
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 32

Xaa Arg Ser Asp Thr Leu Xaa Xaa Glu Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 33

Xaa Arg Ser Asp Thr Leu Xaa Xaa Glu Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
```

```
<223> OTHER INFORMATION: D-1-Nal
<220> FEATURE:
<221> NAME/KEY: MOD_RES
<222> LOCATION: (10)..(10)
<223> OTHER INFORMATION: D-Lys

<400> SEQUENCE: 34

Xaa Arg Ser Asp Thr Leu Xaa Xaa Glu Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-2-Nal
<220> FEATURE:
<221> NAME/KEY: MOD_RES
<222> LOCATION: (10)..(10)
<223> OTHER INFORMATION: D-Lys

<400> SEQUENCE: 35

Xaa Arg Ser Asp Thr Leu Xaa Xaa Glu Lys
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 36

Cys Arg Ser Asp Thr Leu Xaa Trp Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 37

Cys Arg Ser Asp Thr Leu Xaa Trp Lys
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: N-Me-D-Lys

<400> SEQUENCE: 38

Xaa Arg Ser Asp Thr Leu Xaa Xaa Glu Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
```

```
<223> OTHER INFORMATION: 2-Nal
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: N-Me-D-Lys

<400> SEQUENCE: 39

Xaa Arg Ser Asp Thr Leu Xaa Xaa Glu Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: H-Phe
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 40

Xaa Arg Ser Asp Thr Leu Xaa Phe Glu Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
```

<222> LOCATION: (10)..(10)
<223> OTHER INFORMATION: N-Me-D-Lys

<400> SEQUENCE: 41

Xaa Arg Ser Asp Thr Leu Xaa Xaa Glu Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(2,4diCl)
<220> FEATURE:
<221> NAME/KEY: MOD_RES
<222> LOCATION: (10)..(10)
<223> OTHER INFORMATION: D-Lys

<400> SEQUENCE: 42

Xaa Arg Ser Asp Thr Leu Xaa Phe Glu Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(3,4diCl)
<220> FEATURE:
<221> NAME/KEY: MOD_RES
<222> LOCATION: (10)..(10)
<223> OTHER INFORMATION: D-Lys

<400> SEQUENCE: 43

Xaa Arg Ser Asp Thr Leu Xaa Phe Glu Lys
1               5                   10

<210> SEQ ID NO 44
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (10)..(10)
<223> OTHER INFORMATION: N-Me-D-Lys

<400> SEQUENCE: 44

Xaa Arg Ser Asp Thr Leu Xaa Xaa Glu Lys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: H-Phe
<220> FEATURE:
<221> NAME/KEY: MOD_RES
<222> LOCATION: (10)..(10)
<223> OTHER INFORMATION: D-Lys

<400> SEQUENCE: 45

Xaa Arg Ser Asp Thr Leu Xaa Phe Glu Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
```

-continued

```
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 46

Xaa Arg Ser Asp Asp Leu Xaa Trp Glu Lys
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: D-Lys

<400> SEQUENCE: 47

Thr Leu Xaa Trp Glu Lys
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (3)..(3)
<223> OTHER INFORMATION: D-Asp
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 48

Xaa Arg Asp Asp Thr Leu Xaa Trp Glu Lys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (11)..(11)
<223> OTHER INFORMATION: D-Lys

<400> SEQUENCE: 49

Xaa Arg Ser Asp Thr Leu Xaa Trp Glu Pro Lys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: H-Phe
<220> FEATURE:
<221> NAME/KEY: MOD_RES
<222> LOCATION: (10)..(10)
<223> OTHER INFORMATION: D-Lys

<400> SEQUENCE: 50

Xaa Arg Ser Asp Thr Leu Xaa Xaa Phe Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

```
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Aic
<220> FEATURE:
<221> NAME/KEY: MOD_RES
<222> LOCATION: (10)..(10)
<223> OTHER INFORMATION: D-Lys

<400> SEQUENCE: 51

Xaa Arg Ser Asp Thr Leu Xaa Trp Xaa Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: N-Me-Arg
<220> FEATURE:
<221> NAME/KEY: MOD_RES
<222> LOCATION: (8)..(8)
<223> OTHER INFORMATION: Pen

<400> SEQUENCE: 52

Ala Xaa Arg Ser Asp Thr Leu Xaa Trp Glu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: N-Me-Arg
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (10)..(10)
<223> OTHER INFORMATION: D-Glu

<400> SEQUENCE: 53

Ala Xaa Arg Ser Asp Thr Leu Xaa Trp Glu
1               5                   10
```

```
<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: N-Me-Arg
<220> FEATURE:
<221> NAME/KEY: MOD_RES
<222> LOCATION: (8)..(8)
<223> OTHER INFORMATION: Pen

<400> SEQUENCE: 54

Ala Xaa Arg Ser Asp Thr Leu Xaa Trp Glu
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: Dap

<400> SEQUENCE: 55

Xaa Arg Ser Asp Thr Leu Xaa Trp Glu Xaa
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
```

```
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: Dab

<400> SEQUENCE: 56

Xaa Arg Ser Asp Thr Leu Xaa Trp Glu Xaa
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 57

Xaa Arg Ser Asp Thr Leu Xaa Trp Glu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu

<400> SEQUENCE: 58

Xaa Arg Ser Asp Thr Leu Xaa Trp Glu
1               5

<210> SEQ ID NO 59
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Dap

<400> SEQUENCE: 59

Xaa Arg Ser Asp Thr Leu Xaa Trp Glu Xaa
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Dap

<400> SEQUENCE: 60

Xaa Arg Ser Asp Thr Leu Xaa Trp Glu Xaa
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (10)..(10)
<223> OTHER INFORMATION: Dab

<400> SEQUENCE: 61

Xaa Arg Ser Asp Thr Leu Xaa Trp Glu Xaa
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Dab

<400> SEQUENCE: 62

Xaa Arg Ser Asp Thr Leu Xaa Trp Glu Xaa
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: Dap

<400> SEQUENCE: 63

Xaa Arg Ser Asp Thr Leu Xaa Trp Glu Xaa
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: Dab

<400> SEQUENCE: 64

Xaa Arg Ser Asp Thr Leu Xaa Trp Glu Xaa
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 65

Xaa Arg Ser Asp Thr Leu Xaa Trp Glu Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 66

Xaa Arg Ser Asp Thr Leu Xaa Trp Glu Lys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 67

Xaa Arg Ser Asp Thr Leu Xaa Trp Glu Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 68

Xaa Arg Ser Asp Thr Leu Xaa Trp Glu Lys
1               5                   10

<210> SEQ ID NO 69
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (4)..(4)
<223> OTHER INFORMATION: Asp(OMe)
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 69

Xaa Arg Ser Asp Thr Leu Xaa Trp Glu Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 70

Xaa Arg Ser Asp Thr Leu Xaa Trp Glu Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
```

```
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 71

Xaa Arg Ser Asp Thr Leu Xaa Trp Glu Lys
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 72

Xaa Arg Ser Asp Thr Leu Xaa Trp Glu Lys
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (4)..(4)
<223> OTHER INFORMATION: Asp(OMe)
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (10)..(10)
<223> OTHER INFORMATION: D-Lys

<400> SEQUENCE: 73

Xaa Arg Ser Asp Thr Leu Xaa Trp Glu Lys
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 74

Xaa Arg Ser Asp Thr Leu Xaa Trp Glu Lys
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal

<400> SEQUENCE: 75

Xaa Arg Ser Asp Thr Leu Xaa Xaa Glu
1               5

<210> SEQ ID NO 76
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 76

Xaa Arg Ser Asp Thr Leu Xaa Trp Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: N-Me-Lys

<400> SEQUENCE: 77

Xaa Arg Ser Asp Thr Leu Xaa Trp Lys
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys
```

```
<400> SEQUENCE: 78

Xaa Arg Ser Asp Thr Leu Xaa Trp Glu Lys
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Bip
<220> FEATURE:
<221> NAME/KEY: MOD_RES
<222> LOCATION: (10)..(10)
<223> OTHER INFORMATION: D-Lys

<400> SEQUENCE: 79

Xaa Arg Ser Asp Thr Leu Xaa Xaa Xaa Lys
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 80

Xaa Arg Ser Asp Thr Leu Xaa Xaa Glu Lys
```

```
<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 81

Xaa Arg Ser Asp Thr Leu Xaa Trp Glu Lys
 1               5                  10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 82

Xaa Arg Ser Asp Thr Leu Xaa Trp Gln Lys
 1               5                  10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
```

```
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 83

Xaa Arg Ser Asp Thr Leu Xaa Trp Asn Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Cit
<220> FEATURE:
<221> NAME/KEY: MOD_RES
<222> LOCATION: (10)..(10)
<223> OTHER INFORMATION: D-Lys

<400> SEQUENCE: 84

Xaa Arg Ser Asp Thr Leu Xaa Trp Xaa Lys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 85

Xaa Arg Ser Asp Thr Leu Xaa Trp Phe Lys
1               5                   10

<210> SEQ ID NO 86
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Glu(OMe)
<220> FEATURE:
<221> NAME/KEY: MOD_RES
<222> LOCATION: (10)..(10)
<223> OTHER INFORMATION: D-Lys

<400> SEQUENCE: 86

Xaa Arg Ser Asp Thr Leu Xaa Trp Glu Lys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 87

Xaa Arg Ser Asp Thr Leu Xaa Trp Asp Lys
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
```

```
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Lys

<400> SEQUENCE: 88

Xaa Arg Ser Asp Thr Leu Xaa Xaa Lys
1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 89

Xaa Arg Ser Asp Thr Leu Cys Xaa Glu Lys
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Lys
```

<400> SEQUENCE: 90

Xaa Arg Ser Asp Thr Leu Xaa Xaa Lys
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Lys

<400> SEQUENCE: 91

Xaa Arg Ser Asp Thr Leu Xaa Trp Phe Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Tyr
<220> FEATURE:
<221> NAME/KEY: MOD_RES
<222> LOCATION: (10)..(10)
<223> OTHER INFORMATION: D-Lys

<400> SEQUENCE: 92

Xaa Arg Ser Asp Thr Leu Xaa Trp Tyr Lys
1               5                   10

<210> SEQ ID NO 93
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 93

Xaa Arg Ser Asp Thr Leu Cys Xaa Glu Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 94

Xaa Arg Ser Asp Thr Leu Xaa Trp Pro Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
```

<400> SEQUENCE: 95

Xaa Arg Ser Asp Thr Leu Xaa Trp Pro Lys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 96

Xaa Arg Ser Asp Thr Leu Xaa Trp Pro Lys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: Dab

<400> SEQUENCE: 97

Xaa Arg Ser Asp Thr Leu Xaa Trp Glu Xaa
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:

```
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(2-carbamoyl)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 98

Xaa Arg Ser Asp Thr Leu Xaa Phe Glu Lys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(3-carbamoyl)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 99

Xaa Arg Ser Asp Thr Leu Xaa Phe Glu Lys
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
```

```
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 100

Xaa Arg Ser Asp Thr Leu Xaa Phe Glu Lys
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(2,4-Cl)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 101

Xaa Arg Ser Asp Thr Leu Xaa Phe Glu Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (8)..(8)
<223> OTHER INFORMATION: Phe(3,4-Cl)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 102

Xaa Arg Ser Asp Thr Leu Xaa Phe Glu Lys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-OMe)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 103

Xaa Arg Ser Asp Thr Leu Xaa Phe Glu Lys
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (9)..(9)
<223> OTHER INFORMATION: D-His
<220> FEATURE:
<221> NAME/KEY: MOD_RES
<222> LOCATION: (10)..(10)
<223> OTHER INFORMATION: D-Lys

<400> SEQUENCE: 104

Xaa Arg Ser Asp Thr Leu Xaa Trp His Lys
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Phe(4-COOH)
<220> FEATURE:
<221> NAME/KEY: MOD_RES
<222> LOCATION: (10)..(10)
<223> OTHER INFORMATION: D-Lys

<400> SEQUENCE: 105

Xaa Arg Ser Asp Thr Leu Xaa Trp Phe Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys
```

```
<400> SEQUENCE: 106

Xaa Arg Ser Asp Thr Leu Xaa Phe Glu Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-F)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 107

Xaa Arg Ser Asp Thr Leu Xaa Phe Glu Lys
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 108

Xaa Arg Ser Asp Thr Leu Xaa Xaa Glu Lys
```

```
1               5                  10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: D-Lys

<400> SEQUENCE: 109

Xaa Arg Ser Asp Thr Leu Xaa Trp Xaa Lys
1               5                  10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Trp
<220> FEATURE:
<221> NAME/KEY: MOD_RES
<222> LOCATION: (10)..(10)
<223> OTHER INFORMATION: D-Lys

<400> SEQUENCE: 110

Xaa Arg Ser Asp Thr Leu Xaa Trp Trp Lys
1               5                  10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Lys

<400> SEQUENCE: 111

Xaa Arg Ser Asp Thr Leu Xaa Xaa Phe Lys
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-His
<220> FEATURE:
<221> NAME/KEY: MOD_RES
<222> LOCATION: (10)..(10)
<223> OTHER INFORMATION: D-Lys

<400> SEQUENCE: 112

Xaa Arg Ser Asp Thr Leu Xaa Xaa His Lys
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
```

```
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Leu
<220> FEATURE:
<221> NAME/KEY: MOD_RES
<222> LOCATION: (10)..(10)
<223> OTHER INFORMATION: D-Lys

<400> SEQUENCE: 113

Xaa Arg Ser Asp Thr Leu Xaa Xaa Leu Lys
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Lys

<400> SEQUENCE: 114

Xaa Arg Ser Asp Thr Leu Xaa Xaa Arg Lys
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
```

```
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: D-Lys

<400> SEQUENCE: 115

Xaa Arg Ser Asp Thr Leu Xaa Xaa Xaa Lys
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: D-Thr
<220> FEATURE:
<221> NAME/KEY: MOD_RES
<222> LOCATION: (10)..(10)
<223> OTHER INFORMATION: D-Lys

<400> SEQUENCE: 116

Xaa Arg Ser Asp Thr Leu Xaa Xaa Thr Lys
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

-continued

```
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Lys

<400> SEQUENCE: 117

Xaa Arg Ser Asp Thr Leu Xaa Xaa Phe Lys
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-His
<220> FEATURE:
<221> NAME/KEY: MOD_RES
<222> LOCATION: (10)..(10)
<223> OTHER INFORMATION: D-Lys

<400> SEQUENCE: 118

Xaa Arg Ser Asp Thr Leu Xaa Xaa His Lys
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Leu
<220> FEATURE:
<221> NAME/KEY: MOD_RES
<222> LOCATION: (10)..(10)
<223> OTHER INFORMATION: D-Lys

<400> SEQUENCE: 119

Xaa Arg Ser Asp Thr Leu Xaa Xaa Leu Lys
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Lys

<400> SEQUENCE: 120

Xaa Arg Ser Asp Thr Leu Xaa Xaa Arg Lys
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
```

```
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: D-Lys

<400> SEQUENCE: 121

Xaa Arg Ser Asp Thr Leu Xaa Xaa Xaa Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-CF3)
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 122

Xaa Arg Ser Asp Thr Leu Xaa Phe Glu Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
```

-continued

```
<223> OTHER INFORMATION: D-Lys

<400> SEQUENCE: 123

Xaa Arg Ser Asp Thr Leu Xaa Tyr Glu Lys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 124

Xaa Arg Ser Asp Thr Leu Xaa His Glu Lys
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: D-Lys

<400> SEQUENCE: 125

Xaa Arg Ser Asp Thr Leu Xaa Phe Glu Lys
1               5                   10

<210> SEQ ID NO 126
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: N-Me-Lys

<400> SEQUENCE: 126

Xaa Arg Ser Asp Thr Leu Xaa Phe Glu Lys
1               5                   10

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 127

Xaa Arg Ser Asp Thr Leu Xaa Trp
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 128
```

Xaa Arg Ser Asp Thr Leu Xaa Trp Glu
1               5

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (10)..(10)
<223> OTHER INFORMATION: D-Lys

<400> SEQUENCE: 129

Xaa Arg Ser Asp Thr Leu Xaa Phe Glu Lys
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 130

Xaa Arg Ser Asp Thr Leu Xaa Phe Glu Lys
1               5                   10

<210> SEQ ID NO 131
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: D-Lys

<400> SEQUENCE: 131

Xaa Arg Ser Asp Thr Leu Xaa Phe Glu Lys
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 132

Xaa Arg Ser Asp Thr Leu Xaa Phe Glu Lys
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: N-Me-Lys

<400> SEQUENCE: 133

Xaa Arg Ser Asp Thr Leu Xaa Phe Glu Lys
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (10)..(10)
<223> OTHER INFORMATION: D-Lys

<400> SEQUENCE: 134

Xaa Arg Ser Asp Thr Leu Xaa Xaa Glu Lys
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 135

Xaa Arg Ser Asp Thr Leu Xaa Xaa Glu Lys
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (10)..(10)
<223> OTHER INFORMATION: N-Me-Lys

<400> SEQUENCE: 136

Xaa Arg Ser Asp Thr Leu Xaa Xaa Glu Lys
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
```

```
<221> NAME/KEY: MOD_RES
<222> LOCATION: (10)..(10)
<223> OTHER INFORMATION: D-Lys

<400> SEQUENCE: 137

Xaa Arg Ser Asp Thr Leu Xaa Xaa Glu Lys
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 138

Xaa Arg Ser Asp Thr Leu Xaa Xaa Glu Lys
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-CN)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 139

Xaa Arg Ser Asp Thr Leu Xaa Phe Glu Lys
```

```
<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Thr
<220> FEATURE:
<221> NAME/KEY: MOD_RES
<222> LOCATION: (10)..(10)
<223> OTHER INFORMATION: D-Lys

<400> SEQUENCE: 140

Xaa Arg Ser Asp Thr Leu Xaa Xaa Thr Lys
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 141

Xaa Arg Ser Asp Thr Leu Xaa Trp Glu Lys
1               5                   10

<210> SEQ ID NO 142
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 142

Xaa Arg Ser Asp Thr Leu Xaa Xaa Glu Lys
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal

<400> SEQUENCE: 143

Xaa Arg Ser Asp Thr Leu Xaa Xaa Glu
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
```

```
<220> FEATURE:
<221> NAME/KEY: MOD_RES
<222> LOCATION: (7)..(7)
<223> OTHER INFORMATION: Pen

<400> SEQUENCE: 144

Xaa Arg Ser Asp Thr Leu Xaa Trp Glu
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu

<400> SEQUENCE: 145

Xaa Arg Ser Asp Thr Leu Xaa Trp Glu
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 146

Xaa Arg Ser Asp Thr Leu Xaa Trp Glu
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (10)..(10)
<223> OTHER INFORMATION: N-Me-Lys

<400> SEQUENCE: 147

Xaa Arg Ser Asp Thr Leu Xaa Phe Glu Lys
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 148

Xaa Arg Ser Asp Thr Leu Xaa Phe Glu Lys
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
```

```
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 149

Xaa Arg Ser Asp Thr Leu Xaa Phe Glu Lys
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 150

Xaa Arg Ser Asp Thr Leu Xaa Xaa Glu Lys
1               5                   10

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (8)..(8)
<223> OTHER INFORMATION: Phe(4-tBu)

<400> SEQUENCE: 151

Xaa Arg Ser Asp Thr Leu Xaa Phe
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 152

Xaa Arg Ser Asp Thr Leu Xaa Phe Glu
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 153
```

```
Xaa Arg Ser Asp Thr Leu Xaa Phe Glu Lys
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Beta-Homo-Glu

<400> SEQUENCE: 154

Xaa Arg Ser Asp Thr Leu Xaa Xaa Glu
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 155

Xaa Arg Ser Asp Thr Leu Xaa Xaa Glu
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 156

Xaa Arg Ser Asp Val Leu Xaa Xaa Glu
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 157

Xaa Arg Ser Asp Phe Leu Xaa Xaa Glu
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

```
<222> LOCATION: (5)..(5)
<223> OTHER INFORMATION: Cha
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 158

Xaa Arg Ser Asp Xaa Leu Xaa Xaa Glu
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 159

Xaa Arg Ser Asp Leu Leu Xaa Xaa Glu
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
```

```
<221> NAME/KEY: MOD_RES
<222> LOCATION: (9)..(9)
<223> OTHER INFORMATION: D-Glu

<400> SEQUENCE: 160

Xaa Arg Ser Asp Ile Leu Xaa Xaa Glu
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (5)..(5)
<223> OTHER INFORMATION: hLeu
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 161

Xaa Arg Ser Asp Leu Leu Xaa Xaa Glu
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 162

Xaa Arg Ser Asp Thr Phe Xaa Xaa Glu
```

```
<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 163

Xaa Arg Ser Asp Thr Gln Xaa Xaa Glu
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: D-Glu

<400> SEQUENCE: 164

Xaa Arg Ser Asp Thr Tyr Xaa Xaa Glu
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 165

Xaa Arg Ser Asp Thr Leu Xaa Phe Glu
1               5

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 166

Xaa Arg Ser Asp Thr Leu Xaa Phe Glu Lys
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg

```
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 167

Xaa Arg Ser Asp Thr Leu Xaa Phe Glu Lys
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 168

Xaa Arg Ser Asp Thr Leu Xaa Phe Glu Lys
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 169

Xaa Arg Ser Asp Thr Leu Xaa Phe Glu Lys
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 170

Xaa Arg Ser Asp Thr Leu Xaa Phe Glu Lys
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 171

Xaa Arg Ser Asp Thr Leu Xaa Phe Glu Lys
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 172

Xaa Arg Ser Asp Thr Leu Xaa Phe Glu Lys
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
```

```
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 173

Xaa Arg Ser Asp Thr Leu Xaa Phe Glu Lys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 174

Xaa Arg Ser Asp Thr Leu Xaa Phe Glu Lys
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
```

```
<220> FEATURE:
<221> NAME/KEY: MOD_RES
<222> LOCATION: (10)..(10)
<223> OTHER INFORMATION: D-Lys

<400> SEQUENCE: 175

Xaa Arg Ser Asp Thr Leu Xaa Phe Glu Lys
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 176

Xaa Arg Ser Asp Thr Leu Xaa Phe Glu Lys
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
```

<223> OTHER INFORMATION: D-Lys

<400> SEQUENCE: 177

Xaa Arg Ser Asp Thr Leu Xaa Phe Glu Lys
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 178

Xaa Arg Ser Asp Thr Leu Xaa Phe Glu Lys
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 179

```
Xaa Arg Ser Asp Thr Leu Xaa Phe Glu Lys
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 180

Xaa Arg Ser Asp Thr Leu Xaa Phe Glu Lys
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 181

Xaa Arg Ser Asp Thr Leu Xaa Phe Glu Lys
1               5                   10
```

```
<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 182

Xaa Arg Ser Asp Thr Leu Xaa Phe Glu Lys
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 183

Xaa Arg Ser Asp Thr Leu Xaa Phe Glu Lys
1               5                   10

<210> SEQ ID NO 184
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 184

Xaa Arg Ser Asp Thr Leu Xaa Phe Glu Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (6)..(6)
<223> OTHER INFORMATION: 13C(5)Leu
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 185

Xaa Arg Ser Asp Thr Leu Xaa Phe Glu Lys
1               5                   10
```

```
<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 186

Xaa Arg Ser Asp Ile Leu Xaa Phe Glu Lys
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 187

Xaa Arg Ser Asp Thr Gln Xaa Phe Glu Lys
1               5                   10

<210> SEQ ID NO 188
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 188

Xaa Arg Ser Asp Ile Leu Xaa Phe Glu Lys
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 189

Xaa Arg Ser Gln Ile Gln Xaa Phe Glu Lys
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 190

Xaa Arg Ser Gln Ile Gln Xaa Phe Glu Lys
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 191

Xaa Arg Ser Asp Asp Leu Xaa Phe Glu Lys
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 192

Xaa Arg Ser Gln Ile Gln Xaa Phe Glu Lys
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 193

Xaa Arg Ser Asp Asp Leu Xaa Phe Glu Lys
1               5                   10

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Arg Ser Asp Thr Leu Cys Gly Glu
1               5
```

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Arg Ser Asp Thr Leu Cys
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Arg Ser Asp Thr Leu Cys Gly Glu Lys
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Cys Arg Ser Asp Thr Leu Cys Gly Glu Lys
1               5                   10

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg

<400> SEQUENCE: 198

Cys Arg Ser Asp Thr Leu Cys Gly Glu
1               5

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg

<400> SEQUENCE: 199

Cys Arg Ser Asp Thr Leu Cys Gly Glu Lys
1               5                   10

```
<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg

<400> SEQUENCE: 200

Cys Arg Ser Asp Thr Leu Cys Lys
1               5

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg

<400> SEQUENCE: 201

Cys Arg Ser Asp Thr Leu Cys Gly Glu Lys
1               5                   10

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 202

Cys Arg Ser Asp Thr Leu Xaa Lys
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (8)..(8)
<223> OTHER INFORMATION: D-Lys

<400> SEQUENCE: 203

Cys Arg Ser Asp Thr Leu Xaa Lys
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 204

Cys Arg Ser Asp Thr Leu Xaa Trp Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 205

Cys Arg Ser Asp Thr Leu Xaa Glu Lys
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 206
```

```
Xaa Arg Ser Asp Thr Leu Cys Lys
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (8)..(8)
<223> OTHER INFORMATION: D-Lys

<400> SEQUENCE: 207

Xaa Arg Ser Asp Thr Leu Cys Lys
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Lys

<400> SEQUENCE: 208

Xaa Arg Ser Asp Thr Leu Xaa Trp Lys
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
```

```
<223> OTHER INFORMATION: D-Lys

<400> SEQUENCE: 209

Xaa Arg Ser Asp Thr Leu Xaa Trp Lys
1               5

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: D-Lys

<400> SEQUENCE: 210

Xaa Arg Ser Asp Thr Leu Xaa Xaa Glu Lys
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 211

Xaa Arg Ser Asp Thr Leu Xaa Trp Glu Lys
1               5                   10

<210> SEQ ID NO 212
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: D-Lys

<400> SEQUENCE: 212

Xaa Arg Ser Asp Thr Leu Xaa Xaa Glu Lys
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 213

Xaa Arg Ser Asp Thr Leu Xaa Trp Glu Lys
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
```

```
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 214

Xaa Arg Ser Asp Thr Leu Xaa Trp Glu Lys
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 215

Xaa Arg Ser Asp Thr Leu Xaa Trp Glu Lys
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: D-Glu
<220> FEATURE:
<221> NAME/KEY: MOD_RES
<222> LOCATION: (10)..(10)
<223> OTHER INFORMATION: D-Lys

<400> SEQUENCE: 216

Xaa Arg Ser Asp Thr Leu Xaa Trp Glu Lys
1               5                   10
```

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: D-Lys

<400> SEQUENCE: 217

Xaa Arg Ser Asp Thr Leu Xaa Trp Glu Lys
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 218

Xaa Arg Ser Asp Thr Leu Xaa Phe Glu Lys
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 219

Xaa Arg Ser Asp Thr Leu Xaa Trp Glu Lys
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 220

Xaa Arg Ser Asp Thr Leu Xaa Phe Glu Lys
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

```
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 221

Xaa Arg Ser Asp Thr Leu Xaa Trp Glu Lys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 222

Xaa Arg Ser Asp Thr Leu Xaa Xaa Glu Lys
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
```

```
<221> NAME/KEY: MOD_RES
<222> LOCATION: (10)..(10)
<223> OTHER INFORMATION: D-Lys

<400> SEQUENCE: 223

Xaa Arg Ser Asp Thr Leu Xaa Xaa Glu Lys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 224

Xaa Arg Ser Asp Thr Leu Xaa Xaa Glu Lys
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 225

Xaa Arg Ser Asp Thr Leu Xaa Phe Glu Lys
```

```
<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 226

Xaa Arg Ser Asp Thr Leu Xaa Phe Glu Lys
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 227

Xaa Arg Ser Asp Thr Leu Xaa Trp Glu Lys
1               5                   10

<210> SEQ ID NO 228
<211> LENGTH: 10
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 228

Xaa Arg Ser Asp Thr Leu Xaa Xaa Glu Lys
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 229

Xaa Arg Ser Asp Thr Leu Xaa Xaa Glu Lys
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 230

Xaa Arg Ser Asp Thr Leu Xaa Trp Glu Lys
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 231

Xaa Arg Ser Asp Thr Leu Xaa Xaa Glu Lys
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 232

Xaa Arg Ser Asp Thr Leu Xaa Xaa Glu Lys
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 233

Xaa Arg Ser Asp Thr Leu Xaa Trp Glu Lys
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
```

```
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 234

Xaa Arg Ser Asp Thr Leu Xaa Phe Glu Lys
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 235

Xaa Arg Ser Asp Thr Leu Xaa Trp Glu Lys
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 236

Xaa Arg Ser Asp Thr Leu Xaa Xaa Glu Lys
1               5                   10
```

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 237

Xaa Arg Ser Asp Thr Leu Xaa Xaa Glu Lys
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 238

Xaa Arg Ser Asp Thr Leu Xaa Xaa Glu Lys
1               5                   10

<210> SEQ ID NO 239
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 239

Xaa Arg Ser Asp Thr Leu Xaa Phe Glu Lys
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 240

Xaa Arg Ser Asp Thr Leu Xaa Phe Glu Lys
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 241

Xaa Arg Ser Asp Thr Leu Xaa Trp Glu Lys
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 242

Xaa Arg Ser Asp Thr Leu Xaa Xaa Glu Lys
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
```

```
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 243

Xaa Arg Ser Asp Thr Leu Xaa Xaa Glu Lys
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 244

Xaa Arg Ser Asp Thr Leu Xaa Trp Glu Lys
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (10)..(10)
```

<223> OTHER INFORMATION: D-Lys

<400> SEQUENCE: 245

Xaa Arg Ser Asp Thr Leu Xaa Phe Glu Lys
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: D-Lys

<400> SEQUENCE: 246

Xaa Arg Ser Asp Thr Leu Xaa Phe Glu Lys
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 247

Xaa Arg Ser Asp Thr Leu Xaa Phe Glu Lys
1               5                   10

```
<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (10)..(10)
<223> OTHER INFORMATION: N-Me-Lys

<400> SEQUENCE: 248

Xaa Arg Ser Asp Thr Leu Xaa Phe Glu Lys
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (10)..(10)
<223> OTHER INFORMATION: D-Lys

<400> SEQUENCE: 249

Xaa Arg Ser Asp Thr Leu Xaa Xaa Glu Lys
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 250

Xaa Arg Ser Asp Thr Leu Xaa Xaa Glu Lys
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 251

Xaa Arg Ser Asp Thr Leu Xaa Trp Glu Lys
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
```

```
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 252

Xaa Arg Ser Asp Thr Leu Xaa Phe Glu Lys
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 253

Xaa Arg Ser Asp Thr Leu Xaa Trp Glu Lys
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
```

```
<221> NAME/KEY: MOD_RES
<222> LOCATION: (10)..(10)
<223> OTHER INFORMATION: D-Lys

<400> SEQUENCE: 254

Xaa Arg Ser Asp Thr Leu Xaa Xaa Glu Lys
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 255

Xaa Arg Ser Asp Thr Leu Xaa Xaa Glu Lys
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 256

Xaa Arg Ser Asp Thr Leu Xaa Xaa Glu Lys
```

```
<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 257

Xaa Arg Ser Asp Thr Leu Xaa Phe Glu Lys
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 258

Xaa Arg Ser Asp Thr Leu Xaa Phe Glu Lys
1               5                   10
```

```
<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 259

Xaa Arg Ser Asp Thr Leu Xaa Trp Glu Lys
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 260

Xaa Arg Ser Asp Thr Leu Xaa Xaa Glu Lys
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 261

Xaa Arg Ser Asp Thr Leu Xaa Xaa Glu Lys
1               5                   10

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 262

Xaa Arg Ser Asp Thr Leu Xaa Trp Glu Lys
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
```

```
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 263

Xaa Arg Ser Asp Thr Leu Xaa Trp Glu Lys
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 264

Xaa Arg Ser Asp Thr Leu Xaa Phe Glu Lys
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 265
```

Xaa Arg Ser Asp Thr Leu Xaa Trp Glu Lys
1               5                   10

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 266

Xaa Arg Ser Asp Thr Leu Xaa Xaa Glu Lys
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 267

Xaa Arg Ser Asp Thr Leu Xaa Xaa Glu Lys
1               5                   10

```
<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 268

Xaa Arg Ser Asp Thr Leu Xaa Xaa Glu Lys
1               5                   10

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 269

Xaa Arg Ser Asp Thr Leu Xaa Phe Glu Lys
1               5                   10

<210> SEQ ID NO 270
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 270

Xaa Arg Ser Asp Thr Leu Xaa Trp Glu Lys
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 271

Xaa Arg Ser Asp Thr Leu Xaa Xaa Glu Lys
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
```

```
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 272

Xaa Arg Ser Asp Thr Leu Xaa Xaa Glu Lys
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 273

Xaa Arg Ser Asp Thr Leu Xaa Trp Glu Lys
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
```

<400> SEQUENCE: 274

Xaa Arg Ser Asp Thr Leu Xaa Phe Glu
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu

<400> SEQUENCE: 275

Xaa Arg Ser Asp Thr Leu Xaa Phe Glu
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)

<400> SEQUENCE: 276

Xaa Arg Ser Asp Thr Leu Xaa Phe Glu
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 277

Xaa Arg Ser Asp Thr Leu Xaa Phe Glu
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip

<400> SEQUENCE: 278

Xaa Arg Ser Asp Thr Leu Xaa Xaa Glu
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip

```
<220> FEATURE:
<221> NAME/KEY: MOD_RES
<222> LOCATION: (9)..(9)
<223> OTHER INFORMATION: Beta-Homo-Glu

<400> SEQUENCE: 279

Xaa Arg Ser Asp Thr Leu Xaa Xaa Glu
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 280

Xaa Arg Ser Asp Thr Leu Xaa Trp Glu
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 281

Xaa Arg Ser Asp Thr Leu Xaa Trp Glu
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
```

```
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 282

Xaa Arg Ser Asp Thr Leu Xaa Xaa Glu
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu

<400> SEQUENCE: 283

Xaa Arg Ser Asp Thr Leu Xaa Xaa Glu
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
```

<400> SEQUENCE: 284

Xaa Arg Ser Asp Thr Leu Xaa Xaa Glu
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 285

Xaa Arg Ser Asp Thr Leu Xaa Phe Glu
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu

<400> SEQUENCE: 286

Xaa Arg Ser Asp Thr Leu Xaa Phe Glu
1               5

<210> SEQ ID NO 287
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 287

Xaa Arg Ser Asp Thr Leu Xaa Xaa Glu
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu

<400> SEQUENCE: 288

Xaa Arg Ser Asp Thr Leu Xaa Xaa Glu
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
```

```
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal

<400> SEQUENCE: 289

Xaa Arg Ser Asp Thr Leu Xaa Xaa Glu
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 290

Xaa Arg Ser Asp Thr Leu Xaa Trp Glu
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu

<400> SEQUENCE: 291

Xaa Arg Ser Asp Thr Leu Xaa Phe Glu
1               5
```

```
<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 292

Xaa Arg Ser Asp Thr Leu Xaa Trp Glu
1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu

<400> SEQUENCE: 293

Xaa Arg Ser Asp Thr Leu Xaa Xaa Glu
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
```

```
<220> FEATURE:
<221> NAME/KEY: MOD_RES
<222> LOCATION: (8)..(8)
<223> OTHER INFORMATION: 2-Nal

<400> SEQUENCE: 294

Xaa Arg Ser Asp Thr Leu Xaa Xaa Glu
1               5

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 295

Xaa Arg Ser Asp Thr Leu Xaa Trp Glu Lys
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 296

Xaa Arg Ser Asp Thr Leu Xaa Trp Glu Lys
1               5                   10
```

```
<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 297

Xaa Arg Ser Asp Thr Leu Xaa Phe Glu Lys
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-Lys

<400> SEQUENCE: 298

Xaa Arg Ser Asp Thr Leu Xaa Trp Glu Lys
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
```

```
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 299

Xaa Arg Ser Asp Thr Leu Xaa Xaa Glu Lys
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 300

Xaa Arg Ser Asp Thr Leu Xaa Xaa Glu Lys
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
```

```
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 301

Xaa Arg Ser Asp Thr Leu Xaa Xaa Glu Lys
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 302

Xaa Arg Ser Asp Thr Leu Xaa Phe Glu Lys
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
```

```
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 303

Xaa Arg Ser Asp Thr Leu Xaa Phe Glu Lys
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 304

Xaa Arg Ser Asp Thr Leu Xaa Trp Glu Lys
1               5                   10

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
```

```
<221> NAME/KEY: MOD_RES
<222> LOCATION: (10)..(10)
<223> OTHER INFORMATION: N-Me-Lys

<400> SEQUENCE: 305

Xaa Arg Ser Asp Thr Leu Xaa Xaa Glu Lys
1               5                   10

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 306

Xaa Arg Ser Asp Thr Leu Xaa Xaa Glu Lys
1               5                   10

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 307

Xaa Arg Ser Asp Thr Leu Xaa Trp Glu Lys
```

-continued

```
1               5                   10

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 308

Xaa Arg Ser Asp Thr Leu Xaa Trp Glu Lys
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 309

Xaa Arg Ser Asp Thr Leu Xaa Trp Glu Lys
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
```

```
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 310

Xaa Arg Ser Asp Thr Leu Xaa Trp Glu Lys
1               5                   10

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 311

Xaa Arg Ser Asp Thr Leu Xaa Phe Glu Lys
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
```

<220> FEATURE:
<221> NAME/KEY: MOD_RES
<222> LOCATION: (10)..(10)
<223> OTHER INFORMATION: N-Me-Lys

<400> SEQUENCE: 312

Xaa Arg Ser Asp Thr Leu Xaa Trp Glu Lys
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 313

Xaa Arg Ser Asp Thr Leu Xaa Xaa Glu Lys
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)

<223> OTHER INFORMATION: D-Lys

<400> SEQUENCE: 314

Xaa Arg Ser Asp Thr Leu Xaa Xaa Glu Lys
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (10)..(10)
<223> OTHER INFORMATION: N-Me-Lys

<400> SEQUENCE: 315

Xaa Arg Ser Asp Thr Leu Xaa Xaa Glu Lys
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 316

Xaa Arg Ser Asp Thr Leu Xaa Phe Glu Lys
1               5                   10

```
<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 317

Xaa Arg Ser Asp Thr Leu Xaa Phe Glu Lys
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 318

Xaa Arg Ser Asp Thr Leu Xaa Trp Glu Lys
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
           peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 319

Xaa Arg Ser Asp Thr Leu Xaa Xaa Glu Lys
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: N-Me-Lys

<400> SEQUENCE: 320

Xaa Arg Ser Asp Thr Leu Xaa Xaa Glu Lys
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (10)..(10)
<223> OTHER INFORMATION: N-Me-D-Lys

<400> SEQUENCE: 321

Xaa Arg Ser Asp Thr Leu Xaa Trp Glu Lys
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
<221> NAME/KEY: MOD_RES
<222> LOCATION: (10)..(10)
<223> OTHER INFORMATION: D-Lys

<400> SEQUENCE: 322

Xaa Arg Ser Asp Thr Leu Xaa Trp Glu Lys
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu
<220> FEATURE:
```

```
<221> NAME/KEY: MOD_RES
<222> LOCATION: (10)..(10)
<223> OTHER INFORMATION: D-Lys

<400> SEQUENCE: 323

Xaa Arg Ser Asp Thr Leu Xaa Trp Glu Lys
1               5                   10

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 324

Xaa Arg Ser Asp Thr Leu Xaa Trp Glu
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu

<400> SEQUENCE: 325

Xaa Arg Ser Asp Thr Leu Xaa Phe Glu
1               5

<210> SEQ ID NO 326
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen

<400> SEQUENCE: 326

Xaa Arg Ser Asp Thr Leu Xaa Trp Glu
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 327

Xaa Arg Ser Asp Thr Leu Xaa Xaa Glu
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
```

```
<221> NAME/KEY: MOD_RES
<222> LOCATION: (9)..(9)
<223> OTHER INFORMATION: Beta-Homo-Glu

<400> SEQUENCE: 328

Xaa Arg Ser Asp Thr Leu Xaa Xaa Glu
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal

<400> SEQUENCE: 329

Xaa Arg Ser Asp Thr Leu Xaa Xaa Glu
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 330

Xaa Arg Ser Asp Thr Leu Xaa Phe Glu
1               5

<210> SEQ ID NO 331
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 331

Xaa Arg Ser Asp Thr Leu Xaa Trp Glu
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-COOH)
<220> FEATURE:
<221> NAME/KEY: MOD_RES
<222> LOCATION: (9)..(9)
<223> OTHER INFORMATION: Beta-Homo-Glu

<400> SEQUENCE: 332

Xaa Arg Ser Asp Thr Leu Xaa Phe Glu
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
```

```
<400> SEQUENCE: 333

Xaa Arg Ser Asp Thr Leu Xaa Trp Glu
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 334

Xaa Arg Ser Asp Thr Leu Xaa Xaa Glu
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 1-Nal
<220> FEATURE:
<221> NAME/KEY: MOD_RES
<222> LOCATION: (9)..(9)
<223> OTHER INFORMATION: Beta-Homo-Glu

<400> SEQUENCE: 335

Xaa Arg Ser Asp Thr Leu Xaa Xaa Glu
1               5

<210> SEQ ID NO 336
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: 2-Nal

<400> SEQUENCE: 336

Xaa Arg Ser Asp Thr Leu Xaa Xaa Glu
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Phe(4-tBu)
<220> FEATURE:
<221> NAME/KEY: MOD_RES
<222> LOCATION: (9)..(9)
<223> OTHER INFORMATION: Beta-Homo-Glu

<400> SEQUENCE: 337

Xaa Arg Ser Asp Thr Leu Xaa Phe Glu
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (8)..(8)
<223> OTHER INFORMATION: 2-Nal
<220> FEATURE:
<221> NAME/KEY: MOD_RES
<222> LOCATION: (9)..(9)
<223> OTHER INFORMATION: Beta-Homo-Glu

<400> SEQUENCE: 338

Xaa Arg Ser Asp Thr Leu Xaa Xaa Glu
1               5

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (10)..(10)
<223> OTHER INFORMATION: D-Lys

<400> SEQUENCE: 339

Xaa Arg Ser Asp Thr Leu Xaa Xaa Glu Lys
1               5                   10

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (8)..(8)
<223> OTHER INFORMATION: Bip

<400> SEQUENCE: 340

Xaa Arg Ser Asp Thr Leu Xaa Xaa Glu
1               5

<210> SEQ ID NO 341
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 341

Xaa Arg Ser Asp Thr Leu Xaa Trp Glu
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Beta-Homo-Glu

<400> SEQUENCE: 342

Xaa Arg Ser Asp Thr Leu Xaa Trp Glu
1               5

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
```

```
<221> NAME/KEY: MOD_RES
<222> LOCATION: (9)..(9)
<223> OTHER INFORMATION: Glu, D-Glu, Beta-Homo-Glu or absent
<220> FEATURE:
<221> NAME/KEY: MOD_RES
<222> LOCATION: (10)..(10)
<223> OTHER INFORMATION: D-Lys or N-Me-Lys

<400> SEQUENCE: 343

Xaa Arg Ser Asp Thr Leu Xaa Trp Glu Lys
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (6)..(6)
<223> OTHER INFORMATION: Leu or Nle
<220> FEATURE:
<221> NAME/KEY: MOD_RES
<222> LOCATION: (7)..(7)
<223> OTHER INFORMATION: Cys, Pen or D-Pen
<220> FEATURE:
<221> NAME/KEY: MOD_RES
<222> LOCATION: (8)..(8)
<223> OTHER INFORMATION: Trp, Tic, Bip, 1-Nal, 2-Nal, Phe(4-tBu) or
      Phe(4-COOH)
<220> FEATURE:
<221> NAME/KEY: MOD_RES
<222> LOCATION: (9)..(9)
<223> OTHER INFORMATION: Glu, Beta-Homo-Glu, D-Glu or Glu(OMe)
<220> FEATURE:
<221> NAME/KEY: MOD_RES
<222> LOCATION: (10)..(10)
<223> OTHER INFORMATION: Any amino acid

<400> SEQUENCE: 344

Xaa Arg Ser Asp Thr Xaa Xaa Xaa Glu Xaa
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (5)..(5)
<223> OTHER INFORMATION: Thr or Val
<220> FEATURE:
<221> NAME/KEY: MOD_RES
<222> LOCATION: (6)..(6)
```

```
<223> OTHER INFORMATION: Leu or Nle
<220> FEATURE:
<221> NAME/KEY: MOD_RES
<222> LOCATION: (7)..(7)
<223> OTHER INFORMATION: Cys or Pen
<220> FEATURE:
<221> NAME/KEY: MOD_RES
<222> LOCATION: (8)..(8)
<223> OTHER INFORMATION: Trp, Tic, Bip, 1-Nal, 2-Nal, Phe(4-tBu), Phe,
      Tyr or Phe(4-COOH)
<220> FEATURE:
<221> NAME/KEY: MOD_RES
<222> LOCATION: (9)..(9)
<223> OTHER INFORMATION: Glu, Beta-Homo-Glu or D-Glu
<220> FEATURE:
<221> NAME/KEY: MOD_RES
<222> LOCATION: (10)..(10)
<223> OTHER INFORMATION: Any amino acid

<400> SEQUENCE: 345

Xaa Arg Ser Asp Xaa Xaa Xaa Xaa Glu Xaa
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (7)..(7)
<223> OTHER INFORMATION: Pen
<220> FEATURE:
<221> NAME/KEY: MOD_RES
<222> LOCATION: (9)..(9)
<223> OTHER INFORMATION: Glu, D-Glu, Beta-Homo-Glu or absent
<220> FEATURE:
<221> NAME/KEY: MOD_RES
<222> LOCATION: (10)..(10)
<223> OTHER INFORMATION: Any amino acid

<400> SEQUENCE: 346

Xaa Arg Ser Asp Thr Leu Xaa Trp Glu Xaa
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or Pen
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (6)..(6)
<223> OTHER INFORMATION: Leu or Nle
<220> FEATURE:
```

```
<221> NAME/KEY: MOD_RES
<222> LOCATION: (7)..(7)
<223> OTHER INFORMATION: Cys, Pen or D-Pen
<220> FEATURE:
<221> NAME/KEY: MOD_RES
<222> LOCATION: (8)..(8)
<223> OTHER INFORMATION: Trp, Tic, Bip, 1-Nal, 2-Nal, Phe(4-tbu) or
      Phe(4-COOH)
<220> FEATURE:
<221> NAME/KEY: MOD_RES
<222> LOCATION: (9)..(9)
<223> OTHER INFORMATION: Glu, D-Glu, Beta-Homo-Glu or Glu(OMe)
<220> FEATURE:
<221> NAME/KEY: MOD_RES
<222> LOCATION: (10)..(10)
<223> OTHER INFORMATION: Any amino acid

<400> SEQUENCE: 347

Xaa Arg Ser Asp Thr Xaa Xaa Xaa Glu Xaa
1               5                   10

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (8)..(8)
<223> OTHER INFORMATION: Dab

<400> SEQUENCE: 348

Cys Arg Ser Asp Thr Leu Cys Xaa
1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-Me-Arg
<220> FEATURE:
<221> NAME/KEY: MOD_RES
<222> LOCATION: (8)..(8)
<223> OTHER INFORMATION: Dab

<400> SEQUENCE: 349

Cys Arg Ser Asp Thr Leu Cys Xaa
1               5
```

α4α7 PEPTIDE MONOMER AND DIMER ANTAGONISTS

CROSS REFERENCE TO RELATED APPLICATIONS

This application is a Continuation of U.S. application Ser. No. 15/698,407, filed Sep. 7, 2017, which is a Continuation of U.S. application Ser. No. 14/872,975, filed Oct. 1, 2015, now U.S. Pat. No. 9,809,623, issued Nov. 7, 2017; which claims priority to U.S. Provisional Application No. 62/058,506, filed on Oct. 1, 2014; U.S. Provisional Application No. 62/058,510, filed on Oct. 1, 2014; U.S. Provisional Application No. 62/149,257, filed on Apr. 17, 2015; and U.S. Provisional Application No. 62/192,934, filed on Jul. 15, 2015; all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Feb. 3, 2020, is named PRTH-012-06US_SL.txt and is 173 KB in size.

FIELD OF THE INVENTION

The present invention relates to novel compounds having activity useful for treating conditions that arise from or are exacerbated by integrin binding, pharmaceutical compositions comprising the compounds, methods of treatment using the compounds, and methods of blocking or disrupting integrin binding.

BACKGROUND OF THE INVENTION

Integrins are noncovalently associated α/β heterodimeric cell surface receptors involved in numerous cellular processes ranging from cell adhesion and migration to gene regulation (Dubree, et al., Selective α4β7 Integrin Antagonist and Their Potential as Anti-inflammatory Agents, *J. Med. Chem.* 2002, 45, 3451-3457). Differential expression of integrins can regulate a cell's adhesive properties, allowing different leukocyte populations to be recruited to specific organs in response to different inflammatory signals. If left unchecked, integrins-mediated adhesion process can lead to chronic inflammation and autoimmune disease.

The α4 integrins, α4β1 and α4β7, play essential roles in lymphocyte migration throughout the gastrointestinal tract. They are expressed on most leukocytes, including B and T lymphocytes, where they mediate cell adhesion via binding to their respective primary ligands, vascular cell adhesion molecule (VCAM), and mucosal addressin cell adhesion molecule (MAdCAM), respectively. The proteins differ in binding specificity in that VCAM binds both α4β1 and to a lesser extent α4β7, while MAdCAM is highly specific for α4β7. In addition to pairing with the α4 subunit, the β7 subunit also forms a heterodimeric complex with αE subunit to form αEβ7, which is primarily expressed on intraepithelial lymphocytes (IEL) in the intestine, lung and genitourinary tract. αEβ7 is also expressed on dendritic cells in the gut. The αEβ7 heterodimer binds to E-cadherin on the epithelial cells. The IEL cells are thought to provide a mechanism for immune surveillance within the epithelial compartment. Therefore, blocking αEβ7 and α4β7 together may be a useful method for treating inflammatory conditions of the intestine Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis. Id. However, one of these therapies interfered with α4β1 integrin-ligand interactions thereby resulting in dangerous side effects to the patient. Therapies utilizing a dual-specific small molecule antagonists have shown similar side effects in animal models.

Accordingly, there is a need in the art for integrin antagonist molecules having high affinity for the α4β7 integrin and high selectivity against the α4β1 integrin, as a therapy for various gastrointestinal autoimmune diseases.

Such integrin antagonist molecules and related compositions and methods are provided by the present invention.

SUMMARY OF THE INVENTION

The present invention has been developed in response to the present state of the art, and in particular, in response to the problems and needs in the art that have not yet been fully solved by currently available integrin antagonists. Thus, the present invention provides α4β7 antagonist monomer and dimer peptides, e.g., for use as anti-inflammatory and/or immunosuppressive agents. Further, the present invention provides α4β7 antagonist monomer and dimer peptides for use in treating a condition that is associated with a biological function of α4β7 to tissues expressing MAdCAM.

The invention relates to novel peptidic compounds exhibiting integrin antagonist activity. The present invention further relates to novel peptidic compounds exhibiting high specificity for α4β7 integrin, and increased oral stability. In particular embodiments, the present invention relates to novel compounds having activity useful for treating conditions which arise or are exacerbated by integrin binding, pharmaceutical compositions comprising the compounds, methods of treatment using the compounds, and methods of blocking or disrupting integrin binding. The compounds are integrin antagonist molecules having high affinity for the α4β7 integrin, which may be used as a therapy for various gastrointestinal autoimmune diseases.

In certain embodiments, compounds of the present invention are dimers comprising two paired subunits that are linked together by their C- or N-termini via a linking moiety. In certain embodiments, one or both of the dimer subunit peptides of the present invention further comprises two natural or unnatural amino acids that are capable of bridging to form a cyclized structure. Thus, particular compounds of the present invention comprise dimerized peptides, each subunit of the dimer containing a cyclized structure through at least one of a disulfide bridge, an amide bond, or another or equivalent connection. This feature provides increased stability to the compound when administered orally as a therapeutic agent. In addition, this feature further provides for increased specificity and potency.

One having skill in the art will appreciate that the C- and N-terminal linker moieties disclosed herein are non-limiting examples of suitable linkers, and that the present invention may include any suitable linker moiety. Thus, some embodiments of the present invention comprises a homo- or heterodimer molecule comprised of two monomer subunits selected from the peptide molecules described herein and in the accompanying figures and tables, wherein the C- or N-termini of the respective monomers are linked by any suitable linker moiety to provide a dimer molecule having superior integrin antagonist activity.

In another aspect, the present invention provides a composition for treating a subject in need of integrin-antagonist therapy comprising a dimer compound of Formula (I), or any other compound described herein or in the accompanying figures and tables, in combination with a pharmaceutically acceptable carrier.

In yet another aspect, the present invention provides a diagnostic method for visualizing and diagnosing a disease comprising administering an orally stable compound of Formula (I), or any other compound described herein or in the acompanying figures, that is further labeled with at least one of a chelating group and a detectable label for use as an in vivo imaging agent for non-invasive diagnostic procedures.

In certain embodiments, compounds of the present invention are monomers. Each monomer peptide of the present invention further comprises two natural or unnatural amino acids that are capable of bridging to form a cyclized structure. Thus, the compounds of the present invention comprise monomer peptides, each forming a cyclized structure through at least one of a disulfide salt bridge, an amide bond, or an equivalent connection. This feature provides increased stability to the compound when administered orally as a therapeutic agent. This feature further provides for increased specificity and potency as compared to non-cyclized analogs.

In one embodiment, the present invention includes a peptide dimer compound comprising two linked monomer subunits of Formula (I):

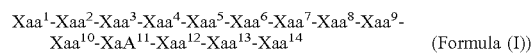

(Formula (I))

or a pharmaceutically acceptable salt thereof,
wherein:
$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidinoguanidino), Phe(4-carbomyl), Cit, Phe(4-$NH_2$), N-Me-homoArg, homoArg, Tyr, Dap, Dab, Arg-Me-sym, Arg-Me-asym, Cav, and His;
$Xaa^6$ is Ser, Gly, Thr or Ile;
$Xaa^7$ is Asp, Asp(OMe) or N-Me-Asp;
$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, cyclopentylAla, Leu, Nle, Cba, homoLeu, Cpa, Aoc, and N-Me-Leu;
$Xaa^{10}$ is any amino acid capable of forming a bond with $Xaa^4$;
$Xaa^{11}$ is absent or selected from the group consisting of: aromatic amino acids, substituted aromatic amino acids, and Tic;
$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val, and corresponding D-amino acids and isosteres;
$Xaa^{13}$ is absent or Pro or any amino acid; and
$Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, HomoGlu, D-homoGlu, N-Me-Glu, N-Me-Asp, N-Me-D-Glu, and N-Me-D-Asp;
wherein $Xaa^4$ and $Xaa^{10}$ are both Pen or Cys;
wherein:
$Xaa^5$ is selected from the group consisting of Cit, Phe(4-carbomylamino), and N-Me-homoArg; $Xaa^8$ is selected from the group consisting of Leu, homoLeu, Nle and Val; $Xaa^9$ is selected from the group consisting of Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gin, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or$Xaa^{13}$ is Pro; and
wherein one or both monomer subunits of the peptide dimer compound comprises a bond between $Xaa^4$ and $Xaa^{10}$.

In one embodiment, $Xaa^4$ is Cys or Pen, $Xaa^{10}$ is Pen or Cys, and $Xaa^4$ and $Xaa^{10}$ are linked by a disulfide bond.

In particular embodiments of compounds comprising Formula (I), the compound further comprises a linker moiety linking the two monomer subunits, wherein the linker moiety is optionally selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, 4-fluoorobenzoic acid, 4-fluorophenylacetic acid, 3-phenylpropionic acid, succinic acid, biotin, glutaric acid, Azelaic acid, Pimelic acid, Dodecanedioic acid, aliphatic amino acids, aromatic amino acids, heteroaromatics, polyethylene glycols having a molecular weight from approximately 400 Da to approximately 40,000 Da, bifunctional linkers, N-Hydroxy succinamine (NHS)-activated diesters, and bis-maleimides.

In particular embodiments compounds comprising Formula I, the N-terminus of each monomer subunit is linked by the linker moiety to provide an N-terminus dimer compound.

In particular embodiments, the C-terminus of each monomer subunit is joined by the linker moiety to provide a C-terminus dimer compound.

In particular embodiments, $Xaa^5$ is N-Me-Arg; $Xaa^6$ is Ser, $Xaa^7$ is Asp, $Xaa^8$ is Thr, and/or $Xaa^9$ is Leu; a$Xaa^{11}$ is Tic, Phe(2-carbomyl), Phe(3-carbomyl), Phe(4-COOH), Phe (4-OMe), or Phe(4-tBu). In one embodiment, $Xaa^5$ is N-Methyl-Arg; $Xaa^6$ is Ser; $Xaa^7$ is Asp; $Xaa^8$ is Thr or Val; $Xaa^9$ is Leu; $Xaa^{11}$ is selected from the group consisting of Trp, Phe, 2-Nal, 1-Nal, Tyr, His, Phe(4-F), Phe(4-$CF_3$), Phe(4-$CH_3$), Phe(4-tBu), Bip, Phe(4-COOH), Gly, 3,3-Di-PhenylGly, 3,3 diPhenyl Ala, Tic, β-homoTrp, D-1-Nal, D-2-Nal, Phe(2,4-diCL), Phe(3,4-diCL), Phe(4-carbomyl), Phe(3-Carbomyl), Tyr(Me), and HomoPhe; $Xaa^{12}$ is selected from the group consisting of: any aromatic amino acid, Glu, D-Glu, and beta-homoGlu; $Xaa^{13}$ is absent; and $Xaa^{14}$ is selected from the group consisting of: D-Lys, N-Me-Lys, and D-N-Me-Lys.

In particular embodiments, $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, HomoGlu, D-homoGlu, N-Me-Glu, N-Me-Asp, N-Me-D-Glu, and N-Me-D-Asp. In particular embodiments, $Xaa^{14}$ also includes D-Cys and D-Pen. In certain embodiments, $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, Cys, homoCys, Pen and D-Orn.

In certain embodiments of Formula (I), $Xaa^5$ is selected from the group consisting of Cit, Phe(4-carbomylamino), and N-Me-homoArg; $Xaa^8$ is selected from the group consisting of Leu, homoLeu, Nle and Val; $Xaa^9$ is selected from the group consisting of Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In certain embodiments of Formula (I), one or both monomer subunits of the peptide dimer compound comprises a disulfide bond, a lactam bond, an olefin bond, a 1,2,3-triazole ring, a selenoether bond, or a diselenide bond between $Xaa^4$ and $Xaa^{10}$.

In certain embodiments, Formula (I) represents a monomer subunit of a dimer molecule, wherein the monomer subunits are linked to form a dimer molecule in accordance with the present invention.

In certain embodiments, $Xaa^4$ is Cys or Pen. In certain embodiments, $Xaa^{10}$ is Cys or Pen. In certain embodiments, both $Xaa^4$ and $Xaa^{10}$ are Cys or Pen. In certain embodiments, Both $Xaa^4$ and $Xaa^{10}$ are Pen. In certain embodiments, the amino acid residue directly C-terminal to $Xaa^{10}$ is an aromatic amino acid.

In certain embodiments wherein the compound is a peptide dimer, $Xaa^{14}$ is any amino acid with amine side chain, Lys, D-Lys, N-Me-Lys, D-N-Me-Lys, Orn, Dab, Dap, HomoLys, D-Dap, D-Dab, or D-Orn. In certain embodiments, $Xaa^{14}$ is Lys, D-Lys, N-Me-Lys, D-N-Me-Lys, Orn, Dab, Dap, HomoLys, D-Dap, D-Dab, or D-Orn. In certain embodiments, $Xaa^{14}$ is Cys, HomoCys, or Pen.

In certain embodiments, one or both monomer subunits of the peptide dimer comprise an intramolecular bind between $Xaa^4$ and $Xaa^{10}$. In particular embodiments, the intramolecular bond is a disulfide bond or a lactam bond.

In certain embodiments, a free amine in the C-terminal amino acid of the peptide monomer is capped, e.g., with an acetyl group For some embodiments, any of $Xaa^1$-$Xaa^5$, $Xaa^7$-$Xaa^9$, and $Xaa^{11}$-$Xaa^{12}$ are N(alpha)Methylated. $Xaa^5$ may further be Arg-Me-sym or Arg-Me-asym, and $Xaa^{11}$ may be O-Me-Tyr, N-Me-Lys(Ac), or 4-Me-Phe. In some instances, any of $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, and/or Asp are used as spacers for acylations. In some instances, Glu or Asp are used as spacers for acylations.

In some embodiments, the N-terminal or C-terminal amino acids of both peptide monomer subunits of a peptide dimer, e.g., $Xaa^1$, $Xaa^2$, $Xaa^3$, $Xaa^{12}$, $Xaa^{13}$ or $Xaa^{14}$, are modified with a suitable linker moiety to form a homo- or hetero-dimer molecule, wherein Formula (I) comprises a dimer formed from two subunits joined by a suitable C- or N-terminal linker.

In certain embodiments of Formula (I), both subunits comprise one of the following sequences:

```
                                                      (SEQ ID NO: 219)
Pen-(N-Me-Arg)-Ser-Asp-Thr-Leu-Pen-Trp-(β-homoGlu)-(D-Lys);

(SEQ ID NO: 220)
Pen-(N-Me-Arg)-Ser-Asp-Thr-Leu-Pen-(Phe-(4-COOH)-(β-homoGlu)-(D-Lys);

(SEQ ID NO: 221)
Pen-(N-Me-Arg)-Ser-Asp-Thr-Leu-Pen-Trp-Glu-(N-Me-Lys);

(SEQ ID NO: 222)
Pen-(N-Me-Arg)-Ser-Asp-Thr-Leu-Pen-2-Nal-(β-homoGlu)-(D-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 224)
Pen-(N-Me-Arg)-Ser-Asp-Thr-Leu-Pen-2-Nal-Glu-(N-Me-Lys);

(SEQ ID NO: 225)
Pen-(N-Me-Arg)-Ser-Asp-Thr-Leu-Pen-Phe(4-tBu)-(β-homoGlu)-(D-Lys);

(SEQ ID NO: 226)
Pen-(N-Me-Arg)-Ser-Asp-Thr-Leu-Pen-Phe(4-tBu)-(β-homoGlu)-(N-Me-Lys);

(SEQ ID NO: 227)
Pen-(N-Me-Arg)-Ser-Asp-Thr-Leu-Pen-Trp-(β-homoGlu)-(N-Me-Lys);

(SEQ ID NO: 228)
Pen-(N-Me-Arg)-Ser-Asp-Thr-Leu-Pen-2-Nal-(β-homoGlu)-(N-Me-Lys);
```

```
                                                      (SEQ ID NO: 223)
Pen-(N-Me-Arg)-Ser-Asp-Thr-Leu-Pen-1-Nal-(β-homoGlu)-(D-Lys);

(SEQ ID NO: 229)
Pen-(N-Me-Arg)-Ser-Asp-Thr-Leu-Pen-1-Nal-(β-homoGlu)-(N-Me-Lys);

(SEQ ID NO: 219)
Pen-(N-Me-Arg)-Ser-Asp-Thr-Leu-Pen-Trp-(β-homoGlu)-(D-Lys); or (SEQ ID NO: 230)
Pen-(N-Me-Arg)-Ser-Asp-Thr-Leu-Pen-Trp-Glu-(N-Me-D-Lys).
```

In certain embodiments, both subunits comprise the same sequences. In particular embodiments, the subunits are linked via DIG at their C-termini.

In particular embodiments the peptide dimer compound 15 has one of the following structures:

```
                                                                      (SEQ ID NO: 213)
[Ac-Pen-(N-Me-Arg)-Ser-Asp-Thr-Leu-Pen-Trp-(β-homoGlu)-(D-Lys)-NH₂]₂-DIG;

(SEQ ID NO: 130)
[Ac-Pen-(N-Me-Arg)-Ser-Asp-Thr-Leu-Pen-(Phe-(4-COOH)-(β-homoGlu)-(D-Lys)-NH₂]₂-DIG;

(SEQ ID NO: 215)
[Ac-Pen-(N-Me-Arg)-Ser-Asp-Thr-Leu-Pen-Trp-Glu-(N-Me-Lys)-NH₂]₂-DIG;

(SEQ ID NO: 137)
[Ac-Pen-(N-Me-Arg)-Ser-Asp-Thr-Leu-Pen-2-Nal-(β-homoGlu)-(D-Lys)-NH₂]₂-DIG;

(SEQ ID NO: 231)
[Ac-Pen-(N-Me-Arg)-Ser-Asp-Thr-Leu-Pen-1-Nal-(β-homoGlu)-(D-Lys)-NH₂]₂-DIG;

(SEQ ID NO: 138)
[Ac-Pen-(N-Me-Arg)-Ser-Asp-Thr-Leu-Pen-2-Nal-Glu-(N-Me-Lys)-NH₂]₂-DIG;

(SEQ ID NO: 218)
[Ac-Pen-(N-Me-Arg)-Ser-Asp-Thr-Leu-Pen-Phe(4-tBu)-(β-homoGlu)-(D-Lys)-NH₂]₂-DIG;

(SEQ ID NO: 149)
[Ac-Pen-(N-Me-Arg)-Ser-Asp-Thr-Leu-Pen-Phe(4-tBu)-(β-homoGlu)-(N-Me-Lys)-NH₂]₂-DIG;

(SEQ ID NO: 141)
[Ac-Pen-(N-Me-Arg)-Ser-Asp-Thr-Leu-Pen-Trp-(β-homoGlu)-(N-Me-Lys)-NH₂]₂-DIG;

(SEQ ID NO: 232)
[Ac-Pen-(N-Me-Arg)-Ser-Asp-Thr-Leu-Pen-2-Nal-(β-homoGlu)-(N-Me-Lys)-NH₂]₂-DIG;

(SEQ ID NO: 231)
[Ac-Pen-(N-Me-Arg)-Ser-Asp-Thr-Leu-Pen-1-Nal-(β-homoGlu)-(D-Lys)-NH₂]₂-DIG;

(SEQ ID NO: 142)
[Ac-Pen-(N-Me-Arg)-Ser-Asp-Thr-Leu-Pen-1-Nal-(β-homoGlu)-(N-Me-Lys)-NH₂]₂-DIG;

(SEQ ID NO: 213)
[Ac-Pen-(N-Me-Arg)-Ser-Asp-Thr-Leu-Pen-Trp-(β-homoGlu)-(D-Lys)-NH₂]₂-DIG;

(SEQ ID NO: 214)
[Ac-Pen-(N-Me-Arg)-Ser-Asp-Thr-Leu-Pen-Trp-Glu-(N-Me-D-Lys)-NH₂]₂-DIG;

(SEQ ID NO: 233)
[Ac-Pen-(N-Me-Arg)-Ser-Asp-Thr-Leu-Pen-Trp-(β-homoGlu)-(D-Lys)-OH]₂-DIG;

(SEQ ID NO: 234)
[Ac-Pen-(N-Me-Arg)-Ser-Asp-Thr-Leu-Pen-(Phe-(4-COOH)-(β-homoGlu)-(D-Lys)-OH]₂-DIG;

(SEQ ID NO: 235)
[Ac-Pen-(N-Me-Arg)-Ser-Asp-Thr-Leu-Pen-Trp-Glu-(N-Me-Lys)-OH]₂-DIG;

(SEQ ID NO: 236)
[Ac-Pen-(N-Me-Arg)-Ser-Asp-Thr-Leu-Pen-2-Nal-(β-homoGlu)-(D-Lys)-OH]₂-DIG;

(SEQ ID NO: 237)
[Ac-Pen-(N-Me-Arg)-Ser-Asp-Thr-Leu-Pen-1-Nal-(β-homoGlu)-(D-Lys)-OH]₂-DIG;

(SEQ ID NO: 238)
[Ac-Pen-(N-Me-Arg)-Ser-Asp-Thr-Leu-Pen-2-Nal-Glu-(N-Me-Lys)-OH]₂-DIG;
```

-continued (SEQ ID NO: 239)
[Ac-Pen-(N-Me-Arg)-Ser-Asp-Thr-Leu-Pen-Phe(4-tBu)-(β-homoGlu)-(D-Lys)-OH]$_2$-DIG;

(SEQ ID NO: 240)
[Ac-Pen-(N-Me-Arg)-Ser-Asp-Thr-Leu-Pen-Phe(4-tBu)-(β-homoGlu)-(N-Me-Lys)-OH]$_2$-DIG;

(SEQ ID NO: 241)
[Ac-Pen-(N-Me-Arg)-Ser-Asp-Thr-Leu-Pen-Trp-(β-homoGlu)-(N-Me-Lys)-OH]$_2$-DIG;

(SEQ ID NO: 242)
[Ac-Pen-(N-Me-Arg)-Ser-Asp-Thr-Leu-Pen-2-Nal-(β-homoGlu)-(N-Me-Lys)-OH]$_2$-DIG;

(SEQ ID NO: 237)
[Ac-Pen-(N-Me-Arg)-Ser-Asp-Thr-Leu-Pen-1-Nal-(β-homoGlu)-(D-Lys)-OH]$_2$-DIG;

(SEQ ID NO: 243)
[Ac-Pen-(N-Me-Arg)-Ser-Asp-Thr-Leu-Pen-1-Nal-(β-homoGlu)-(N-Me-Lys)-OH]$_2$-DIG;

(SEQ ID NO: 233)
[Ac-Pen-(N-Me-Arg)-Ser-Asp-Thr-Leu-Pen-Trp-(β-homoGlu)-(D-Lys)-OH]$_2$-DIG; or (SEQ ID NO: 244)
[Ac-Pen-(N-Me-Arg)-Ser-Asp-Thr-Leu-Pen-Trp-Glu-(N-Me-D-Lys)-OH]$_2$-DIG, wherein there is a disulfide bond between the two Pen residues in the monomer subunits.

In particular embodiments, the peptide dimer compound comprises an C-terminal OH.

In particular embodiments, the peptide dimer compound comprises N(alpha)methylation at one or more positions selected from the group consisting of Xaa$^3$, Xaa$^5$, Xaa$^7$-Xaa$^9$, and Xaa$^{11}$-Xaa$^{13}$; or acylation at one or more position selected from the group consisting of Xaa$^1$-Xaa$^3$ and Xaa$^{11}$-Xaa$^{14}$. In one embodiment, Xaa$^1$ and Xaa$^2$ are absent, and Xaa$^3$ is Ac. In one embodiment, one or more of Xaa$^{11}$, Xaa$^{12}$ and Xaa$^{13}$ is absent.

In a related embodiment, the present invention includes a peptide monomer compound of Formula (IV):

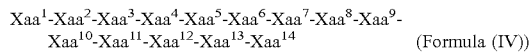

or a pharmaceutically acceptable salt thereof,
wherein:
Xaa$^1$ is absent, Ac, or any amino acid;
Xaa$^2$ is absent, Ac, or any amino acid;
Xaa$^3$ is absent, Ac, or any amino acid;
Xaa$^4$ is any amino acid capable of binding to Xaa$^{10}$;
Xaa$^5$ is selected from the group consisting of: N-Me-Arg, Arg, N-Me-Lys, Phe(4-guanidino), Phe(4-carbomylamino), Cit, Phe(4-NH$_2$), N-Me-homoArg, homoArg, Tyr, Dap, Dab, Arg-Me-sym, Arg-Me-asym, Cav, and His;
Xaa$^6$ is Ser, Gly, Thr, or Ile;
Xaa$^7$ is Asp, Asp(OMe), or N-Me-Asp;
Xaa$^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
Xaa$^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, cyclopentylAla, Leu, Nle, Cpa, Cba, homoLeu, Aoc, and N-Me-Leu;
Xaa$^{10}$ is any amino acid capable of binding to Xaa$^4$;
Xaa$^{11}$ is absent or selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenyl Ala, Tic, b-homoTrp, D-1-Nal, D-2-Nal, Phe(2,4-diCl), Phe(3,4-diCl), Phe(4-carbomyl), Phe(3-Carbomyl), Phe(2-carbomyl), Tyr(Me), homoPhe, N-Me-Phe, N-Me-Tyr, Ser, Sar, Dihydro Trp, Ile, Leu, Arg, Thr, aromatic amino acids, substituted aromatic amino acids, and Tic;
Xaa$^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val, and corresponding D-amino acids and isosteres;
Xaa$^{13}$ is absent or Pro or any amino acid; and
Xaa$^{14}$ is any amino acid, wherein
Xaa$^5$ is selected from the group consisting of Cit, Phe(4-carbomyl), and N-Me-HomoArg;
Xaa$^8$ is selected from the group consisting of Leu, homoLeu, Nle and Val;
Xaa$^9$ is selected from the group consisting of: Cba, homo-Leu, and Cpa;
Xaa$^{11}$ is selected from the group consisting of Tic, Phe(2-carbomyl), Phe(3-carbomyl), Phe(4-COOH), Phe(4-OMe), and Phe(4-tBu);
Xaa$^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or Xaa$^{13}$ is Pro;
wherein Xaa$^4$ and Xaa$^{10}$ are linked by a bond; and wherein
Xaa$^5$ is selected from the group consisting of Cit, Phe(4-carbomyl), and N-Me-HomoArg;
Xaa$^8$ is selected from the group consisting of Leu, homoLeu, Nle and Val;
Xaa$^9$ is selected from the group consisting of: Cba, homo-Leu, and Cpa;
Xaa$^{11}$ is selected from the group consisting of Tic, Phe(2-carbomyl), Phe(3-carbomyl), Phe(4-COOH), Phe(4-OMe), and Phe(4-tBu);
Xaa$^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or Xaa$^{13}$ is Pro.

In particular embodiments, Xaa$^4$ is Cys or Pen, Xaa$^{10}$ is Cys or Pen, and Xaa$^4$ and Xaa$^{10}$ are linked by a disulfide bond.

In particular embodiments, $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and suitable isosteres.

In particular embodiments, $Xaa^{13}$ is absent or Pro.

In particular embodiments, $Xaa^5$ is N-Me-Arg.

In particular embodiments, $Xaa^1$ and $Xaa^2$ are absent, and $Xaa^3$ is Ac, and/or wherein one or more of $Xaa^{11}$, $Xaa^{12}$ and $Xaa^{13}$ is absent.

In particular embodiments of Formula (IV), $Xaa^5$ is selected from the group consisting of Cit, Phe(4-carbomyl), and N-Me-HomoArg; $Xaa^8$ is selected from the group consisting of Leu, homoLeu, Nle and Val; $Xaa^9$ is selected from the group consisting of: Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In particular embodiments, the peptide monomer compound comprises a disulfide bond, a lactam bond, an olefin bond, a 1,2,3-triazole ring, a selenoether bond, or a diselenide bond between $Xaa^4$ and $Xaa^{10}$.

In certain embodiments, a monomer peptide comprises a disulfide bond, a lactam bond, an olefin bond, a 1,2,3-triazole ring, a selenoether bond, or a diselenide bond between $Xaa^4$ and $Xaa^{10}$.

In certain embodiments, $Xaa^4$ is Cys or Pen. In certain embodiments, $Xaa^{10}$ is Cys or Pen. In certain embodiments, both $Xaa^4$ and $Xaa^{10}$ are Cys or Pen. In certain embodiments, both $Xaa^4$ and $Xaa^{10}$ are Pen.

In certain embodiments, the amino acid residue directly C-terminal to $Xaa^{10}$ is an aromatic amino acid.

In certain embodiments, $Xaa^{14}$ or the C-terminal amino acid does not comprise a free amine.

In certain embodiments, $Xaa^{14}$ is absent or any amino acid with an amine side chain, Lys, D-Lys, N-Me-Lys, D-N-Me-Lys, Orn, Dab, Dap, HomoLys, D-Dap, D-Dab, or D-Orn. In certain embodiments, $Xaa^{14}$ is Lys, D-Lys, N-Me-Lys, D-N-Me-Lys, Orn, Dab, Dap, HomoLys, D-Dap, D-Dab, or D-Orn.

In certain embodiments wherein the compound is peptide monomer, $Xaa^{14}$ or the C-terminus comprises an $NH_2$ or an OH.

In certain embodiments, a free amine in the C-terminal amino acid of the peptide monomer is capped, e.g., with an acetyl group.

In certain embodiments, the peptide monomer comprises an intramolecular bind between $Xaa^4$ and $Xaa^{10}$. In particular embodiments, the intramolecular bond is a disulfide bond or a lactam bond.

For some embodiments, any of $Xaa^1$-$Xaa^5$, $Xaa^7$-$Xaa^9$, and $Xaa^{11}$-$Xaa^{12}$ are N(alpha)Methylated. $Xaa^5$ may further be Arg-Me-sym or Arg-Me-asym, and $Xaa^{11}$ may be O-Me-Tyr, N-Me-Lys(Ac), or 4-Me-Phe. In some instances, any of $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

The invention also includes a peptide monomer compound of Formula (V):

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10} \quad \text{(Formula (V))}$$

or a pharmaceutically acceptable salt thereof, wherein the peptide compound comprises a disulfide bond $Xaa^1$ and Xaa;

wherein $Xaa^1$-$Xaa^{10}$ of Formula (V) corresponds to $Xaa^4$-$Xaa^3$ of Formula (IV), and wherein $Xaa^1$ is Pen or Cys;

$Xaa^2$ is selected from the group consisting of Cit, Phe(4-carbomyl), and N-Me-HomoArg $Xaa^3$ is Ser, Gly, Thr, or Ile;

$Xaa^4$ is Asp, D-Asp, Asp(OMe), or N-Me-Asp;

$Xaa^5$ is selected from the group consisting of Leu, HomoLeu, Nle and Val;

$Xaa^6$ is selected from the group consisting of: Cba, HomoLeu, and Cpa;

$Xaa^7$ is Pen or Cys;

$Xaa^8$ is selected from the group consisting of Tic, Phe(2-carbomyl), Phe(3-carbomyl), Phe(4-COOH), Phe(4-OMe), and Phe(4-tBu);

$Xaa^9$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; and $Xaa^{10}$ is Pro.

In certain embodiments, the peptide monomer compound comprises one of the following sequences or structures:

```
                                                              (SEQ ID NO: 245)
Pen-(N-Me-Arg)-Ser-Asp-Thr-Leu-Pen-(Phe(4-COOH))-(Glu)-(D-Lys);

(SEQ ID NO: 220)
Pen-(N-Me-Arg)-Ser-Asp-Thr-Leu-Pen-(Phe(4-COOH))-(β-homo-Glu)-(D-Lys);

(SEQ ID NO: 246)
Pen-(N-Me-Arg)-Ser-Asp-Thr-Leu-Pen-(Phe(4-tBu))-Glu-(D-Lys);

(SEQ ID NO: 247)
Pen-(N-Me-Arg)-Ser-Asp-Thr-Leu-Pen-(Phe(4-tBu))-(β-homo-Glu)-(D-Lys);

(SEQ ID NO: 248)
Pen-(N-Me-Arg)-Ser-Asp-Thr-Leu-Pen-(Phe(4-tBu))-Glu-(N-Me-Lys);

(SEQ ID NO: 249)
Pen-(N-Me-Arg)-Ser-Asp-Thr-Leu-Pen-Bip-Glu-(D-Lys);
```

-continued

Pen-(N-Me-Arg)-Ser-Asp-Thr-Leu-Pen-Bip-(β-homo-Glu)-(D-Lys); (SEQ ID NO: 250)

Pen-(N-Me-Arg)-Ser-Asp-Thr-Leu-Pen-Trp-(β-homoGlu)-(D-Lys); (SEQ ID NO: 219)

Pen-(N-Me-Arg)-Ser-Asp-Thr-Leu-Pen-(Phe(4-COOH)-(β-homoGlu)-(D-Lys); (SEQ ID NO: 220)

Pen-(N-Me-Arg)-Ser-Asp-Thr-Leu-Pen-Trp-Glu-(N-Me-Lys); (SEQ ID NO: 221)

Pen-(N-Me-Arg)-Ser-Asp-Thr-Leu-Pen-2-Nal-(β-homoGlu)-(D-Lys); (SEQ ID NO: 222)

Pen-(N-Me-Arg)-Ser-Asp-Thr-Leu-Pen-1-Nal-(β-homoGlu)-(D-Lys); (SEQ ID NO: 223)

Pen-(N-Me-Arg)-Ser-Asp-Thr-Leu-Pen-2-Nal-Glu-(N-Me-Lys); (SEQ ID NO: 224)

Pen-(N-Me-Arg)-Ser-Asp-Thr-Leu-Pen-Phe(4-tBu)-(β-homoGlu)-(D-Lys); (SEQ ID NO: 225)

Pen-(N-Me-Arg)-Ser-Asp-Thr-Leu-Pen-Phe(4-tBu)-(β-homoGlu)-(N-Me-Lys); (SEQ ID NO: 226)

Pen-(N-Me-Arg)-Ser-Asp-Thr-Leu-Pen-Trp-(β-homoGlu)-(N-Me-Lys); (SEQ ID NO: 227)

Pen-(N-Me-Arg)-Ser-Asp-Thr-Leu-Pen-2-Nal-(β-homoGlu)-(N-Me-Lys); (SEQ ID NO: 228)

Pen-(N-Me-Arg)-Ser-Asp-Thr-Leu-Pen-1-Nal-(β-homoGlu)-(D-Lys); (SEQ ID NO: 223)

Pen-(N-Me-Arg)-Ser-Asp-Thr-Leu-Pen-1-Nal-(β-homoGlu)-(N-Me-Lys); (SEQ ID NO: 229)

Pen-(N-Me-Arg)-Ser-Asp-Thr-Leu-Pen-Trp-(β-homoGlu)-(D-Lys); (SEQ ID NO: 219)

Pen-(N-Me-Arg)-Ser-Asp-Thr-Leu-Pen-Trp-Glu-(N-Me-D-Lys); (SEQ ID NO: 230)

Ac-Pen-(N-Me-Arg)-Ser-Asp-Thr-Leu-Pen-Trp-(β-homoGlu)-(D-Lys)-OH; (SEQ ID NO: 251)

Ac-Pen-(N-Me-Arg)-Ser-Asp-Thr-Leu-Pen-(Phe(4-COOH)-(β-homoGlu)-(D-Lys)-OH; (SEQ ID NO: 252)

Ac-Pen-(N-Me-Arg)-Ser-Asp-Thr-Leu-Pen-Trp-Glu-(N-Me-Lys)-OH; (SEQ ID NO: 253)

Ac-Pen-(N-Me-Arg)-Ser-Asp-Thr-Leu-Pen-2-Nal-(β-homoGlu)-(D-Lys)-OH; (SEQ ID NO: 254)

Ac-Pen-(N-Me-Arg)-Ser-Asp-Thr-Leu-Pen-1-Nal-(β-homoGlu)-(D-Lys)-OH; (SEQ ID NO: 255)

Ac-Pen-(N-Me-Arg)-Ser-Asp-Thr-Leu-Pen-2-Nal-Glu-(N-Me-Lys)-OH; (SEQ ID NO: 256)

Ac-Pen-(N-Me-Arg)-Ser-Asp-Thr-Leu-Pen-Phe(4-tBu)-(β-homoGlu)-(D-Lys)-OH; (SEQ ID NO: 257)

Ac-Pen-(N-Me-Arg)-Ser-Asp-Thr-Leu-Pen-Phe(4-tBu)-(β-homoGlu)-(N-Me-Lys)-OH; (SEQ ID NO: 258)

Ac-Pen-(N-Me-Arg)-Ser-Asp-Thr-Leu-Pen-Trp-(β-homoGlu)-(N-Me-Lys)-OH; (SEQ ID NO: 259)

Ac-Pen-(N-Me-Arg)-Ser-Asp-Thr-Leu-Pen-2-Nal-(β-homoGlu)-(N-Me-Lys)-OH; (SEQ ID NO: 260)

Ac-Pen-(N-Me-Arg)-Ser-Asp-Thr-Leu-Pen-1-Nal-(β-homoGlu)-(D-Lys)-OH; (SEQ ID NO: 255)

Ac-Pen-(N-Me-Arg)-Ser-Asp-Thr-Leu-Pen-1-Nal-(β-homoGlu)-(N-Me-Lys)-OH; (SEQ ID NO: 261)

-continued (SEQ ID NO: 251)
Ac-Pen-(N-Me-Arg)-Ser-Asp-Thr-Leu-Pen-Trp-(β-homoGlu)-(D-Lys)-OH;

(SEQ ID NO: 262)
Ac-Pen-(N-Me-Arg)-Ser-Asp-Thr-Leu-Pen-Trp-Glu-(N-Me-D-Lys)-OH;

(SEQ ID NO: 263)
Ac-Pen-(N-Me-Arg)-Ser-Asp-Thr-Leu-Pen-Trp-(β-homoGlu)-(D-Lys)-NH$_2$;

(SEQ ID NO: 264)
Ac-Pen-(N-Me-Arg)-Ser-Asp-Thr-Leu-Pen-(Phe-(4-COOH)-(β-homoGlu)-(D-Lys)-NH$_2$;

(SEQ ID NO: 265)
Ac-Pen-(N-Me-Arg)-Ser-Asp-Thr-Leu-Pen-Trp-Glu-(N-Me-Lys)-NH$_2$;

(SEQ ID NO: 266)
Ac-Pen-(N-Me-Arg)-Ser-Asp-Thr-Leu-Pen-2-Nal-(β-homoGlu)-(D-Lys)-NH$_2$;

(SEQ ID NO: 267)
Ac-Pen-(N-Me-Arg)-Ser-Asp-Thr-Leu-Pen-1-Nal-(β-homoGlu)-(D-Lys)-NH$_2$;

(SEQ ID NO: 268)
Ac-Pen-(N-Me-Arg)-Ser-Asp-Thr-Leu-Pen-2-Nal-Glu-(M-Me-Lys)-NH$_2$;

(SEQ ID NO: 153)
Ac-Pen-(N-Me-Arg)-Ser-Asp-Thr-Leu-Pen-Phe(4-tBu)-(β-homoGlu)-(D-Lys)-NH$_2$;

(SEQ ID NO: 269)
Ac-Pen-(N-Me-Arg)-Ser-Asp-Thr-Leu-Pen-Phe(4-tBu)-(β-homoGlu)-(N-Me-Lys)-NH$_2$;

(SEQ ID NO: 270)
Ac-Pen-(N-Me-Arg)-Ser-Asp-Thr-Leu-Pen-Trp-(β-homoGlu)-(N-Me-Lys)-NH$_2$;

(SEQ ID NO: 271)
Ac-Pen-(N-Me-Arg)-Ser-Asp-Thr-Leu-Pen-2-Nal-(β-homoGlu)-(N-Me-Lys)-NH$_2$;

(SEQ ID NO: 267)
Ac-Pen-(N-Me-Arg)-Ser-Asp-Thr-Leu-Pen-1-Nal-(β-homoGlu)-(D-Lys)-NH$_2$;

(SEQ ID NO: 272)
Ac-Pen-(N-Me-Arg)-Ser-Asp-Thr-Leu-Pen-1-Nal-(β-homoGlu)-(N-Me-Lys)-NH$_2$;

(SEQ ID NO: 263)
Ac-Pen-(N-Me-Arg)-Ser-Asp-Thr-Leu-Pen-Trp-(β-homoGlu)-(D-Lys)-NH$_2$;

(SEQ ID NO: 273)
Ac-Pen-(N-Me-Arg)-Ser-Asp-Thr-Leu-Pen-Trp-Glu-(N-Me-D-Lys)-NH$_2$;
or (SEQ ID NO: 274)
Pen-(N-Me-Arg)-Ser-Asp-Thr-Leu-Pen-(Phe(4-COOH))-(Glu);

(SEQ ID NO: 275)
Pen-(N-Me-Arg)-Ser-Asp-Thr-Leu-Pen-(Phe(4-COOH)-(β-homo-Glu);

(SEQ ID NO: 276)
Pen-(N-Me-Arg)-Ser-Asp-Thr-Leu-Pen-(Phe(4-tBu))-Glu;

(SEQ ID NO: 277)
Pen-(N-Me-Arg)-Ser-Asp-Thr-Leu-Pen-(Phe(4-tBu))-(β-homo-Glu);

(SEQ ID NO: 276)
Pen-(N-Me-Arg)-Ser-Asp-Thr-Leu-Pen-(Phe(4-tBu))-Glu;

(SEQ ID NO: 278)
Pen-(N-Me-Arg)-Ser-Asp-Thr-Leu-Pen-Bip-Glu;

(SEQ ID NO: 279)
Pen-(N-Me-Arg)-Ser-Asp-Thr-Leu-Pen-Bip-(β-homo-Glu);

(SEQ ID NO: 280)
Pen-(N-Me-Arg)-Ser-Asp-Thr-Leu-Pen-Trp-(β-homoGlu);

(SEQ ID NO: 275)
Pen-(N-Me-Arg)-Ser-Asp-Thr-Leu-Pen-(Phe(4-COOH))-(β-homoGlu);

(SEQ ID NO: 281)
Pen-(N-Me-Arg)-Ser-Asp-Thr-Leu-Pen-Trp-Glu;

(SEQ ID NO: 282)
Pen-(N-Me-Arg)-Ser-Asp-Thr-Leu-Pen-2-Nal-(β-homoGlu);

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-2-Nal-Glu; (SEQ ID NO: 284)

Pen-(N-Me-Arg)-Ser-Asp-Thr-Leu-Pen-Phe(4-tBu)-(β-homoGlu); (SEQ ID NO: 285)

Pen-(N-Me-Arg)-Ser-Asp-Thr-Leu-Pen-Phe(4-tBu)-(β-homoGlu); (SEQ ID NO: 285)

Pen-(N-Me-Arg)-Ser-Asp-Thr-Leu-Pen-Trp-(β-homoGlu); (SEQ ID NO: 280)

Pen-(N-Me-Arg)-Ser-Asp-Thr-Leu-Pen-2-Nal-(β-homoGlu); (SEQ ID NO: 282)

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-Trp-(β-homoGlu); (SEQ ID NO: 280)

Pen-(N-Me-Arg)-Ser-Asp-Thr-Leu-Pen-Trp-Glu; (SEQ ID NO: 281)

Ac-Pen-(N-Me-Arg)-Ser-Asp-Thr-Leu-Pen-Trp-(β-homoGlu)-OH; (SEQ ID NO: 146)

Ac-Pen-(N-Me-Arg)-Ser-Asp-Thr-Leu-Pen-(Phe-(4-COOH)-(β-homoGlu)-OH; (SEQ ID NO: 286)

Ac-Pen-(N-Me-Arg)-Ser-Asp-Thr-Leu-Pen-Trp-Glu-OH; (SEQ ID NO: 128)

Ac-Pen-(N-Me-Arg)-Ser-Asp-Thr-Leu-Pen-2-Nal-(β-homoGlu)-OH; (SEQ ID NO: 287)

Ac-Pen-(N-Me-Arg)-Ser-Asp-Thr-Leu-Pen-1-Nal-(β-homoGlu)-OH; (SEQ ID NO: 288)

Ac-Pen-(N-Me-Arg)-Ser-Asp-Thr-Leu-Pen-2-Nal-Glu-OH; (SEQ ID NO: 289)

Ac-Pen-(N-Me-Arg)-Ser-Asp-Thr-Leu-Pen-Phe(4-tBu)-(β-homoGlu)-OH; (SEQ ID NO: 152)

Ac-Pen-(N-Me-Arg)-Ser-Asp-Thr-Leu-Pen-Phe(4-tBu)-(β-homoGlu)-OH; (SEQ ID NO: 152)

Ac-Pen-(N-Me-Arg)-Ser-Asp-Thr-Leu-Pen-Trp-(β-homoGlu)-OH; (SEQ ID NO: 146)

Ac-Pen-(N-Me-Arg)-Ser-Asp-Thr-Leu-Pen-2-Nal-(β-homoGlu)-OH; (SEQ ID NO: 287)

Ac-Pen-(N-Me-Arg)-Ser-Asp-Thr-Leu-Pen-1-Nal-(β-homoGlu)-OH; (SEQ ID NO: 288)

Ac-Pen-(N-Me-Arg)-Ser-Asp-Thr-Leu-Pen-1-Nal-(β-homoGlu)-OH; (SEQ ID NO: 288)

Ac-Pen-(N-Me-Arg)-Ser-Asp-Thr-Leu-Pen-Trp-(β-homoGlu)-OH; (SEQ ID NO: 146)

Ac-Pen-(N-Me-Arg)-Ser-Asp-Thr-Leu-Pen-Trp-Glu-OH; (SEQ ID NO: 128)

Ac-Pen-(N-Me-Arg)-Ser-Asp-Thr-Leu-Pen-Trp-(β-homoGlu)-NH$_2$; (SEQ ID NO: 290)

Ac-Pen-(N-Me-Arg)-Ser-Asp-Thr-Leu-Pen-(Phe-(4-COOH)-(β-homoGlu)-NH$_2$; (SEQ ID NO: 291)

Ac-Pen-(N-Me-Arg)-Ser-Asp-Thr-Leu-Pen-Trp-Glu-NH$_2$; (SEQ ID NO: 292)

```
                                                                (SEQ ID NO: 155)
Ac-Pen-(N-Me-Arg)-Ser-Asp-Thr-Leu-Pen-2-Nal-(β-homoGlu)-NH₂;

(SEQ ID NO: 293)
Ac-Pen-(N-Me-Arg)-Ser-Asp-Thr-Leu-Pen-1-Nal-(β-homoGlu)-NH₂;

(SEQ ID NO: 294)
Ac-Pen-(N-Me-Arg)-Ser-Asp-Thr-Leu-Pen-2-Nal-Glu-NH₂;

(SEQ ID NO: 165)
Ac-Pen-(N-Me-Arg)-Ser-Asp-Thr-Leu-Pen-Phe(4-tBu)-(β-homoGlu)-NH₂;

(SEQ ID NO: 165)
Ac-Pen-(N-Me-Arg)-Ser-Asp-Thr-Leu-Pen-Phe(4-tBu)-(β-homoGlu)-NH₂;

(SEQ ID NO: 290)
Ac-Pen-(N-Me-Arg)-Ser-Asp-Thr-Leu-Pen-Trp-(β-homoGlu)-NH₂;

(SEQ ID NO: 155)
Ac-Pen-(N-Me-Arg)-Ser-Asp-Thr-Leu-Pen-2-Nal-(β-homoGlu)-NH₂;

(SEQ ID NO: 293)
Ac-Pen-(N-Me-Arg)-Ser-Asp-Thr-Leu-Pen-1-Nal-(β-homoGlu)-NH₂;

(SEQ ID NO: 293)
Ac-Pen-(N-Me-Arg)-Ser-Asp-Thr-Leu-Pen-1-Nal-(β-homoGlu)-NH₂;

(SEQ ID NO: 290)
Ac-Pen-(N-Me-Arg)-Ser-Asp-Thr-Leu-Pen-Trp-(β-homoGlu)-NH₂;
or
                                                                (SEQ ID NO: 292)
Ac-Pen-(N-Me-Arg)-Ser-Asp-Thr-Leu-Pen-Trp-Glu-NH₂,
``` wherein in certain embodiments, there is a disulfide bond between the two Pen residues of the peptide or peptide monomer compound.

In certain embodiments, any of the compounds are detectably labeled.

The present invention further includes pharmaceutical composition comprising any of the compounds of the invention. In one embodiment, the pharmaceutical composition comprises an enteric coating, wherein the enteric coating protects and releases the pharmaceutical composition within a subject's lower gastrointestinal system The invention further includes a method for treating a subject afflicted with a condition that is associated with a biological function of an α4β7 integrin, the method comprising administering to the human an effective amount of a compound or compoids of the present invention.

In certain embodiments, the condition is selected from the group consisting of Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease. In particular embodiments, the condition is an inflammatory bowel disease, such as ulcerative colitis or Crohn's disease.

In particular embodiments, the peptide dimer compound or peptide monomer compound of the invention inhibits binding of α4β7 to MAdCAM, and/or selectively inhibits binding of α4β7 to MAdCAM.

In certain embodiments, the subject is a human.

In certain embodiments, the peptide dimer compound or peptide monomer compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In particular embodiments, the peptide dimer compound or peptide monomer compound is administered as an initial does followed by one or more subsequent doses and the minimum interval between any two doses is a period of less than 1 day, and wherein each of the doses comprises an effective amount of the peptide dimer compound.

In particular embodiments, the effective amount of peptide dimer compound or peptide monomer compound is sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In particular embodiments, the compound or pharmaceutical composition is administered orally, parenterally, or topically. In particular embodiments, it is administered at an interval selected from the group consisting of around the clock, hourly, every four hours, once daily, twice daily, three times daily, four times daily, every other day, weekly, bi-weekly, and monthly.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIGS. 3A and 3B provide schematics, each showing a pair of integrin antagonist monomer subunits wherein the subunits are aligned and linked at their respective C-termini (3A) or N-termini (3B) by a linker. In certain embodiments, the linker connects two sulfur-containing amino-acids to form a peptide dimer compound. The two sulfur containing amino acids may be connected by a linker comprising a di-halide, an aliphatic chain, or a PEG. For example, the linker can connect two monomeric subunits by connecting sulfur containing C-terminal amino acids at the C-terminus of each monomer subunit, or it can connect two monomer subunits by connecting sulfur containing N-terminal amino acids at the N-terminus of each monomer subunit. In certain embodiments, the linker connects two amine-containing amino acids to form a peptide dimer compound. The two amine-containing amino acids may be connected by a linker, e.g., comprising a di-halide, an aliphatic chain, or a PEG. For example, the linker can connect two monomeric subunits by connecting amine-containing C-terminal amino acids at the C-terminus of each monomer subunit, or it can connect two monomer subunits by connecting amine-containing N-terminal amino acids at the N-terminus of each monomer subunit.

FIG. 5 provides a summary of stability data generated for Peptide X, demonstrating that Peptide X is stable to a variety of GI fluids, metabolic enzymes and intestinal bacteria.

DETAILED DESCRIPTION

The present invention relates generally to peptides that have been shown to have integrin antagonist activity, including both peptide monomer compounds and peptide dimer compounds. As demonstrated herein, peptides of the present invention are selective antagonists of α4β7 integrin with minimal systemic exposure when administered orally, and are effective in blocking T cell homing and preventing mucosal damage in murine models of IBD. In murine colitis models, peptide compounds of the present invention blocked T cell trafficking and reduce histopathology.

Figure 2:
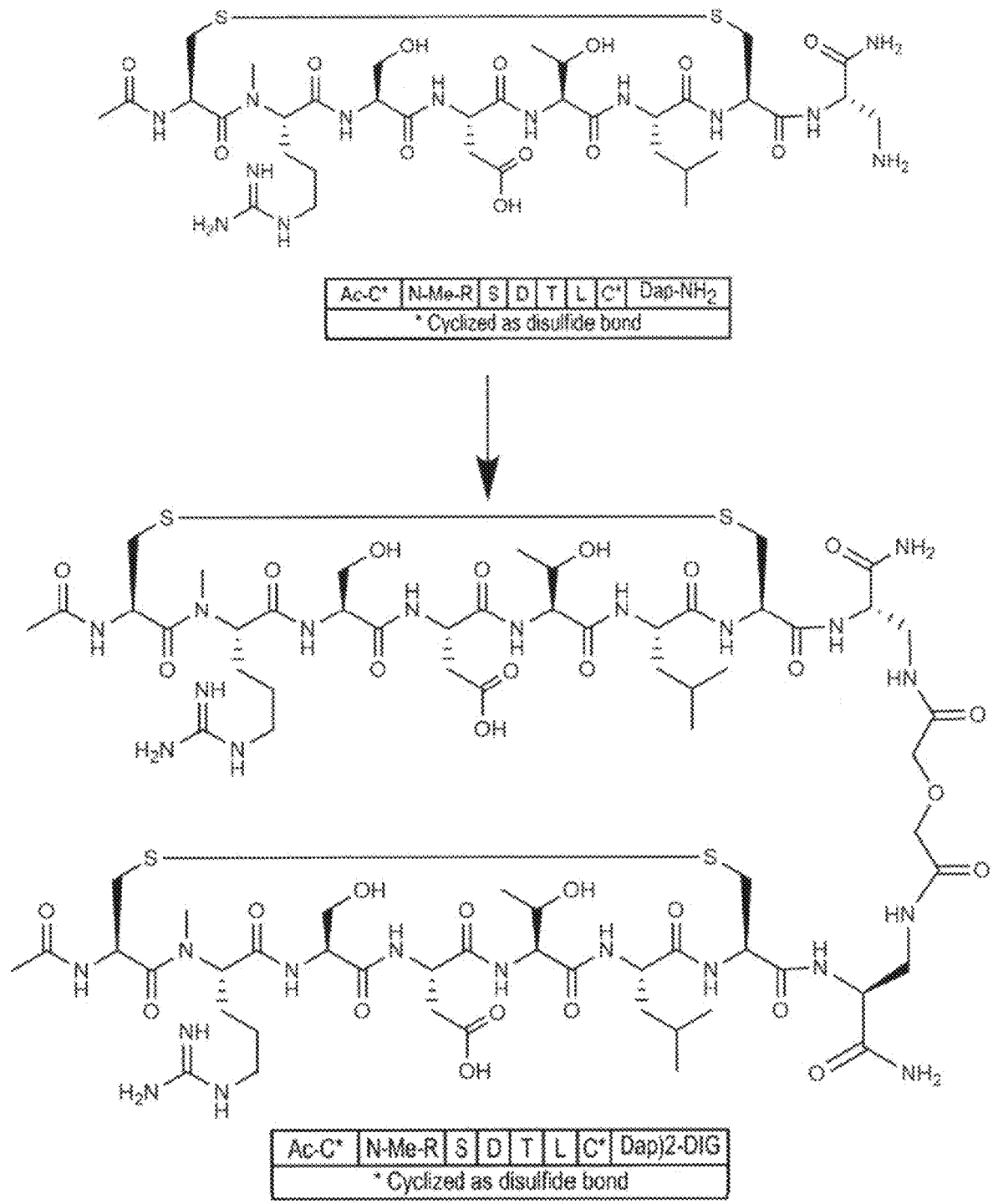
FIG. 2 is a schematic showing a pair of integrin antagonist monomer subunits (SEQ ID NOs: 348 and 349, respectively, in order of appearance), wherein the subunits are aligned and linked at their respective C-termini by a DIG linker in accordance with a representative embodiment of the present invention.
Figure 3B:
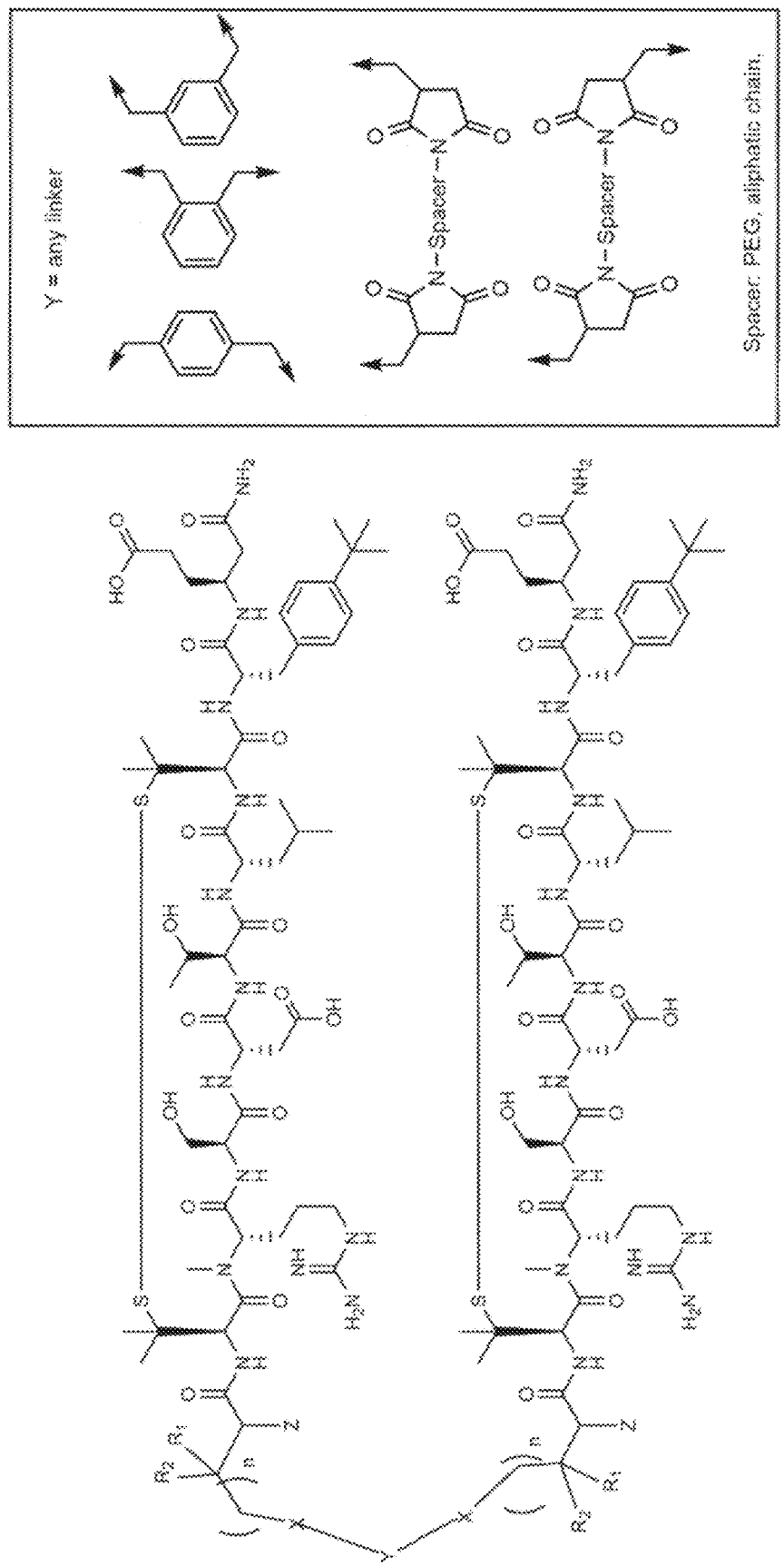
Figure 4:
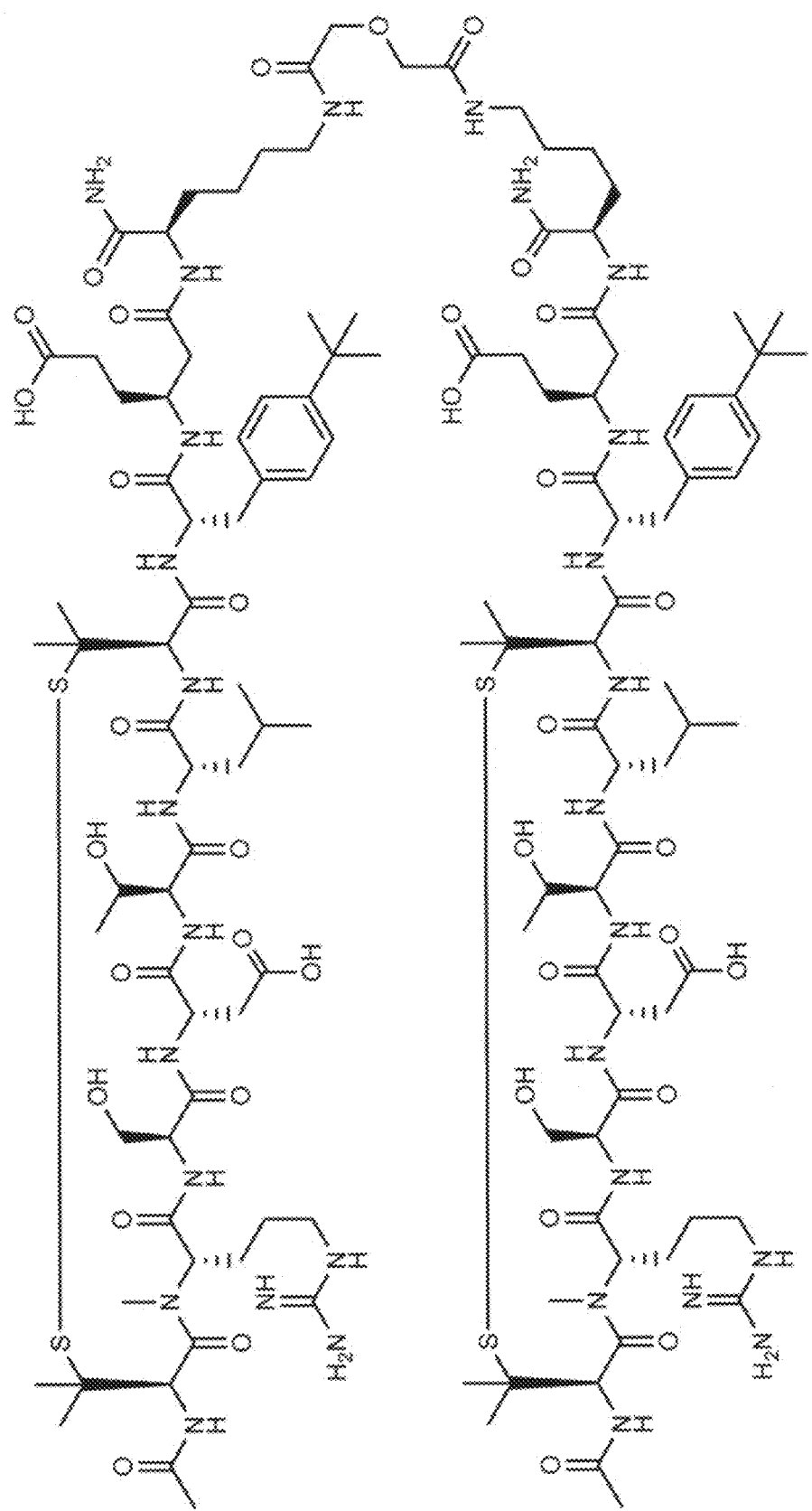
FIG. 4 shows the structure of Peptide X.
Figure 6:
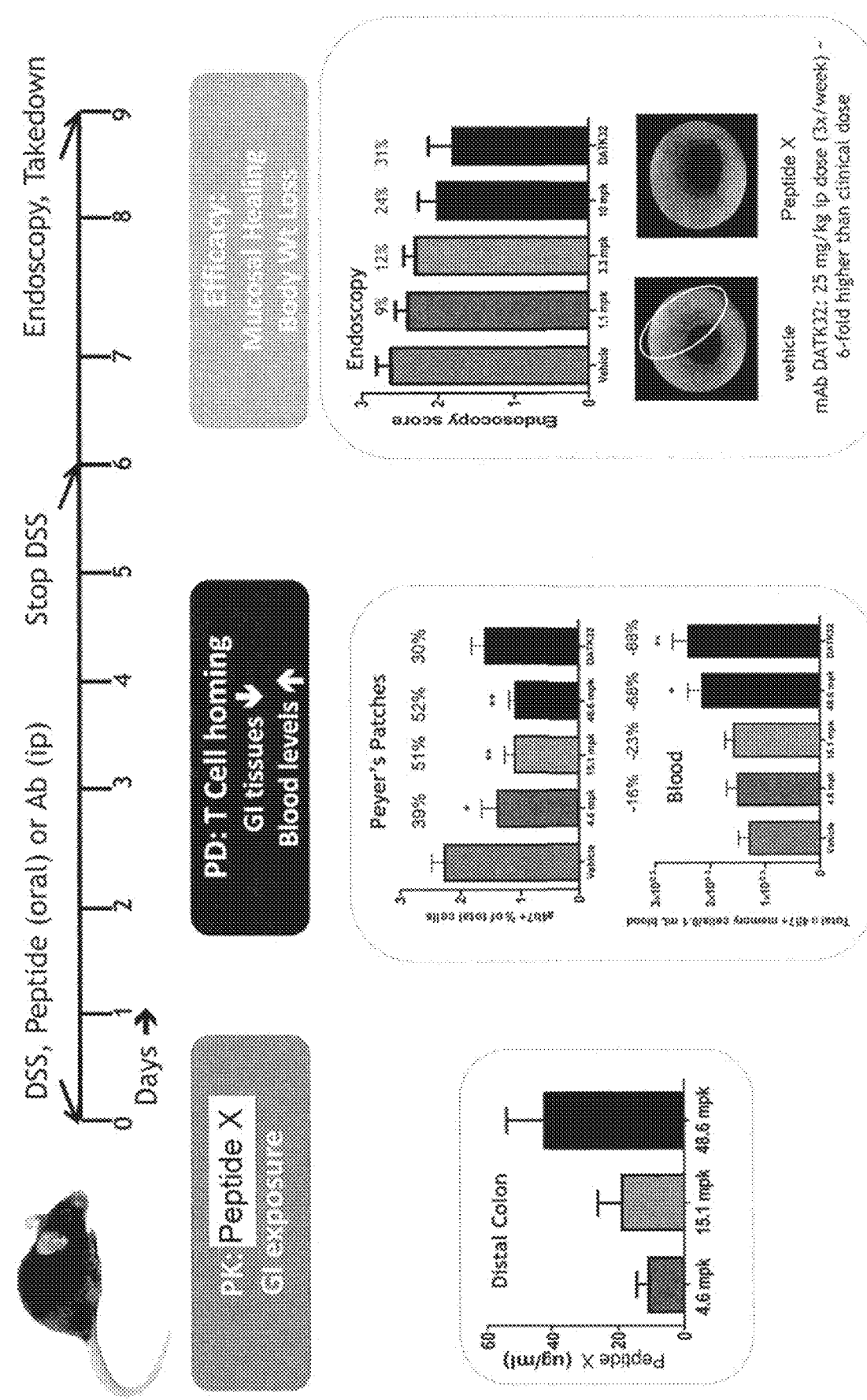
FIG. 6 shows the results of pre-clinical animal studies of Peptide X, showing dose proportional PK-PD-efficacy correlations in colitis mice.
Figure 7A:
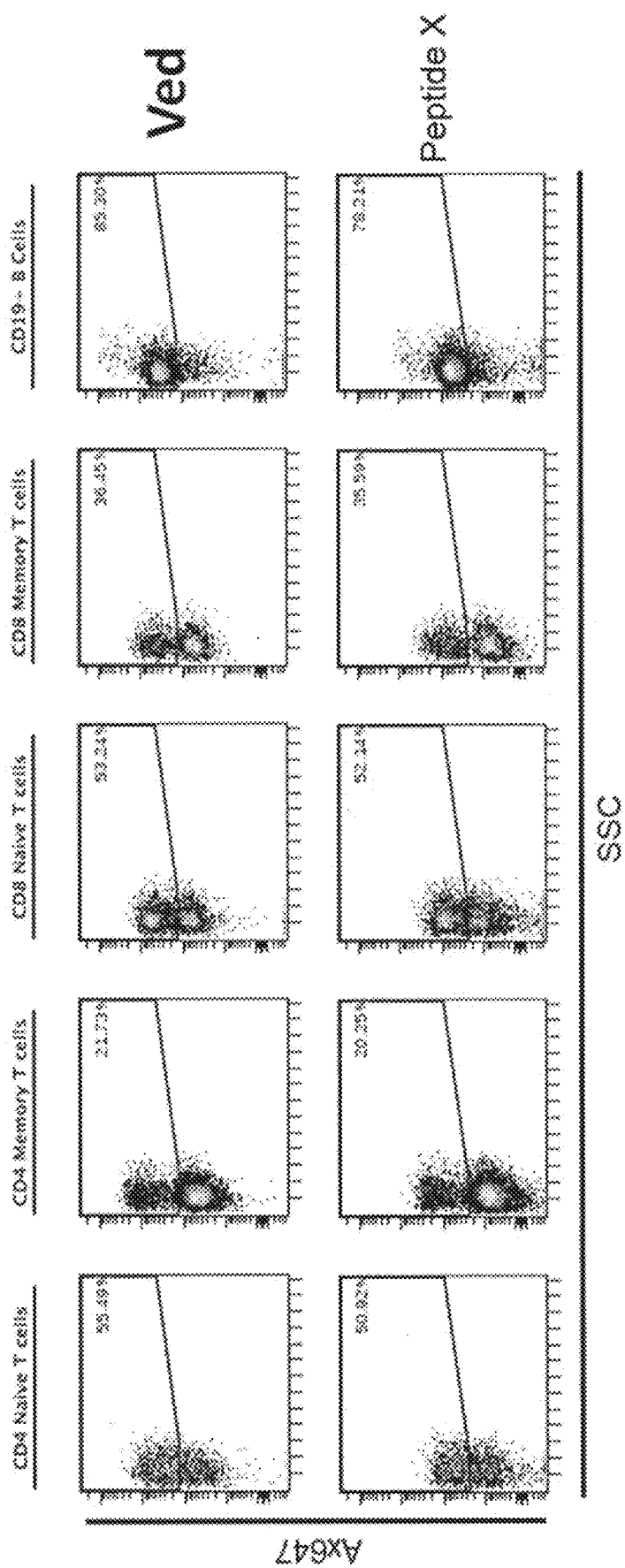
FIGS. 7A and 7B provide graphs showing the binding specificities of Peptide X and vedolizumab to various cells in human whole blood as measured by FACS. For each cell type, vedolizumab results are shown in the top graph, and Peptide X results are shown in the bottom graph.
Figure 7B:
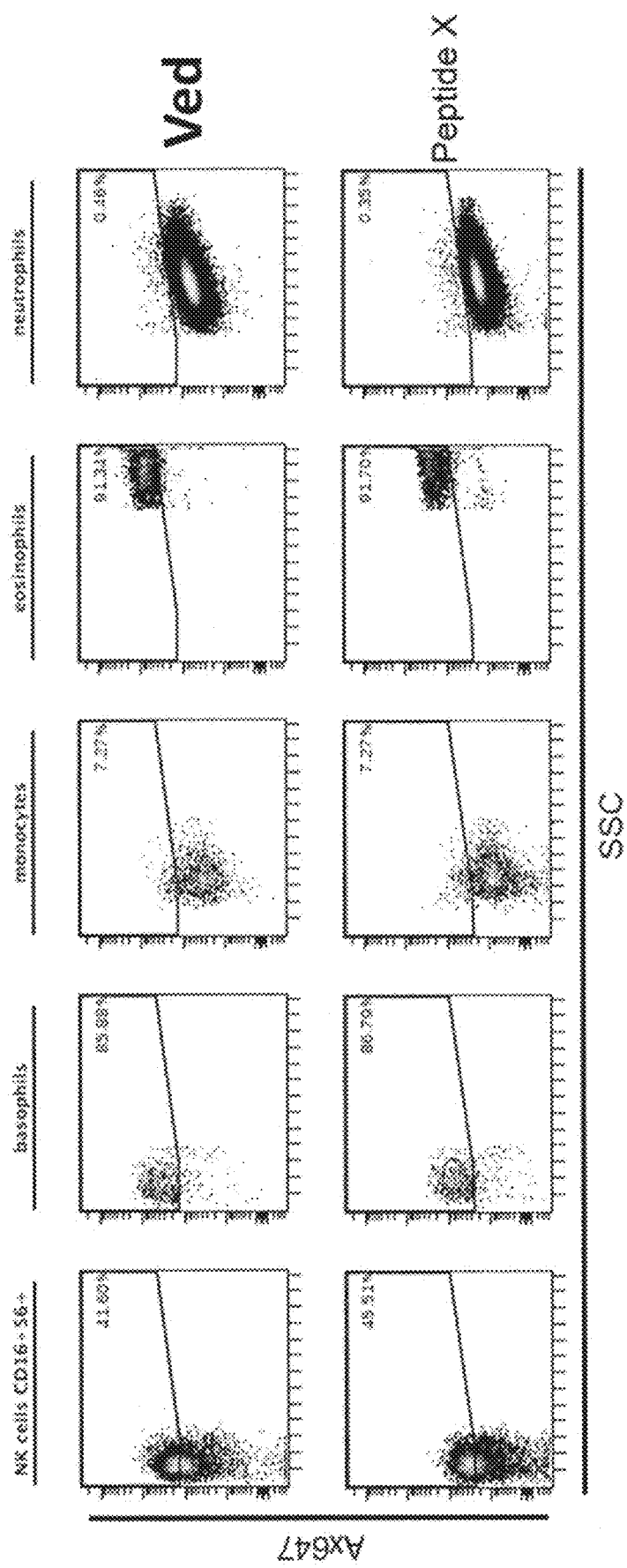

In particular embodiments, the present invention relates to various peptide monomer compounds or peptide dimer compounds comprising hetero- or homo-monomer subunits, which form cyclized structures through a disulfide bond, lactam bond, olefin bond, triazole bond, selenoether bond or diselenide bond. In certain embodiments, a peptide monomer compounds or one or both monomer subunits of a peptide dimer compound comprises an intramolecular bond to form a cyclized peptide monomer compound or cyclized monomer subunit. The cyclized structure of peptide monomer compounds and monomer subunits of peptide dimer compounds has been shown to increase potency and selectivity, and also increase stability for oral delivery. A non-limiting, representative illustration of the cyclized structure of a peptide monomer subunit and peptide dimer compound is shown in FIG. 2.

Definitions

As used herein, the singular forms "a," "and" and "the" include plural references unless the context clearly dictates otherwise.

As used in the present specification the following terms have the meanings indicated:

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring.

The term "DRP," as used herein, refers to disulfide rich peptides.

The term "dimer," as used herein, refers broadly to a peptide comprising two or more subunits, wherein the subunits are peptides, e.g., DRPs, linked at their C- or N-termini. Dimers also include peptides comprising two subunits that are linked via one or more internal amino acid residues or derivatives thereof. Each of the subunits may be linked to the other via its N-terminus, C-terminus, or through an internal amino acid or derivate thereof, which may be different for each of the two subunits. Dimers of the present invention may include homodimers and heterodimers and function as integrin antagonists. Peptide dimer compounds may be described herein using the following nomenclature: $[X_n]_2$, which indicates that the peptide dimer comprises two monomer subunits defined within the brackets (e.g., $X_n$, where X represents an amino acid and n indicates the number of amino acids in the peptide). A linker moiety linking the two peptide subunits may be shown as follows: $[X_n]_2$-L or L-$[X_n]_2$, where L is the linker. Other chemical moieties, such as detectable labels may be shown in a similar manner as for the linker.

The term "L-amino acid," as used herein, refers to the "L" isomeric form of an amino acid, and conversely the term "D-amino acid" refers to the "D" isomeric form of an amino acid. The amino acid residues described herein are preferred to be in the "L" isomeric form, however, residues in the "D" isomeric form can be substituted for any L-amino acid residue, as long as the desired functional is retained by the peptide.

The term "$NH_2$," as used herein, refers to the free amino group present at the amino terminus of a polypeptide. The term "OH," as used herein, refers to the free carboxy group present at the carboxy terminus of a peptide. Further, the term "Ac," as used herein, refers to Acetyl protection through acylation of the C- or N-terminus of a polypeptide, or any amino acid in the peptide. The term "$NH_2$" may also be used herein to refer to a C-terminal amide group, e.g., in the context of a $CONH_2$.

The term "carboxy," as used herein, refers to —$CO_2H$.

The term "isostere" or "isostere replacement," as used herein, refers to any amino acid or other analog moiety having physiochemical and/or structural properties similar to a specified amino acid. In particular embodiments, an "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Illustrative charged amino acid residues include lysine (+), arginine (+), aspartate (−) and glutamate (−). Illustrative polar amino acids include serine, threonine, asparagine, glutamine, histidine and tyrosine. Illustrative hydrophobic amino acids include alanine, valine, leucine, isoleucine, proline, phenylalanine, tryptophane, cysteine and methionine. The amino acid glycine does not have a side chain and is hard to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. In certain embodiments, an isostere is a derivative of an amino acid, e.g., a derivative having one or more modified side chains as compared to the reference amino acid.

The term "cyclized," as used herein, refers to a reaction in which one part of a polypeptide molecule becomes linked to another part of the polypeptide molecule to form a closed ring, such as by forming a disulfide bridge or other similar bond, e.g. a lactam bond. In particular embodiments, peptide monomer compounds or monomer subunits of peptide dimer compounds described herein are cyclized via an intramolecular bond between two amino acid residues present in the peptide monomer or monomer subunit.

The term "subunit," as used herein, refers to one of a pair of polypeptides monomers that are joined at the C- or N-terminus to form a dimer peptide composition.

The term "linker," as used herein, refers broadly to a chemical structure that is capable of linking together a plurality of peptide monomer subunits to form a dimer.

The term "receptor," as used herein, refers to chemical groups of molecules on the cell surface or in the cell interior that have an affinity for a specific chemical group or molecule. Binding between dimer peptides and targeted integrins can provide useful diagnostic tools.

The term "integrin-related diseases," as used herein, refer to indications that manifest as a result of integrin binding, and which may be treated through the administration of an integrin antagonist.

As used herein, the terms "disease," "disorder," and "condition" may be used interchangeably.

As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, 'prevent" or "prevention" includes (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. In certain embodiments, any of the peptide momoner compounds or peptide dimer compounds described herein are salt forms, e.g., acetate salts.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds", as used herein refers to various compounds with carboxylic acid functionality e.g. which may be used to acylate the N-terminus of an amino acid subunit prior to forming a C-terminal dimer. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, 3-Fluoromethylbutyric acid, Tetrahedro-2H-Pyran-4-carboxylic acid.

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide. Peptide sequences may be shown in tables, which may further disclose additional moieties, such as N-terminal or C-terminal chemical modifications, linkers, conjugates, and/or labels, which are present in certain embodiments of the compounds of the invention.

It is noted that the term "comprising" is intended to be open and permits but does not require the inclusion of additional elements or steps. When the term "comprising" is used herein, the term "consisting of" is thus also encompassed and disclosed.

The term "amino acid" or "any amino acid" as used here refers to any and all amino acids, including naturally occurring amino acids (e.g., α-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
|---|---|
| DIG | DiGlycolic acid (Linker) |
| Dap | Diaminopropionic acid |
| Dab | Diaminobutyric acid |
| Pen | Penicillamine |
| Sar | Sarcosine |
| Cit | Citroline |
| Cav | Cavanine |
| Phe(4-Guanidino) or 4-Guan | 4-Guanidine-Phenylalanine |
| N-Me-Arg; N(alpha)Methylation | N-Methyl-Arginine |
| Ac- | Acetyl |
| 2-Nal | 2-Napthylalanine |
| 1-Nal | 1-Napthylalanine |
| Bip | Biphenylalanine |
| O-Me-Tyr | Tyrosine (O-Methyl) |
| N-Me-Lys | N-Methyl-Lysine |
| N-Me-Lys (Ac) | N-e-Acetyl-D-lysine |
| 3,3-DiphenylAla | 3,3 DiPhenylAlanine |
| 3,3-DiphenylGly | 3,3-DiphenylGlycine |
| $NH_2$ | Free Amine |
| $CONH_2$ | Amide |
| COOH | Acid |
| Phe(4-F) | 4-Fluoro-Phenlanine |
| PEG13 | Bifunctional PEG linker with 13 PolyEthylene Glycol units |
| PEG25 | Bifunctional PEG linker with 25 PolyEthylene Glycol units |
| PEG1K | Bifunctional PEG linker with PolyEthylene Glycol Mol wt of 1000Da |
| PEG2K | Bifunctional PEG linker with PolyEthylene Glycol Mol wt of 2000Da |
| PEG3.4K | Bifunctional PEG linker with PolyEthylene Glycol Mol wt of 3400Da |
| PEG5K | Bifunctional PEG linker with PolyEthylene Glycol Mol wt of 5000Da |
| IDA | β-Ala-Iminodiacetic acid (Linker) |
| IDA-Palm | β-Ala (Palmityl)-Iminodiacetic acid |
| HPhe homoPhe | homo Phenylalanine |
| Ahx | Aminohexanoic acid |
| Me | Methyl |
| Triazine | Amino propyl Triazine di-acid |
| Boc-Triazine | Boc-Triazine di-acid |
| Trifluorobutyric acid | Acylated with 4,4,4-Trifluorobutyric acid |
| 2-Methly-trifluorobutyric acid | acylated with 2-Methy-4,4,4-Butyric acid |
| Trifluorpentanoic acid | Acylated with 5,5,5-Trifluoropentanoic acid |
| 1,4-Phenylenediacetic acid | para-Phenylenediacetic acid (Linker) |
| 1,3-Phenylenediacetic acid | meta-Phenylenediacetic acid (Linker) |
| DTT | Dithiothreotol |
| Nle | Norleucine |
| β-HTrp or β-homoTrp | β-homoTrypophane |
| β-HPhe or β-homoPhe | β-homophenylalanine |
| Phe(4-CF3) | 4-Trifluoromethyl Phenylalanine |
| β-Asp | β-Aspartic acid |
| | 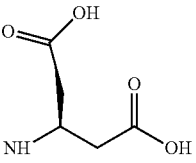 |
| β-HGlu beta-homoGlu | β-homoglutamic acid |
| | 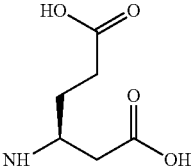 [SMILES: N[C@@H](CCC(=O)O)CC(=O)O] |

TABLE 1-continued

Definitions and Abbreviations

| Abbreviation | Definition |
| --- | --- |
| 2-2-Indane | 2-Aminoindane-2-carboxylic acid |
| 1-1-Indane | 1-Aminoindane-1-carboxylic acid |
| Cpa | CyclopentylAlanine |
| Orn | Ornithine |
| Aoc | 2-Amino octonoic acid |
| Cba | Cyclobutyl alanine |
| HCha | homocyclohexyl Alanine |
| Cyclobutyl | Cyclobutylalanine |
| β-HPhe or β-homoPhe | P-homophenylalanine |
| HAsp or homoAsp | HomoAspartic acid |
| HLys or homoLys | homoLysine |
| HCys or homoCys | HomoCysteine |
| HGlu or homoGlu | homoGlutamic acid |
| HomoLeu or homoLeu | homoLeucine |
| Gla | Gama-Carboxy-Glutamic acid |
| Tic | (3S-)-1,2,3,4-tetrahydroisoquinoline-3-carboxylic acid |
| | [structure: tetrahydroisoquinoline with COOH and NH] |
| Phe(4CF3) | Phe(4-trifluoromethyl 3-(4-trifluoromethyl-phenyl)propionic acid |
| Phe(2,4-diCl) | (S)-Fmoc-2-amino-3-(2,4-dichlorophenyl)propionic acid |
| Phe(3,4-diCl) | (S)-Fmoc-2-amino-3-(3,4-dichlorophenyl)propionic acid |
| Pen(=O) | Penicillamine sulfoxide |
| Aic | aminoindan-2-carboxylic acid |
| Phe(2-carbomyl) | L-2-carbamoylphenylalanine |
| Phe(3-carbomyl) | L-3-carbamoylphenylalanine |
| Phe(4-carbomyl) | L-4-carbomylphenylalanine |
| Phe(4-COOH) | (4-carboxy-tert-butyl)-L-phenylalanine |
| Phe(4-OMe) | (S)-4-methoxyphenylalanine |
| Phe(4-tBu) | 2-amino-3-(4-tert-butyl-phenyl)propionic acid |
| Phe(4-F) | 4-fluoro-L-phenylalanine |
| Glu(OMe) | L-glutamic acid g-methyl ester |
| β-azido-Ala-OH | β-azido-Alanine |
| Aoc | 8-amino-octanoic acid |

Figure 1:
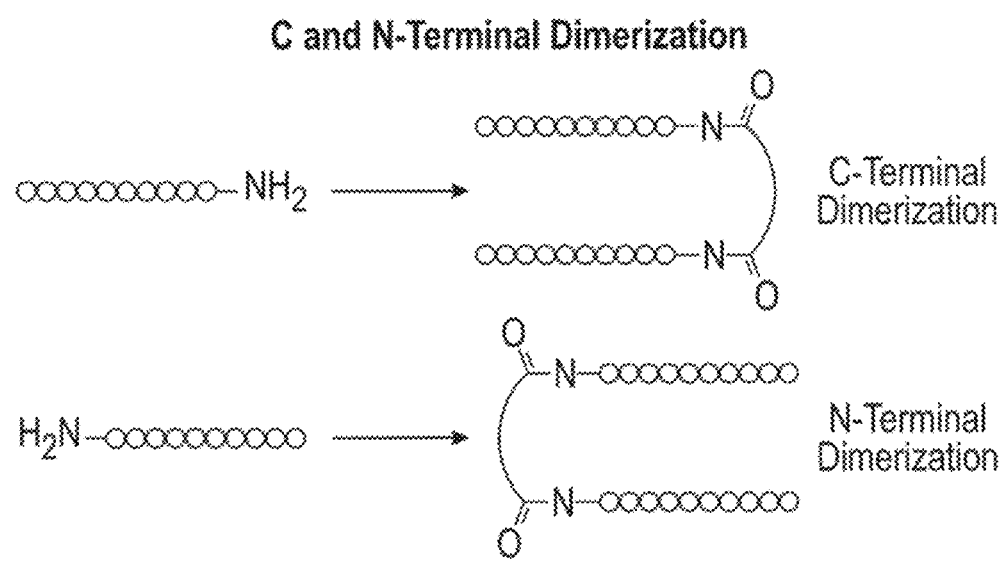
FIG. 1 is a schematic showing C and N-terminal dimerizations.

Aspects of the present invention include peptide dimer compounds comprising two monomer subunits, wherein the peptide dimer compounds are antagonists of α4β7 integrin. Related aspects of the present invention include monomer subunits of peptide antagonists. Monomer subunits present in peptide dimer compounds are linked at either their C- or N-terminus, e.g., as shown in FIG. 1, or via internal amino acid residues, e.g., by a linker moiety. In particular embodiments, both monomer subunits are linked via their respective N-termini, both monomer subunits are linked via their respective C-termini, or both monomer subunits are linked via internal amino acid residues. In further embodiments, one monomer subunit is linked via any of its N-terminus, C-terminus, or an internal amino acid to another monomer subunit via any of its N-terminus, C-terminus or an internal amino acid, and linkages may occur via the same or different amino acid residues on two monomer subunits of a peptide dimer compound. In further related embodiments, monomer subunits of peptide dimer compounds of the present invention are linked via both their N-terminus and their C-terminus. In one embodiments the two N-termini of the monomer subunits are linked; in one embodiment, the two C-termini of the monomer subunits are linked; and in one embodiment, the N-terminus of the first monomer subunit is linked to the C-terminus of the second monomer subunit of a peptide dimer compound, and the C-terminus of the first monomer subunit is linked to the N-terminus of the second monomer subunit of the peptide dimer compound.

The linker moieties of the present invention may include any structure, length, and/or size that is compatible with the teachings herein. In certain embodiments, a linker moiety is selected from the non-limiting group consisting of DIG, PEG13, PEG25, PEG1K, PEG2K, PEG3.4K, PEG4K, PEG5K, IDA, IDA-Palm, IDA-Boc, IDA-Ac, IDA-Isovaleric acid, ADA Triazine, Triazine-Boc, Isophthalic acid, 1,3-phenylenediacetic acid, Glu, Asp, D-Glu, D-Asp, 1,4-phenylenediacetic acid, Biphenyl diacetic acid, cyclopropylacetic acid, succinic acid, glutaric acid, Dodecanedioic acid, suitable aliphatic diacids, suitable aromatic diacids, heteroaromatics, and polyethylene glycols having a molecular weight from approximately 400 Da to approximately 40,000 Da. When the linker is IDA, ADA or any linker with free amine it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations.

In certain embodiments, the linker connects two monomer subunits by connecting two sulfur containing C- or N-terminal amino acids. In some embodiments, the two sulfur containing amino acids are connected by a linker comprising a di-halide, an aliphatic chain, or a PEG. In certain embodiments, the linker connects two monomeric subunits by connecting sulfur containing C-terminal amino acids at the C-terminus of each monomer subunit. In certain embodiments, the linker connects two monomeric subunits by connecting sulfur containing N-terminal amino acids at the N-terminus of each monomer subunit. In certain embodiments, the linker connects two monomeric subunits by connecting a sulfur containing C-terminal amino acid of one monomer subunit to a sulfur-containing N-terminal amino acid of the other monomer subunit. In some embodiments, the two sulfur containing amino acids are connected by a linker comprising Homobifunctional maleimide crosslinkers, di-halide, 1,2-Bis(bromomomethyl)benzene, 1,2-Bis(chloromomethyl)benzene, 1,3-Bis(bromomomethyl) benzene, 1,3-Bis(chloromomethyl)benzene, 1,4-Bis (bromomomethyl)benzene, 1,4-Bis(chloromomethyl) benzene, 3,3'-bis-bromomethyl-biphenyl, or 2,2'-bis-bromomethyl-biphenyl. Particular haloacetyl crosslinkers contain an iodoacetyl or a bromoacetyl group. These homo bifunctional linkers may contain spacers comprising PEG or an aliphatic chain. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

In certain embodiments, the linker is selected from the group consisting of DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, aliphatics, aromatics, heteroaromatics, and polyethylene glycol based linkers having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds. Non-limiting examples of suitable linker moieties are provided in Table 2.

In particular embodiments, any of the peptide dimer compounds described herein e.g., peptide dimer compounds according to Formula (I) (including any of I-A, I-B, I-C, I-D, I-E, I-F, I-G, I-H, I-I, and I-J), Formula (II), Formula (III), Formula (A), Formula (B), Formula (C), Formula (D), Formula (S), Formula (X), or Formula (H), comprise two monomer subunits that are linked by any of the linkers described herein; and any of the peptide monomer compounds described herein, e.g., peptide monomer compounds according to Formula (IV) (including any of IV-A, IV-B, IV-C, IV-D, IV-E, IV-F, IV-G, IV-H, IV-I and IV-J), Formula (V) (including V-A), Formula (VI), Formula (A), Formula (B), Formula (C), or Formula (D) comprise any of the linkers described herein.

TABLE 2

Illustrative Linker Moieties

| Abbreviation | Description | Structure |
|---|---|---|
| DIG | DIGlycolic acid | (structure shown) |
| PEG4 | Bifunctional PEG linker with 4 PolyEthylene Glycol units | (structure shown with subscript 8) |
| PEG13 | Bifunctional PEG linker with 13 PolyEthylene Glycol units | (structure shown with subscript 12) |
| PEG25 | Bifunctional PEG linker with 25 PolyEthylene Glycol units | (structure shown with subscript 24) |
| PEG1K | Bifunctional PEG linker with PolyEthylene Glycol Mol wt of 1000Da | — |
| PEG2K | Bifunctional PEG linker with PolyEthylene Glycol Mol wt of 2000Da | — |
| PEG3.4K | Bifunctional PEG linker with PolyEthylene Glycol Mol wt of 3400Da | — |
| PEG5K | Bifunctional PEG linker with PolyEthylene Glycol Mol wt of 5000Da | — |

TABLE 2-continued

Illustrative Linker Moieties

| Abbreviation | Description | Structure |
|---|---|---|
| IDA | β-Ala-Iminodiacetic acid | 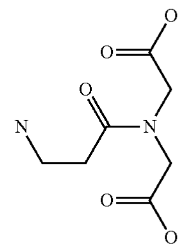 [SMILES: NCCC(=O)N(CC(=O)O)CC(=O)O] |
| Boc-IDA | Boc-β-Ala-Iminodiacetic acid | 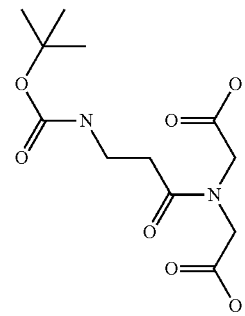 [SMILES: CC(C)(C)OC(=O)NCCC(=O)N(CC(=O)O)CC(=O)O] |
| Ac-IDA | Ac-β-Ala-Iminodiacetic acid | 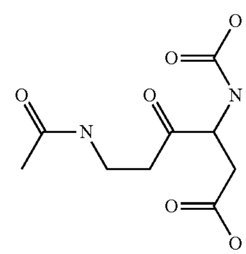 [SMILES: CC(=O)NCCC(=O)C(CC(=O)O)NC(=O)O] |
| IDA-Palm | Palmityl-β-Ala-Iminodiacetic acid | 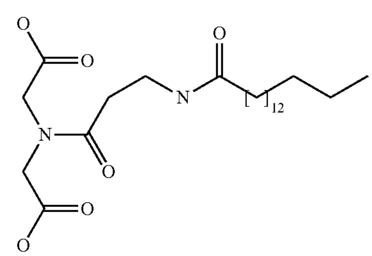 |
| GTA | Glutaric acid | 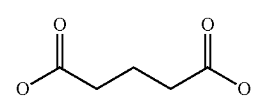 |
| PMA | Pemilic acid | 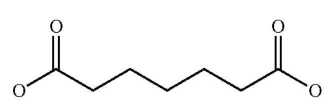 [SMILES: O=C(O)CCCCCC(=O)O] |
| AZA | Azelaic acid | 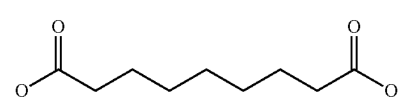 [SMILES: O=C(O)CCCCCCCC(=O)O] |
| DDA | Dodecanedioic acid | 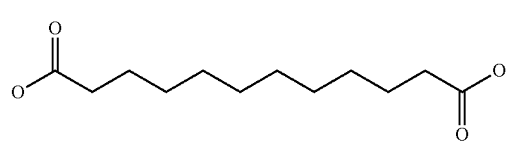 [SMILES: O=C(O)CCCCCCCCCCC(=O)O] |

TABLE 2-continued
Illustrative Linker Moieties
| Abbreviation | Description | Structure |
|---|---|---|
| IPA | Isopthalic aicd | 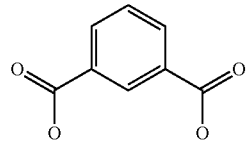 [SMILES: O=C(O)c1cccc(C(=O)O)c1] |
| 1,3-PDA | 1,3-Phenylenediacetic acid | 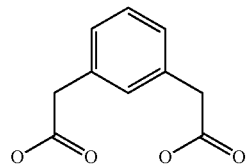 [SMILES: O=C(O)Cc1cccc(CC(=O)O)c1] |
| 1,4-PDA | 1,4-Phenylenediacetic acid | 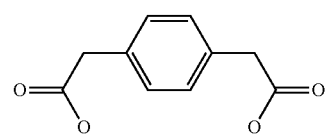 [SMILES: O=C(O)Cc1ccc(CC(=O)O)cc1] |
| 1,2-PDA | 1,2-Phenylenediacetic acid | 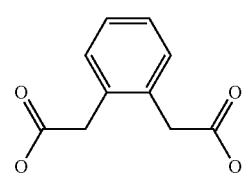 [SMILES: O=C(O)Cc1ccccc1CC(=O)O] |
| Triazine | Amino propyl Triazine di-acid | 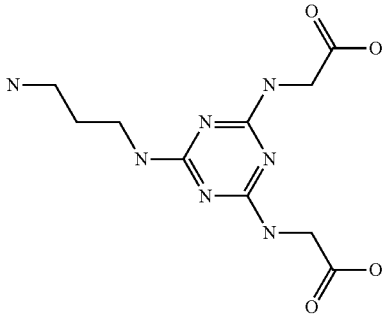 [SMILES: NCCCNc1nc(NCC(=O)O)nc(NCC(=O)O)n1] |
| Boc-Triazine | Boc-Triazine di-acid | 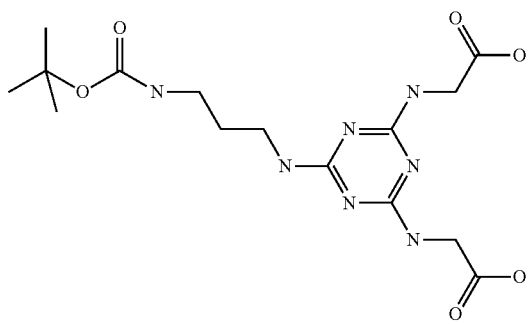 [SMILES: CC(C)(C)OC(=O)NCCCNc1nc(NCC(=O)O)nc(NCC(=O)O)n1] |
| ADA | Amino diacetic acid | 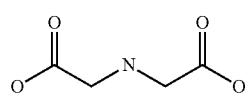 |
| AADA | n-Acetyl amino acetic acid | 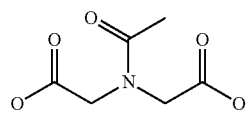 |

TABLE 2-continued

Illustrative Linker Moieties

| Abbreviation | Description | Structure |
| --- | --- | --- |
| PEG4-Biotin | PEG4-Biotin (Product number 10199, QuantaBioDesign) | 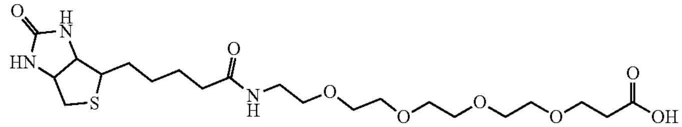 [SMILES: O=C(O)CCOCCOCCOCCOCCNC(=O)CCCCC1SCC2NC(=O)NC21] |
| 1,4 BMB | 1,4-Bis(halo-momethyl)benzene | X = Cl, Br |
| 1,2 BMB | 1,2-Bis(halo-momethyl)benzene | X—Cl, Br |
| 1,3 BMB | 1,3-Bis(halo-momethyl)benzene | X = Cl, Br |
| 1,3 BMBip | 3,3'-Bis-Halomethyl-Biphenyl | X = Cl, Br |
| IDA-Biotin | N-Biotin-β-Ala-Iminodiacetic acid | 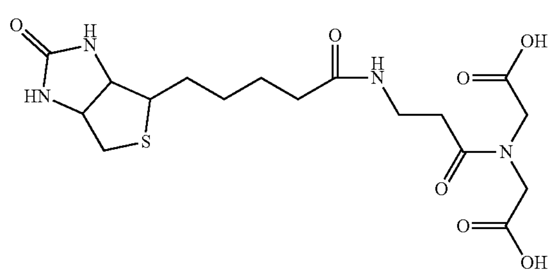 [SMILES: O=C(O)CN(CC(=O)O)C(=O)CCNC(=O)CCCCC1SCC2NC(=O)NC21] |

TABLE 2-continued

Illustrative Linker Moieties

| Abbreviation | Description | Structure |
|---|---|---|
| 2,2 BMBip | 2,2'-Bis-Halomethyl-Biphenyl | 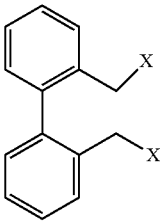 X = Cl, Br |
| BMal | Bis-Mal-dPEG | 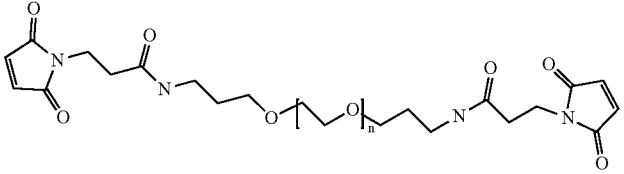 n = 1 to 20 |

When the linker is IDA, ADA or any linker with a free amine, it can be acylated, e.g. with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances, small PEG (PEG4-PEG13), Glu, IsoGlu or Asp is used as spacer before acylations. It is understood that once bound to a linker or another amino acid, an amino acid reisdue of the peptide compound may undergo structural changes, e.g., an acid may become an amide. Reference to a particular amino acid residue encompasses the amino acid residue in any altered structural form upon binding to a linker or forming an intramolecular bond with another amino acid of the peptide compound.

Aspects of the present invention relate to various peptide monomer compounds that form cyclized structures through a disulfide bond, lactam bond, olefin bond, triazole bond, selenoether bond or diselenide bond. The cyclized structure of each peptide monomer has been shown to increase potency and selectivity of the molecules.

In particular embodiments, the peptide monomer compounds and peptide dimer compounds (also referred to herein collectively as "the peptide compounds") of the instant invention may comprise one or more terminal modifying groups. In certain embodiments, a terminal end of a peptide compound is modified to include a terminal modifying group selected from the non-limiting group consisting of DIG, PEG4, PEG13, PEG25, PEG1K, PEG2K, PEG4K, PEG5K, Polyethylene glycol having molecular weight from 400 Da to 40,000 Da, IDA, ADA, Glutaric acid, Succinic acid, Isophthalic acid, 1,3-phenylenediacetic acid, 1,4-phenylenediacetic acid, 1,2-phenylenediacetic acid, AADA, and aliphatics, aromatics, and heteroaromatics. In certain embodiments the N- or C-terminus of the peptide compound is linked to a modifying group. In certain embodiments, the N-terminus of a peptide compound is modified by one to three suitable groups, e.g., as represented by $Xaa^1$, $Xaa^2$, and $Xaa^3$, e.g., of Formula (I) or (I-A). The N-terminus may further be acylated. In some instances, the N-terminus further comprises a linker moiety or other modifying group. Similarly, in certain embodiments, the C-terminus of a peptide is modified by a suitable group. For example, the C-terminus may be acylated. In some instances, the C-terminus further comprises a linker moiety, such as but not limited to any of those disclosed herein. In certain embodiments, the C-terminus comprises $NH_2$ or OH.

The present invention further includes various peptide monomer compounds and peptide dimer compound having peptides that have been substituted with various modified amino acids. For example, some peptides include Tic, Phe (2-carbamoyl), Phe(3-carbamoyl), Phe(4-COOH), Phe(4-OMe), Phe(4-tBu), Homo-Phe, Aic, Cit, Glu(OMe), Dab, Dap, Pen, Sar, Cit, Cav, homoLeu, 2-Nal, D-1-Nal, D-2-Nal, Bip, O-Me-Tyr, β-homoTrp, β-homoPhe, β-homoGlu Phe (4-$CF_3$), 2-2-Indane, 1-1-Indane, Cyclobutyl, Gla, Phe(4-$NH_2$), homoPhe, 1-Nal, Nle, homo amino acids, D-amino acids, 3-3-diPhe, cyclobutyl-Ala, HCha, Bip, β-Glu, Phe(4-guanidino), Phe(4-carbomyl) and various N-methylated amino acids. Additional non-limiting examples of non-natural amino acids contemplated by the present invention are shown in Table 1. One having skill in the art will appreciate that additional substitutions may be made to achieve similar desired results, and that such substitutions are within the teaching and spirit of the present invention.

In one aspect, the present invention provides a peptide dimer compound comprising two linked subunits of Formula (I):

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula (I))

or a pharmaceutically acceptable salt thereof,
wherein one or both subunits of the peptide dimer compound comprises a disulfide bond, a lactam bond, an olefin bond, a triazole bond, a selenoether bond, or a diselenide bond between $Xaa^4$ and $Xaa^{10}$, and further wherein Formula (I) represents a monomer subunit of a dimer molecule, the monomer subunits are linked to form the peptide dimer compound, and wherein:

$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidinoguanidino), Phe(4-carbomyl), Cit, Phe(4-NH$_2$), N-Me-homoArg, homoArg, Tyr, Dap, Dab, Arg-Me-sym, Arg-Me-asym, Cav, and His;
$Xaa^6$ is Ser, Gly, Thr or Ile;
$Xaa^7$ is Asp, D-Asp, Asp(OMe) or N-Me-Asp;
$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, cyclopentylAla, Leu, Nle, Cba, homoLeu, Cpa, Aoc, and N-Me-Leu;
$Xaa^{10}$ is any amino acid capable of forming a bond with $Xaa^4$;
$Xaa^{11}$ is absent or selected from the group consisting of: aromatic amino acids, substituted aromatic amino acids, and Tic;
$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val, and corresponding D-amino acids and isosteres;
$Xaa^{13}$ is absent or Pro or any amino acid; and
$Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp.

In certain embodiments of Formula (I), $Xaa^7$ is Asp, D-Asp, or N-Me-Asp. In certain embodiments of Formula (I), $Xaa^7$ is Asp, Asp(OMe) or N-Me-Asp. In certain embodiments, $Xaa^7$ is Asp or N-Me-Asp. In certain embodiments, $Xaa^7$ is Asp.

In certain embodiments of Formula (I), $Xaa^{11}$ is selected from the group consisting of Tic, Phe(2-carbomyl), Phe(3-carbomyl), Phe(4-COOH), Phe(4-OMe), Phe(4-tBu), Phe(4-CF$_3$), Phe(3-CF$_3$), Phe(CF$_3$), homo-Phe, D-Phe, Phe(2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe(2,4-di-Phe), beta-MethylPhe, and biphenyl-Ala.

In particular embodiments of Formula (I), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val.

In particular embodiments of Formula (I), $Xaa^{12}$ is selected from the group consisting of aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In particular embodiments of Formula (I), $Xaa^{14}$ is selected from the group consisting of: any amino acid with an amine side chain, Lys, D-Lys, N-Me-Lys, D-N-Me-Lys, Orn, Dab, Dap, homoLys, D-Dap, D-Dab, D-Orn, Cys, homoCys, Pen, D-homoCys, D-Cys, and D-Pen.

In particular embodiments of Formula (I), $Xaa^{14}$ is selected from the group consisting of: any amino acid with an amine side chain, Lys, D-Lys, N-Me-Lys, D-N-Me-Lys, Orn, Dab, Dap, homoLys, D-Dap, D-Dab, Cys, homoCys, Pen, and D-Orn.

In one embodiment of Formula (I), $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer.

In another embodiment of Formula (I), $Xaa^{14}$ is selected from the group consisting of: Asp, Glu, homoGlu, D-Asp, D-Glu, D-homoGlu, N-Me-Glu, N-Me-Asp, N-Me-D-Glu, and N-Me-D-Asp.

In particular embodiments of Formula (I), the two C-terminal amino acids of each subunit of a peptide dimer compound possess acid functionality, and they are linked through retroinverse linking by a diamine linker.

In particular embodiments of Formula (I), $Xaa^5$ is selected from the group consisting of Cit, Phe(4-carbomyl), and N-Me-homoArg; $Xaa^8$ is selected from the group consisting of Leu, homoLeu, Nle and Val; $Xaa^9$ is selected from the group consisting of: Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, and Val; or $Xaa^{13}$ is Pro.

In particular embodiments of Formula (I), $Xaa^5$ is selected from the group consisting of Cit, Phe(4-carbomyl), and N-Me-homoArg. In particular embodiments of Formula (I), $Xaa^8$ is selected from the group consisting of Leu, homoLeu, Nle and Val. In particular embodiments of Formula (I), $Xaa^9$ is selected from the group consisting of: Cba, homoLeu, and Cpa. In particular embodiments of Formula (I), $Xaa^{11}$ is selected from the group consisting of Tic, Phe(2-carbomyl), Phe(3-carbomyl), Phe(4-COOH), Phe(4-OMe), and Phe(4-tBu). In particular embodiments of Formula (I), $Xaa^{12}$ is selected from the group consisting of Aic, Gln, Cit, Glu (OMe), D-His, Tic, Phe(3-COOH), D-Arg, Bip, D-Trp, Phe, D-Phe, D-Val, D-Thr, D-1-Nal, D-2-Nal, Thr, and Val. In particular embodiments of Formula (I), $Xaa^{13}$ is Pro.

In particular embodiments of Formula (I), $Xaa^{11}$ is selected from the group consisting of Tic, Phe(2-carbomyl), Phe(3-carbomyl), Phe(4-COOH), Phe(4-OMe), Phe(4-tBu), Phe(4-CF$_3$), Phe(3-CF$_3$), Phe(CF$_3$), homo-Phe, D-Phe, Phe (2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe(2,4-di-Phe), beta-MethylPhe, or biphenyl-Ala.

In particular embodiments of Formula (I), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val.

In particular embodiments of Formula (I), $Xaa^7$ is Asp, D-Asp or N-Me-Asp; $Xaa^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, Leu, Nle, Cba, homoLeu, Aoc, and N-Me-Leu; $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and isosteres; $Xaa^{13}$ is absent or Pro; and $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, and Pen.

In particular embodiments of Formula (I), $Xaa^7$ is Asp, Asp(OMe) or N-Me-Asp.

In certain embodiments, the amino acid directly C-terminal to $Xaa^{10}$ is selected from aromatic amino acids, substituted aromatic amino acids, and Tic. In certain embodiments, the amino acid directly C-terminal to $Xaa^{10}$ is an aromatic amino acid. In certain embodiments wherein the compound is a peptide dimer, $Xaa^{14}$ is Lys, D-Lys, N-Me-Lys, D-N-Me-Lys, Orn, Dab, Dap, homoLys, D-Dap, D-Dab, or D-Orn. In certain embodiments, $Xaa^{14}$ is Cys, homoCys, or Pen. In certain embodiments, $Xaa^{14}$ or the C-terminus comprises an $NH_2$ or an OH.

In certain embodiments, a free amine in the C-terminal amino acid is capped, e.g., with an acetyl group.

In certain embodiments of any of the formulas described herein, $Xaa^1$, $Xaa^2$ or $Xaa^3$ can only be Ac when located at the N-terminus of the peptide compound, e.g., bound to the N-terminal amino acid of the peptide compound. In particular embodiments of any of the compounds of any of the various formulas described herein, $Xaa^1$ is Ac, and $Xaa^2$ and $Xaa^3$ are both absent or any amino acid.

In certain embodiments, $Xaa^4$ and $Xaa^{10}$ are amino acid residues capable of binding to each other. Amino acids capable of binding to each other are known in the art, and various examples of specific amino acid residues that bind to each other and the bonds formed are described herein. In particular embodiments, $Xaa^4$ and $Xaa^{10}$ are capable of binding each other via a covalent bond. In certain embodiments, the covalent bond occurs through side chain groups on $Xaa^4$ and $Xaa^{10}$. In particular embodiments, the bond is a disulfide bond.

In certain embodiments of any one of Formula (I) (including any of I-A, I-B, I-C, I-D, I-E, I-F, I-G, I-H, and I-I), one or both peptide dimer subunit(s) comprises an intramolecular bond between $Xaa^4$ and $Xaa^{10}$. In certain embodiments of any one of Formula (II) (including II-A), Formula (III), Formula (A), Formula (B), Formula (C), or Formula (D), one or both peptide dimer subunit(s) comprises an intramolecular bond between $Xaa^1$ and $Xaa^7$. In certain embodiments, the bond is a disulfide bond, a lactam bond, an olefin bond, a triazole, a selenoether, or a diselenide bond. In certain embodiments, the bond occurs directly between the two amino acid residues.

In certain embodiments of Formula (I), $Xaa^4$ is selected from the group consisting of: Cys, Pen, HomoCys, D-Cys, D-Pen, D-HomoCys, Asp, Glu, HomoGlu, β-Asp, β-Glu, Lys, HomoLys, Orn, Dap, Dap, 2-allylglycine, 2-(3'-butenyl) glycine, 2-(4'-pentenyl)glycine, or 2-(5'-hexenyl)glycine, corresponding D-amino acids and sutiable isosteres, and $Xaa^{10}$ is selected from the group consisting of: Cys, Asp, Lys, Glu, Pen, HomoAsp, HomoGlu, HomoCys, D-Cys, D-Pen, HomoLys, Orn, β-Asp, β-Glu, Dap, Dab, D-Homo-Cys, 2-allylglycine, 2-(3'-butenyl)glycine, 2-(4'-pentenyl) glycine, or 2-(5'-hexenyl)glycine, corresponding D-amino acids and suitable isosteres.

In certain embodiments of Formula (I), a peptide subunit comprises a disulfide bond between $Xaa^4$ and $Xaa^{10}$, and $Xaa^4$ and $Xaa^{10}$ are each selected from the group consisting of: Cys and Pen. In certain embodiments, both $Xaa^4$ and $Xaa^{10}$ are Pen.

In certain embodiments of Formula (I), $Xaa^{10}$ is selected from the group consisting of Asp, homoAsp, Glu, and homoGlu, homoLys, and $Xaa^4$ is selected from the group consisting of Lys, Dap, Dab, homoLys, Orn, and homoGlu. In certain embodiments, $Xaa^{10}$ is selected from the group consisting of Lys, Dap, Dab, homoLys, Orn, and homoGlu, and $Xaa^4$ is selected from the group consisting of Asp, homoAsp, Glu, homoGlu, and homoLys.

In certain embodiments of Formula (I), $Xaa^4$ is selected from the group consisting of Asp, homoAsp, Glu, homoGlu, andhomoLys, $Xaa^{10}$ is selected from the group consisting of Lys, Dap, Dab, homoLys, Orn, and HGlu, and $Xaa^4$ and $Xaa^{10}$ are cyclized through an amide bond.

In certain embodiments of Formula (I) wherein a peptide subunit comprises an olefin bond between $Xaa^4$ and $Xaa^{10}$, $Xaa^4$ and $Xaa^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/ "stapled peptide."

In certain embodiments of Formula (I), $Xaa^4$ is Cys, Pen, homoCys, D-Pen, D-Cys or D-homoCys. In certain embodiments, $Xaa^{10}$ is Cys, Pen, homoCys, D-Pen, D-Cys or D-homoCys.

In certain embodiments of Formula (I), $Xaa^4$ and $Xaa^{10}$ are each β-azido-Ala-OH or propargylglycine, and the peptide dimer subunit(s) is cyclized through click chemistry leading to a triazole ring.

In particular embodiments of Formula (I), the intramolecular bond is a disulfide bond or a lactam bond.

In some embodiments, the N-terminal or C-terminal amino acids of both peptide monomer subunits of a peptide dimer, e.g., $Xaa^1$, $Xaa^2$, $Xaa^3$, $Xaa^{11}$, $Xaa^{12}$, $Xaa^{13}$ or $Xaa^{14}$, are modified with a suitable linker moiety to form a homo- or hetero-dimer molecule, wherein Formula (I) comprises a dimer formed from two subunits joined by a suitable C- or N-terminal linker.

In one aspect, the present invention provides a peptide dimer compound comprising two linked subunits of Formula (I'):

$Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$-$Xaa^{11}$-$Xaa^{12}$-$Xaa^{13}$-$Xaa^{14}$ (Formula I')

or a pharmaceutically acceptable salt thereof, wherein:
$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidino), Phe(4-carbomyl), Cit, Phe(4-$NH_2$), N-Me-homoArg, homoArg, Tyr, Dap, Dab, Arg-Me-sym, Arg-Me-asym, Phe(4-guanidino), Cav, and His;
$Xaa^6$ is Ser, Gly, Thr, or Ile;
$Xaa^7$ is Asp or D-Asp, Asp(OMe), or N-Me-Asp;
$Xaa^8$ is selected from the group consisting of: Thr, Val, Ile, Leu, homoLeu, HomoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pentyl Ala, N-hexyl Ala, cyclobutyl Ala, cyclopentylAla, Leu, Nle, Cpa, Cba, homoLeu, Aoc, and N-Me-Leu;

Xaa¹⁰ is any amino acid capable of forming a bond with Xaa⁴;

Xaa¹¹ is absent or selected from the group consisting of: aromatic amino acids, substituted aromatic amino acids and Tic;

Xaa¹² is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and suitable isosteres;

Xaa¹³ is absent or Pro; and

Xaa¹⁴ is selected from the group consisting of: any amino acid with an amine side chain, Lys, D-Lys, N-Me-Lys, D-N-Me-Lys, Orn, Dab, Dap, homoLys, D-Dap, D-Dab, Cys, homoCys, Pen, and D-Orn.

In particular embodiments of peptide dimer compounds comprising peptide monomer subunits of Formula (I'), Xaa⁵ and Xaa¹⁰ are linked via an intramolecular bond, e.g., a disulfide bond, a lactam bond, an olefin bond, a triazole bond, a selenoether bond, or a diselenide bond.

In certain embodiments of Formula (I'), Xaa⁵ is selected from the group consisting of Cit, Phe(4-carbomyl), and N-Me-homoArg; Xaa⁸ is selected from the group consisting of Leu, homoLeu, Nle and Val; Xaa⁹ is selected from the group consisting of: Cba, homoLeu, and Cpa; Xaa¹¹ is selected from the group consisting of Tic, Phe(2-carbomyl), Phe(3-carbomyl), Phe(4-COOH), Phe(4-OMe), and Phe(4-tBu); Xaa¹² is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or Xaa¹³ is Pro.

In various embodiments, any of the further limitations described for Formula (I) may be present in Formula (I'). Reference throughout to embodiments of Formula (I) also apply to any alternative embodiments of Formula (I) and also to Formula I.

In one aspect, the present invention provides a peptide dimer compound comprising two linked subunits of Formula (II):

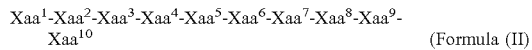

Xaa¹-Xaa²-Xaa³-Xaa⁴-Xaa⁵-Xaa⁶-Xaa⁷-Xaa⁸-Xaa⁹-Xaa¹⁰    (Formula (II)

or a pharmaceutically acceptable salt thereof, wherein one or both subunits of the peptide dimer compound comprises a disulfide bond, a lactam bond, an olefin bond, a triazole bond, a selenoether bond, or a diselenide bond between Xaa¹ and Xaa⁷, and further wherein Formula (II) represents a monomer subunit of a dimer molecule, the monomer subunits are linked to form a dimer molecule in accordance with the present invention, and wherein Xaa¹-Xaa¹⁰ of Formula (II) correspond to Xaa⁴-Xaa¹³ of Formula (I).

In particular embodiments of Formula (II), Xaa¹ and Xaa⁷ are both Cys or Pen; in particular embodiments, both Xaa¹ and Xaa⁷ are Pen.

In particular embodiments of Formula (II), Xaa¹⁰ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer.

In particular embodiments of Formula (II), Xaa¹⁰ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, and D-Pen.

In certain embodiments of Formula (II), Xaa² is selected from the group consisting of Cit, Phe(4-carbomyl), and N-Me-homoArg; Xaa⁵ is selected from the group consisting of Leu, HomoLeu, Nle and Val; Xaa⁶ is selected from the group consisting of: Cba, HomoLeu, and Cpa; Xaa⁸ is selected from the group consisting of Tic, Phe(2-carbomyl), Phe(3-carbomyl), Phe(4-COOH), Phe(4-OMe), and Phe(4-tBu); Xaa⁹ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or Xaa¹⁰ is Pro. In certain embodiments of Formula (II), Xaa² is selected from the group consisting of Cit, Phe(4-carbomyl), and N-Me-homoArg. In certain embodiments of Formula (II), Xaa⁵ is selected from the group consisting of Leu, HomoLeu, Nle and Val. In certain embodiments of Formula (II), Xaa⁶ is selected from the group consisting of: Cba, HomoLeu, and Cpa. In certain embodiments of Formula (II), Xaa⁸ is selected from the group consisting of Tic, Phe(2-carbomyl), Phe(3-carbomyl), Phe(4-COOH), Phe(4-OMe), and Phe(4-tBu). In certain embodiments of Formula (II), Xaa⁹ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val. In certain embodiments of Formula (II), Xaa¹⁰ is Pro.

In particular embodiments, one or both subunit of Formula (I) and Formula (II) comprises a disulfide bond, a lactam bond, an olefin bond, a triazole bond, a selenoether bond, or a diselenide bond between Xaa⁴ and Xaa¹⁰ of Formula (I), or Xaa¹ and Xaa⁷ of Formula (II). In particular embodiments, the intramolecular bond is a disulfide bond or a lactam bond. In certain embodiments, a peptide dimer comprises one or more monomer subunits selected from of any one of Formula (I) (including any of I-A, I-B, I-C, I-D, I-E, I-F, I-G, I-H, I-I and I-J).

In one embodiment of Formula (I), herein referred to as Formula (I-A),

Xaa¹ is absent, Ac, or any amino acid;

Xaa² is absent, Ac, or any amino acid;

Xaa³ is absent, Ac, or any amino acid;

Xaa⁴ is Pen;

Xaa⁵ is selected from the group consisting of: Arg, N-Me-Arg, Arg, N-Me-Lys, Phe(4-guanidino), Phe(4-carbomylamino), Cit, Phe(4-NH₂), N-Me-HomoArg, HomoArg, Tyr and His;

Xaa⁶ is Ser, Ile, Gly or Thr;

Xaa⁷ is Asp, D-Asp or N-Me-Asp;

Xaa⁸ is selected from the group consisting of: Thr, Val, Ile, Leu, homoLeu, Nle, and Val;

Xaa⁹ is selected from the group consisting of: Leu, Nle, Cpa, Cba, HomoLeu, Ile, cyclobutyl Ala, cyclopentylAla, Aoc, and N-Me-Leu;

Xaa¹⁰ is Pen;

Xaa¹¹ is absent or selected from the group consisting of: Trp, Phe, 2-Nal, 1-Nal, Tyr, His, Phe(4-F), Phe(4-CF₃), Phe(4-CH₃), Phe(4-tBu), Bip, Phe(4-COOH), Gly, 3,3-DiPhenylGly, 3,3-diPhenylAla, Tic, β-homoTrp, D-1-Nal, D-2-Nal, Phe(2,4-diCl), Phe(3,4-diCl), Phe(4-carbomyl), Phe(3-carbomyl), Phe(2-carbomyl), Tyr(Me), homoPhe, N-Me-Phe, N-Me-Tyr, Ser, Sar, 2,3-dihydroTrp, Ile, Leu, Ser, Arg, and Thr;

Xaa¹² is absent or selected from the group consisting of Glu, D-Glu, homoGlu, Asp, D-Asp, D-homoGlu, D-Asp, Gla, beta-homoGlu, corresponding D-amino acid, any aromatic amino acid, and isosteres thereof, $Xaa^{13}$ is absent or any amino acid; and
$Xaa^{14}$ is selected from the group consisting of: any amino acid with a free amino group on a side chain, Lys, D-Lys, N-Me-Lys, D-N-Me-Lys, Orn, Dab, Dap, HomoLys, D-Dap, D-Dab, or D-Orn.

In certain embodiments of Formula (I-A), $Xaa^4$ and $Xaa^{10}$ are linked, e.g. via a disulfide bond.

In certain embodiments of Formula (I-A), $Xaa^7$ is Asp or N-Me-Asp.

In one embodiment of Formula (I), herein referred to as Formula (I-B),
$Xaa^1$ is absent, Ac, or any amino acid;
$Xaa^2$ is absent, Ac, or any amino acid;
$Xaa^3$ is absent, Ac, or any amino acid;
$Xaa^4$ is Pen;
$Xaa^5$ is N-Me-Arg;
$Xaa^6$ is Ser;
$Xaa^7$ is Asp or D-Asp;
$Xaa^8$ is selected from the group consisting of: Thr, Val, Ile, Leu, homoLeu and Nle;
$Xaa^9$ is selected from the group consisting of: Leu, Nle, Cpa, Cba, homoLeu, Aoc, and N-Me-Leu;
$Xaa^{10}$ is Pen;
$Xaa^{11}$ is selected from the group consisting of: Trp, Phe, 2-Nal, 1-Nal, Tyr, His, Phe(4-F), Phe(4-CF$_3$), Phe(4-CH$_3$). Phe(4-tBu), Bip, Phe(4-COOH), Gly, 3,3-diPhenylGly, 3,3-diPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Ser, Arg, and Thr;
$Xaa^{12}$ is selected from the group consisting of: any aromatic amino acid, Glu, D-Glu, homoGlu, Asp, D-Asp, D-homo-Glu, Gla, beta-homoGlu, corresponding D-amino acid and isosteres thereof;
$Xaa^{13}$ is absent or any amino acid; and
$Xaa^{14}$ is selected from the group consisting of: Lys, D-Lys, N-Me-Lys, D-N-Me-Lys, Orn, Dab, Dap, HomoLys, D-Dap, D-Dab, and D-Orn.

In certain embodiments of Formula (I-B), $Xaa^4$ and $Xaa^{10}$ are linked, e.g. via a disulfide bond.

In certain embodiments of Formula (I-B), $Xaa^7$ is Asp.

In one embodiment of Formula (I), herein referred to as Formula (I-C),
$Xaa^1$ is absent, Ac, or any amino acid;
$Xaa^2$ is absent, Ac, or any amino acid;
$Xaa^3$ is absent, Ac, or any amino acid;
$Xaa^4$ is Pen;
$Xaa^5$ is N-Me-Arg;
$Xaa^6$ is Ser;
$Xaa^7$ is Asp or D-Asp;
$Xaa^8$ is selected from the group consisting of: Thr, Val, Ile, Leu, homoLeu and Nle;
$Xaa^9$ is selected from the group consisting of: Leu, Nle, Cpa, Cba, HomoLeu, Aoc, and N-Me-Leu;
$Xaa^{10}$ is Pen;
$Xaa^{11}$ is selected from the group consisting of: Trp, Phe, 2-Nal, 1-Nal, Tyr, His, Phe(4-F), Phe(4-CF$_3$), Phe(4-CH$_3$). Phe(4-tBu), Bip, Phe(4-COOH), Gly, 3,3-DiPhenylGly, 3,3-DiPhenyl Ala, Tic, β-homoTrp, D-1-Nal, D-2-Nal, Phe(2,4-diCl), Phe(3,4-diCl), Phe(4-carbomyl), Phe(3-carbomyl), Tyr(Me), HomoPhe, N-Me-Phe, N-Me-Tyr, Ser, Sar, 2,3-dihydroTrp, Ile, Leu, Ser, Arg, and Thr;
$Xaa^{12}$ is selected from the group consisting of: Glu, D-Glu, homoGlu, Asp, D-Asp, D-homoGlu, Gla, beta-homoGlu, corresponding D-amino acid and any aromatic amino acid and corresponding isosteres thereof;
$Xaa^{13}$ is absent or is any amino acid; and
$Xaa^{14}$ is selected from the group consisting of: Lys, D-Lys, N-Me-Lys, D-N-Me-Lys, Orn, Dab, Dap, HomoLys, D-Dap, D-Dab, and D-Orn.

In certain embodiments of Formula (I-C), $Xaa^4$ and $Xaa^{10}$ are linked, e.g. via a disulfide bond.

In certain embodiments of Formula (I-C), $Xaa^7$ is Asp.

In one embodiment of Formula (I), herein referred to as Formula (I-D),
$Xaa^1$ is absent, Ac, or any amino acid;
$Xaa^2$ is absent, Ac, or any amino acid;
$Xaa^3$ is absent, Ac, or any amino acid;
$Xaa^4$ is Pen;
$Xaa^5$ is N-Me-Arg;
$Xaa^6$ is Ser;
$Xaa^7$ is Asp or D-Asp;
$Xaa^8$ is Thr or Val;
$Xaa^9$ is selected from the group consisting of: Leu, Nle, Cpa, Cba, homoLeu, Aoc, and N-Me-Leu;
$Xaa^{10}$ is Pen;
$Xaa^{11}$ is selected from the group consisting of: Trp, Phe, 2-Nal, 1-Nal, Tyr, His, Phe(4-F), Phe(4-CF$_3$), Phe(4-CH$_3$). Phe(4-tBu), Bip, Phe(4-COOH), Gly, 3,3-DiPhenylGly, 3,3-DiPhenylAla, Tic, b-homoTrp, D-1-Nal, D-2-Nal, Phe(2,4-diCl), Phe(3,4-diCl), Phe(4-carbomyl), Phe(3-carbomyl), Tyr(Me), HomoPhe, N-Me-Phe, N-Me-Tyr, Ser, Sar, 2,3-dihydroTrp, Ile, Leu, Ser, Arg, and Thr;
$Xaa^{12}$ is absent or selected from the group consisting of: any aromatic amino acid, Glu, D-Glu, homoGlu, Asp, D-Asp, D-homoGlu, Gla, beta-homoGlu, corresponding D-amino acid and isosteres thereof;
$Xaa^{13}$ is absent; and
$Xaa^{14}$ is selected from the group consisting of: Lys, D-Lys, N-Me-Lys, D-N-Me-Lys, Orn, Dab, Dap, HomoLys, D-Dap, D-Dab, and D-Orn.

In certain embodiments of Formula (I-D), $Xaa^4$ and $Xaa^{10}$ are linked, e.g. via a disulfide bond.

In certain embodiments of Formula (I-D), $Xaa^7$ is Asp.

In one embodiment of Formula (I), herein referred to as Formula (I-E),
$Xaa^1$ is absent, Ac, or any amino acid;
$Xaa^2$ is absent, Ac, or any amino acid;
$Xaa^3$ is absent, Ac, or any amino acid;
$Xaa^4$ is Pen;
$Xaa^5$ is N-Me-Arg;
$Xaa^6$ is Ser;
$Xaa^7$ is Asp or D-Asp;
$Xaa^8$ is Thr or Val;
$Xaa^9$ is selected from the group consisting of: Leu, Nle, Cpa, Cba, homoLeu, Aoc, and N-Me-Leu;
$Xaa^{10}$ is Pen;
$Xaa^{11}$ is selected from the group consisting of: Trp, Phe, 2-Nal, 1-Nal, Tyr, His, Phe(4-F), Phe(4-CF$_3$), Phe(4-CH$_3$). Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Ser, Arg, and Thr;
$Xaa^{12}$ is absent or selected from the group consisting of: any aromatic amino acid, Glu, D-Glu, and beta-homoGlu;
$Xaa^{13}$ is absent; and
$Xaa^{14}$ is selected from the group consisting of: Lys, D-Lys, N-Me-Lys, D-N-Me-Lys, Orn, Dab, Dap, HomoLys, D-Dap, D-Dab, or D-Orn.

In certain embodiments, $Xaa^4$ and $Xaa^{10}$ are linked, e.g. via a disulfidebond.

In certain embodiments of Formula (I-E), $Xaa^7$ is Asp.

In one embodiment of Formula (I), herein referred to as Formula (I-F),
Xaa$^1$ is absent, Ac, or any amino acid;
Xaa$^2$ is absent, Ac, or any amino acid;
Xaa$^3$ is absent, Ac, or any amino acid;
Xaa$^4$ is Pen;
Xaa$^5$ is N-Me-Arg;
Xaa$^6$ is Ser;
Xaa$^7$ is Asp or D-Asp;
Xaa$^8$ is Thr or Val;
Xaa$^9$ is Leu;
Xaa$^{10}$ is Pen;
Xaa$^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3 diPhenyl Ala, Tic, b-homoTrp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, and Thr;
Xaa$^{12}$ is selected from the group consisting of: any aromatic amino acid, Glu, D-Glu, beta-homoGlu, corresponding D-amino acid, and isosteres thereof;
Xaa$^{13}$ is absent; and
Xaa$^{14}$ is selected from the group consisting of: Lys, D-Lys, N-Me-Lys, D-N-Me-Lys, Orn, Dab, Dap, HomoLys, D-Dap, D-Dab, and D-Orn.

In certain embodiments of Formula (I-F), Xaa$^{14}$ is selected from the group consisting of: Lys, D-Lys, N-Me-Lys, and D-N-Me-Lys.

In certain embodiments of Formula (I-F), Xaa$^4$ and Xaa$^{10}$ are linked, e.g. via a disulfide or a lactam bond.

In certain embodiments of Formula (I-F), Xaa$^7$ is Asp.

In one embodiment of Formula (I), herein referred to as Formula (I-G),
Xaa$^1$ is absent, Ac, or any amino acid;
Xaa$^2$ is absent, Ac, or any amino acid;
Xaa$^3$ is absent, Ac, or any amino acid;
Xaa$^4$ is Pen;
Xaa$^5$ is N-Me-Arg;
Xaa$^6$ is Ser;
Xaa$^7$ is Asp or D-Asp;
Xaa$^8$ is Thr or Val;
Xaa$^9$ is Leu;
Xaa$^{10}$ is Pen;
Xaa$^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Ser, Arg, and Thr
Xaa$^{12}$ is selected from the group consisting of: any aromatic amino acid, Glu, D-Glu, and beta-homoGlu;
Xaa$^{13}$ is absent; and
Xaa$^{14}$ is selected from the group consisting of: Lys, D-Lys, N-Me-Lys, D-N-Me-Lys, Orn, Dab, Dap, HomoLys, D-Dap, D-Dab, or D-Orn.

In certain embodiments of Formula (I-G), Xaa$^{14}$ is selected from the group consisting of: D-Lys, N-Me-Lys, and D-N-Me-Lys.

In certain embodiments of Formula (I-G), Xaa$^4$ and Xaa$^{10}$ are linked, e.g. via a disulfide bond.

In certain embodiments of Formula (I-G), Xaa$^7$ is Asp.

In one embodiment of Formula (I), herein referred to as Formula (I-H),
Xaa$^1$ is absent, Ac, or any amino acid;
Xaa$^2$ is absent, Ac, or any amino acid;
Xaa$^3$ is absent, Ac, or any amino acid;
Xaa$^4$ is Pen;
Xaa$^5$ is N-Me-Arg;
Xaa$^6$ is Ser;
Xaa$^7$ is Asp;
Xaa$^8$ is Thr or Val;
Xaa$^9$ is Leu;
Xaa$^{10}$ is Pen;
Xaa$^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, b-homoTrp, D-1-Nal, D-2-Nal, Phe(2,4-diCl), Phe(3,4-diCl), Phe(4-carbomyl), Phe(3-carbomyl), Tyr(Me), HomoPhe, N-Me-Phe, N-Me-Tyr, Ser, Sar, 2,3-dihydroTrp, Ile, Leu, Ser, Arg, and Thr;
Xaa$^{12}$ is selected from the group consisting of: any aromatic amino acid, Glu, D-Glu, and beta-homoGlu;
Xaa$^{13}$ is absent; and
Xaa$^{14}$ is selected from the group consisting of: D-Lys, N-Me-Lys, and D-N-Me-Lys.

In certain embodiments of Formula (I-H), Xaa$^4$ and Xaa$^{10}$ are linked, e.g. via a disulfide bond.

In one embodiment of Formula (I), herein referred to as Formula (I-I),
Xaa$^1$ is absent, Ac, or any amino acid;
Xaa$^2$ is absent, Ac, or any amino acid;
Xaa$^3$ is absent, Ac, or any amino acid;
Xaa$^4$ is Pen;
Xaa$^5$ is N-Me-Arg;
Xaa$^6$ is Ser;
Xaa$^7$ is Asp or D-Asp;
Xaa$^8$ is Thr or Val;
Xaa$^9$ is Leu;
Xaa$^{10}$ is Pen;
Xaa$^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), and homoPhe;
Xaa$^{12}$ is selected from the group consisting of: any aromatic amino acid, Glu, D-Glu, and beta-homoGlu;
Xaa$^{13}$ is absent; and
Xaa$^{14}$ is selected from the group consisting of: D-Lys, N-Me-Lys, and D-N-Me-Lys.

In certain embodiments of Formula (I-I), Xaa$^4$ and Xaa$^{10}$ are linked, e.g. via a disulfide bond.

In certain embodiments of Formula (I-I), Xaa$^7$ is Asp.

In one embodiment of Formula (I), herein referred to as Formula (I-J),
Xaa$^1$ is absent, Ac or any amino acid;
Xaa$^2$ is absent, Ac or any amino acid;
Xaa$^3$ is absent, Ac or any amino acid;
Xaa$^4$ is Pen;
Xaa$^5$ is N-Me-Arg;
Xaa$^6$ is Ser;
Xaa$^7$ is Asp;
Xaa$^8$ is Thr;
Xaa$^9$ is Leu;
Xaa$^{10}$ is Pen;
Xaa$^{11}$ is Phe(4-tBu)
Xaa$^{12}$ is beta-homoGlu;
Xaa$^{13}$ is absent;
and Xaa$^{14}$ is D-Lys.

In particular embodiments, of Formula (I-J), Xaa$^4$ and Xaa$^{10}$ are linked via a disulfide bond, and the two monomer subunits are linked via a linker. In particular embodiments, they are linked via their respective C-termini. In one embodiment, the linker is DIG.

In certain embodiments of any one of Formulas (I), (I-A), (I-B), (I-C), (I-D), (I-E), (I-F), (I-G), (I-H), (I-I), or (I-J), $Xaa^{14}$ is selected from the group consisting of: Lys, D-Lys, N-Me-Lys, and D-N-Me-Lys.

In certain embodiments of any one of Formulas (II), (III), (A), (B), or (C), $Xaa^{10}$ is selected from the group consisting of: Lys, D-Lys, N-Me-Lys, and D-N-Me-Lys.

In certain embodiments of any one of Formulas (I), (I-A), (I-B), (I-C), (I-D), (I-E), (I-F), (I-G), (I-H), (I-I), or (I-J), $Xaa^{14}$ is selected from the group consisting of: Lys, D-Lys, N-Me-Lys, and D-N-Me-Lys.

In alternative embodiments of any one of Formulas (I), (I-A), (I-B), (I-C), (I-D), (I-E), (I-F), (I-G), (I-H), (I-I), or (I-J), $Xaa^{14}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In other alternative embodiments, $Xaa^{14}$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments, of these alternatives of Formula (I), (I-A), (I-B), (I-C), (I-D), (I-E), (I-F), (I-G), (I-H), (I-I), or (I-J), the two C-terminal amino acids of each subunit of a peptide dimer compound possess acid functionality, and they are linked through retroinverse linking by a diamine linker.

In alternative embodiments of any one of Formulas (II), (III), (A), (B), or (C), $Xaa^{10}$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In other alternative embodiments, $Xaa^{10}$ is selected from the group consisting of: Asp, Glu, homoGlu, D-Asp, D-Glu, D-homoGlu, N-Me-Glu, N-Me-Asp, N-Me-D-Glu, and N-Me-D-Asp. In particular embodiments of these alternatives of Formulas (II), (III), (A), (B), or (C), the two C-terminal amino acids of each subunit of a peptide dimer compound possess acid functionality, and they are linked through retroinverse linking by a diamine linker.

In other embodiments, the present invention includes peptide dimers comprising two peptide subunits of any one of Formulas (I-A), (I-B), (I-C), (I-D), (I-E), (I-F), (I-G), (I-H), (I-I), or (I-J), but wherein one or both of the Pen residues at $Xaa^4$ and $Xaa^{10}$ are substituted with Cys. In particular embodiments, both Pen residues at $Xaa^4$ and $Xaa^{10}$ are substituted with Cys. In particular embodiments, one or both subunits comprise a disulfide bond between $Xaa^4$ and $Xaa^{10}$.

In particular embodiments of any of Formulas (I), (II), (III) (I-A), (I-B), (I-C), (I-D), (I-E), (I-F), (I-G), (I-H), (I-I), (I-J), (A), (B), (C), (S), or related peptides, the two peptide subunits are linked via their respective C-termini, e.g., via a linker bound to $Xaa^{13}$ or $Xaa^{14}$ of each subunit.

In particular embodiments of any of Formulas (I), (II), (III), (I-A), (I-B), (I-C), (I-D), (I-E), (I-F), (I-G), (I-H), (I-I) or (I-J), (A), (B), (C), (S), or related peptides, the two peptide subunits are linked via their respective N-termini, e.g., via a linker bound to $Xaa^1$, $Xaa^2$, or $Xaa^3$ of each subunit.

In particular embodiments of any of Formulas (I), (I-A), (I-B), (I-C), (I-D), (I-E), (I-F), (I-G), (I-H), (I-I) or (I-J), or related peptides, $Xaa^1$ is Ac, and $Xaa^2$ and $Xaa^3$ are absent or any amino acid. In certain embodiments, $Xaa^1$ and $Xaa^2$ are absent and $Xaa^3$ is Ac.

In particular embodiments of any of Formulas (I), (I-A), (I-B), (I-C), (I-D), (I-E), (I-F), (I-G), (I-H), (I-I) or (I-J), or related peptides, any one or more of $Xaa^1$, $Xaa^2$, or $Xaa^3$ is selected from the group consisting of: any amino acid with an amine side chain, Lys, D-Lys, N-Me-Lys, D-N-Me-Lys, Orn, Dab, Dap, HomoLys, D-Dap, D-Dab, Cys, homoCys, Pen, and D-Orn. In particular embodiments when $Xaa^1$, $Xaa^2$ or $Xaa^3$ are absent, the two monomer subunits of the peptide dimer compounds are linked with α-amine of the N-terminal amino acid. In particular embodiments, the two sununits are linked with side chain amine, thio group or any functionality capable of linking through the linker of amino acid or the α-amine group of $Xaa^1$, $Xaa^2$ or $Xaa^3$. In particular embodiments, $Xaa^1$, $Xaa^2$ or $Xaa^3$ is D-Lys, N-Me-Lys, or D-N-Me-Lys. In particular embodiments, $Xaa^1$, $Xaa^2$ or $Xaa^3$ is D-Lys, N-Me-Lys, or D-N-Me-Lys, and is located at the N-terminus of the peptide. In particular embodiments, both subunits of a peptide dimer compound comprise an $Xaa^1$, $Xaa^2$ or $Xaa^3$ selected from one of these residues, and the two subunits are linked via their respective N-termini.

In particular embodiments of any of Formulas (I), (I-A), (I-B), (I-C), (I-D), (I-E), (I-F), (I-G), (I-H), (I-I) or (I-J), or related peptides, any one or more of $Xaa^1$, $Xaa^2$, or $Xaa^3$ is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In particular embodiments, this residue is located at the N-terminus of the peptide. In certain embodiments, $Xaa^1$, $Xaa^2$ or $Xaa^3$ is selected from the group consisting of: Asp, Glu, homoGlu, D-Asp, D-Glu, D-homo-Glu, N-Me-Glu, N-Me-Asp, N-Me-D-Glu, and N-Me-D-Asp. In particular embodiments, this residue is located at the N-terminus of the peptide. In particular embodiments, the two N-terminal amino acids of each subunit of a peptide dimer compound possess acid functionality, and they are linked through retroinverse linking by a diamine linker. In particular embodiments, both subunits of a peptide dimer compound comprise an $Xaa^1$, $Xaa^2$ or $Xaa^3$ selected from one of these residues, and the two subunits are linked via their respective N-termini.

In particular embodiments of any of Formulas (I), (I-A), (I-B), (I-C), (I-D), (I-E), (I-F), (I-G), (I-H), (I-I) or (I-J), or related peptides including monomer subunits thereof, $Xaa^4$ and $Xaa^{10}$ are Pen, and $Xaa^5$ is N-Me-Arg. In further embodiments of any of these formulas or peptide, $Xaa^4$ and $Xaa^{10}$ are Pen, $Xaa^5$ is N-Me-Arg, and $Xaa^{11}$ is selected from the group consisting of Tic, Phe(2-carbomyl), Phe(3-carbomyl), Phe(4-COOH), Phe(4-OMe), and Phe(4-tBu).

In certain embodiments of any one of Formulas (II), (III), (A), (B), or (C), $Xaa^{10}$ is selected from the group consisting of: Lys, D-Lys, N-Me-Lys, and D-N-Me-Lys.

In one embodiment, a peptide dimer compound or peptide monomer compound of the present invention comprises one or more peptide subunits of Formula (A):

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10} \quad \text{(Formula (A))}$$

or a pharmaceutically acceptable salt thereof, wherein

Xaa¹ is Cys or Pen;
Xaa² is N-Methyl-Arg;
Xaa³ is Ser;
Xaa⁴ is Asp;
Xaa⁵ is Thr or Val;
Xaa⁶ is Leu or Nle;
Xaa⁷ is Cys or Pen;
Xaa⁸ is Trp, Tic, Bip, 1-Nal, 2-Nal, Phe(4-tBu), Phe, Tyr, or Phe(4-COOH);
Xaa⁹ is Glu, β-homoGlu, or D-Glu, and
Xaa¹⁰ is any amino acid,
wherein the peptide molecule comprises a disulfide bond between Xaa¹ and Xaa⁷.

In particular embodiments of Formula (A), Xaa¹⁰ is D-Lys, N-Me-Lys or N-Me-D-Lys. In particular embodiments, Xaa¹ and/or Xaa⁷ are Pen. In certain embodiments of Formula (A), Xaa¹⁰ is selected from the group consisting of: any amino acid with an amine side chain, Lys, D-Lys, N-Me-Lys, D-N-Me-Lys, Orn, Dab, Dap, HomoLys, D-Dap, D-Dab, Cys, homoCys, Pen, and D-Orn.

In certain embodiments, Xaa¹⁰ or the C-terminus of the peptide comprises an NH₂ or an OH.

Embodiments include peptide dimer compounds comprising the following structure:

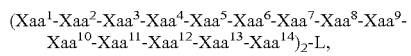

wherein Xaa¹-Xaa¹⁴ are defined as shown herein for any of Formulas (I), including (I-A), (I-B), (I-C), (I-D), (I-E), (I-F), (I-G), (I-H), (I-I), and (I-J), and wherein L is any linker moiety linking the C-termini of the two monomer subunits. In particular embodiments, L is selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thio-ether, di-thio, or ether bonds. In particular embodiments, L is selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, succinic acid, glutaric acid, Dodecanedioic acid, suitable aliphatics, suitable aromatics, heteroaromatics, and polyethylene glycols having a molecular weight from approximately 400 Da to approximately 40,000 Da. In one embodiment, the linked is DIG. In other embodiments, L is any of the linkers described herein.

Other embodiments include a peptide dimer compound comprising the following structure:

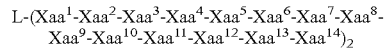

wherein Xaa¹-Xaa¹⁴ are defined as shown here for any of Formulas (I), including (I-A), (I-B), (I-C), (I-D), (I-E), (I-F), (I-G), (I-H), (I-I), and (I-J), and wherein L is selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thio-ether, di-thio, or ether bonds. In particular embodiments, L is selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, succinic acid, glutaric acid, Dodecanedioic acid, suitable aliphatics, suitable aromatics, heteroaromatics, and polyethylene glycols having a molecular weight from approximately 400 Da to approximately 40,000 Da. In one embodiment, the linked is DIG.

Some sequences of the present invention are derived from the general sequences provided in Formula (I) (including any of I-A, I-B, I-C, I-D, I-E, I-F, I-G, I-H, I-I, I-J), Formula (II) (including II-A), Formula (III), Formula (A), Formula (B), Formula (C), Formula (D) or Formula (S). For example, the N-terminus of a decapeptide represented by Xaa⁴-Xaa¹³ of Formula (I) or Xaa¹-Xaa¹⁰ of Formula (II) can be modified by one to three suitable groups, as represented by Xaa¹, Xaa², and Xaa³ of Formula (I). The N-terminus may further be acylated. In particular embodiments, the N-terminus may be acylated with an acylating organic compound selected from the group consisting of 2-Methyl-4,4,4-Trifluorobutyl, Trifluoropentyl, Acetyl, Octonyl, Butyl, Pentyl, Hexyl, Palmityl, Lauryl, Oleoyl, Trifluoromethyl butyl, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In some instances, the N-terminus further comprises a suitable linker moiety to facilitate linking together two monomer subunits to form an N-terminal dimer molecule.

In certain embodiments of any peptide dimer copound, e.g., wherein the peptide dimer compound is linked via the N-terminus of one or both monomer subunits, the N-terminal amino acid is any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In certain embodiments, the N-terminal amino acid residue of the monomer subunit is an amino acid with an amine side chain, or an amino acid selected from Lys, D-Lys, N-Me-Lys, D-N-Me-Lys, Orn, Dab, Dap, HomoLys, D-Dap, D-Dab, Cys, homoCys, Pen, and D-Orn. In particular embodiments, it is D-Lys, N-Me-Lys, or D-N-Me-Lys.

In addition, as described above for any of the various embodiments of Formula (I), $Xaa^1$, $Xaa^2$ and/or $Xaa^3$ may be an amino acid with an amine side chain, or an amino acid selected from Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In certain embodiments, it is Lys, D-Lys, N-Me-Lys, D-N-Me-Lys, Orn, Dab, Dap, HomoLys, D-Dap, D-Dab, Cys, homoCys, Pen, and D-Orn, and it may participate in the linkage. The residue participating in the linkage may be located at the N-terminus of the peptide monomer, or it may be an internal amino acid, i.e., not the N-terminal or C-terminal amino acid.

The present invention further includes peptide dimer compounds having subunits based on any of the Formulas described herein, e.g., Formula (I) (including any of I-A, I-B, I-C, I-D, I-E, I-F, I-G, I-H, I-I and I-J), Formula (II) (including II-A), Formula (III), Formula (A), Formula (B), Formula (C), Formula (D), or Formula (S), wherein the subunits are linked via one or more internal amino acid residue. For example, an internal amino acid residue of one or more subunits could be modified to include an amino acid or derivative, such as an amino acid with an amine side chain, or an amino acid selected from Lys, D-Lys, N-Me-Lys, D-N-Me-Lys, Orn, Dab, Dap, HomoLys, D-Dap, D-Dab, Cys, homoCys, Pen, and D-Orn, capable of forming a bond with a linker. In addition, internal amino acid residues of the monomer subunits may be directly linked to each other (or to a linker) to form a peptide dimer compound. For example, internal lysine residues present in each monomer subunit may bind to each other to form a peptide dimer compound.

In some embodiments, $Xaa^1$, $Xaa^2$, and $Xaa^3$ of Formula (I) (including any of I-A, I-B, I-C, I-D, I-E, I-F, I-G, I-H, I-I and I-J) are absent. In other embodiments, $Xaa^1$ is absent, and $Xaa^2$ and $Xaa^3$ represent suitable groups for modifying the N-terminus of the peptide, e.g., the decapeptide represented by residues $Xaa^4$-$Xaa^{13}$ of Formula (I), and residues $Xaa^1$-$Xaa^{10}$ of Formula (II). Further, in some embodiments $Xaa^1$ and $Xaa^2$ of Formula (I) (including any of I-A, I-B, I-C, I-D, I-E, I-F, I-G, I-H, I-I and I-J) are absent, and $Xaa^3$ of Formula (I) (including any of I-A, I-B, I-C, I-D, I-E, I-F, I-G, I-H, I-I and I-J) represents a single suitable group for modifying the N-terminus of the decapeptide subunit. In some embodiments, $Xaa^1$ and $Xaa^2$ of Formula (I) (including any of I-A, I-B, I-C, I-D, I-E, I-F, I-G, I-H, I-I and I-J) are absent, and $Xaa^3$ of Formula (I) is Ac. In some embodiments, the N-terminal amino acid residue of peptide dimers of either Formula (I) (including any of I-A, I-B, I-C, I-D, I-E, I-F, I-G, I-H, I-I and I-J), Formula (II) (including 2-A), Formula (III), Formula (A), Formula (B), Formula (C), Formula (D) or Formula (S) is acylated. In particular embodiments, the N-terminus may be acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

Similarly, the C-terminus of the peptide, e.g., the decapeptide represented by Formula (I) (including any of I-A, I-B, I-C, I-D, I-E, I-F, I-G, I-H, I-I and I-J), Formula (II), Formula (III), Formula (A) Formula (B), Formula (C), Formula (D), or Formula (S) can be modified by a suitable group. The C-terminus may further be acylated, e.g., in the context of peptides dimer subunits that are dimerized via their N-terminus or peptide monomer compounds, e.g., as described herein. In particular embodiments, the C-terminus may be acylated, e.g., on an amino acid with a free amine, with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In some instances, the C-terminus further comprises a suitable linker moiety to facilitate linking together two monomer subunits to form a C-terminal dimer molecule.

In certain embodiments of the peptides of Formula (I) (including any of I-A, I-B, I-C, I-D, I-E, I-F, I-G, I-H, I-I and I-J), $Xaa^{11}$, $Xaa^{12}$ and $Xaa^{13}$ are absent. In other embodiments, $Xaa^{12}$ and $Xaa^{13}$ are absent. In other embodiments, $Xaa^{13}$ is absent. In particular embodiments, $Xaa^{14}$ is the C-terminal amino acid of the peptide monomer subunit of the peptide dimer. In particular embodiments, $Xaa^{14}$ is modified. In certain embodiments, $Xaa^{14}$ is Lysine, D-Lysine, N-methyl-Lysine, Dap or Dab. In particular embodiments, $Xaa^{14}$ is Dap or Dab. In certain embodiments, $Xaa^4$ comprises an $NH_2$ moiety.

In some embodiments, the N-terminal residue of Formula (I) (including any of I-A, I-B, I-C, I-D, I-E, I-F, I-G, I-H, I-I and I-J), Formula (II), Formula (III), Formula (A), Formula (B), Formula (C), Formula (D), or Formula (S) further comprises a linker moiety, e.g., one selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, cyclopropylacetic acid, succinic acid, glutaric acid, Dodecanedioic acid, suitable aliphatics, suitable aromatics, heteroaromatics, and polyethylene glycols having a molecular weight from approximately 400 Da to approximately 40,000 Da. Further, in some embodiments, any one or more of $Xaa^1$-$Xaa^4$ are acylated. In particular embodiments, any one or more of $Xaa^1$-$Xaa^4$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

In certain embodiments where $Xaa^4$ and $Xaa^{10}$ are both Cys or Pen, the peptide monomer, or each subunit of the peptide dimer, is cyclized though a disulfide bond between $Xaa^4$ and $Xaa^{10}$. Preferably, in one embodiment $Xaa^4$ is Cys. In another embodiment, preferably $Xaa^4$ is Pen. In particular embodiments, $Xaa^4$ is Pen; in other embodiments, $Xaa^{10}$ is Pen; in other embodiments, both $Xaa^4$ and $Xaa^{10}$ are Pen.

In certain embodiments of any of the formulas described herein, e.g., Formula (I) (including any of I-A, I-B, I-C, I-D, I-E, I-F, I-G, I-H, I-I and I-J), $Xaa^5$ is N-Me-Arg. In certain embodiments, $Xaa^6$ is Ser. In certain embodiments, $Xaa^7$ is Asp. In certain embodiments, $Xaa^8$ is Thr. In certain embodiments, $Xaa^9$ is Leu. In one embodiment $Xaa^{10}$ is Pen. In another embodiment, $Xaa^{10}$ is Cys. In particular embodiments, $Xaa^{11}$ is selected from the group consisting of Tic, Phe(2-carbomyl), Phe(3-carbomyl), Phe(4-COOH), Phe-(4-OMe), Phe(4-tBu), Phe(4-CN), N-Me-Phe, N-Me-Tyr, b-homoTrp, and Pentafluro-Phe. In certain embodiments, $Xaa^{11}$ is an aromatic amino acid. In particular embodiments, $Xaa^{12}$ is Aic. In particular embodiments, $Xaa^{13}$ is Pro, and $Xaa^{11}$ and/or $Xaa^{12}$ are present. In particular embodiments, $Xaa^{14}$ is an amino acyl residue selected from the group consisting of natural amino acids, Dap, Dab, Orn, D-Orn, N-Me-Orn, N-Me-Dap, N-Me-Dab, N-Me Lys, D-Dap, D-Dab, D-Lys, N-Me-D-Lys, suitable isostere replacements, corresponding D-amino acids, and corresponding N-Methyl amino acids. In at least one embodiment, $Xaa^{14}$ is the C-terminus. When $Xaa^{14}$ is the C-terminus of the subunit, $Xaa^{14}$ may be modified to include a linker moiety in accordance with the present invention. Further, in some embodiments $Xaa^{14}$ is N(alpha)Methylated. For some embodiments, any of $Xaa^1$-$Xaa^5$, $Xaa^7$-$Xaa^9$, and $Xaa^{11}$-$Xaa^{12}$ are N(alpha)Methylated. $Xaa^5$ may further be Arg-Me-sym or Arg-Me-asym, and $Xaa^{11}$ may be O-Me-Tyr, N-Me-Lys(Ac), or 4-Me-Phe. In some instances, any of $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

In certain alternative embodiments of peptides of Formula (I) (including any of I-A, I-B, I-C, I-D, I-E, I-F, I-G, I-H, I-I and I-J), $Xaa^{14}$ is Cys, HomoCys or Pen, instead of the amino acids listed.

In particular embodiments of any of the peptides described herein, including but not limited to those of Formula (I) (including any of I-A, I-B, I-C, I-D, I-E, I-F, I-G, I-H, I-I and I-J) (or the corresponding residues of Formula (II), (II-A), (III), (A), (B), (C), (D), (S), (X), or (H), $Xaa^5$ is selected from the group consisting of N-Me-Ar, Phe(4-guanidino), Phe(4-NH$_2$), N-Me-HomoArg, HomoArg, Tyr and His; $Xaa^8$ is selected from the group consisting of Leu, HomoLeu, Nle and Val; $Xaa^9$ is CPA or Aoc; $Xaa^{11}$ is selected from the group consisting of Tic, Phe(2-carbomyl), Phe(3-carbomyl), Phe(4-carbomyl), Phe(4-COOH), Phe(4-OMe), and Phe(4-tBu) $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro. In particular embodiments of of any of the compounds and genuses described herein, $Xaa^5$ is selected from the group consisting of Cit, Phe(4-carbomyl), and N-Me-HomoArg; $Xaa^8$ is selected from the group consisting of Leu, HomoLeu, Nle and Val; $Xaa^9$ is selected from the group consisting of: Cba, HomoLeu, and Cpa; $Xaa^{11}$ is selected from the group consisting of Tic, Phe(2-carbomyl), Phe(3-carbomyl), Phe (4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In some embodiments, the N-terminal residue or C-terminal residue of any of the peptides described herein, e.g., Formula (I) (including any of I-A, I-B, I-C, I-D, I-E, I-F, I-G, I-H, I-I, and I-J) or Formula (II) (including II-A) or Formula (III), Formula (A), Formula (B), or Formula (C), Formula (D), or Formula (S) further comprises a conjugated moiety, e.g., a linker moiety, including but not limited to any of those described herein. In particular embodiments, the linker is selected from the group consisting of DIG, bifunctional PEG13, bifunctional PEG25, bifunctional PEG1K, bifunctional PEG2K, bifunctional PEG3.4K, bifunctional PEG4K, bifunctional PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da. When the linker is IDA, ADA or any linker with free amine, it can be acylated with acylating organic compound selected from the group consisting of 2-me-Trifluorobutyl, Trifluoropentyl, Acetyl, Octonyl, Butyl, Pentyl, Hexyl, Palmityl, Lauryl, Oleoyl, Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid, straight chain aliphatic acids with 10 to 20 carbon units, cholic acid and other bile acids. In some instances small PEG (PEG4-PEG13), Glu, IsoGlu or Asp is used as spacer before acylations. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

Some embodiments of the present invention further include a peptide homodimer or heterodimer molecule, wherein each subunit of the dimer molecule comprises, consists essentially of, or consists of an amino acid sequence represented by at least one of the sequences shown in the accompanying figures and tables.

The invention further includes monomer subunits of any of the peptide dimers described herein (which includes the accompanying figures).

In addition, the present invention includes compounds, including peptide dimer compounds, peptide monomer compound, and monmer subunits, comprising, consisting essentially of, or consisting of one or more (e.g., two) of any of the amino acid sequences described herein, e.g., in any of the formulas, or shown in any of the accompanying tables or figures, e.g., without requiring the presence of any N-terminal modification such as Ac or any C-terminal modification such as NH$_2$.

The present invention further includes any of the compounds described herein having an alternative N-terminal or C-terminal group. For example, those compounds that show an N-terminal Ac group are also encompassed when their N-terminus is either the unaltered N-terminus of an amino acid, or when a different group is present, and those copmounds that show a C-terminal NH$_2$ group are also encompassed when their C-terminus is either the unaltered C-terminus of an amino acid, or when a different group is present.

Additional embodiments of the present invention include peptide dimer compounds, peptide monomer compounds, and peptides comprising any of the amino acid sequences shown in any of the formulas, tables or figures herein, and which may include one or more additional amino acid residues. In particular embodiments, the monomer subunits of peptide dimer compounds, the peptide monomer compounds, and the peptides comprise from 7 to 35 amino acid residuesm from 7 to 30 amino acid residues, from 7 to 25 amino acid residues, from 7 to 20 amino acid residues, 7 to 19 amino acid residues, 7 to 18 amino acid residues, 7 to 17 amino acid residues, 7 to 16 amino acid residues, 7 to 15 amino acid residues, 7 to 14 amino acid residues, 7 to 13 amino acid residues, or 7 to 12 amino acid residues. In particular embodiments, the invention includes a peptide comprising the amino acid residues shown for SEQ ID Nos: 1-193 of Table 3 or SEQ ID Nos:194-218 of Table 4, wherein the peptide does not necessarily include (but may include) any of the N-terminal or C-terminal modifications, intramolecular bonds, linkers, or other modifications shown therein. In particular embodiments, the peptide comprises an intramolecular bond, e.g., a disulfide bond between two resisdues, e.g., two Pen residues. The invention further includes peptide monomer compounds, peptide dimer compounds, and other compounds comprising a peptide comprising an amino acid sequence described herein.

The invention further includes a method of manufacturing a peptide compound of the present invention, comprising synthesizing a peptide having a sequence as described herein, and introducing an intramolecular bond between two residues of the peptide (or allowing the intramolecular bond to form). In particular embodiments, the method further includes modifying one or both of the C-terminus and N-terminus of the peptide. In further embodiments, the method includes conjugating a linker to the peptide. In related embodiments, the invention includes a method of preparing a peptide dimer compound comprising: (i) synthesizing a peptide having a sequence as described herein, and introducing an intramolecular bond between two residues of the peptide (or allowing the intramolecular bond to form), and conjugating a linker to the peptide; (ii) synthesizing a peptide having a sequence as described herein (e.g., the same sequence as for step (i)), and introducing an intramolecular bond between two residues of the peptide (or allowing the intramolecular bond to form); and (iii) conjugating the peptide of step (i) to the peptide of step (ii) via the linker attached to the peptide of step (i).

In particular embodiments, the present invention includes a polynucleotide encoding any of the peptide sequences disclosed herein. In particular embodiments, the polynucleotide is DNA, RNA, cDNA, or mRNA, including single-stranded, double-stranded polynucleotide forms thereof, and modified forms thereof. In certain embodiments, the invention includes a vector, e.g., an expression vector or gene therapy vector, comprising a polynucleotide encoding any of the peptides described herein. The vector may further include a promoter and/or other regulatory sequences operably linked to the sequence encoding the peptide sequence described herein. The present invention further includes cells comprising an exogenous or introduced peptide or polynucleotide described herein.

In particular embodiments, the present invention includes peptide dimer compounds comprising two linker monomer subunits, each having the following structure of Formula (S):

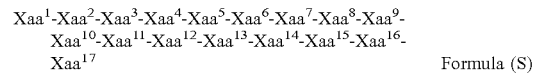

Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$-Xaa$^{14}$-Xaa$^{15}$-Xaa$^{16}$-Xaa$^{17}$    Formula (S)

wherein Xaa$^1$-Xaa$^{13}$ correspond to the residues defined at those positions in one of the formulas described herein, e.g., any of Formulas (I), (IV) and wherein Xaa$^{13}$ Xaa$^{14}$, Xaa$^{15}$, Xaa$^{16}$ and Xaa$^{17}$ are absent or any amino acid, with the proviso that the C-terminal amino acid corresponds to the residues defined for Xaa$^{14}$ in the same formula for which Xaa$^1$-Xaa$^{13}$ were defined. In particular embodiments, Xaa$^4$ and Xaa$^{10}$ are linked via a disulfide bond, a lactam bond, an olefin bond, a triazole bond, a selenoether bond, or a diselenide bond.

In particular embodiments, the present invention includes peptide dimer compounds comprising two linker monomer subunits, each having the following structure of Formula (S'):

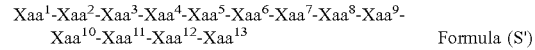

Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$-Xaa$^{11}$-Xaa$^{12}$-Xaa$^{13}$    Formula (S')

wherein Xaa$^1$-Xaa$^9$ correspond to the residues defined at those positions in one of the formulas described herein, e.g., any of Formulas (II), (III), A, B, C or D and wherein Xaa$^{10}$, Xaa$^{11}$, Xaa$^{12}$, and Xaa$^{13}$ are absent or any amino acid, with the proviso that the C-terminal amino acid corresponds to the residues defined for Xaa$^{10}$ in the same formula for which Xaa$^7$-Xaa$^{10}$ were defined. In particular embodiments, Xaa$^1$ and Xaa$^7$ are linked via a disulfide bond, a lactam bond, an olefin bond, a triazole bond, a selenoether bond, or a diselenide bond.

In certain embodiments, the peptides further comprise one or more modifying group and/or linker. In certain embodiments, one or both of the N- or C-terminus of the peptides is modified. In particular embodiments, the N-terminus is acylated; and in particular embodiments, the C-terminus comprises a free amine, e.g., NH$_2$. In particular embodiments, the C-terminus comprises an —OH group. In particular embodiments, the peptide comprises an intramolecular linkage between Xaa$^4$ and Xaa$^{10}$ of Formula (I) (including any of I-A, I-B, I-C, I-D, I-E, I-F, I-G, I-H, I-I, and I-J) (or Xaa$^1$ and Xaa$^7$ in Formula (II), (III), (A), (B), (C), or (D)). The present invention also includes compounds having any of the structures described herein or shown in any of the accompanying figures.

Further, some embodiments of the present invention comprise a peptide homodimer or hetereodimer molecule, wherein each subunit of the dimer molecule is cyclized through a disulfide bond or a lactam bond, and wherein each monomer subunit of the dimer molecule comprises, consists essentially of, or consists of an amino acid sequence represented by at least one of the sequences shown in the accompanying figures and tables.

In certain embodiments, the present invention provides a peptide dimer compound comprising one or two linked subunits of Formula (III):

Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$(SEQ ID NO: 343)  (Formula (III))

or a pharmaceutically acceptable salt thereof,
wherein each subunit comprises a disulfide bond between Xaa$^1$ and Xaa$^7$, and further wherein Formula (III) represents a monomer subunit of a dimer molecule, wherein the monomer subunits are linked to form a dimer molecule in accordance with the present invention, and wherein:
Xaa$^1$ is Pen;
Xaa$^2$ is N-Me-Arg;
Xaa$^3$ is Ser;
Xaa$^4$ is Asp;
Xaa$^5$ is Thr;
Xaa$^6$ is Leu;
Xaa$^7$ is Pen;
Xaa$^8$ is Trp;
Xaa$^9$ is absent or selected from the group consisting of: Glu, D-Glu, β-homoGlu; and
Xaa$^{10}$ is selected from the group consisting of D-Lys and N-Me-Lys.

In particular embodiments, Xaa$^9$ is present. In particular embodiments of Formula (III), Xaa$^1$ is acylated. In particular embodiments of Formula (III), Xaa$^{10}$ comprises NH$_2$ or OH. In particular embodiments of dimers of Formula (III), the two monomer subunits are linked via their respective C-termini via a linker moiety, e.g., DIG. In particular embodiments, the peptide dimer compound is a homodimer.

In one embodiment, a peptide monomer compound or a peptide dimer compound of the present invention comprises a peptide molecule of Formula (B):

Xaa$^1$-Xaa$^2$-Xaa$^3$-Xaa$^4$-Xaa$^5$-Xaa$^6$-Xaa$^7$-Xaa$^8$-Xaa$^9$-Xaa$^{10}$(SEQ ID NO: 344)  (Formula (B))

or a pharmaceutically acceptable salt thereof, wherein
Xaa$^1$ is Cys or Pen;
Xaa$^2$ is N-methyl-Arg;
Xaa$^3$ is Ser;
Xaa$^4$ is Asp;
Xaa$^5$ is Thr;
Xaa$^6$ is Leu or Nle;
Xaa$^7$ is Cys, Pen or D-Pen;
Xaa$^8$ is Trp, Tic, Bip, 1-Nal, 2-Nal, Phe(4-tBu), or Phe(4-COOH);
Xaa$^9$ is Glu, β-homoGlu, D-Glu, or Glu(OMe); and
Xaa$^{10}$ is any amino acid,
wherein the peptide molecule comprises a disulfide bond between Xaa$^1$ and Xaa$^7$.

In particular embodiments, of Formula (B), one or both of Xaa$^1$ and Xaa$^7$ are Pen.

In particular embodiments of Formula (B), Xaa$^{10}$ is D-Lys or N-Me-Lys.

In particular embodiments, a peptide dimer comprises two monomer subunits of Formula (B). In particular embodiments, the one or both subunits of the dimer comprise an intramolecular bond between Xaa$^1$ and Xaa$^7$, e.g., a disulfide bond.

Illustrative peptide dimer compounds of the present invention are shown in the Examples and accompanying figures. Peptide dimer compounds are generally shown by providing the amino acid sequence of the monomer subunits of the peptide dimer compound in parentheses, followed by a lower case 2, which indicates that the peptide dimer compound comprises two subunits having the depicted amino acid sequence. The linker may also be shown at the C-terminus of the sequence to indicate that the two monomer subunits are linked via their C-termini, or it is shown at the N-terminus of the sequence to indicate that the two monomer subunits are linked via their N-termini.

The present invention further includes peptide monomer subunits having any of the Formula described herein. In certain embodiments, the peptide monomer subunits are bound to a linker.

The peptide dimer and peptide monomer compounds of the present invention may be free acids or they may be pharmaceutically acceptable salts. In particular embodiments, they are acetate salts.

In certain embodiments, the present invention includes peptide dimer compounds, including pharmaceutically acceptable salts thereof, wherein the two monomer subunits are linked via their C-termini, having a structure of Formula (X):

Formula (X)

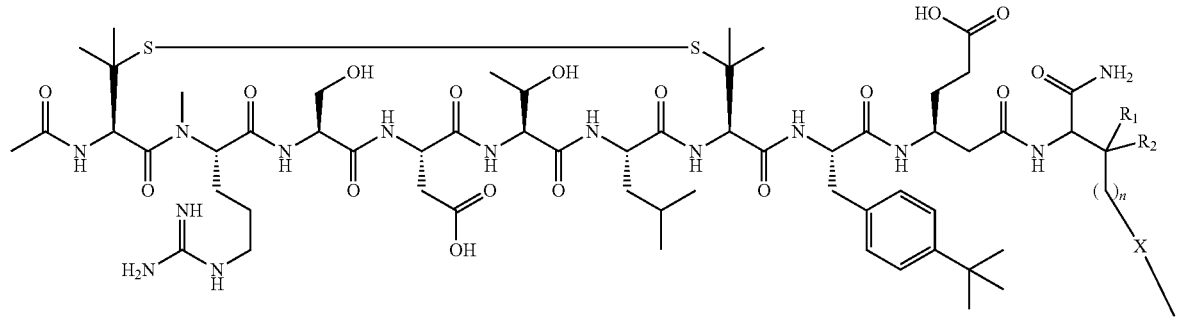

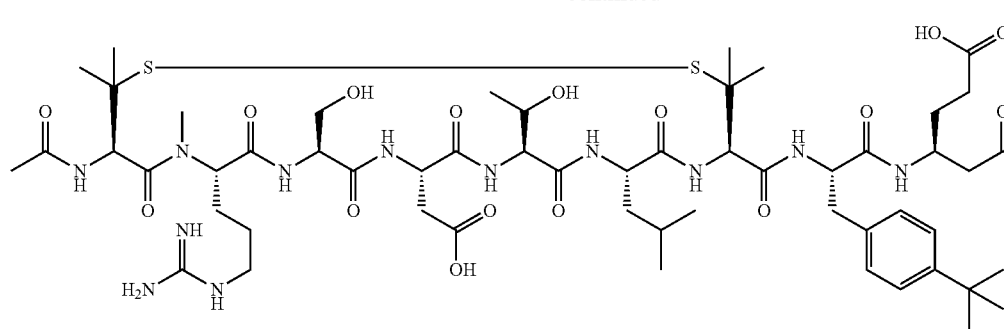 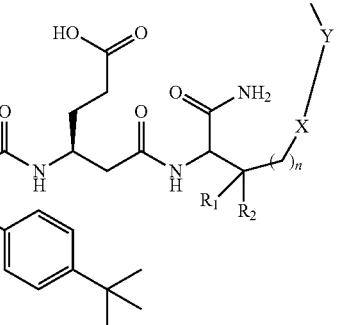

wherein $R_1$ and $R_2$ are H or Me;
n is any integer from 2 to 10;
X is $CH_2$, NHCO, CONH, S—S, C=O, CHOH, S, S=O, NH, or O; and
Y is a linker moiety.

In particular embodiments, the linker moiety, Y, is any of those shown herein, including but not limited to any of those shown below. In particular embodiments, the linker moiety is selected from DIG, PEG13, PEG25, PEG1K, PEG2K, PEG3.4K, PEG4K, PEG5K, IDA, IDA-Palm, IDA-Boc, IDA-Ac, IDA-Isovaleric acid, ADA Triazine, Triazine-Boc, Isophthalic acid, 1,3-phenylenediacetic acid, Glu, Asp, D-Glu, D-Asp, 1,4-phenylenediacetic acid, Biphenyl diacetic acid, cyclopropylacetic acid, succinic acid, glutaric acid, Dodecanedioic acid, suitable aliphatic diacids, suitable aromatic diacids, heteroaromatics, and polyethylene glycols having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

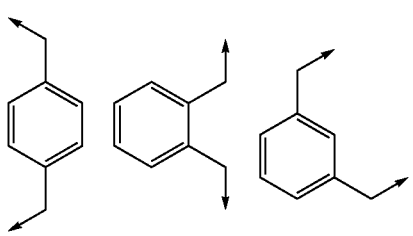

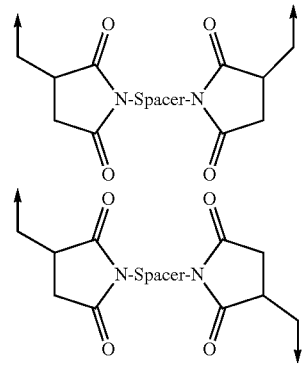

Y = any linker
Spacer: PEG, aliphatic chain,

In certain embodiments, a peptide dimer compound of Formula (X) has the structure shown below (Compound X).

Compound X

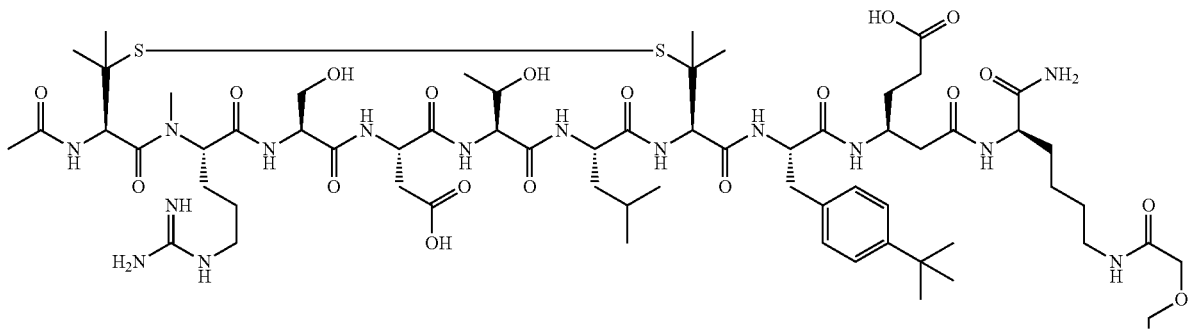

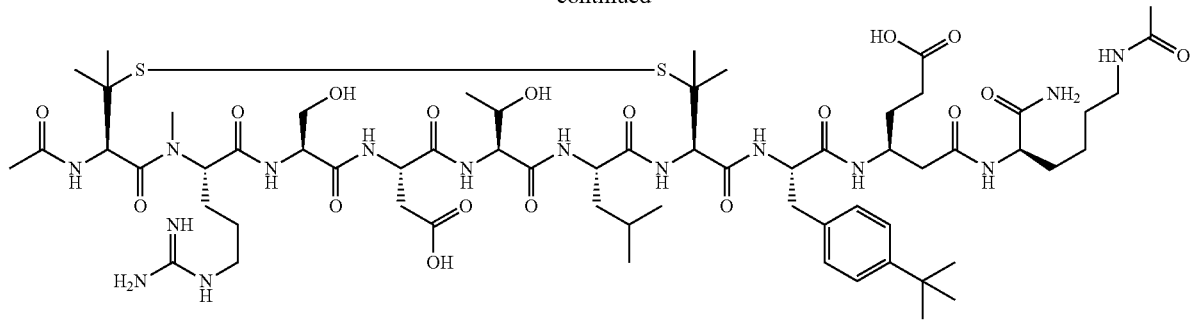

In particular embodiments, compounds of Formula (X) and Compound X are salt forms. In one embodiment, they are acetate salts.

In certain embodiments, the present invention includes peptide dimer compounds, including pharmaceutically acceptable salts thereof, wherein the two monomer subunits are linked via their N-termini, having a structure of Formula (H):

diacetic acid, cyclopropylacetic acid, succinic acid, glutaric acid, Dodecanedioic acid, suitable aliphatic diacids, suitable aromatic diacids, heteroaromatics, and polyethylene glycols having a molecular weight from approximately 400 Da to approximately 40,000 Da. In particular embodiments, the linker is a bifunctional linker (e.g., di-acid, di-amine, dihalide, N-Hydroxy succinamine (NHS)-activated diesters, bis-maleimides, which may be capable of linking two monomer subunits through amine, ester, thioether, di-thio, or ether bonds.

Formula (H)

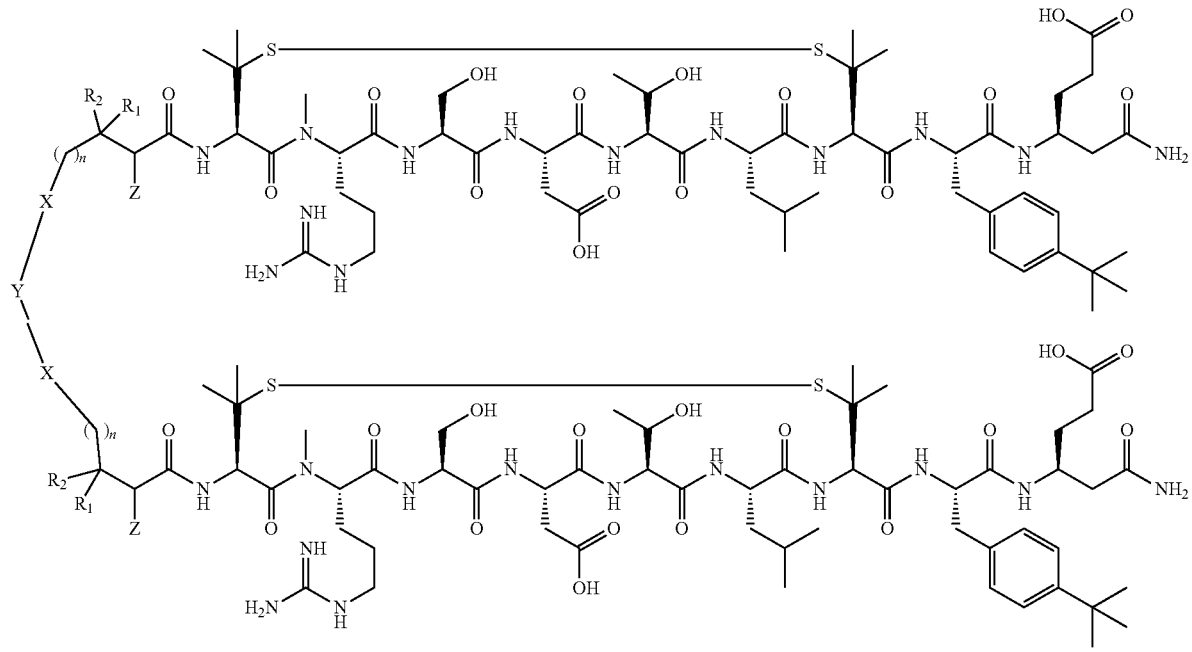

wherein $R_1$ and $R_2$ are H or Me;
n is any integer from 2 to 10;
X is $CH_2$, NHCO, CONH, S—S, C=O, CHOH, S, S=O, NH, or O;
Y is a linker moiety; and
Z is NHAc, absent or H.

In particular embodiments, the linker moiety is any of those shown herein, including but not limited to those shown below. In particular embodiments, the linker moiety is selected from DIG, PEG13, PEG25, PEG1K, PEG2K, PEG3.4K, PEG4K, PEG5K, IDA, IDA-Palm, IDA-Boc, IDA-Ac, IDA-Isovaleric acid, ADA Triazine, Triazine-Boc, Isophthalic acid, 1,3-phenylenediacetic acid, Glu, Asp, D-Glu, D-Asp, 1,4-phenylenediacetic acid, Biphenyl

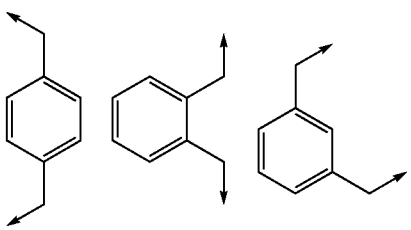

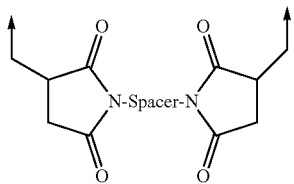

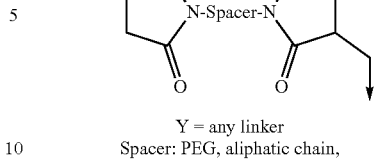

Y = any linker
Spacer: PEG, aliphatic chain,

In certain embodiments, a peptide dimer compound of Formula (H) has the structure shown below (Compound H):

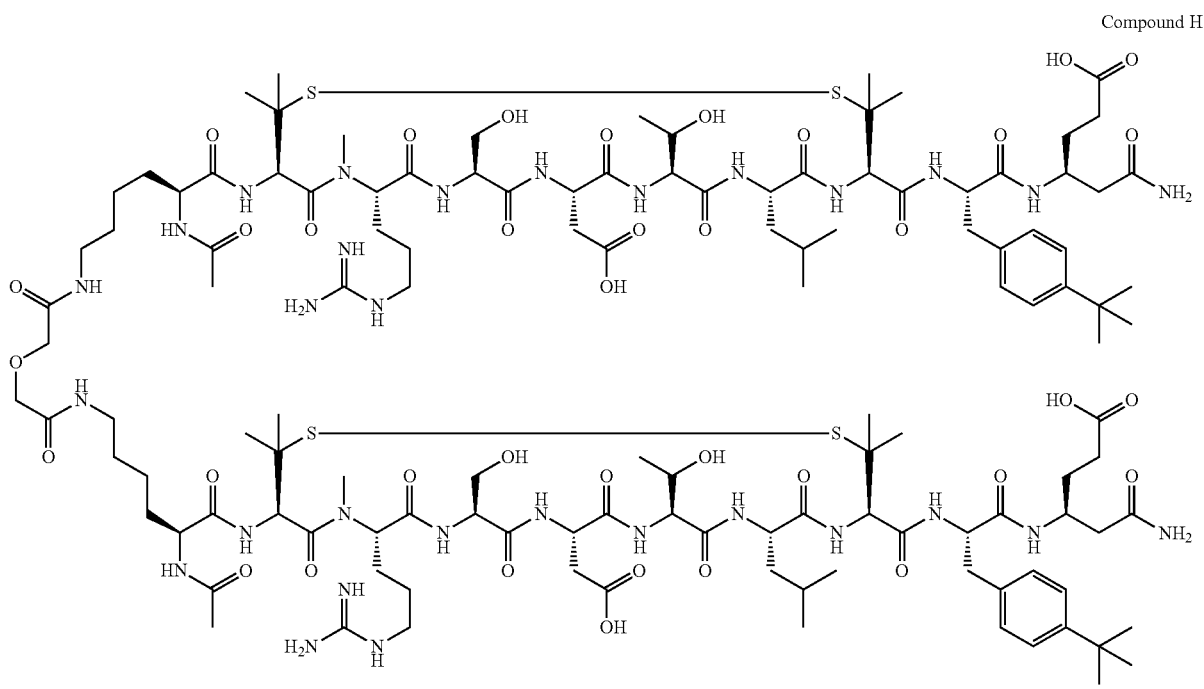 [SMILES: CC(=O)N[C@@H](CCCCNC(=O)COCC(=O)NCCCC[C@H](NC(C)=O)C(=O)N[C@@H]1C(=O)N(C)[C@@H](CCCNC(=N)N)C(=O)N[C@@H](CO)C(=O)N[C@@H](CC(=O)O)C(=O)N[C@@H](C(C)O)C(=O)N[C@@H](CC(C)C)C(=O)N[C@H](C(=O)N[C@@H](Cc2ccc(C(C)(C)C)cc2)C(=O)N[C@@H](CCC(=O)O)CC(N)=O)C(C)(C)SSC1(C)C)C(=O)N[C@@H]1C(=O)N(C)[C@@H](CCCNC(=N)N)C(=O)N[C@@H](CO)C(=O)N[C@@H](CC(=O)O)C(=O)N[C@@H](C(C)O)C(=O)N[C@@H](CC(C)C)C(=O)N[C@H](C(=O)N[C@@H](Cc2ccc(C(C)(C)C)cc2)C(=O)N[C@@H](CCC(=O)O)CC(N)=O)C(C)(C)SSC1(C)C]

Compound H

Embodiments of the invention include pharmaceutically acceptable salt forms of Compound H, e.g., acetate salts of Compound H.

In certain particular embodiments, the present invention includes peptide dimer compounds comprising one or two monomer subunits comprising one of the following amino acid sequences, wherein the monomer subunits of the peptide dimer are linked via their C-terminus:

```
                                                          (SEQ ID NO: 219)
Pen-(N-Me-Arg)-Ser-Asp-Thr-Leu-Pen-Trp-(β-homoGlu)-(D-Lys);

(SEQ ID NO: 220)
Pen-(N-Me-Arg)-Ser-Asp-Thr-Leu-Pen-(Phe(4-COOH)-(β-homoGlu)-(D-Lys);

(SEQ ID NO: 221)
Pen-(N-Me-Arg)-Ser-Asp-Thr-Leu-Pen-Trp-Glu-(N-Me-Lys);

(SEQ ID NO: 222)
Pen-(N-Me-Arg)-Ser-Asp-Thr-Leu-Pen-2-Nal-(β-homoGlu)-(D-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 224)
Pen-(N-Me-Arg)-Ser-Asp-Thr-Leu-Pen-2-Nal-Glu-(N-Me-Lys);
```

```
                                                         (SEQ ID NO: 225)
Pen-(N-Me-Arg)-Ser-Asp-Thr-Leu-Pen-Phe(4-tBu)-(β-homoGlu)-(D-Lys);

(SEQ ID NO: 226)
Pen-(N-Me-Arg)-Ser-Asp-Thr-Leu-Pen-Phe(4-tBu)-(β-homoGlu)-(N-Me-Lys);

(SEQ ID NO: 227)
Pen-(N-Me-Arg)-Ser-Asp-Thr-Leu-Pen-Trp-(β-homoGlu)-(N-Me-Lys);

(SEQ ID NO: 228)
Pen-(N-Me-Arg)-Ser-Asp-Thr-Leu-Pen-2-Nal-(β-homoGlu)-(N-Me-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 229)
Pen-(N-Me-Arg)-Ser-Asp-Thr-Leu-Pen-1-Nal-(β-homoGlu)-(N-Me-Lys);

(SEQ ID NO: 219)
Pen-(N-Me-Arg)-Ser-Asp-Thr-Leu-Pen-Trp-(β-homoGlu)-(D-Lys);
or
                                                         (SEQ ID NO: 230)
Pen-(N-Me-Arg)-Ser-Asp-Thr-Leu-Pen-Trp-Glu-(N-Me-D-Lys),
``` and wherein there is a disulfide bond between the two Pen residues of the monomer subunits.

In particular embodiments, the peptides of the monomer subunit further comprise an N-terminal Ac and/or a C-terminal NH$_2$ or OH. In particular embodiments, there is an disulfide bond between the two Pen residues of the monomer subunit.

In certain particular embodiments, the present invention includes peptide dimer compounds comprising one or two monomer subunits comprising one of the following amino acid sequences, wherein the monomer subunits of the peptide dimer are linked via their N-termini or their C-termini:

```
                                                         (SEQ ID NO: 280)
Pen-(N-Me-Arg)-Ser-Asp-Thr-Leu-Pen-Trp-(β-
homoGlu);

(SEQ ID NO: 275)
Pen-(N-Me-Arg)-Ser-Asp-Thr-Leu-Pen-(Phe-(4-
COOH)-(β-homoGlu);

(SEQ ID NO: 281)
Pen-(N-Me-Arg)-Ser-Asp-Thr-Leu-Pen-Trp-Glu;

(SEQ ID NO: 282)
Pen-(N-Me-Arg)-Ser-Asp-Thr-Leu-Pen-2-Nal-(β-
homoGlu);

(SEQ ID NO: 283)
Pen-(N-Me-Arg)-Ser-Asp-Thr-Leu-Pen-1-Nal-(β-
homoGlu);

(SEQ ID NO: 284)
Pen-(N-Me-Arg)-Ser-Asp-Thr-Leu-Pen-2-Nal-Glu;

(SEQ ID NO: 285)
Pen-(N-Me-Arg)-Ser-Asp-Thr-Leu-Pen-Phe(4-tBu)-
(β-homoGlu);

(SEQ ID NO: 285)
Pen-(N-Me-Arg)-Ser-Asp-Thr-Leu-Pen-Phe(4-tBu)-
(β-homoGlu);

(SEQ ID NO: 280)
Pen-(N-Me-Arg)-Ser-Asp-Thr-Leu-Pen-Trp-(β-
homoGlu);

(SEQ ID NO: 282)
Pen-(N-Me-Arg)-Ser-Asp-Thr-Leu-Pen-2-Nal-(β-
homoGlu);

(SEQ ID NO: 283)
Pen-(N-Me-Arg)-Ser-Asp-Thr-Leu-Pen-1-Nal-(β-
homoGlu);

(SEQ ID NO: 283)
Pen-(N-Me-Arg)-Ser-Asp-Thr-Leu-Pen-1-Nal-(β-
homoGlu);

(SEQ ID NO: 280)
Pen-(N-Me-Arg)-Ser-Asp-Thr-Leu-Pen-Trp-(β-
homoGlu);
or
                                                         (SEQ ID NO: 281)
Pen-(N-Me-Arg)-Ser-Asp-Thr-Leu-Pen-Trp-Glu,
``` wherein a disulfide bond links the Pen residues within a monomer dimer subunit.

In particular embodiments wherein the monomer subunits are linked via their N-termini, they are linked by a linker that binds to the N-terminal Pen residue of each monomer subunit. In other embodiments where the monomer subunits are linked via their N-termini, the monomer subunits comprise at least one additional N-terminal amino acid, and wherein the N-terminal amino acid of the monomer subunit is linked by a linker to the other monomer subunit. In particular embodiments, the additional N-terminal amino acid is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In particular embodiments, the peptides of the monomer subunit further comprise an N-terminal Ac and/or a C-terminal NH$_2$ or OH.

In one aspect, the present invention provides a peptide monomer compound of Formula (IV):

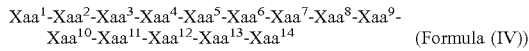

or a pharmaceutically acceptable salt thereof, wherein the peptide compound comprises a disulfide bond, a lactam bond, an olefin bond, a triazole bond, a selenoether bond, or a diselenide bond between $Xaa^4$ and $Xaa^{10}$, wherein:

$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Phe(4-guanidino), Phe(4-carbomyl), Cit, Phe(4-NH$_2$), N-Me-HomoArg, homoArg, Tyr, Dap, Dab, Arg-Me-sym, Arg-Me-asym, Cav, and His;
$Xaa^6$ is Ser, Gly, Thr, or Ile;
$Xaa^7$ is Asp, D-Asp, Asp(OMe), or N-Me-Asp;
$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butyl Ala, N-pental Ala, N-hexyl Ala, cyclobutyl Ala, cyclopentylAla, Leu, Nle, Cba, homoLeu, Cpa, Aoc, and N-Me-Leu;
$Xaa^{10}$ is any amino acid capable of forming a bond with $Xaa^4$;
$Xaa^{11}$ is absent or selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Phe(2-carbomyl), Tyr(Me), HomoPhe, N-Me-Phe, N-Me-Tyr, Ser, Sar, 2,3-dihydro-Trp, Ile, Leu, Arg, Thr, aromatic amino acids, substituted aromatic amino acids, and Tic;
$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, Aic, Gln, Cit, Glu(OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, homoPhe, D-1-Nal, D-2-Nal, Thr, and Val, and corresponding D-amino acids and isosteres;
$Xaa^{13}$ is absent, Pro, or any amino acid; and
$Xaa^{14}$ is any amino acid.

In certain embodiments of Formula (IV), $Xaa^7$ is Asp, Asp(OMe), or N-Me-Asp.

In certain embodiments of Formula (IV), $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In certain embodiments of Formula (IV), $Xaa^{11}$ is selected from the group consisting of Tic, Phe(2-carbomyl), Phe(3-carbomyl), Phe(4-COOH), Phe(4-OMe), Phe(4-tBu), Phe(4-CF$_3$), Phe(3-CF$_3$), Phe(CF$_3$), homo-Phe, D-Phe, Phe(2,3-di-Cl), Phe(3,4-di-Cl), N-Me-Tyr, N-Me-Phe, Phe(4-F), Phe(3-F), Phe(4-Me), Phe(3-Me), Phe(2-Me), Phe(3,4-di-Me), Phe (2,4-di-Phe), beta-MethylPhe, and biphenyl-Ala.

In particular embodiments of Formula (IV), $Xaa^{12}$ is selected from the group consisting of Aic, Gln, Cit, Glu (OMe), Asn, D-His, Tic, Phe(3-COOH), D-Arg, Bip, D-Trp, Phe, D-Phe, D-Val, D-Thr, D-Tyr, D-Lys, D-Ile, D-His, N-Me-Glu, N-Me-Asp, alpha-homoGlu, Biphenyl-Gly, Biphenyl-Ala, Homo-Phe, D-1-Nal, D-2-Nal, Thr, and Val.

In particular embodiments of Formula (IV), $Xaa^{12}$ is selected from the group consisting of aromatic amino acids, substituted aromatic amino acids, Glu, D-Glu, homoGlu, Asp, D-Asp, D-homoGlu, Gla, beta-homoGlu, Tic, and corresponding D-amino acids and isosteres.

In certain embodiments of Formula (IV), $Xaa^5$ is selected from the group consisting of Cit, Phe(4-carbomyl), and N-Me-HomoArg; $Xaa^8$ is selected from the group consisting of Leu, HomoLeu, Nle and Val; $Xaa^9$ is selected from the group consisting of: Cba, HomoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro. In particular embodiments, the intramolecular bond is a disulfide bond.

In particular embodiments of Formula (IV), $Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and suitable isosteres; and $Xaa^{13}$ is absent or Pro.

In certain embodiments, the amino acid directly C-terminal to $Xaa^{10}$ is selected from aromatic amino acids, substituted aromatic amino acids, and Tic. In certain embodiments, the amino acid directly C-terminal to $Xaa^{10}$ is an aromatic amino acid.

In certain embodiments, $Xaa^{14}$ or the C-terminal amino acid does not comprise a free amine.

In certain embodiments, $Xaa^{14}$ is Lys, D-Lys, N-Me-Lys, D-N-Me-Lys, Orn, Dab, Dap, HomoLys, D-Dap, D-Dab, or D-Orn.

In certain embodiments, $Xaa^{14}$ or the C-terminus comprises an NH$_2$ or an OH.

In certain embodiments, a free amine in the C-terminal amino acid is capped, e.g., with an acetyl group.

In certain embodiments, the peptide comprises an intramolecular bond between $Xaa^4$ and $Xaa^{10}$. In certain embodiments, the bond is a disulfide bond, a lactam bond, an olefin bond, a triazole, a selenoether, or a diselenide bond. In certain embodiments, the bond occurs directly between the two amino acid residues.

In certain embodiments, $Xaa^4$ is selected from the group consisting of: Cys, Pen, HomoCys, D-Cys, D-Pen, D-HomoCys, Asp, Glu, HomoGlu, β-Asp, β-Glu, Lys, HomoLys, Orn, Dap, Dap, 2-allylglycine, 2-(3'-butenyl)glycine, 2-(4'-pentenyl)glycine, or 2-(5'-hexenyl)glycine, corresponding D-amino acids and suitable isosteres, and $Xaa^{10}$ is selected from the group consisting of: Cys, Asp, Lys, Glu, Pen, HomoAsp, HomoGlu, D-Cys, D-Pen, HomoLys, Orn, β-Asp, β-Glu, Dap, Dab, D-HomoCys, 2-allylglycine, 2-(3'-butenyl)glycine, 2-(4'-pentenyl)glycine, or 2-(5'-hexenyl) glycine, corresponding D-amino acids and suitable isosteres.

In certain embodiments wherein the cyclic peptide comprises a disulfide bond between $Xaa^4$ and $Xaa^{10}$, $Xaa^4$ and $Xaa^{10}$ are each selected from the group consisting of: Cys and Pen. In certain embodiments, both $Xaa^4$ and $Xaa^{10}$ are Pen.

In certain embodiments wherein the cyclic peptide comprises a lactam bond between $Xaa^4$ and $Xaa^{10}$, $Xaa^4$ and $Xaa^{10}$ are each selected from the group consisting of: Lys, HomoLys, Orn, Dap, Dab, Asp, Glu, HomoGlu, D-Dap, D-Dab, D-Asp, D-Glu or D-Lys. In certain embodiments, $Xaa^{10}$ is Lys, HomoLys, Orn, Dap or Dab; and $Xaa^4$ is Asp, Glu, or HomoGlu. In certain embodiments, $Xaa^4$ is Lys, HomoLys, Orn, Dap or Dab; and $Xaa^{10}$ is Asp, Glu, or HomoGlu.

In certain embodiments wherein the cyclic peptide comprises a lactam bond between $Xaa^4$ and $Xaa^{10}$, $Xaa^{10}$ is selected from the group consisting of Asp, HAsp, Glu, and HGlu, HLys, and $Xaa^4$ is selected from the group consisting of Lys, Dap, Dab, HLys, Orn, and HGl. In certain embodiments, $Xaa^{10}$ is selected from the group consisting of Lys, Dap, Dab, HLys, Orn, and HGlu, and $Xaa^4$ is selected from the group consisting of Asp, HAsp, Glu, HGlu, and HLys.

In certain embodiments, $Xaa^4$ is selected from the group consisting of Asp, HAsp, Glu, HGlu, and Hlys, $Xaa^{10}$ is selected from the group consisting of Lys, Dap, Dab, HLys, Orn, and HGlu, and $Xaa^4$ and $Xaa^{10}$ are cyclized through an amide bond.

In certain embodiments wherein the cyclic peptide comprises an olefin bond between $Xaa^4$ and $Xaa^{10}$, $Xaa^4$ and $Xaa^{10}$ are each selected from the group consisting of: 2-allylglycine, 2-(3'-butenyl)glycine, 2-(4'-pentenyl)glycine, or 2-(5'-hexenyl)glycine, and the peptide is cyclized via ring closing methasis to give the corresponding olefin/"stapled peptide."

In certain embodiments, $Xaa^4$ is Cys, Pen, or homoCys. In certain embodiments, $Xaa^4$ and $Xaa^{10}$ are each β-azido-Ala-OH or propargylglycine, and the peptide is cyclized through click chemistry leading to a triazole ring.

In particular embodiments, the intramolecular bond is a disulfide bond or a lactam bond.

In one aspect, the present invention provides a peptide monomer compound of Formula (IV'):

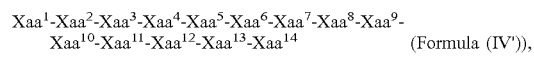

or a pharmaceutically acceptable salt thereof, wherein:
$Xaa^1$ is absent, Ac, or any amino acid;
$Xaa^2$ is absent, Ac, or any amino acid;
$Xaa^3$ is absent, Ac, or any amino acid;
$Xaa^4$ is any amino acid capable of forming a bond with $Xaa^{10}$;
$Xaa^5$ is selected from the group consisting of: N-Me-Arg, Arg, N-Me-Lys, Ph (4-guanidino), Phe(4-carbomyl), Cit, Phe(4-NH$_2$), N-Me-homoArg, homoArg, Tyr Dap, Dab, Arg-Me-sym, Arg-Me-asym, Cav, and His;
$Xaa^6$ is Ser Gly, Thr, or Ile;
$Xaa^7$ is Asp or D-Asp, Asp(OMe), or N-Me-Asp;
$Xaa^8$ is selected from the group consisting of: Thr, Val, Ile, Leu, homoLeu, Gln, Ser, Asp, Pro, Gly, His, Ala, Phe, Lys, Arg, Asn, Glu, Tyr, Trp, Met, Nle, and N-methyl amino acids, including N-Me-Thr;
$Xaa^9$ is selected from the group consisting of: Gln, Ser, Asp, Pro, Gly, Ala, Phe, Glu, Ile, Val, N-butylAla, N-pentylAla, N-hexyl Ala, cyclobutyl Ala, cyclopentyl-Ala, Leu, Nle, Cpa, Cba, homoLeu, Aoc, and N-Me-Leu;
$Xaa^{10}$ is any amino acid capable of forming a bond with $Xaa^4$; and
$Xaa^{11}$ is absent or selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, beta-homoTrp, D-1-Nal, D-2-Nal, Phe(2,4-diCl), Phe(3,4-diCl), Phe(4-carbomyl), Phe(3-carbomyl), Phe(2-carbomyl), Tyr(Me), homoPhe, N-Me-Phe, N-Me-Tyr, Ser, Sar, Dihydro Trp, Ile, Leu, Ser, Arg, Thr, aromatic amino acids, substituted aromatic amino acids, and Tic;

$Xaa^{12}$ is absent or selected from the group consisting of: aromatic amino acids, substituted aromatic amino acids, Glu, D-Glu, homoGlu, Asp, D-Asp, D-homoGlu, Gla, beta-homoGlu, Tic, and corresponding D-amino acids and suitable isosteres;
$Xaa^{13}$ is absent or Pro; and
$Xaa^{14}$ is any amino acid.

In particular embodiments of Formula (IV'), $Xaa^5$ is selected from the group consisting of Cit, Phe(4-carbomyl), and N-Me-homoArg; $Xaa^8$ is selected from the group consisting of Leu, homoLeu, Nle and Val; $Xaa^9$ is selected from the group consisting of: Cba, homoLeu, and Cpa; $Xaa^{11}$ is selected from the group consisting of Tic, Phe(2-carbomyl), Phe(3-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In various embodiments, any of the features or limitations described for Formula (IV) may be present in Formula (IV').

In one aspect, the present invention provides a peptide compound of Formula (V):

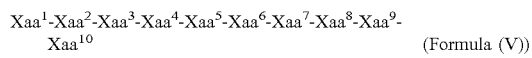

or a pharmaceutically acceptable salt thereof, wherein the peptide compound comprises a disulfide bond, a lactam bond, an olefin bond, a triazole bond, a selenoether bond, or a diselenide bond between $Xaa^1$ and $Xaa^7$, wherein $Xaa^1$-$Xaa^{10}$ of Formula (V) corresponds to $Xaa^4$-$Xaa^{13}$ of Formula (IV).

In certain embodiments of Formula (V), $Xaa^2$ is selected from the group consisting of Cit, Phe(4-carbomyl), and N-Me-homoArg; $Xaa^5$ is selected from the group consisting of Leu, HomoLeu, Nle and Val; $Xaa^6$ is selected from the group consisting of: Cba, homoLeu, and Cpa; $Xaa^8$ is selected from the group consisting of Tic, Phe(2-carbomyl), Phe(3-carbomyl), Phe(4-COOH), Phe(4-OMe), and Phe(4-tBu); $Xaa^9$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{10}$ is Pro. In particular embodiments, the intramolecular bond is a disulfide bond or a lactam bond.

In one embodiment of Formula (IV), herein referred to as Formula (IV-A),
$Xaa^1$ is absent, Ac, or any amino acid;
$Xaa^2$ is absent, Ac, or any amino acid;
$Xaa^3$ is absent, Ac, or any amino acid;
$Xaa^4$ is Pen;
$Xaa^5$ is selected from the group consisting of: N-Me-Arg, Arg, N-Me-Lys, Phe(4-guanidino), Phe(4-carbomylamino), Cit, Phe(4-NH$_2$), N-Me-homoArg, homoArg, Tyr and His;
$Xaa^6$ is Ser, Gly, Thr, Ile;
$Xaa^7$ is Asp or D-Asp;
$Xaa^8$ is selected from the group consisting of: Thr, Val, Ile, Leu, homoLeu, Nle, and Val;
$Xaa^9$ is selected from the group consisting of: Ile, cyclobutyl Ala, cyclopentylAla, Leu, Nle, Cpa, homoLeu, Aoc, and N-Me-Leu;
$Xaa^{10}$ is Pen;
$Xaa^{11}$ is absent or selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3- carbomyl), Phe(2-carbomyl), Tyr(Me), homoPhe, N-Me-Phe, N-Me-Tyr, Ser, Sar, 2,3-dihydroTrp, Ile, Leu, Arg, and Thr;

$Xaa^{12}$ is absent or selected from the group consisting of: Glu, D-Glu, homoGlu, Asp, D-Asp, D-homoGlu, D-Asp, Gla, beta-homoGlu, corresponding D-amino acid, any aromatic amino acid, and isosteres;

$Xaa^{13}$ is absent or any amino acid; and $Xaa^{14}$ is any amino acid.

In certain embodiments, $Xaa^4$ and $Xaa^{10}$ are linked, e.g. via a disulfide bond.

In certain embodiments, $Xaa^7$ is Asp.

In one embodiment of Formula (IV), herein referred to as Formula (IV-B), $Xaa^1$ is absent, Ac, or any amino acid;

$Xaa^2$ is absent, Ac, or any amino acid;

$Xaa^3$ is absent, Ac, or any amino acid;

$Xaa^4$ is Pen or Cys;

$Xaa^5$ is N-Me-Arg;

$Xaa^6$ is Ser;

$Xaa^7$ is Asp or D-Asp;

$Xaa^8$ is selected from the group consisting of: Thr, Val, Ile, Leu, homoLeu and Nle;

$Xaa^9$ is selected from the group consisting of: Leu, Nle, Cpa, Cba, homoLeu, Aoc, and N-Me-Leu;

$Xaa^{10}$ is Pen or Cys;

$Xaa^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Arg, Thr, any substituted aromatic amino acid, and corresponding D-amino acids;

$Xaa^{12}$ is selected from the group consisting of: Glu, D-Glu, homoGlu, Asp, D-Asp, D-homoGlu, Gla, beta-homoGlu, corresponding D-amino acid and any aromatic amino acid and corresponding isosteres;

$Xaa^{13}$ is absent; and $Xaa^{14}$ is any amino acid. In certain embodiments, $Xaa^4$ and $Xaa^{10}$ are linked, e.g. via a disulfide or a lactam bond.

In particular embodiments, $Xaa^7$ is Asp.

In one embodiment of Formula (IV), herein referred to as Formula (IV-C), $Xaa^1$ is absent, Ac, or any amino acid;

$Xaa^2$ is absent, Ac, or any amino acid;

$Xaa^3$ is absent, Ac, or any amino acid;

$Xaa^4$ is Pen;

$Xaa^5$ is N-Me-Arg;

$Xaa^6$ is Ser, Gly, Thr, Ile;

$Xaa^7$ is Asp or D-Asp;

$Xaa^8$ is selected from the group consisting of: Thr, Val, Ile, Leu, homoLeu and Nle;

$Xaa^9$ is selected from the group consisting of: Leu, Nle, Cpa, Cba, homoLeu, Aoc, and N-Me-Leu;

$Xaa^{10}$ is Pen;

$Xaa^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-Carbomyl), Tyr(Me), HomoPhe, N-Me-Phe, N-Me-Tyr, Ser, Sar, Dihydro Trp, Ile, Leu, Ser, Arg, and Thr;

$Xaa^{12}$ is selected from the group consisting of: Glu, D-Glu, homoGlu, Asp, D-Asp, D-homoGlu, Gla, beta-homoGlu, corresponding D-amino acid and any aromatic amino acid and corresponding isosteres;

$Xaa^{13}$ is absent or is any amino acid; and $Xaa^{14}$ is any amino acid.

In certain embodiments, $Xaa^4$ and $Xaa^{10}$ are linked, e.g. via a disulfide or a lactam bond.

In particular embodiments, $Xaa^7$ is Asp.

In one embodiment of Formula (IV), herein referred to as Formula (IV-D), $Xaa^1$ is absent, Ac, or any amino acid;

$Xaa^2$ is absent, Ac, or any amino acid;

$Xaa^3$ is absent, Ac, or any amino acid;

$Xaa^4$ is Pen;

$Xaa^5$ is N-Me-Arg;

$Xaa^6$ is Ser;

$Xaa^7$ is Asp or D-Asp;

$Xaa^8$ is Thr or Val;

$Xaa^9$ is selected from the group consisting of: Leu, Nle, Cpa, Cba, HomoLeu, Aoc, and N-Me-Leu;

$Xaa^{10}$ is Pen;

$Xaa^{11}$ is selected from the group consisting of: Trp, Phe, 2-Nal, 1-Nal, Tyr, His, Phe(4-F), Phe(4-CF$_3$), Phe(4-CH$_3$), Phe(4-tBu), Bip, Phe(4-COOH), Gly, 3,3-DiPhenylGly, 3,3-DiPhenylAla, Tic, b-homoTrp, D-1-Nal, D-2-Nal, Phe(2,4-diCl), Phe(3,4-diCl), Phe(4-carbomyl), Phe(3-carbomyl), Tyr(Me), HomoPhe, N-Me-Phe, N-Me-Tyr, Ser, Sar, 2,3-dihydroTrp, Ile, Leu, Arg, and Thr;

$Xaa^{12}$ is absent or selected from the group consisting of: any aromatic amino acid, Glu, D-Glu, homoGlu, Asp, D-Asp, D-homoGlu, Gla, beta-homoGlu, corresponding D-amino acid and isosteres thereof;

$Xaa^{13}$ is absent; and $Xaa^{14}$ is any amino acid.

In certain embodiments, $Xaa^4$ and $Xaa^{10}$ are linked, e.g. via a disulfide bond.

In particular embodiments, $Xaa^7$ is Asp.

In one embodiment of Formula (IV), herein referred to as Formula (IV-E), $Xaa^1$ is absent, Ac, or any amino acid;

$Xaa^2$ is absent, Ac, or any amino acid;

$Xaa^3$ is absent, Ac, or any amino acid;

$Xaa^4$ is Pen;

$Xaa^5$ is N-Me-Arg;

$Xaa^6$ is Ser;

$Xaa^7$ is Asp or D-Asp;

$Xaa^8$ is Thr or Val;

$Xaa^9$ is selected from the group consisting of: Leu, Nle, Cpa, Cba, homoLeu, Aoc, and N-Me-Leu;

$Xaa^{10}$ is Pen;

$Xaa^{11}$ is selected from the group consisting of: Trp, Phe, 2-Nal, 1-Nal, Tyr, His, Phe(4-F), Phe(4-CF$_3$), Phe(4-CH$_3$) Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Arg, and Thr;

$Xaa^{12}$ is absent or selected from the group consisting of: any aromatic amino acid, Glu, D-Glu, and beta-homoGlu;

$Xaa^{13}$ is absent; and $Xaa^{14}$ is any amino acid.

In certain embodiments, $Xaa^4$ and $Xaa^{10}$ are linked, e.g. via a disulfide or a lactam bond.

In particular embodiments, $Xaa^7$ is Asp.

In one embodiment of Formula (IV), herein referred to as Formula (IV-F), $Xaa^1$ is absent, Ac, or any amino acid;

$Xaa^2$ is absent, Ac, or any amino acid;

$Xaa^3$ is absent, Ac, or any amino acid;

$Xaa^4$ is Pen;

Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen;
Xaa¹¹ is selected from the group consisting of: Trp, Phe, 2-Nal, 1-Nal, Tyr, His, Phe(4-F), Phe(4-CF₃), Phe(4-CH₃), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dihydroTrp, Ile, Leu, Arg, and Thr;
Xaa¹² is selected from the group consisting of: any aromatic amino acid, Glu, D-Glu, beta-homoGlu, and corresponding D-amino acid and isosteres thereof;
Xaa¹³ is absent; and
Xaa¹⁴ is any amino acid.

In certain embodiments, Xaa⁴ and Xaa¹⁰ are linked, e.g. via a disulfide or a lactam bond.

In particular embodiments, Xaa⁷ is Asp.

In one embodiment of Formula (IV), herein referred to as Formula (IV-G),
Xaa¹ is absent, Ac, or any amino acid;
Xaa² is absent, Ac, or any amino acid;
Xaa³ is absent, Ac, or any amino acid;
Xaa⁴ is Pen;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen;
Xaa¹¹ is selected from the group consisting of: Trp, Phe, 2-Nal, 1-Nal, Tyr, His, Phe(4-F), Phe(4-CF₃), Phe(4-CH₃), Phe(4-tBu), Bip, Phe(4-COOH), Gly, 3,3-DiPhenylGly, 3,3-DiPhenylAla, Tic, b-homoTrp, D-1-Nal, D-2-Nal, Phe(2,4-diCl), Phe(3,4-diCl), Phe(4-carbomyl), Phe(3-carbomyl), Tyr(Me), homoPhe, N-Me-Phe, N-Me-Tyr, Ser, Sar, 2,3-dDihydroTrp, Ile, Leu, Arg, and Thr;
Xaa¹² is selected from the group consisting of: any aromatic amino acid, Glu, D-Glu, and beta-homoGlu;
Xaa¹³ is absent; and
Xaa¹⁴ is any amino acid.

In certain embodiments, Xaa⁴ and Xaa¹⁰ are linked, e.g. via a disulfide or a lactam bond.

In particular embodiments, Xaa⁷ is Asp.

In one embodiment of Formula (IV), herein referred to as Formula (IV-H),
Xaa¹ is absent, Ac, or any amino acid;
Xaa² is absent, Ac, or any amino acid;
Xaa³ is absent, Ac, or any amino acid;
Xaa⁴ is Pen;
Xaa⁵ is N-Me-Arg;
Xaa⁶ is Ser;
Xaa⁷ is Asp;
Xaa⁸ is Thr or Val;
Xaa⁹ is Leu;
Xaa¹⁰ is Pen;
Xaa¹¹ is selected from the group consisting of: Trp, Phe, 2-Nal, 1-Nal, Tyr, His, Phe(4-F), Phe(4-CF₃), Phe(4-CH₃), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), HomoPhe, N-Me-Phe, N-Me-Tyr, Ser, Sar, 2,3-dihydroTrp, Ile, Leu, Ser, Arg, or Thr;
Xaa¹² is selected from the group consisting of: any aromatic amino acid, Glu, D-Glu, and beta-homoGlu;
Xaa¹³ is absent; and
Xaa¹⁴ is any amino acid.

In certain embodiments, Xaa⁴ and Xaa¹⁰ are linked, e.g. via a disulfide bond.

In one embodiment of Formula (IV), herein referred to as Formula (IV-I),
Xaa¹ is absent, Ac, or any amino acid;
Xaa² is absent, Ac, or any amino acid;
Xaa³ is absent, Ac, or any amino acid;
Xaa⁴ is Pen;
Xaa⁵ is N-Me-Arg;
Xaa⁶ is Ser;
Xaa⁷ is Asp or D-Asp;
Xaa⁸ is Thr or Val;
Xaa⁹ is Leu;
Xaa¹⁰ is Pen;
Xaa¹¹ is selected from the group consisting of: Trp, Phe, 2-Nal, 1-Nal, Tyr, His, Phe(4-F), Phe(4-CF₃), Phe(4-CH₃), Phe(4-tBu), Bip, Phe(4-COOH), Gly, 3,3-DiPhenylGly, 3,3-DiPhenylAla, Tic, β-homoTrp, D-1-Nal, D-2-Nal, Phe(2,4-diCl), Phe(3,4-diCl), Phe(4-carbomyl), Phe(3-carbomyl), Tyr(Me), and homoPhe;
Xaa¹² is selected from the group consisting of: any aromatic amino acid, Glu, D-Glu, and beta-homoGlu;
Xaa¹³ is absent; and
Xaa¹⁴ is any amino acid. In certain embodiments, Xaa⁴ and Xaa¹⁰ are linked, e.g. via a disulfide or a lactam bond.

In particular embodiments, Xaa⁷ is Asp.

In one embodiment of Formula (IV), herein referred to as Formula (IV-J),
Xaa¹ is absent, Ac or any amino acid;
Xaa² is absent, Ac or any amino acid;
Xaa³ is absent, Ac or any amino acid;
Xaa⁴ is Pen;
Xaa⁵ is N-Me-Arg;
Xaa⁶ is Ser;
Xaa⁷ is Asp;
Xaa⁸ is Thr;
Xaa⁹ is Leu;
Xaa¹⁰ is Pen;
Xaa¹¹ is Phe(4-tBu)
Xaa¹² is beta-homoGlu;
Xaa¹³ is absent;
and Xaa¹⁴ is D-Lys.

In particular embodiments of Formula (IV-J), Xaa⁴ and Xaa¹⁰ are linked via a disulfide bond.

In certain embodiments of any one of Formulas (IV-A), (IV-B), (IV-C), (IV-D), (IV-E), (IV-F), (IV-G), (IV-H), (IV-I) or (IV-J), Xaa¹⁴ is selected from the group consisting of: Lys, D-Lys, N-Me-Lys, D-N-Me-Lys.

In one embodiment, a peptide monomer compound or peptide dimer compound of the present invention comprises a peptide molecule of Formula (C):

$$\text{Xaa}^1\text{-Xaa}^2\text{-Xaa}^3\text{-Xaa}^4\text{-Xaa}^5\text{-Xaa}^6\text{-Xaa}^7\text{-Xaa}^8\text{-Xaa}^9\text{-Xaa}^{10}(\text{SEQ ID NO: 345}) \quad \text{(Formula (C))}$$

or a pharmaceutically acceptable salt thereof, wherein.
Xaa¹ is Cys or Pen;
Xaa² is N-methyl-Arg;
Xaa³ is Ser;
Xaa⁴ is Asp;
Xaa⁵ is Thr or Val;
Xaa⁶ is Leu or Nle;
Xaa⁷ is Cys or Pen;

$Xaa^8$ is Trp, Tic, Bip, 1-Nal, 2-Nal, Phe(4-tBu), Phe, Tyr, or Phe(4-COOH);
$Xaa^9$ is Glu, β-homoGlu, or D-Glu; and
$Xaa^{10}$ is any amino acid,
wherein the peptide molecule comprises a disulfide bond between $Xaa^1$ and $Xaa^7$.

In particular embodiments of Formula (C), $Xaa^{10}$ is D-Lys, N-Me-Lys or N-Me-D-Lys. In particular embodiments, $Xaa^1$ and/or $Xaa^7$ are Pen.

In certain embodiments, $Xaa^{10}$ or the C-terminus of the peptide comprises an $NH_2$ or an OH.

In certain embodiments, a free amine in the C-terminal amino acid is capped, e.g., with an acetyl group.

Illustrative peptide monomer compounds of the present invention are shown in the Examples and accompanying figures. In certain embodiments, a peptide monomer compound has the structure shown below (Compound U). In particular embodiments, Compound U is a pharmaceutically acceptable salt form. In one embodiment, it is an acetate salt.

any of IV-A, IV-B, IV-C, IV-D, IV-E, IV-F, IV-G, IV-H, IV-I, and IV-J) represents a single suitable group for modifying the N-terminus of the decapeptide subunit. In some embodiments, $Xaa^1$ and $Xaa^2$ of Formula (IV) (including any of IV-A, IV-B, IV-C, IV-D, IV-E, IV-F, IV-G, IV-H, IV-I, and IV-J) are absent, and $Xaa^3$ of Formula (IV) is Ac. In some embodiments, the N-terminal amino acid residue of the peptide of either Formula (IV), (V), (VI), (A), (B), (C), or (D) is acylated. In particular embodiments, the N-terminus may be acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

Compound U

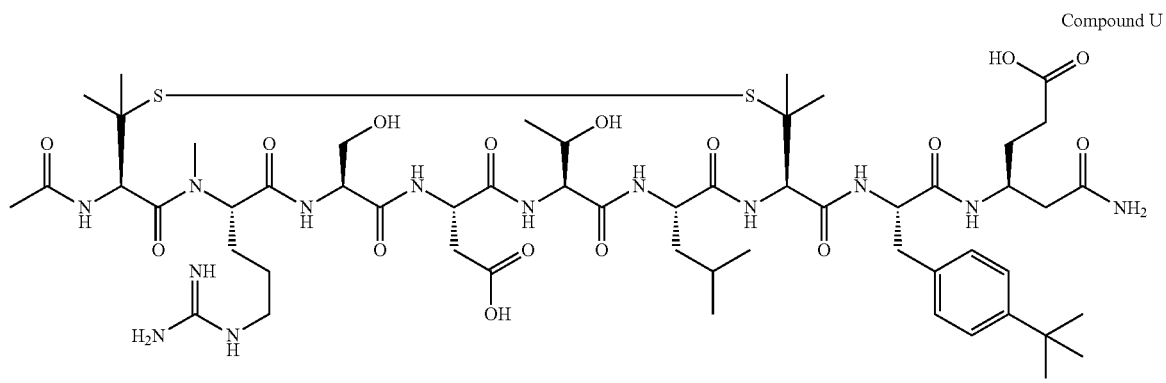 [SMILES: CC(=O)N[C@@H]1C(=O)N(C)[C@@H](CCCNC(=N)N)C(=O)N[C@@H](CO)C(=O)N[C@@H](CC(=O)O)C(=O)N[C@@H](C(C)O)C(=O)N[C@@H](CC(C)C)C(=O)N[C@H](C(=O)N[C@@H](Cc2ccc(C(C)(C)C)cc2)C(=O)N[C@@H](CCC(=O)O)CC(N)=O)C(C)(C)SSC1(C)C]

Some sequences of the present invention are derived from the general sequences provided in Formula (IV) (including any of IV-A, IV-B, IV-C, IV-D, IV-E, IV-F, IV-G, IV-H, IV-I, and IV-J), Formula (V), Formula (A), (Formula (B), Formula (C), or Formula (D). For example, the N-terminus of a decapeptide represented by $Xaa^4$-$Xaa^{13}$ of Formula (IV) or $Xaa^1$-$Xaa^{10}$ of Formula (V), (VI), (A), (B), (C), or (D) can be modified by one to three suitable groups, as represented by $Xaa^1$, $Xaa^2$, and $Xaa^3$ of Formula (IV). The N-terminus may further be acylated. In particular embodiments, the N-terminus may be acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In some embodiments, $Xaa^1$, $Xaa^2$, and $Xaa^3$ of Formula (IV) (including any of I-A, I-B, I-C, I-D, I-E, I-F, I-G, I-H, and I-I) are absent. In other embodiments, $Xaa^1$ is absent, and $Xaa^2$ and $Xaa^3$ represent suitable groups for modifying the N-terminus of the peptide, e.g., the decapeptide represented by residues $Xaa^4$-$Xaa^{13}$ of Formula (IV), and residues $Xaa^1$-$Xaa^{10}$ of Formula (V). Further, in some embodiments, $Xaa^1$ and $Xaa^2$ of Formula (IV) (including any of IV-A, IV-B, IV-C, IV-D, IV-E, IV-F, IV-G, IV-H, IV-I, and IV-J) are absent, and $Xaa^3$ of Formula (IV) (including Similarly, the C-terminus of the peptide, e.g., the peptide represented by Formula (IV) (including any of IV-A, IV-B, IV-C, IV-D, IV-E, IV-F, IV-G, IV-H, IV-I, and IV-J), Formula (V), Formula (VI), Formula (A), Formula (B), Formula (C) or Formula (D) can be modified by a suitable group. The C-terminus may further be acylated. In particular embodiments, the C-terminus may be acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In certain embodiments of the peptides of Formula (IV) (including any of IV-A, IV-B, IV-C, IV-D, IV-E, IV-F, IV-G, IV-H, IV-I, and IV-J, $Xaa^{11}$, $Xaa^{12}$ and $Xaa^{13}$ are absent. In other embodiments, $Xaa^{12}$ and $Xaa^{13}$ are absent. In other embodiments, $Xaa^{13}$ is absent. In particular embodiments, $Xaa^{14}$ is the C-terminal amino acid of the peptide. In particular embodiments, $Xaa^{14}$ is modified. In certain embodiments, $Xaa^{14}$ is Lysine, D-Lysine, N-methyl-Lysine, Dap or Dab. In particular embodiments, $Xaa^{14}$ is Dap or Dab. In certain embodiments, $Xaa^{14}$ comprises an $NH_2$ moiety.

In some embodiments, any one or more of $Xaa^1$-$Xaa^4$ are acylated. In particular embodiments, any one or more of $Xaa^1$-$Xaa^4$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

In certain embodiments where $Xaa^4$ and $Xaa^{10}$ are both either Cys or Pen, the peptide is cyclized though a disulfide bond or a lactam bond between $Xaa^4$ and $Xaa^{10}$. Preferably, in one embodiment $Xaa^4$ is Cys. In another embodiment, preferably $Xaa^4$ is Pen. In particular embodiments, $Xaa^4$ is Pen; in other embodiments, $Xaa^{10}$ is Pen; in other embodiments, both $Xaa^4$ and $Xaa^{10}$ are Pen.

In certain embodiments of any of the peptide dimer or monomer compounds described herein, $Xaa^5$ is N-Me-Arg. In certain embodiments, $Xaa^6$ is Ser. In certain embodiments, $Xaa^7$ is Asp. In certain embodiments, $Xaa^8$ is Thr. In certain embodiments, $Xaa^9$ is Leu. In one embodiment, $Xaa^{10}$ is Pen. In another embodiment, $Xaa^{10}$ is Cys. In particular embodiments, $Xaa^{11}$ is selected from the group consisting of Tic, Phe(2-carbomyl), Phe(3-carbomyl), Phe (4-COOH), Phe-(4-OMe), Phe(4-tBu), Phe(4-F), Phe(4-CN), N-Me-Phe, N-Me-Tyr, β-homoTrp, and Pentafluro-Phe. In particular embodiments, $Xaa^{12}$ Glu, D-Glu, beta homoGlu, In particular embodiments, $Xaa^{13}$ is Pro, and $Xaa^{11}$ and/or $Xaa^{12}$ are present In particular embodiments, $Xaa^{14}$ is an amino acyl residue selected from the group consisting of natural amino acids, Dap, Dab, Orn, D-Orn, N-Me-Orn, N-Me-Dap, N-Me-Dab, N-Me Lys, D-Dap, D-Dab, D-Lys, N-Me-D-Lys, isostere replacements, corresponding D-amino acids, and corresponding N-Methyl amino acids. In at least one embodiment, $Xaa^{14}$ is the C-terminus. When $Xaa^{14}$ is the C-terminus of the subunit, $Xaa^{14}$ may be modified to include a linker moiety in accordance with the present invention. Further, in some embodiments $Xaa^{14}$ is N(alpha)Methylated. For some embodiments, any of $Xaa^1$-$Xaa^5$, $Xaa^7$-$Xaa^9$, and $Xaa^{11}$-$Xaa^{12}$ are N(alpha)Methylated. $Xaa^5$ may further be Arg-Me-sym or Arg-Me-asym, and $Xaa^{11}$ may be O-Me-Tyr, N-Me-Lys (Ac), or 4-Me-Phe. In some instances, any of $Xaa^1$-$Xaa^4$, and $Xaa^{11}$-$Xaa^{14}$ are acylated. For example, in some instances one or more residues at positions $Xaa^1$-$Xaa^4$, and $Xaa^{11}$-$Xaa^{14}$ are acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations.

In particular embodiments of any of the peptides described herein, including but not limited to those of Formula (IV) (including any of IV-A, IV-B, IV-C, IV-D, IV-E, IV-F, IV-G, IV-H, and IV-I) (or the corresponding residues of Formula (V), (IV-A), (A), (B), (C), or (D), $Xaa^5$ is selected from the group consisting of N-Me-Arg, Phe(4-guanidino), Phe(4-NH$_2$), N-Me-homoArg, homoArg, Tyr and His; $Xaa^8$ is selected from the group consisting of Leu, homoLeu, Nle and Val; $Xaa^9$ is CPA or Aoc; $Xaa^{11}$ is selected from the group consisting of Tic, Phe(2-carbomyl), Phe(3-carbomyl), Phe(4-carbomyl), Phe(4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In particular embodiments of any of the compounds and genuses described herein, $Xaa^5$ is selected from the group consisting of Cit, Phe(4-carbomyl), and N-Me-homoArg; $Xaa^8$ is selected from the group consisting of Leu, homoLeu, Nle and Val; $Xaa^9$ is selected from the group consisting of: Cba, homoLeu, and Cpa; $Xaa^{11}$ is selected from the group consisting of Tic, Phe(2-carbomyl), Phe(3-carbomyl), Phe (4-COOH), Phe(4-OMe), and Phe(4-tBu); $Xaa^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or $Xaa^{13}$ is Pro.

In some embodiments, the C-terminal residue of any of the peptides described herein, e.g., Formula (IV) (including any of IV-A, IV-B, IV-C, IV-D, IV-E, IV-F, IV-G, IV-H, and IV-I) or Formula (V) (including V-A), Formula (VI), Formula (A), Formula (B), Formula (C), or Formula (D) further comprises a linker moiety selected from the group consisting of DIG, PEG13, PEG25, PEG1K, PEG2K, PEG3.4K, PEG4K, PEG5K, IDA, IDA-Palm, IDA-Boc, IDA-Isovaleric acid, Triazine, Triazine-Boc, Isophthalic acid, 1,3-phenylenediacetic acid, 1,4-phenylenediacetic acid, glutaric acid, Azelaic acid, Pimelic acid, Dodecanedioic acid, suitable aliphatics, aromatics, heteroaromatics, and polyethylene glycol based linkers having a molecular weight from approximately 400 Da to approximately 40,000 Da.

Some embodiments of the present invention further include a peptide monomer, wherein the peptide monomer comprises, consists essentially of, or consists of an amino acid sequence represented by at least one of the sequences shown in the accompanying figures and tables.

In addition, the present invention includes compounds comprising, consisting essentially of, or consisting of any of the amino acid sequences described herein or shown in any of the accompanying figures. In certain embodiments, the peptides further comprise one or more modifying group and/or linker. In certain embodiments, one or both of the N- or C-terminus of the peptides is modified. In particular embodiments, the N-terminus is acylated. In some embodiments, the N-terminus is acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In particular embodiments, the C-terminus comprises a free amine, e.g., NH$_2$. In particular embodiments, the peptide comprises an intramolecular linkage, e.g., between $Xaa^4$ and $Xaa^{10}$ of Formula (IV) (or $Xaa^1$ and $Xaa^7$ in Formulas (V), (VI), (A), (B), (C), and (D). The present invention also includes compounds having any of the structures described herein or shown in any of the accompanying figures.

In certain embodiments, the present invention provides a peptide of Formula (VI):

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10}\text{(SEQ ID NO: 346)}$$ (Formula (VI))

or a pharmaceutically acceptable salt thereof, comprising a disulfide bond between $Xaa^1$ and $Xaa^7$, and wherein:

Xaa¹ is Pen;
Xaa² is N-Me-Arg;
Xaa³ is Ser;
Xaa⁴ is Asp;
Xaa⁵ is Thr;
Xaa⁶ is Leu;
Xaa⁷ is Pen;
Xaa⁸ is Trp;
Xaa⁹ is absent or selected from the group consisting of: Glu, D-Glu, β-homoGlu; and
Xaa¹⁰ is any amino acid.

In particular embodiments, Xaa¹ and Xaa⁷ are linked via a disulfide bond.

In particular embodiments, Xaa¹⁰ is selected from the group consisting of D-Lys, N-Me-Lys, and D-N-Me-Lys.

In particular embodiments, Xaa⁹ is present.

In particular embodiments of Formula (VI), Xaa¹ is acylated. In some embodiments, Xaa¹ is acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are use as spacer for acylations. In particular embodiments of Formula (VI), Xaa¹⁰ comprises NH₂ or OH.

In one embodiment, a peptide monomer compound or a peptide dimer compound of the present invention comprises a peptide molecule of Formula (D):

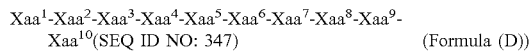

Xaa¹-Xaa²-Xaa³-Xaa⁴-Xaa⁵-Xaa⁶-Xaa⁷-Xaa⁸-Xaa⁹-Xaa¹⁰(SEQ ID NO: 347)  (Formula (D))

or a pharmaceutically acceptable salt thereof, wherein
Xaa¹ is Cys or Pen;
Xaa² is N-methyl-Arg;
Xaa³ is Ser;
Xaa⁴ is Asp;
Xaa⁵ is Thr;
Xaa⁶ is Leu or Nle;
Xaa⁷ is Cys, Pen or D-Pen;
Xaa⁸ is Trp, Tic, Bip, 1-Nal, 2-Nal, Phe(4-tBu), or Phe(4-COOH);
Xaa⁹ is Glu, β-homoGlu, D-Glu, or Glu(OMe); and
Xaa¹⁰ is any amino acid,
wherein the peptide molecule comprises a bond between Xaa¹ and Xaa⁷.

In particular embodiments, of Formula (D), one or both of Xaa¹ and Xaa⁷ are Pen.

In particular embodiments of Formula (D), Xaa⁷ is Cys or Pen.

In particular embodiments of Formula (D), Xaa¹⁰ is D-Lys or N-Me-Lys.

In certain embodiments of Formula (D), Xaa¹⁰ or the C-terminus of the peptide comprises an NH₂ or an OH. In certain embodiments, a free amine in the C-terminal amino acid is capped, e.g., with an acetyl group. In particular embodiments of Formula (D), Xaa¹ is acylated. In some embodiments, Xaa¹ is acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In particular embodiments of Formula (D), Xaa¹⁰ comprises NH₂ or OH.

In alternative embodiments any of the peptide monomer compounds herein, including peptide monomer compounds of any one of Formula (IV), including (IV-A)-(IV-J), Formula (V), Formula (VI), Formula (C) and Formula (D), the C-terminal amino acid (e.g., Xaa¹⁴ or Xaa¹⁰) is selected from the group consisting of: any amino acid with an amine side chain, Lys, D-Lys, N-Me-Lys, D-N-Me-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu and HomoSer, Asp, Glu, homoGlu, D-Asp, D-Glu, D-homoGlu, N-Me-Glu, N-Me-Asp, N-Me-D-Glu, and N-Me-D-Asp. In other alternative embodiments of peptide monomer compounds herein, including peptide monomer compounds of any one of Formula (IV), including (IV-A)-(IV-J), Formula (V), Formula (VI), Formula (C) and Formula (D), the C-terminal amino acid (e.g., Xaa¹⁴ or Xaa¹⁰), the C-terminal residue is selected from the group consisting of: Asp, Glu, homoGlu, D-Asp, D-Glu, D-homoGlu, N-Me-Glu, N-Me-Asp, N-Me-D-Glu, and N-Me-D-Asp.

In further embodiments, the present invention includes any of the peptide monomers comprising an amino acid sequence or having a structure shown in the Examples or in any of the accompanying figures. In certain embodiments, these sequences may include different amino acid residues at the positions that form intramolecular bonds, e.g., Xaa⁴ and Xaa¹⁰ of Formula (IV), including any of those described herein to allow the formation of particular types of bonds, e.g., disulfide, lactam, olefin, triazole (e.g., Click chemistry), selenother, or diselenide bonds.

The present invention further comprises peptides comprising or consisting of any of the amino acid sequences described herein, e.g. any of the amino acid sequences shown in the accompanying tables or figures, but absent any linker. In addition it includes such petides having natural N-termini and/or C-termini, N-terminal and/or C-terminal modifications depicted herein, or other N-terminal or C-terminal modifications.

In certain embodiments, Xaa¹⁰ or the C-terminus of the peptide comprises an NH₂ or an OH. In certain embodiments, a free amine in the C-terminal amino acid is capped, e.g., with an acetyl group. In particular embodiments of Formula (B), Xaa¹ is acylated. In some embodiments, Xaa¹ is acylated with an acylating organic compound selected from the group consisting of 2-me-Trifluorobutyl, Trifluoropentyl, Acetyl, Octonyl, Butyl, Pentyl, Hexyl, Palmityl, Lauryl, Oleoyl, and Lauryl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, small PEG (e.g., PEG4-PEG13) is used as spacer before acylations. In some instances Glu, IsoGlu, or Asp are used as spacer for acylations. In particular embodiments of Formula (B), Xaa¹⁰ comprises NH₂ or OH. In particular embodiments of dimers of Formula (B), the two monomer subunits are linked via their respective C-termini via a linker moiety, e.g., DIG. In various embodiment, the peptide may further comprise one or more linkers or other modifying groups, e.g., attached to the C- and/or N-terminus.

In further embodiments, the present invention includes any of the peptide monomers comprising an amino acid sequence or having a structure shown in any of the Examples and accompanying figures. In certain embodiments, these sequences may include different amino acid residues at the positions that form intramolecular bonds, e.g., Xaa$^4$ and Xaa$^{10}$ of Formula (IV), inlcuding any of those described herein to allow the formation of particular types of bonds, e.g., disulfide, lactam, olefin, triazole (e.g., Click chemistry), selenother, or diselenide bonds.

In further embodiments, Xaa$^4$ is selected from the group consisting of Cys or Pen. In some embodiments, Xaa$^{10}$ is selected from the group consisting of Cys or Pen. In particular embodiments, Xaa$^5$ is selected from the group consisting of Phe(4-guanidino), Phe(4-NH$_2$), N-Me-homoArg, homoArg, Tyr and His; Xaa$^8$ is selected from the group consisting of Leu, homoLeu, Nle and Val; Xaa$^9$ is CPA or Aoc; Xaa$^{10}$ is homoCys; Xaa$^{11}$ is selected from the group consisting of Tic, Phe(2-carbomyl), Phe(3-carbomyl), Phe (4-carbomyl), Phe(4-COOH), Phe(4-OMe), and Phe(4-tBu); Xaa$^{12}$ is selected from the group consisting of Aic, Gln, Cit, Glu(OMe), D-His, Tic, Phe(3-COOH), D-Arg, Bip, D-Trp, Phe, D-Phe, D-Val, D-Thr, D-1-Nal, D-2-Nal, Thr, Val; or Xaa$^{13}$ is Pro.

In addition, it is understood that any of the specific features described for any of the compounds or Formulas described herein may be incorporated to any other compound or Formula described herein. In addition, any of the compositions or methods described herein may be practiced using any of the compounds or compounds of any of the Formulas described herein.

In particular embodiments of any of the various formulas described herein, peptides having the same structure or sequence as disclosed in PCT/US2013/064439, PCT/US2014/032391 or PCT/US2014/032392 are excluded.

In certain embodiments, the present invention includes a peptide comprising any of the amino acid sequences present in any of the peptides described herein. In particular embodiments, the present invention includes a peptide comprising or consisting of one of the following amino acid sequences. In particular embodiments, the present invention includes a peptide monomer compound comprising or consisting of one of the following amino acid sequences. In particular embodiments, the present invention includes a peptide dimer compound comprising or consisting of monomer subunits comprising one of the following amino acid sequences:

```
                                                   (SEQ ID NO: 219)
Pen-(N-Me-Arg)-Ser-Asp-Thr-Leu-Pen-Trp-(β-homoGlu)-(D-Lys);

(SEQ ID NO: 220)
Pen-(N-Me-Arg)-Ser-Asp-Thr-Leu-Pen-(Phe(4-COOH)-(β-homoGlu)-(D-Lys);

(SEQ ID NO: 221)
Pen-(N-Me-Arg)-Ser-Asp-Thr-Leu-Pen-Trp-Glu-(N-Me-Lys);

(SEQ ID NO: 222)
Pen-(N-Me-Arg)-Ser-Asp-Thr-Leu-Pen-2-Nal-(β-homoGlu)-(D-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 224)
Pen-(N-Me-Arg)-Ser-Asp-Thr-Leu-Pen-2-Nal-Glu-(N-Me-Lys);

(SEQ ID NO: 225)
Pen-(N-Me-Arg)-Ser-Asp-Thr-Leu-Pen-Phe(4-tBu)-(β-homoGlu)-(D-Lys);

(SEQ ID NO: 226)
Pen-(N-Me-Arg)-Ser-Asp-Thr-Leu-Pen-Phe(4-tBu)-(β-homoGlu)-(N-Me-Lys);

(SEQ ID NO: 227)
Pen-(N-Me-Arg)-Ser-Asp-Thr-Leu-Pen-Trp-(β-homoGlu)-(N-Me-Lys);

(SEQ ID NO: 228)
Pen-(N-Me-Arg)-Ser-Asp-Thr-Leu-Pen-2-Nal-(β-homoGlu)-(N-Me-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 229)
Pen-(N-Me-Arg)-Ser-Asp-Thr-Leu-Pen-1-Nal-(β-homoGlu)-(N-Me-Lys);

(SEQ ID NO: 219)
Pen-(N-Me-Arg)-Ser-Asp-Thr-Leu-Pen-Trp-(β-homoGlu)-(D-Lys);
or
                                                   (SEQ ID NO: 230)
Pen-(N-Me-Arg)-Ser-Asp-Thr-Leu-Pen-Trp-Glu-(N-Me-D-Lys).
```

In certain embodiments, any of the peptides of the invention comprise 10-35, 10-30, 10-25, 10-20 or 10-15 amino acids. In particular embodiments, the Pen residues within the peptide are linked via a disulfide bond.

In certain embodiments, the present invention includes a peptide monomer compound comprising a peptide comprising any of the following sequences, wherein in certain embodiments the peptide monomer compound further comprises an N-terminal Ac and/or a C-terminal NH$_2$ or OH.:

```
                                                   (SEQ ID NO: 280)
Pen-(N-Me-Arg)-Ser-Asp-Thr-Leu-Pen-Trp-(β-homoGlu);

(SEQ ID NO: 275)
Pen-(N-Me-Arg)-Ser-Asp-Thr-Leu-Pen-(Phe-(4-COOH)-
(β-homoGlu);
```

Pen-(N-Me-Arg)-Ser-Asp-Thr-Leu-Pen-Trp-Glu; (SEQ ID NO: 281)

Pen-(N-Me-Arg)-Ser-Asp-Thr-Leu-Pen-2-Nal-(β-homoGlu); (SEQ ID NO: 282)

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-2-Nal-Glu; (SEQ ID NO: 284)

Pen-(N-Me-Arg)-Ser-Asp-Thr-Leu-Pen-Phe(4-tBu)-(β-homoGlu); (SEQ ID NO: 285)

Pen-(N-Me-Arg)-Ser-Asp-Thr-Leu-Pen-Phe(4-tBu)-(β-homoGlu); (SEQ ID NO: 285)

Pen-(N-Me-Arg)-Ser-Asp-Thr-Leu-Pen-Trp-(β-homoGlu); (SEQ ID NO: 280)

Pen-(N-Me-Arg)-Ser-Asp-Thr-Leu-Pen-2-Nal-(β-homoGlu); (SEQ ID NO: 282)

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-1-Nal-(β-homoGlu); (SEQ ID NO: 283)

Pen-(N-Me-Arg)-Ser-Asp-Thr-Leu-Pen-Trp-(β-homoGlu); (SEQ ID NO: 280)
or

Pen-(N-Me-Arg)-Ser-Asp-Thr-Leu-Pen-Trp-Glu. (SEQ ID NO: 281)

In particular embodiments, the Pen residues within a peptide monomer compound are linked via a disulfide bond.

Peptide Structure and Biological Activity

The present invention provides various novel antagonist peptides. These compounds have been tested to more clearly characterize the increased affinity for α4β7 binding, increased selectivity against α4β1, and increased stability in simulated intestinal fluid (SIF). These novel antagonist molecules demonstrate high binding affinity with α4β7, thereby preventing binding between α4β7 and the MAdCAM ligand. Accordingly, these antagonist peptides have shown to be effective in eliminating and/or reducing the inflammation process in various experiments.

The present invention thus provides various monomer and dimer peptide compounds which bind or associate with the α4β7 integrin, in serum and SIF, to disrupt or block binding between α4β7 and the MAdCAM ligand. The various peptide compounds of the invention may be constructed solely of natural amino acids. Alternatively, the peptide compounds may include non-natural amino acids including, but not limited to, modified amino acids. Modified amino acids include natural amino acids which have been chemically modified to include a group, groups, or chemical moiety not naturally present on the amino acid. The peptide compounds of the invention may additionally include D-amino acids. Still further, the peptide compounds of the invention may include amino acid analogs.

In certain embodiments, peptide molecules of the present invention inhibit or reduced binding between between α4β7 and the MAdCAM ligand. In certain embodiments, a peptide of the present invention reduces binding of α4β7 and the MAdCAM ligand by at least 20%, at least 30%, at least 40%, at least 50%, at least 60%, at least 70%, at least 80%, or at least 90% as compared to a negative control peptide. Methods of determining binding are known in the art and include ELISA assays, for example.

In certain embodiments, a peptide molecule of the present invention has an IC50 of <500 nM, <250 nM, <100 nM, <50 nM, <25 nM, <10 nM, <5 nM, <3 nM, or <2 nM, e.g., in binding to α4β7 or inhibiting α4β7 from binding its receptor. Methods of determining activity are known in the art and include any of those described in the accompanying Examples.

Certain peptide dimer compound and peptide monomer compounds, e.g., disulfide-containing dimers and monomers, have been shown to be gastrointestinal stable and provide high levels of specificity and affinity for the α437 integrin. Some embodiments of the present invention provide a peptide monomer compound or peptide dimer compound having a half-life of greater than 60 minutes when exposed to simulated intestinal fluids (SIF). Some implementations further provide a peptide monomer compound or peptide dimer compound having a half-life from approximately 1 minute to approximately 60 minutes in SIF. Some embodiments of the present invention provide a peptide molecule comprising a half-life of greater than 180 minutes when exposed to SIF. Some implementations further provide a peptide molecule comprising a half-life from approximately 60 minutes to approximately 180 minutes in SIF. Similarly, these peptides are stable under reduced conditions and, in certain embodiments, have half-life >120 min when tested in DTT (Dithiothreitol) assay.

In certain embodiments, a peptide monomer or dimer of the present invention has increased stability, increased gastrointestinal stability, increased stability in stimulated intestinal fluid (SIF), or increased stability in simulated gastric fluid (SGF), as compared to a control peptide. In particular embodiments, a control peptide is a peptide having the identical or a highly related amino acid sequence (e.g., >90% sequence identity) as the peptide, but which does not form a cyclized structure, e.g., through a disulfide or lactam bond. In particular embodiments, a control peptide is a peptide having the identical or a highly related amino acid sequence (e.g., >90% sequence identity) as the peptide, but which forms a disulfide bond through two Cys residues (e.g., as opposed to two Pen residues). In particular embodiments, the only difference between the peptide and the control peptide is that the peptide comprises one or more amino acid substitutions that introduce one or more amino acid residues into the peptide, wherein the introduced residue(s) forms a disulfide or lactam bond with another residue in the peptide.

Methods of determining the stability of a peptide are known in the art. In certain embodiments, the stability of a peptide is determined using an SIF assay, an SGF assay, A DTT assay, or a Cys/CysS assay, e.g., as described in the accompanying Examples. In particular embodiments, a peptide of the present invention has a half-life under a given set of conditions (e.g., temperature) of greater than 1 minute, greater than 10 minutes, greater than 20 minutes, greater than 30 minutes, greater than 60 minutes, greater than 90 minutes, greater than 120 minutes, greater than 3 hours, or greater than four hours when exposed to SIF or SGF. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of a peptide of the present invention is determined by incubating the peptide with pre-warmed human serum (Sigma) at 37° C. Samples are taken at various time points, typically up to 24 hours, and the stability of the sample is analyzed by separating the peptide monomer or dimer from the serum proteins and then analyzing for the presence of the peptide of interest using LC-MS.

In some embodiments, a peptide of the present invention exhibits improved solubility or improved aggregation characteristics as compared to a control peptide. Solubility may be determined via any suitable method known in the art. In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a control peptide.

In some embodiments, the peptides of the present invention have less degradation (i.e., more degradation stability), e.g., greater than or about 10% less, greater than or about 20% less, greater than or about 30% less, greater than or about 40% less, or greater than or about 50% less degradation than a control peptide. In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent peptide monomer or dimer molecules with enhanced shelf lives.

In certain embodiments, peptides of the present invention inhibit or reduce α4β7-mediated inflammation. In related embodiments, peptides of the present invention inhibit or reduce α4β7-mediated secretion of one or more cytokines. Methods of determining inhibition of cytokine secretion and inhibition of signaling molecules are known in the art.

In certain embodiments, peptides of the present invention demonstrate increased binding selectivity. In certain instances, peptides of the present invention binds to α4β7 with at least a two-fold, three-fold, five-fold, or ten-fold greater affinity than the peptides bind to α4β1.

In certain embodiments, peptide antagonists show limited systemic exposure and/or GI-restricted localization following oral administration. In particular embodiments, greater than 50%, greater than 60%, greater than 70%, greater than 80%, or greater than 90% of orally administered peptide inhibitor is localized to gastrointestinal organs and tissues. In particular embodiments, blood plasma levels of orally administered peptide inhibitor are less than 20%, less than 10%, less than 5%, less than 2%, less than 1% or less than 0.5% the levels of peptide inhibitor found in the small intestine, colon, or proximal colon.

In certain embodiments, peptide antagonists of the present invention are efficacious in the treatment of colitis, e.g., ulcerative colitis, and have an IC50 for α4β7 of less than 2 nm or less than 1 nM as determined by ELISA or T cell assay, have a half-life of greater than 4 h, greater than 5 h, greater than 6 h, greater than 12 h or greater than 24 h in simulated intestinal fluid (SIF), rat intestingal fluid (RIW), human intestinal fluid (HIF), colonic wash (CW), intestinal mucosal homogenate (IMH), colonic mucosal homogenate (CMH), simulated gastric fluid (SGF), plasma, Hu S9 or RL S9. In particular embodiments, they are stable after 12 h, 24 h, or 48 h incubation in anaerobic cultures of *C. difficile, B. fragilis, E. coli, B. bifidum*, and *L. acidophilus*. In particular embodiments, they show no significant antimicrobial activity against intestinal bacteria grown under anaerobic conditions. In particular embodiments, upon oral administration, the peptide antagonists show minimal exposure in plasma/urine, and exhibit approximately equal exposure in the GI of normal and colitis-diseased animals.

α4β7 integrin present on gut-specific homing lymphocytes is a specific and clinically validated target for IBD. The recently approved α4β7 antagonist antibody drug, Entyvio (vedolizumab) has been described as the future front-line targeted therapy because of its combined efficacy and safety. The present invention provides novel, potent, target specific and orally stable peptides against this integrin target, including selective oral peptide antagonists of α4β7 integrin with limited systemic exposure, and which are effective in blocking T cell homing, preventing mucosal damage in murine models of IBD, and engaging the integrin target as assessed by receptor occupancy in blood cells and in the gastrointestinal tissue. Certain peptides antagonists of the present invention, including Peptide X described in the accompanying examples, have comparable potency and selectivity to vedolizumab in a variety of in vitro cell binding assays. However, the peptide antagonists of the present invention, including Peptide X, are distinguished as oral drugs and by their marked drug exposure in the small intestine and colon, with the potential for expanding the population of IBD patients being treated with targeted therapies.

The compounds of the present invention are peptide homo- or heterodimers formed by linking two subunit monomers at their C- or N-termini. Dimerization of the monomer subunits demonstrate increased potency over their non-dimerized, monomer analogs. Some peptide monomer and peptide dimer compounds of the present invention demonstrated further increased potency as a result of substituting various natural amino acyl residues with N-methylated analog residues. Further still, some peptide monomers and dimer compounds of the present invention comprise monomer subunits that undergo independent cyclization, whereby the cyclized structures demonstrate increased stability over their non-cyclized dimer analogs.

Referring now to Tables 3 and 4, charts are provided which include various data illustrating increased stability for various non-limiting peptide molecules in accordance with the instant invention. Simulated Intestinal Fluid (SIF) Stability assays were performed for the majority of the instant peptide molecules. A selective sampling of these results is provided in Tables 3 and 4.

According to the protocols discussed herein, applicant successfully synthesized and purified integrin antagonist peptide monomer molecules and successfully synthesized, purified, and dimerized the majority of the integrin antagonist peptide dimer molecules shown in the accompanying figures and tables. For those peptides wherein data is not shown, it is expected that they will have an IC50<100 nM in α4β7 ELISA or cell adhesion assays.

Further, substitutions at arginine with N-Me-Arg increased half-life substantially in SIF. In some embodiments, substitution of Cys with Penicillamine (Pen) increased stability significantly in simulated intestinal fluids (SIF). The substitution of Cys with Pen also increased stability under reduced conditions (DTT) indicating improved gastric stability.

Referring now to Tables 3 and 4, charts are provided which include various data illustrating increased potency, selectivity and/or stability for various non-limiting sample peptide dimer molecules in accordance with the instant invention. The peptides also demonstrate low efficacy for α4β1 when compared to α4β7, thereby indicating selectivity against α4β7.

Dimerization of the monomer peptides subunits generally demonstrated increased affinity for α4β7 and/or decreased affinity for α4β1 leading to increased selectivity against α4β1, as compared to the monomer disulfide subunit peptides.

Upon C- and N-terminal dimerization, a significant improvement in potency for α4β7 was also frequently observed. In addition, dimerization also lead to either decrease of potency for a4β1 or no significant change in potency leading to increased selectivity for α4β7 in ELISA and cell adhesion assays.

When Arg is replaced with N-Me-Arg, a significant improvement in potency for α4β7 was shown in both ELISA and cell adhesion assays. N(alpha)methylation further demonstrated increased molecular stability. One having skill in the art will appreciate that methylated isosteres of arginine may further demonstrate similar increases in potency and/or stability.

The invention provides a method for stabilizing a peptide dimer compound or peptide monomer compound, the method comprising a step for substituting $Xaa^4$ and $Xaa^{10}$ with an amino acid residue selected from the group consisting of Cys and Pen, wherein $Xaa^4$ and $Xaa^{10}$ form a cyclized structure through a disulfide bond.

One embodiment includes a method for stabilizing a peptide dimer compound or peptide monomer compound, by substituting $Xaa^4$ and $Xaa^{10}$ (or $Xaa^1$ and $Xaa^7$ in Formulas (II), (III), (IV), (V), (VI), (A), (B), (C), or (D)) with compatible amino acid residues that are capable of forming a cyclized structure through at least one of disulfide bond or lactam bond. In certain embodiments, the compatible amino acids are selected from the group consisting of Cys and Pen, and $Xaa^4$ and $Xaa^{10}$ form a cyclized structure through a disulfide bond. In certain embodiments, $Xaa^4$ is selected from the group consisting of Lys, HLys, Orn, Dap, and Dab, $Xaa^{10}$ is selected from the group consisting of Asp, Glu, HGlu, β-Asp, and β-Glu, and $Xaa^4$ and $Xaa^{10}$ are cyclized through a lactam bond.

Certain embodiments include a method for increasing SIF stability of a peptide dimer or peptide monomer compound of the present invention, comprising a step for substituting N-Me-Arg for one or more unmethylated arginine residues. Other embodiments include a method for increasing SIF stability of a peptide monomer compound of the present invention, comprising a step for substituting Pen for one or more cysteine residues.

Further embodiments include method for increasing redox stability of a peptide dimer compound or peptide monomer compound according to the present invention, comprising a step for substituting Pen for one or more cysteine residues.

Methods of Treatment and Pharmaceutical Compositions

As discussed above, integrins are heterodimers that function as cell adhesion molecules. The α4 integrins, α4β1 and α4β7, play essential roles in lymphocyte migration throughout the gastrointestinal tract. They are expressed on most leukocytes, including B and T lymphocytes, monocytes, and dendritic cells, where they mediate cell adhesion via binding to their respective primary ligands, namely vascular cell adhesion molecule (VCAM) and mucosal addressin cell adhesion molecule (MAdCAM). VCAM and MAdCAM differ in binding specificity, in that VCAM binds both α4β1 and α4β7, while MAdCAM is highly specific for α4β7.

Differences in the expression profiles of VCAM and MAdCAM provide the most convincing evidence of their role in inflammatory diseases. Both are constitutively expressed in the gut; however, VCAM expression extends into peripheral organs, while MAdCAM expression is confined to organs of the gastrointestinal tract. In addition, elevated MAdCAM expression in the gut has now been correlated with several gut-associated inflammatory diseases, including Crohn's disease, ulcerative colitis, and hepatitis C.

The compounds of the invention, including but not limited to those specified in the accompanying examples, possess integrin-antagonist activity. In one embodiment, the condition or medical indication comprises at least one of Inflammatory Bowel Disease (IBD) (including adult IBD, pediatric IBD and adolescent IBD), ulcerative colitis, Crohn's disease, Celiac disease (e.g., nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease (GVDH) (including intestinal GVDH), colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease. In addition, these compounds may be useful in the prevention or reversal of these diseases when used in combination with currently available therapies, medical procedures, and therapeutic agents.

The compounds of the invention may be used in combination with other compositions and procedures for the treatment of disease. Additionally, the compounds of the present invention may be combined with pharmaceutically acceptable excipients, carriers and diluent, and optionally sustained-release matrices, such as biodegradable polymers, to form therapeutic compositions.

In some embodiments, the present invention provides a method for treating an individual afflicted with a condition or indication characterized by integrin binding, wherein the method comprises administering to the individual an integrin antagonist dimer molecule according to Formula (I) (including any of I-A, I-B, I-C, I-D, I-E, I-F, I-G, I-H, I-I, and I-J), Formula (II), Formula (III), Formula (A), Formula (B), Formula (C), Formula (D), Formula (S), Formula (X), or Formula (H) or an integrin antagonist monomer molecule according to Formula (IV) (including any of IV-A, IV-B, IV-C, IV-D, IV-E, IV-F, IV-G, IV-H, IV-I and IV-J), Formula (V) (including V-A), Formula (VI), Formula (A), Formula (B), Formula (C), or Formula (D), or any of the compounds described herein.

In one embodiment, a method is provided for treating an individual afflicted with a condition or indication characterized by inappropriate trafficking of cells expressing α4β7 to tissues comprising cells expressing MAdCAM, comprising administering to the individual an α4β7-antagonist dimer molecule according to at least one of Formula (I) Formula (II), Formula (III), Formula (A), Formula (B), Formula (C), Formula (D), Formula (S), Formula (X), or Formula (H), or an α4β7-antagonist monomer molecule according to at least one of Formula (IV) Formula (V), Formula (VI), Formula (A), Formula (B), Formula (C), or Formula (D), or any of the compounds described herein, in an amount sufficient to inhibit (partially or fully) the trafficking of cells expressing α4β7 to tissues comprising cells expressing MAdCAM.

In related embodiments, the present invention provides methods for inhibiting adhesion of CD4+ memory T cells to MAdCAM-1 and/or primary leukocytes in blood, comprising providing to a subject in need thereof an effective amount of a peptide dimer compound or peptide monomer compound of the present invention. The present invention further provides methods of selectively inhibiting adhesion of CD4$^+$ memory T cells to tissues expressing MAdCAM-1 in the GI tract, or inhibiting infiltration of α4β7+ cells into the small intestine and the colon (e.g., the distal colon), comprising providing to a subject in need thereof an effective amount of a peptide dimer compound or peptide monomer compound of the present invention.

In another embodiment, the present invention provides a method of inhibiting binding of MAdCAM-1 to α4β7 integrin, comprising contacting the MAdCAM-1 with an integrin antagonist of the present invention. Various embodiments of methods of the present invention may be carried out in vitro, ex vivo, or in vivo. In particular embodiments, exposure of the administered peptide antagonist in GI tissues is at least 10-fold, at least 20-fold, at least 50-fold, or at least 100-fold greater than the exposure in the blood.

In further related embodiments, the present invention provides a method for reducing α4β7+ T cells in the GI tract, e.g., in MLN, isolated lymphoid follicles, and/or Peyers Patches, comprising providing to a subject in need thereof an effective amount of a peptide dimer compound or peptide monomer compound of the present invention. In particular embodiments, the method also causes concomitant increases in α4β7+ T cells in the spleen and/or blood.

In a further related embodiment, the present invention provides a method for increasing receptor occupancy of α4β7+ leukocytes, including memory T cells and/or increasing the percentage of circulating α4β7+ memory T cells in blood, comprising providing to a subject in need thereof an effective amount of a peptide dimer compound or peptide monomer compound of the present invention.

In some embodiments, the present invention provides a method whereby a pharmaceutical composition comprising an integrin antagonist dimer molecule according to Formula (I) (including any of I-A, I-B, I-C, I-D, I-E, I-F, I-G, I-H, I-I, and I-J), Formula (II) (including II-A), Formula (III), Formula (A), Formula (B), Formula (C), Formula (D), Formula (S), Formula (X), Formula (H), or an integrin antagonist monomer molecule according to Formula (IV) (including any of IV-A, IV-B, IV-C, IV-D, IV-E, IV-F, IV-G, IV-H, IV-I, and IV-J), Formula (V) (including V-A), Formula (VI), Formula (A), Formula (B), Formula (C), or Formula (D), or any of the compounds described herein, is administered to a subject as a first treatment. In another embodiment, the method further comprises administering to the subject a second treatment. In another embodiment, the second treatment is administered to the subject before and/or simultaneously with and/or after the pharmaceutical composition is administered to the subject. In other embodiment, the second treatment comprises an anti-inflammatory agent. In another embodiment, the second pharmaceutical composition comprises an agent selected from the group consisting of non-steroidal anti-inflammatory drugs, steroids, and immune modulating agents. In another embodiment, the method comprises administering to the subject a third treatment.

In one embodiment, a method is provided for treating an individual afflicted with a condition or indication characterized by α4β7 integrin binding, wherein the method comprises administering to the individual an effective amount of a peptide dimer compound or peptide monomer compound of the invention, e.g., an α4β7 integrin antagonist dimer molecule containing subunits of Formula (I) (including any of I-A, I-B, I-C, I-D, I-E, I-F, I-G, I-H, I-I and I-J), Formula (II) (including II-A), Formula (III), Formula (A), Formula (B), Formula (C), Formula (D), Formula (S), Formula (X), or Formula (H), or any of the compounds described herein. In some instances, an α4β7 integrin antagonist dimer molecule having subunits selected from and corresponding to Formula (I), Formula (II) Formula (III), Formula (A), Formula (B), Formula (C), Formula (D), Formula (S), Formula (X), or Formula (H), or an α4β7 integrin antagonist monomer molecule according to Formula (IV) (including any of IV-A, IV-B, IV-C, IV-D, IV-E, IV-F, IV-G, IV-H, IV-I, and IV-J), Formula (V) (including V-A), Formula (VI), Formula (A), Formula (B), Formula (C), or Formula (D), or any of the compounds described herein, and having high specificity for α4β7 is administered to an individual as part of a therapeutic treatment for a condition or indication characterized by α4β7 integrin binding.

Yet another aspect of the present invention provides a composition for treating a subject in need of α4β7-specific antagonist therapy comprising providing to the subject a peptide dimer compound of Formula (I), or any other compound described herein or in the accompanying figures and tables, having high selectivity for α4β7 integrin in combination with a pharmaceutically acceptable carrier.

Yet another aspect of the present invention provides a composition for treating a subject in need of α4β7-specific antagonist therapy comprising providing to the subject a compound of Formula (I), or any other compound described herein or in the accompanying figures and tables, having high selectivity for α4β7 against α4β1 integrins in combination with a pharmaceutically acceptable carrier.

Yet another aspect of the present invention provides a composition for treating a subject in need of α4β7-specific antagonist therapy comprising providing to the subject a compound of Formula (I), or any other compound described herein or in the accompanying figures or tables, having high selectivity for α4β7 against αEβ7 integrins in combination with a pharmaceutically acceptable carrier.

Yet another aspect of the present invention provides a composition for treating a subject in need of α4β7-specific antagonist therapy comprising providing to the subject a compound of Formula (I), or any other compound described herein or in the accompanying figures or tables, having low selectivity for α4β7 against αEβ7 integrins in combination with a pharmaceutically acceptable carrier.

Yet another aspect of the present invention provides a method for treating a subject in need of integrin-antagonist therapy comprising providing to the subject a peptide of Formula (I), or any other compound described herein or in the accompanying figures and tables.

Some embodiments of the present invention further provide a method for treating an individual with an α4β7 integrin antagonist monomer or dimer molecule that is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

In some aspects, the invention provides a pharmaceutical composition for oral delivery. The various embodiments and monomer and dimer compositions of the instant invention may be prepared for oral administration according to any of the methods, techniques, and/or delivery vehicles described herein. Further, one having skill in the art will appreciate that the monomer and the dimer compositions of the instant invention may be modified or integrated into a system or delivery vehicle that is not disclosed herein, yet is well known in the art and compatible for use in oral delivery of small dimer peptide molecules.

Oral dosage forms or unit doses compatible for use with the monomer or dimer peptides of the present invention may include a mixture of peptide active drug components, and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of dimer peptide having subunits selected from and corresponding to Formula (I) (including any of I-A, I-B, I-C, I-D, I-E, I-F, I-G, I-H, I-I, and I-J), Formula (II) (including II-A), Formula (III), Formula (A), Formula (B), Formula (C), Formula (D), Formula (S), Formula (X), or Formula (H) or a monomer peptide selected from and corresponding to Formula (IV) (including any of IV-A, IV-B, IV-C, IV-D, IV-E, IV-F, IV-G, IV-H, IV-I, IV-J), Formula (V) (including V-A), Formula (VI), Formula (A), Formula (B), Formula (C), or Formula (D), or any of the compounds described herein, wherein the dosage form comprises at least one of a pill, a tablet, a capsule, a gel, a paste, a drink, a syrup, ointment, and suppository. In some instances, an oral dosage form is provided that is designed and configured to achieve delayed release of the peptide dimer in the subjects small intestine and/or colon In one embodiment, an oral pharmaceutical composition according to any of the formulas described herein comprises an enteric coating that is designed to delay release of the peptide in the small intestine. In at least some embodiments, a pharmaceutical composition is provided which comprises a peptide dimer compound having subunits selected from and corresponding to Formula (I) (including any of I-A, I-B, I-C, I-D, I-E, I-F, I-G, I-H, I-I, and I-J), Formula (II) (including II-A), Formula (III), Formula (A), or Formula (B), Formula (C), Formula (D), Formula (S), Formula (X), or Formula (H) or a monomer peptide selected from and corresponding to Formula (IV) (including any of IV-A, IV-B, IV-C, IV-D, IV-E, IV-F, IV-G, IV-H, IV-I, and IV-J), Formula (V) (including V-A), Formula (VI), Formula (A), Formula (B), Formula (C), or Formula (D), or any of the compounds described herein, and a protease inhibitor, such as aprotinin, in a delayed release pharmaceutical formulation. In some instances it is preferred that a pharmaceutical composition of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition having subunits selected from and corresponding to Formula (I) (including any of I-A, I-B, I-C, I-D, I-E, I-F, I-G, I-H, I-I and I-J), Formula (II) (including II-A), Formula (III), Formula (A), or Formula (B), Formula (C), Formula (D), Formula (S), Formula (X), or Formula (H) or a monomer peptide selected from and corresponding to Formula (IV) (including any of IV-A, IV-B, IV-C, IV-D, IV-E, IV-F, IV-G, IV-H, IV-I, IV-J), Formula (V) (including V-A), Formula (VI), Formula (A), Formula (B), Formula (C), or Formula (D), or any of the compounds described herein, is provided in an enteric coating, the enteric coating being designed to protect and release the pharmaceutical composition in a controlled manner within the subjects lower gastrointestinal system, and to avoid systemic side effects. In addition to enteric coatings, the monomer or dimer peptides of the instant invention may be encapsulated, coated, engaged or otherwise associated within any compatible oral drug delivery system or component. For example, in some embodiments a peptide of the present invention is provided in a lipid carrier system comprising at least one of polymeric hydrogels, nanoparticles, microspheres, micelles, and other lipid systems.

To overcome peptide degradation in the small intestine, some implementations of the present invention comprise a hydrogel polymer carrier system in which a peptide monomer or dimer in accordance with the present invention is contained, whereby the hydrogel polymer protect the peptide from proteolysis in the small intestine and/or colon. The peptides of the present invention may further be formulated for compatible use with a carrier system that is designed to increase the dissolution kinetics and enhance intestinal absorption of the peptides. These methods include the use of liposomes, micelles and nanoparticles to increase GI tract permeation of peptides.

Various bioresponsive systems may also be combined with one or more peptide monomers or dimers of the present invention to provide a pharmaceutical agent for oral delivery. In some embodiments, a peptide monomer or dimer of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a peptide monomer or dimer disclosed herein, wherein the surface of the peptide monomer or dimer is modified to comprise mucoadhesive properties through hydrogen bonds, polymers with linked mucins or/and hydrophobic interactions. These modified monomer or dimer molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the dimer peptide.

Other embodiments comprise a method for oral delivery of a dimer peptide having subunits selected from and corresponding to Formula (I) (including any of I-A, I-B, I-C, I-D, I-E, I-F, I-G, I-H, I-I, and I-J), Formula (II) (including II-A), Formula (III), Formula (A), or Formula (B), Formula (C), Formula (D), Formula (S), Formula (X), or Formula (H), or a monomer peptide selected from and corresponding to Formula (IV) (including any of IV-A, IV-B, IV-C, IV-D, IV-E, IV-F, IV-G, IV-H, IV-I and I-J), Formula (V) (including V-A), Formula (VI), Formula (A), Formula (B), Formula (C), or Formula (D), or any of the compounds described herein, wherein the dimer peptide is used in combination with permeation enhancers that promote the transport of the dimer peptides across the intestinal mucosa by increasing paracellular or transcellular permeation. For example, in one embodiment a permeation enhancer is combined with a dimer peptide having subunits selected from and corresponding to Formula (I) (including any of I-A, I-B, I-C, I-D, I-E, I-F, I-G, I-H, I-I, and I-J), Formula (II) (including II-A), Formula (III), Formula (A), or Formula (B), Formula (C), Formula (D), Formula (S), Formula (X), or Formula (H), or a monomer peptide selected from and corresponding to Formula (IV) (including any of IV-A, IV-B, IV-C, IV-D, IV-E, IV-F, IV-G, IV-H, IV-I, IV-J), Formula (V) (including V-A), Formula (VI), Formula (A), Formula (B), Formula (C), or Formula (D), or any of the compounds described herein, wherein the permeation enhancer comprises at least one of a long-chain fatty acid, a bile salt, an amphiphilic surfactant, and a chelating agent. In one embodiment, a permeation enhancer comprising sodium N-[hydroxybenzoyl)amino] caprylate is used to form a weak noncovalent association with the dimer peptide of the instant invention, wherein the permeation enhancer favors membrane transport and further dissociation once reaching the blood circulation. In another embodiment, a peptide dimer of the present invention is conjugated to oligoarginine, thereby increasing cellular penetration of the monomer or dimer peptides into various cell types. Further, in at least one embodiment a noncovalent bond is provided between a monomer or dimer peptide having subunits selected from and corresponding to Formula (I) (including any of I-A, I-B, I-C, I-D, I-E, I-F, I-G, I-H, I-I, I-J), Formula (II) (including II-A), Formula (III), Formula (A), or Formula (B), Formula (C), Formula (D), Formula (S), Formula (X), or Formula (H), or a monomer peptide selected from and corresponding to Formula (IV) (including any of IV-A, IV-B, IV-C, IV-D, IV-E, IV-F, IV-G, IV-H, IV-I, and IV-J), Formula (V) (including V-A), Formula (VI), Formula (A), Formula (B), Formula (C), or Formula (D), or any of the compounds described herein, and a permeation enhancer selected from the group consisting of a cyclodextrin (CD) and a dendrimer, wherein the permeation enhancer reduces peptide aggregation and increasing stability and solubility for the peptide molecule.

Particular embodiments include a method for treating a condition in a subject comprising administering a pharmaceutical composition comprising a peptide dimer compound or peptide monomer compound described herein to the subject, wherein the condition is treatable by reducing the activity (partially or fully) of $\alpha4\beta7$ in the subject. In certain embodiments, the subject is a human being. In certain embodiments, the condition is an inflammatory condition of the gastrointestinal system.

Other embodiments include a method for treating a human afflicted with a condition that is associated with a biological function $\alpha4\beta7$ and comprise administering to the individual a peptide dimer compound or peptide monomer compound described herein in an amount sufficient to inhibit (partially or fully) the biological function of $\alpha4\beta7$ in one or more tissues expressing MAdCAM. In one embodiment, the condition is an inflammatory bowel disease. In certain embodiments, the condition is selected from the group consisting of Inflammatory Bowel Disease (IBD) (including adult IBD, pediatric IBD and adolescent IBD), ulcerative colitis, Crohn's disease, Celiac disease (e.g., nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease (GVDH) (including intestinal GVDH), colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease.

In various embodiments of any of the methods of treatment described herein, the peptide dimer compound or peptide monomer compound is administered to the individual by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In particular embodiments, the $\alpha4\beta7$ integrin antagonist molecule comprises an increased half-life. In one embodiment, the increased half-life is at least one day in vitro or in vivo. In further embodiments, the increased half-life is equal to or greater than a period consistent with no more frequent than twice daily dosing in vivo, the $\alpha4\beta7$ integrin antagonist peptide dimer compound or peptide monomer compound comprises or is present in a pharmaceutical composition that is administered orally. In certain embodiments, the increased half-life is from approximately 12 hours to greater than 24 in vivo, and the α4β7 integrin antagonist peptide dimer compound or peptide monomer compound comprises or is present in a pharmaceutical composition that is administered parenterally. In certain embodiments, the increased half-life is from approximately 12 hours to greater than 24 hours in vivo, and the α4β7 integrin antagonist peptide monomer compound comprises or is present in a pharmaceutical preparation that is administered topically.

Related embodiments of the invention provide a method for treating an individual in need thereof with an α4β7 integrin antagonist monomer or dimer molecule having an increased half-life. In one aspect, the present invention provides an integrin antagonist monomer or dimer molecule having a half-life of at least several hours to one day in vitro or in vivo (e.g., when administered to a human subject) sufficient for daily (q.d.), twice daily (b.i.d.), or thrice daily (t.i.d.) dosing of a therapeutically effective amount. In another embodiment, the monomer or dimer molecule has a half-life of three days or longer sufficient for weekly (q.w.) dosing of a therapeutically effective amount. Further, in another embodiment the monomer or dimer molecule has a half-life of eight days or longer sufficient for bi-weekly (b.i.w.) or monthly dosing of a therapeutically effective amount. In another embodiment, the monomer or dimer molecule is derivatized or modified such that is has a longer half-life as compared to the underivatized or unmodified dimer molecule. In another embodiment, the monomer or dimer molecule contains one or more chemical modifications to increase serum half-life.

When used in at least one of the treatments or delivery systems described herein, a therapeutically effective amount of one of the compounds of the present invention may be employed in pure form or, where such forms exist, in pharmaceutically acceptable salt form. As used herein, a "therapeutically effective amount" of the compound of the invention is meant to describe a sufficient amount of the peptide monomer or dimer compound to treat an integrin-related disease, (for example, to reduce inflammation associated with IBD) at a desired benefit/risk ratio applicable to any medical treatment. It will be understood, however, that the total daily usage of the compounds and compositions of the present invention will be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the subject; d) the time of administration, route of administration, and rate of excretion of the specific compound employed; e) the duration of the treatment; f) drugs used in combination or coincidental with the specific compound employed, and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracistemally, intravaginally, intraperitoneally, intrarectally, topically (as by powders, ointments, drops, suppository, or transdermal patch), or buccally. The term "parenteral" as used herein refers to modes of administration which include intravenous, intramuscular, intraperitoneal, intrastemal, subcutaneous, intradermal and intraarticular injection and infusion.

Pharmaceutical compositions for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical lung administration, including those for inhalation and intranasal, may involve solutions and suspensions in aqueous and non-aqueous formulations and can be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids, including the phosphatidyl cholines (lecithins) and serines, both natural and synthetic. Methods to form liposomes are known in the art.

Total daily dose of the compositions of the invention to be administered to a human or other mammal host in single or divided doses may be in amounts, for example, from 0.0001 to 300 mg/kg body weight daily and more usually 1 to 300 mg/kg body weight.

Non-Invasive Detection of Intestinal Inflammation

The peptides of the invention may be used for detection, assessment and diagnosis of intestinal inflammation by microPET imaging using an orally stable compound described herein, and that is further labeled with at least one of a chelating group and a detectable label as part of a non-invasive diagnostic procedure. In one embodiment, an integrin antagonist monomer or dimer molecule is conjugated with a bifunctional chelator to provide an orally stable monomer or dimer molecule. In another embodiment, an integrin antagonist monomer or dimer molecule is radiolabeled to provide an orally stable monomer or dimer molecule. The orally stable, chelated or radiolabeled monomer or dimer molecule is then administered to a subject orally or rectally. In one embodiment, the orally stable monomer or dimer molecule is included in drinking water. Following uptake of the monomer or dimer molecules, microPET imaging may be used to visualize inflammation throughout the subject's bowels and digestive track.

Methods for Determining Receptor Occupancy and Integrin Expression

The peptides of the invention may be used for determining binding and $\alpha 4\beta 7$ integrin receptor occupancy of a peptide, e.g., on CD4 T cells, naïve CD4 T cells, or B cells. For example, receptor occupancy of blood cells may be determined using blood obtained from a subject (e.g., a mammal or human) having been administered a peptide dimer compound or peptide monomer compound of the present invention, e.g., when the compound was orally administered to the subject. Alternatively, receptor occupancy may be determined based on in vitro binding and competition of a peptide dimer compound or peptide monomer compound of the present invention.

In certain embodiments for FACS analysis, heparinized whole blood from animals *e.g., cyanos) is stained with each of two panels of antibodies to evaluate (1) the extent of $\alpha 4\beta 7$ receptor occupancy in samples treated with a peptide dimer compound or peptide monomer compound described herein; and (2) the abundance of circulating $\alpha 4\beta 7+$, $\alpha E\beta 7+$, and $\alpha 4\beta 7+\alpha E\beta 7+$ lymphocyte subsets. Receptor occupancy and integrin expression are assessed within memory CD4 T cells, naïve CD4 T cells, and B cells. To evaluate receptor occupancy, whole blood samples are first treated with 1 mM $MnCl_2$ to allow peptide binding, and then pre-incubated+/−1 uM unlabeled peptide to fully occupy (i.e., block) the $\alpha 4\beta 7$ receptor. Blocked and unblocked samples were stained with 1 nM Alexa 647-labeled peptide, followed by staining with antibodies against $\alpha 4\beta 7$, CD45, CD4, CD45RA, and CD19. Samples are processed to lyse erythrocytes and fix leukocytes, followed by staining with a second-step reagent (streptavidin-BV421) and wash steps. To assess integrin expression and cell subset abundance, whole blood samples are stained with antibodies against $\alpha 4$, $\beta 7$, and $\alpha E$, in addition to antibodies against CD45, CD4, CD45RA, and CD19. Samples are processed to lyse erythrocytes and fix leukocytes, followed by staining with a second-step reagent (streptavidin-BV421) and wash steps. The stained samples are analyzed by flow cytometry, collecting a constant sample volume to allow calculation of absolute cell counts.

In one embodiment for determining receptor occupancy, a blood sample obtained from a subject having been administered (e.g., orally) a peptide dimer compound or peptide monomer compound of the present invention is incubated with a detectably labeled version of the same peptide dimer compound or peptide monomer compound, under conditions and for a time sufficient to allow binding of the labeled peptide to cells within the blood sample. The samples are then stained with antibodies and/or other reagents that bind to $\alpha 4\beta 7$ integrin, and other markers of CD4 Tcells, naïve CD4 T cells and/or B cells. The samples are then processed to lyse erythrocytes and fix leukoctyes, stained with a second-step reagent, e.g., to allow antibody detection and/or cell sorting, washed, and analyzed by flow cytometry to determine the amount of competitor peptide binding to the CD4 Tcells, naïve CD4 T cells and/or B cells. The receptor occupancy of the peptide dimer compound or peptide monomer compound may be determined based upon the amount of labeled peptide detected bound to the cells, optionally further in view of the amount of $\alpha 4\beta 7$ detected on the cells.

In another embodiment for determining receptor occupancy, a blood sample obtained from a donor animal (e.g., a mammal or human not treated with the peptide) is incubated with an unlabeled peptide dimer compound or peptide monomer compound of the present invention, or with a negative control (such as buffer only or an unrelated peptide), under conditions and for a time sufficient to allow binding of the unlabeled peptide to cells within the blood sample. The samples are then stained with a detectably-labeled version of the same peptide dimer compound or peptide monomer compound of the present invention (under conditions and for a time sufficient to allow binding of the labeled peptide to cells within the blood sample), followed by staining with antibodies and/or other reagents that bind to $\alpha 4\beta 7$ integrin, and other markers of CD4 Tcells, naive CD4 T cells and/or B cells. The samples are then processed to lyse erythrocytes and fix leukoctyes, stained with a second-step reagent, e.g., to allow antibody detection and/or cell sorting, washed, and analyzed by flow cytometry to determine the amount of competitor peptide binding to the CD4 Tcells, naive CD4 T cells and/or B cells. The receptor occupancy of the test peptide may be determined based upon the amount of labeled peptide detected bound to the cells, optionally further in view of the amount of α4β7 detected on the cells.

In another embodiment for evaluating receptor occupancy of a test peptide, a blood sample is incubated with an unlabeled test peptide or a negative control (such as buffer only or an unrelated peptide), under conditions and for a time sufficient to allow binding of the test peptide to cells within the blood sample. The samples are then stained with a detectably-labeled peptide dimer compound or peptide monomer compound of the present invention (competitor peptide), followed by staining with antibodies and/or other reagents that bind to α4β7 integrin, and other markers of CD4 Tcells, naive CD4 T cells and/or B cells. The samples are then processed to lyse erythrocytes and fix leukoctyes, stained with a second-step reagent, e.g., to allow antibody detection and/or cell sorting, washed, and analyzed by flow cytometry to determine the amount of competitor peptide binding to the CD4 Tcells, naive CD4 T cells and/or B cells. The receptor occupancy of the test peptide may be determined based upon the amount of competitor peptide detected bound to the cells, further in view of the amount of α4β7 detected on the cells.

In one example, whole blood samples (e.g., mouse, rat or human blood) are first treated with 1 mM MnCl2 to allow test peptide binding, and then pre-incubated +/−1 uM unlabeled Peptide X to bind (i.e., block) the α4β7 receptor, or with no peptide or a negative control peptide (unblocked). Blocked and unblocked samples are stained with 1 nM Alexa 647-labeled Peptide X, followed by staining with antibodies against α4β7, CD45, CD4, CD45RA, and CD19. Samples are processed to lyse erythrocytes and fix leukocytes, followed by staining with a second-step reagent (streptavidin-BV421) and wash steps. All stained samples were analyzed by flow cytometry, collecting a constant sample volume to allow calculation of absolute cell counts.

To assess integrin expression and cell subset abundance, whole blood samples are stained with antibodies against α4, β7, and αE, in addition to antibodies against CD45, CD4, CD45RA, and CD19. Samples are processed to lyse erythrocytes and fix leukocytes, followed by staining with a second-step reagent (streptavidin-BV421) and wash steps. All stained samples were analyzed by flow cytometry, collecting a constant sample volume to allow calculation of absolute cell counts.

In particular embodiments, to prevent receptor internalization, cells are kept cold during all steps prior to fizzation, and incubations are performed at 4 degrees C. (except for red blood cell lysis).

Detailed description of one embodiment of the assay is described below.

MnCl$_2$ is added to each blood sample (about 100 uL) at a final concentration of about 1 mM; the sample is mixed and incubated at 4 degrees C. for 10-15 minutes.

Unlabeled peptide (or control) is added to the sample at a final concentration of luM or DMSO vehicle control (matching concentration of DMSO) to the appropriate blood samples, mixed, and incubated at 4 degrees C. for 60 minutes.

Labeled peptide is added at a final concentration of lnM to the appropriate blood samples mixed, and incubated at 4 degrees C. for 60 minutes.

Antibody staining cocktail is added to each blood sample, e.g., integrin a4/b7/ae cocktail including labeled antibodies that bind CD45 (C45 V500), CD4 (CD4 Ax700), CD45RA (CD45RA FITC), CD19 (C19 PE-CF$_{594}$), integrin α4 (integrin (a4 biotin), integrin J37 (integrin J37 PE), or integrin αE (integrin αE PE-Cy7); or receptor occupancy staining cocktail including CD45 V500, CD4 Ax700, CD45Ra FITc, CD19 PE-CF594, vedolizumab-biotin, and integrin αE PE-Cy7; mixed, and incubated at 4 degrees C. for 30 minutes.

Samples are then treated with a 10-volume excess of 1×FACS Lysing Solution (diluted from 10× stock) to lyse red blood cells, mixed thoroughly, and incubated at Room Temperature for 10 minutes. Samples are centrifuged at 400×g for 5 min, supernatant is removed, and cells are resuspended in PBS/BSA/MnCl2 to wash. Cells are centrifuged again similarly and supernatant removed; washing is repeated.

Cells are stained with Streptavidin BV421 at a final dilution of 1:1000 in PBS/BSA/MnCl$_2$, mixed thoroughly, and incubated at 4 degrees C. for 30 minutes.

Cells are washed twice with PBS/BSA/MnCl$_2$ as above, and then resuspended in PBS/BSA/MnCl$_2$ Samples are run on a flow cytometer, collecting a consistent sample volume across all samples to allow calculation of absolute event counts through FACs analysis. Receptor occupancy of the test peptide may be determined based on the relative amount of competitor peptide that binds to unblocked samples as compared to samples blocked with the test peptide.

In another specific example, heparinized whole blood from human donors is stained with each of two panels of antibodies to evaluate (1) the extent of α4β7 receptor occupancy in peptide-treated samples and (2) the abundance of circulating α4β7$^+$, αEβ7$^+$, and α4β7+αEβ7$^+$ lymphocyte subsets. Receptor occupancy and integrin expression are assessed within memory CD4 T cells, naïve CD4 T cells, and B cells.

To evaluate receptor occupancy, whole blood samples are first treated with 1 mM MnCl$_2$ to allow peptide binding and then pre-incubated +/−1 uM unlabeled peptide to fully occupy (i.e., block) the α4β7 receptor. Blocked and unblocked samples are stained with 1 nM Alexa 647-labeled peptide, followed by staining with antibodies against α4β7, CD45, CD4, CD45RA, and CD19. Samples are then processed to lyse erythrocytes and fix leukocytes, followed by staining with a second-step reagent (streptavidin-BV421) and wash steps.

To assess integrin expression and cell subset abundance, whole blood samples are stained with antibodies against α4, β7, and αE, in addition to antibodies against CD45, CD4, CD45RA, and CD19. Samples are then processed to lyse erythrocytes and fix leukocytes, followed by staining with a second-step reagent (streptavidin-BV421) and wash steps.

All stained samples are analyzed by flow cytometry, collecting a constant sample volume to allow calculation of absolute cell counts. In one, receptor occupancy is determined by determining an amount of labeled peptide that binds to the blood cells after the blood cells have been contacted with unlabeled peptide, and determining an amount of α4β7 present on the cells, wherein the difference between the amount of $^a$4β7 present on the cells and the amount bound by the labeled peptide represents receptor occupancy by the unlabeled peptide.

In certain embodiments, the present invention includes a labeled (e.g., detectably-labeled) compound or peptide described here, including but not limited to any of the peptide dimer compounds described herein e.g., peptide dimer compounds according to Formula (I) (including any of I-A, I-B, I-C, I-D, I-E, I-F, I-G, I-H, I-I, and I-J), Formula (II), Formula (III), Formula (A), Formula (B), Formula (C), Formula (D), Formula (S), Formula (X), or Formula (H), or any of the peptide monomer compounds described herein, e.g., peptide monomer compounds according to Formula (IV) (including any of IV-A, IV-B, IV-C, IV-D, IV-E, IV-F, IV-G, IV-H, IV-I and IV-J), Formula (V) (including V-A), Formula (VI), Formula (A), Formula (B), Formula (C), or Formula (D). In particular embodiments, the peptide compound or peptide is fluorescently labeled.

In certain embodiments, the present invention includes a detectably labeled peptide, peptide monomer compound or peptide dimer compound of the present invention, comprising any of the amino acid sequences present in any of the peptides described herein. In particular embodiments, the peptide compound or peptide is fluorescently labeled.

In particular embodiments, the present invention includes a peptide, peptide dimer compound, or peptide monomer compound comprising any of the following amino acid sequences:

```
                                                   (SEQ ID NO: 219)
Pen-(N-Me-Arg)-Ser-Asp-Thr-Leu-Pen-Trp-(β-homoGlu)-(D-Lys);

(SEQ ID NO: 220)
Pen-(N-Me-Arg)-Ser-Asp-Thr-Leu-Pen-(Phe-(4-COOH)-(β-homoGlu)-(D-Lys);

(SEQ ID NO: 221)
Pen-(N-Me-Arg)-Ser-Asp-Thr-Leu-Pen-Trp-Glu-(N-Me-Lys);

(SEQ ID NO: 222)
Pen-(N-Me-Arg)-Ser-Asp-Thr-Leu-Pen-2-Nal-(β-homoGlu)-(D-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 224)
Pen-(N-Me-Arg)-Ser-Asp-Thr-Leu-Pen-2-Nal-Glu-(N-Me-Lys);

(SEQ ID NO: 225)
Pen-(N-Me-Arg)-Ser-Asp-Thr-Leu-Pen-Phe(4-tBu)-(β-homoGlu)-(D-Lys);

(SEQ ID NO: 226)
Pen-(N-Me-Arg)-Ser-Asp-Thr-Leu-Pen-Phe(4-tBu)-(β-homoGlu)-(N-Me-Lys);

(SEQ ID NO: 227)
Pen-(N-Me-Arg)-Ser-Asp-Thr-Leu-Pen-Trp-(β-homoGlu)-(N-Me-Lys);

(SEQ ID NO: 228)
Pen-(N-Me-Arg)-Ser-Asp-Thr-Leu-Pen-2-Nal-(β-homoGlu)-(N-Me-Lys);

(SEQ ID NO: 223)
Pen-(N-Me-Arg)-Ser-Asp-Thr-Leu-Pen-1-Nal-(β-homoGlu)-(D-Lys);

(SEQ ID NO: 229)
Pen-(N-Me-Arg)-Ser-Asp-Thr-Leu-Pen-1-Nal-(β-homoGlu)-(N-Me-Lys);

(SEQ ID NO: 295)
Pen-(N-Me-Arg)-Ser-Asp-Thr-Leu-Pen-Trp-(β-homoGlu)-(D-Lys);
or
                                                   (SEQ ID NO: 230)
Pen-(N-Me-Arg)-Ser-Asp-Thr-Leu-Pen-Trp-Glu-(N-Me-D-Lys),
``` wherein there is optionally a disulfide bond between the two Pen reisdues.

In particular embodiments, the peptide dimer compound comprises one of the following sequences or structures:

```
                                                   (SEQ ID NO: 296)
[Ac-Pen-(N-Me-Arg)-Ser-Asp-Thr-Leu-Pen-Trp-(β-homoGlu)-(D-Lys)]₂-DIG;

(SEQ ID NO: 297)
[Ac-Pen-(N-Me-Arg)-Ser-Asp-Thr-Leu-Pen-(Phe-(4-COOH)-(β-homoGlu)-(D-Lys)]₂-DIG;

(SEQ ID NO: 298)
[Ac-Pen-(N-Me-Arg)-Ser-Asp-Thr-Leu-Pen-Trp-Glu-(N-Me-Lys)]₂-DIG;

(SEQ ID NO: 299)
[Ac-Pen-(N-Me-Arg)-Ser-Asp-Thr-Leu-Pen-2-Nal-(β-homoGlu)-(D-Lys)]₂-DIG;

(SEQ ID NO: 300)
[Ac-Pen-(N-Me-Arg)-Ser-Asp-Thr-Leu-Pen-1-Nal-(β-homoGlu)-(D-Lys)]₂-DIG;
```

-continued (SEQ ID NO: 301)
[Ac-Pen-(N-Me-Arg)-Ser-Asp-Thr-Leu-Pen-2-Nal-Glu-(N-Me-Lys)]₂-DIG;

(SEQ ID NO: 302)
[Ac-Pen-(N-Me-Arg)-Ser-Asp-Thr-Leu-Pen-Phe(4-tBu)-(β-homoGlu)-(D-Lys)]₂-DIG;

(SEQ ID NO: 303)
[Ac-Pen-(N-Me-Arg)-Ser-Asp-Thr-Leu-Pen-Phe(4-tBu)-(β-homoGlu)-(N-Me-Lys)]₂-DIG;

(SEQ ID NO: 304)
[Ac-Pen-(N-Me-Arg)-Ser-Asp-Thr-Leu-Pen-Trp-(β-homoGlu)-(N-Me-Lys)]₂-DIG;

(SEQ ID NO: 305)
[Ac-Pen-(N-Me-Arg)-Ser-Asp-Thr-Leu-Pen-2-Nal-(β-homoGlu)-(N-Me-Lys)]₂-DIG;

(SEQ ID NO: 300)
[Ac-Pen-(N-Me-Arg)-Ser-Asp-Thr-Leu-Pen-1-Nal-(β-homoGlu)-(D-Lys)]₂-DIG;

(SEQ ID NO: 306)
[Ac-Pen-(N-Me-Arg)-Ser-Asp-Thr-Leu-Pen-1-Nal-(β-homoGlu)-(N-Me-Lys)]₂-DIG;

(SEQ ID NO: 307)
[Ac-Pen-(N-Me-Arg)-Ser-Asp-Thr-Leu-Pen-Trp-(β-homoGlu)-(D-Lys)]₂-DIG;

(SEQ ID NO: 308)
[Ac-Pen-(N-Me-Arg)-Ser-Asp-Thr-Leu-Pen-Trp-Glu-(N-Me-D-Lys)]₂-DIG;

(SEQ ID NO: 213)
[Ac-Pen-(N-Me-Arg)-Ser-Asp-Thr-Leu-Pen-Trp-(β-homoGlu)-(D-Lys)-NH₂]₂-DIG;

(SEQ ID NO: 130)
[Ac-Pen-(N-Me-Arg)-Ser-Asp-Thr-Leu-Pen-(Phe-(4-COOH)-(β-homoGlu)-(D-Lys)-NH₂]₂-DIG;

(SEQ ID NO: 215)
[Ac-Pen-(N-Me-Arg)-Ser-Asp-Thr-Leu-Pen-Trp-Glu-(N-Me-Lys)-NH₂]₂-DIG;

(SEQ ID NO: 137)
[Ac-Pen-(N-Me-Arg)-Ser-Asp-Thr-Leu-Pen-2-Nal-(β-homoGlu)-(D-Lys)-NH₂]₂-DIG;

(SEQ ID NO: 231)
[Ac-Pen-(N-Me-Arg)-Ser-Asp-Thr-Leu-Pen-1-Nal-(β-homoGlu)-(D-Lys)-NH₂]₂-DIG;

(SEQ ID NO: 138)
[Ac-Pen-(N-Me-Arg)-Ser-Asp-Thr-Leu-Pen-2-Nal-Glu-(N-Me-Lys)-NH₂]₂-DIG;

(SEQ ID NO: 218)
[Ac-Pen-(N-Me-Arg)-Ser-Asp-Thr-Leu-Pen-Phe(4-tBu)-(β-homoGlu)-(D-Lys)-NH₂]₂-DIG;

(SEQ ID NO: 149)
[Ac-Pen-(N-Me-Arg)-Ser-Asp-Thr-Leu-Pen-Phe(4-tBu)-(β-homoGlu)-(N-Me-Lys)-NH₂]₂-DIG;

(SEQ ID NO: 141)
[Ac-Pen-(N-Me-Arg)-Ser-Asp-Thr-Leu-Pen-Trp-(β-homoGlu)-(N-Me-Lys)-NH₂]₂-DIG;

(SEQ ID NO: 232)
[Ac-Pen-(N-Me-Arg)-Ser-Asp-Thr-Leu-Pen-2-Nal-(β-homoGlu)-(N-Me-Lys)-NH₂]₂-DIG;

(SEQ ID NO: 231)
[Ac-Pen-(N-Me-Arg)-Ser-Asp-Thr-Leu-Pen-1-Nal-(β-homoGlu)-(D-Lys)-NH₂]₂-DIG;

(SEQ ID NO: 142)
[Ac-Pen-(N-Me-Arg)-Ser-Asp-Thr-Leu-Pen-1-Nal-(β-homoGlu)-(N-Me-Lys)-NH₂]₂-DIG;

(SEQ ID NO: 213)
[Ac-Pen-(N-Me-Arg)-Ser-Asp-Thr-Leu-Pen-Trp-(β-homoGlu)-(D-Lys)-NH₂]₂-DIG;

(SEQ ID NO: 214)
[Ac-Pen-(N-Me-Arg)-Ser-Asp-Thr-Leu-Pen-Trp-Glu-(N-Me-D-Lys)-NH₂]₂-DIG;

(SEQ ID NO: 233)
[Ac-Pen-(N-Me-Arg)-Ser-Asp-Thr-Leu-Pen-Trp-(β-homoGlu)-(D-Lys)-OH]₂-DIG;

(SEQ ID NO: 234)
[Ac-Pen-(N-Me-Arg)-Ser-Asp-Thr-Leu-Pen-(Phe-(4-COOH)-(β-homoGlu)-(D-Lys)-OH]₂-DIG;

(SEQ ID NO: 235)
[Ac-Pen-(N-Me-Arg)-Ser-Asp-Thr-Leu-Pen-Trp-Glu-(N-Me-Lys)-OH]₂-DIG;

(SEQ ID NO: 236)
[Ac-Pen-(N-Me-Arg)-Ser-Asp-Thr-Leu-Pen-2-Nal-(β-homoGlu)-(D-Lys)-OH]₂-DIG;

```
                                                            (SEQ ID NO: 237)
[Ac-Pen-(N-Me-Arg)-Ser-Asp-Thr-Leu-Pen-1-Nal-(β-homoGlu)-(D-Lys)-OH]₂-DIG;

(SEQ ID NO: 238)
[Ac-Pen-(N-Me-Arg)-Ser-Asp-Thr-Leu-Pen-2-Nal-Glu-(N-Me-Lys)-OH]₂-DIG;

(SEQ ID NO: 239)
[Ac-Pen-(N-Me-Arg)-Ser-Asp-Thr-Leu-Pen-Phe(4-tBu)-(β-homoGlu)-(D-Lys)-OH]₂-DIG;

(SEQ ID NO: 240)
[Ac-Pen-(N-Me-Arg)-Ser-Asp-Thr-Leu-Pen-Phe(4-tBu)-(β-homoGlu)-(N-Me-Lys)-OH]₂-DIG;

(SEQ ID NO: 241)
[Ac-Pen-(N-Me-Arg)-Ser-Asp-Thr-Leu-Pen-Trp-(β-homoGlu)-(N-Me-Lys)-OH]₂-DIG;

(SEQ ID NO: 242)
[Ac-Pen-(N-Me-Arg)-Ser-Asp-Thr-Leu-Pen-2-Nal-(β-homoGlu)-(N-Me-Lys)-OH₂]₂-DIG;

(SEQ ID NO: 237)
[Ac-Pen-(N-Me-Arg)-Ser-Asp-Thr-Leu-Pen-1-Nal-(β-homoGlu)-(D-Lys)-OH]₂-DIG;

(SEQ ID NO: 243)
[Ac-Pen-(N-Me-Arg)-Ser-Asp-Thr-Leu-Pen-1-Nal-(β-homoGlu)-(N-Me-Lys)-OH]₂-DIG;

(SEQ ID NO: 309)
[Ac-Pen-(N-Me-Arg)-Ser-Asp-Thr-Leu-Pen-Trp-(β-homoGlu)-(D-Lys)-OH]₂-DIG;
or
                                                            (SEQ ID NO: 244)
[Ac-Pen-(N-Me-Arg)-Ser-Asp-Thr-Leu-Pen-Trp-Glu-(N-Me-D-Lys)-OH]₂-DIG,
``` wherein in certain embodiments, there is a disulfide bond between the two Pen residues.

In particular embodiments, the peptide monomer compound comprises one of the following sequences or structures:

```
                                                            (SEQ ID NO: 310)
Ac-Pen-(N-Me-Arg)-Ser-Asp-Thr-Leu-Pen-Trp-(β-homoGlu)-(D-Lys);

(SEQ ID NO: 311)
Ac-Pen-(N-Me-Arg)-Ser-Asp-Thr-Leu-Pen-(Phe-(4-COOH)-(β-homoGlu)-(D-Lys);

(SEQ ID NO: 312)
Ac-Pen-(N-Me-Arg)-Ser-Asp-Thr-Leu-Pen-Trp-Glu-(N-Me-Lys);

(SEQ ID NO: 313)
Ac-Pen-(N-Me-Arg)-Ser-Asp-Thr-Leu-Pen-2-Nal-(β-homoGlu)-(D-Lys);

(SEQ ID NO: 314)
Ac-Pen-(N-Me-Arg)-Ser-Asp-Thr-Leu-Pen-1-Nal-(β-homoGlu)-(D-Lys);

(SEQ ID NO: 315)
Ac-Pen-(N-Me-Arg)-Ser-Asp-Thr-Leu-Pen-2-Nal-Glu-(N-Me-Lys);

(SEQ ID NO: 316)
Ac-Pen-(N-Me-Arg)-Ser-Asp-Thr-Leu-Pen-Phe(4-tBu)-(β-homoGlu)-(D-Lys);

(SEQ ID NO: 317)
Ac-Pen-(N-Me-Arg)-Ser-Asp-Thr-Leu-Pen-Phe(4-tBu)-(β-homoGlu)-(N-Me-Lys);

(SEQ ID NO: 318)
Ac-Pen-(N-Me-Arg)-Ser-Asp-Thr-Leu-Pen-Trp-(β-homoGlu)-(N-Me-Lys);

(SEQ ID NO: 319)
Ac-Pen-(N-Me-Arg)-Ser-Asp-Thr-Leu-Pen-2-Nal-(β-homoGlu)-(N-Me-Lys);

(SEQ ID NO: 314)
Ac-Pen-(N-Me-Arg)-Ser-Asp-Thr-Leu-Pen-1-Nal-(β-homoGlu)-(D-Lys);

(SEQ ID NO: 320)
Ac-Pen-(N-Me-Arg)-Ser-Asp-Thr-Leu-Pen-1-Nal-(β-homoGlu)-(N-Me-Lys);

(SEQ ID NO: 310)
Ac-Pen-(N-Me-Arg)-Ser-Asp-Thr-Leu-Pen-Trp-(β-homoGlu)-(D-Lys);

(SEQ ID NO: 321)
Ac-Pen-(N-Me-Arg)-Ser-Asp-Thr-Leu-Pen-Trp-Glu-(N-Me-D-Lys);
```

-continued

```
                                                   (SEQ ID NO: 251)
Ac-Pen-(N-Me-Arg)-Ser-Asp-Thr-Leu-Pen-Trp-(β-homoGlu)-(D-Lys)-OH;

(SEQ ID NO: 252)
Ac-Pen-(N-Me-Arg)-Ser-Asp-Thr-Leu-Pen-(Phe-(4-COOH)-(β-homoGlu)-(D-Lys)-OH;

(SEQ ID NO: 253)
Ac-Pen-(N-Me-Arg)-Ser-Asp-Thr-Leu-Pen-Trp-Glu-(N-Me-Lys)-OH;

(SEQ ID NO: 254)
Ac-Pen-(N-Me-Arg)-Ser-Asp-Thr-Leu-Pen-2-Nal-(β-homoGlu)-(D-Lys)-OH;

(SEQ ID NO: 255)
Ac-Pen-(N-Me-Arg)-Ser-Asp-Thr-Leu-Pen-1-Nal-(β-homoGlu)-(D-Lys)-OH;

(SEQ ID NO: 256)
Ac-Pen-(N-Me-Arg)-Ser-Asp-Thr-Leu-Pen-2-Nal-Glu-(N-Me-Lys)-OH;

(SEQ ID NO: 257)
Ac-Pen-(N-Me-Arg)-Ser-Asp-Thr-Leu-Pen-Phe(4-tBu)-(β-homoGlu)-(D-Lys)-OH;

(SEQ ID NO: 258)
Ac-Pen-(N-Me-Arg)-Ser-Asp-Thr-Leu-Pen-Phe(4-tBu)-(β-homoGlu)-(N-Me-Lys)-OH;

(SEQ ID NO: 259)
Ac-Pen-(N-Me-Arg)-Ser-Asp-Thr-Leu-Pen-Trp-(β-homoGlu)-(N-Me-Lys)-OH;

(SEQ ID NO: 260)
Ac-Pen-(N-Me-Arg)-Ser-Asp-Thr-Leu-Pen-2-Nal-(β-homoGlu)-(N-Me-Lys)-OH;

(SEQ ID NO: 255)
Ac-Pen-(N-Me-Arg)-Ser-Asp-Thr-Leu-Pen-1-Nal-(β-homoGlu)-(D-Lys)-OH;

(SEQ ID NO: 261)
Ac-Pen-(N-Me-Arg)-Ser-Asp-Thr-Leu-Pen-1-Nal-(β-homoGlu)-(N-Me-Lys)-OH;

(SEQ ID NO: 322)
Ac-Pen-(N-Me-Arg)-Ser-Asp-Thr-Leu-Pen-Trp-(β-homoGlu)-(D-Lys)-OH;

(SEQ ID NO: 262)
Ac-Pen-(N-Me-Arg)-Ser-Asp-Thr-Leu-Pen-Trp-Glu-(N-Me-D-Lys)-OH;

(SEQ ID NO: 263)
Ac-Pen-(N-Me-Arg)-Ser-Asp-Thr-Leu-Pen-Trp-(β-homoGlu)-(D-Lys)-NH$_2$;

(SEQ ID NO: 264)
Ac-Pen-(N-Me-Arg)-Ser-Asp-Thr-Leu-Pen-(Phe-(4-COOH)-(β-homoGlu)-(D-Lys)-NH$_2$;

(SEQ ID NO: 265)
Ac-Pen-(N-Me-Arg)-Ser-Asp-Thr-Leu-Pen-Trp-Glu-(N-Me-Lys)-NH$_2$;

(SEQ ID NO: 266)
Ac-Pen-(N-Me-Arg)-Ser-Asp-Thr-Leu-Pen-2-Nal-(β-homoGlu)-(D-Lys)-NH$_2$;

(SEQ ID NO: 267)
Ac-Pen-(N-Me-Arg)-Ser-Asp-Thr-Leu-Pen-1-Nal-(β-homoGlu)-(D-Lys)-NH$_2$;

(SEQ ID NO: 268)
Ac-Pen-(N-Me-Arg)-Ser-Asp-Thr-Leu-Pen-2-Nal-Glu-(N-Me-Lys)-NH$_2$;

(SEQ ID NO: 153)
Ac-Pen-(N-Me-Arg)-Ser-Asp-Thr-Leu-Pen-Phe(4-tBu)-(β-homoGlu)-(D-Lys)-NH$_2$;

(SEQ ID NO: 269)
Ac-Pen-(N-Me-Arg)-Ser-Asp-Thr-Leu-Pen-Phe(4-tBu)-(β-homoGlu)-(N-Me-Lys)-NH$_2$;

(SEQ ID NO: 270)
Ac-Pen-(N-Me-Arg)-Ser-Asp-Thr-Leu-Pen-Trp-(β-homoGlu)-(N-Me-Lys)-NH$_2$;

(SEQ ID NO: 271)
Ac-Pen-(N-Me-Arg)-Ser-Asp-Thr-Leu-Pen-2-Nal-(β-homoGlu)-(N-Me-Lys)-NH$_2$;

(SEQ ID NO: 267)
Ac-Pen-(N-Me-Arg)-Ser-Asp-Thr-Leu-Pen-1-Nal-(β-homoGlu)-(D-Lys)-NH$_2$;

(SEQ ID NO: 272)
Ac-Pen-(N-Me-Arg)-Ser-Asp-Thr-Leu-Pen-1-Nal-(β-homoGlu)-(N-Me-Lys)-NH$_2$;
```

Ac-Pen-(N-Me-Arg)-Ser-Asp-Thr-Leu-Pen-Trp-(β-homoGlu)-(D-Lys)-NH₂;
(SEQ ID NO: 323)

or

Ac-Pen-(N-Me-Arg)-Ser-Asp-Thr-Leu-Pen-Trp-Glu-(N-Me-D-Lys)-NH₂;
(SEQ ID NO: 273)

wherein in certain embodiments, there is a disulfide bond between the two Pen residues.

In particular embodiments, the peptide, peptide monomer compound, or peptide dimer compound, is labeled, for example, detectably labeled, e.g., fluorescently labeled with a fluorophore or radiolabeled with a radioisotope. A variety of detectable molecules may be used, such as a radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody).

The use of detectable labels is well known in the art. Detectable labels may be used according to the invention. Methods for conjugating polypeptides and detectable labels are well known in the art, as are methods for imaging using detectable labels. Chimeric polypeptide sensors tagged with a detectable label may be employed in a wide variety of assays, employing a wide variety of labels. In some embodiments of the present invention, detection of a species of ubiquitin protein or ubiquitin like protein can facilitated by attaching a detectable label to the chimeric polypeptide sensor. In some embodiments, detection of a species of ubiquitin protein or species of ubiquitin like protein can be facilitated by attaching a detectable label to a competitor ubiquitin protein or a competitor ubiquitin-like protein.

Examples of detectable labels include but are not limited to radionucleotides, enzymes, coenzymes, fluorescers, chemiluminescers, chromogens, enzyme substrates or cofactors, enzyme inhibitors, prosthetic group complexes, free radicals, particles, dyes, and the like. Several radioisotopes can be used as detectable molecules for labeling peptides including, for example, 32P, 33P, 35S, 3H, and 125I. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, coumarin, Alexa488, Oregon green 488, rhodamine green, Alexa 532, Cy3, Bodipy 588/586, Alexa586, TAMRA, Rox, Alexa 594, Texas red, Bodipy 630/650, Cy5, Alexa647, IR Dye 680, IR Dye 680, IR Dye 700 DX, Cy5.5, Alexa 750, IR Dye 800CW, IR Dye 800, Atto 532, Atto 465; an example of a luminescent material is luminol; examples of bioluminescent materials include luciferase, luciferin, and aequorin; and examples of suitable radioactive material include 125 I, 131 I, 35 S, or 3 H. In some embodiments, the detectable labels include fluorescent proteins. Suitable fluorescent proteins include TagBFP, mTagBFP2, Azurite, EBFP2, mKalamal, Sirius, Sapphire, T-Sapphire, ECFP, Cerulean, SCFP3A, mnTurquoise, miTurquoise2, monomeric Midorii-shi-cyan, TagCFP, mTFP1, GFP, EGFP, Emeral, Superfolder GFP, monomeric Azanmi Green, TagGFP2, mUKG, mWasabi, Clover, mNeonGreen, EYFP, YFP, Citrine, Venus, SYFP2, TagYFP, monomeric Kusabira Orange, MKOK mKO2, mOrange, mOrange2, mRaspberry, mCherry, mStrawberry, mTangerine, tdTomato, TagRFP, TagRFPI, mApple, mRuby, mRuby2, TagRFP675, IFP1.4, iFRP, mKeima Red, LSS-mKate1, LSS-mKate2, mBeRFP, PA-GFP, PAmCherryl, PATagRFP, Kaede green, Kaede red, KikGR1 green, KikGR1 red, PS-CFP2, mEos2 green, mEos2 red, mnEos3.2 green, mEos3.2 red, PSmOrange. In some embodiments of the present invention, detectable labels also include quenchers suitable for fluorescence resonance energy transfer (FRET) pairings. Examples of suitable quenchers include Dabcyl, BHQ1, BHQ2, BHQ3, CY5Q, CY7Q, lowablack FQ, lowablack RQ, IR Dye QC-1, QSY35, QSKY7, QXL570, QXL610, QXL680.

EXAMPLES

Example 1

Synthesis of Peptide Molecules

The peptide monomer compounds and peptide dimer compounds of the present invention may be synthesized by many techniques that are known to those skilled in the art. Novel peptide monomer and peptide dimer subunits were synthesized, purified, and dimerized using the techniques provided herein.

Synthesis

The peptides of the present invention were synthesized using the Merrifield solid phase synthesis techniques on Protein Technology's Symphony multiple channel synthesizer using standard Fmoc chemistryThe amino acids used are Fmoc amino acids with a standard side chain protecting group compatible with Fmoc chemistry. The peptides were assembled using HBTU (O-Benzotriazole-N,N,N',N'-tetramethyl-uronium-hexafluoro-phosphate), Diisopropylethylamine (DIEA) coupling conditions. For some amino acid couplings, PyAOP (7-Azabenzotriazol-1-yloxy)tripyrrnolidinophosponium hexafluorophosphate) and DIEA conditions were used. For some amino acid couplings Oxyma (Ethyl (hydroxyimino)cyanoacetate) and DIC conditions were used. Rink Amide MBHA resin (100-200mesh 0.57 mmol/g) was used for peptides with C-terminal amides and pre-loaded Wang Resin with N-α-Fmoc protected amino acid was used for peptides with C-terminal acids. The coupling reagents (HBTU and DIEA prenmixed) were prepared at 100 mmol concentration. Similarly, amino acids solutions were prepared at 100 mmol concentration.

Assembly

The peptides were assembled using standard Symphony synthesizer protocols for Fmoc chemistry. The peptide sequences were assembled as follows: Resin (250 mg, 0.14 mmol) in each reaction vial was washed twice with 4 ml of DMF followed by treatment with 2.5 ml of 20% 4-methyl piperidine (Fmoc de-protection) for 10 min. The resin was then filtered and washed two times with DMF (4 ml) and re-treated with N-methyl piperifine for an additional 30 minute. The resin was again washed three times with DMF (4 ml) followed by addition of 2.5 ml of amino acid and 2.5 m of HBTU-DIEA mixture. After 45 min of frequent agitations, the resin was filtered and washed three times with DMF (4 ml each). After completing the coupling reaction, the resin was washed three times with DMF (4 m each) before proceeding to the next amino acid coupling. Fmoc deprotection and amino acid coupling cycles were repeated for the specific number of amino acids in the peptide sequence. For Pen (Trt) coupling coupling to the N-Me-Arg, 2.0 eq amino acid, 2.2 eq oxyma, and 2.0 eq DIC was used, and completion of the reaction was monitored using Chloranil test.

Cleavage

Following completion of the peptide assembly, the peptide was cleaved from the resin by treatment with a cleavage reagent, such as reagent K (82.5% trigluoroacetic acid, 5% water, 5% thioanisole, 5% phenol, 2.5% 1,2-ethanedithiol). The cleavage reagent was able to successfully cleave the peptide from the resin, as well as all remaining side chain protecting groups.

The cleaved peptides were precipitated in cold diethyl ether followed by two washings with ethyl ether. The filtrate was poured off and a second aliquot of cold ether was added, and the procedure was repeated. The crude peptide was dissolved in a solution of acetonitrile:water (7:3 with 1% TFA) and filtered. The quality of linear peptide was then verified using electrospray ionization mass spectrometry (ESI-MS) (Micromass/Waters ZQ) before being purified.

Disulfide Bond Formation via Oxidation 50 mg of crude, cleaved peptide was dissolved in 20 ml of water:acetonitrile. Saturated Iodine in acetic acid was then added drop wise with stirring until yellow color persisted. The solution was stirred for 15 minutes, and the reaction was monitored with analytic HPLC and LCMS. When the reaction was completed, solid ascorbic acid was added until the solution became clear. The solvent mixture was then purified by first being diluted with water and then loaded onto a reverse phase HPLC machine (Luna C18 support, 10 u, 100A, Mobile phase A: water containing 0.1% TFA, mobile phase B: Acetonitrile (ACN) containing 0.1% TFA, gradient began with 5% B, and changed to 50% B over 60 minutes at a flow rate of 15 ml/min). Fractions containing pure product were then freeze-dried on a lyophilyzer.

Lactam Bond Formation 100 mg of crude, cleaved peptide (approx. 0.12 mmol) was dissolved in 100 ml of anhydrous dichloromethane. HOBt (1-Hydroxybenzotriazole hydrate) (0.24 mmol, 2 equivalents) was added followed by DIEA (N,N-Diisopropylethylamine) (1.2 mmol, 10equivalents) and TBTU (O-(Benzotriazol-1-yl)-N,N,N',N'-tetramethyluronium tetrafluoroborate)(0.24 mmol, 2 equivalents). The mixture was stirred overnight and followed the reaction by HPLC. When the reaction was completed, dichloromethane was evaporated and diluted with water and Acetonitrile and then loaded onto a reverse phase HPLC machine (Luna C18 support, 10 u, 100A, Mobile phase A: water containing 0.1% TFA, mobile phase B: Acetonitrile (ACN) containing 0.1% TFA, gradient began with 5% B, and changed to 50% B over 60 minutes at a flow rate of 15 ml/min). Fractions containing pure product were then freeze-dried on a lyophilyzer.

Purification

Analytical reverse-phase, high performance liquid chromatography (HPLC) was performed on a Gemini C18 column (4.6 mm×250 mm) (Phenomenex). Semi-Preparative reverse phase HPLC was performed on a Gemini 10 μm C18 column (22 mm×250 mm) (Phenomenex) or Jupiter 10 μm, 300 A ° C.18 column (21.2 mm×250 mm) (Phenomenex). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative).

Linker Activation and Dimerization

Small Scale DIG Linker Activation Procedure:

5 mL of NMP was added to a glass vial containing IDA diacid (304.2 mg, 1 mmol), N-hydroxysuccinimide (NHS, 253.2 mg, 2.2 eq. 2.2 mmol) and a stirring bar. The mixture was stirred at room temperature to completely dissolve the solid starting materials. N, N'-Dicyclohexylcarbodiimide (DCC, 453.9 mg, 2.2 eq., 2.2 mmol) was then added to the mixture. Precipitation appeared within 10 min and the reaction mixture was further stirred at room temperature overnight. The reaction mixture was then filtered to remove the precipitated dicyclohexylurea (DCU). The activated linker was kept in a closed vial prior to use for dimerization. The nominal concentration of the activated linker was approximately 0.20 M.

For dimerization using PEG linkers, there is no preactivation step involved. Commercially available pre-activated bi-functional PEG linkers were used.

Dimerization Procedure:

2 mL of anhydrous DMF was added to a vial containing peptide monomer (0.1 mmol). The pH of the peptide was the adjusted to 8~9 with DIEA. Activated linker (DIG, IDA or PEG13, PEG 25) (0.48eq relative to monomer, 0.048 mmol) was then added to the monomer solution. The reaction mixture was stirred at room temperature for one hour. Completion of the dimerization reaction was monitored using analytical HPLC. The time for completion of dimerization reaction varied depending upon the linker. After completion of reaction, the peptide was precipitated in cold ether and centrifuged. The supernatant ether layer was discarded. The precipitation step was repeated twice. The crude dimer was then purified using reverse phase HPLC (Luna C18 support, 10 u, 100A, Mobile phase A: water containing 0.1% TFA, mobile phase B: Acetonitrile (ACN) containing 0.1% TFA, gradient of 15% B and changed to 45% B over 60 min, flow rate 15 ml/min). Fractions containing pure product were then freeze-dried on a lyophilyzer.

Example 2

Characterization of Peptide Dimer Molecules

The stability, potency, and selectivity of certain peptide monomer compounds and peptide dimer compounds was determined using a variety of in vitro and in vivo assays.

α4β7-MAdCAM Competition ELISA

A nickel coated plate (Pierce #15442) was coated with rh integrin α4β7 (R&D Systems #5397-A30) at 800 ng/well and incubated at room temperature with shaking for 1 hr. The solution was then removed by shaking and blocked with assay buffer (50 mM Tris-HCl pH7.6, 150 mM NaCl, 1 mM MnCl$_2$ or MgCl$_2$, 0.05% Tween-20 and 0.5% BSA) at 250 ul/well. The plate was then incubated at room temperature for 1 hr. Each well was washed 3 times with wash buffer (50 mM Tris-HCl pH7.6, 100 mM NaCl, 1 mM MnCl$_2$ or MgCl$_2$, 0.05% Tween-20). To each well was added 25 ul of a serial dilution (3-fold dilutions in assay buffer) of peptide starting at 20 μM. 25 ul of recombinant human MAdCAM-1 (R&D Systems #6056-MC) was then added to each well at a fixed concentration 20 nM. The final starting peptide concentration was 1 μM, and the final MAdCAM-1 concentration was 10 nM. The plates were then incubated at room temperature for 1 hr to reach binding equilibrium. The wells were then washed three times with wash buffer. 50 ul of mouse anti-human IgG1-HRP (Invitrogen #A10648) diluted in 1:2000 in assay buffer was then added to each well. The wells were incubated at room temperature for 45 min with shaking. The wells were then washed 3 times with wash buffer. 100 ul of 3,3',5,5'-Tetramethylbenzidine (TMB) were then added to each well and closely observe during development time. The reaction was stopped with 2N $H_2SO_4$ and absorbance was read at 450 nm.

TMB is a chromogenic substrate suitable for use in ELISA procedures, which utilize horseradish peroxidase conjugates. This substrate produces a soluble end product that is blue in color and can be read spectrophotometrically at 370 or 655 nm. The reaction maybe stopped with 2 M $H_2SO_4$, resulting in a yellow solution that is read at 450 nm. Each tablet contains 1 mg of TMB substrate. To prepare TMB Substrate Solution, dissolve one 3,3',5,5'-tetramethylbenzidine tablet in 1 ml of DMSO and add to 9 ml of 0.05 M Phosphate-Citrate Buffer, pH 5.0. Add 2 µl of fresh 30% hydrogen peroxide (Product No. H 1009) per 10 ml of substrate buffer solution, immediately prior to use.

α4β1-VCAM Competition ELISA

A Nunc MaxiSorp plate was coated with rh VCAM-1/CD106 Fc chimera (R&D #862-VC) at 400 ng/well in 50 ul per well in 1×PBS and incubated overnight at 4° C. The solution was removed by shaking and then blocked with 250 ul of 1% BSA in 1×PBS per well. The wells were then incubated at room temperature for 1 hr with shaking. Each well was then washed once with wash buffer (50 mM Tris-HCl pH7.6, 100 mM NaCL, 1 mM $MnCl_2$ or $MgCl_2$, 0.05% Tween-20). 25 ul of serial dilutions of peptides starting at 200 µM in assay buffer (Assay buffer: 50 mM Tris-HCl pH7.6, 100 mM NaCl, 1 mM $MnCl2$ or $MgCl_2$, 0.05% Tween-20) was added to each well. Additionally, 25 ul of α4β1 (R&D Systems #5668-A4) was added to each well at a fixed concentration of 120 nM. The final peptide and α4β1 concentrations were 100 µM and 60 nM, respectively. The plates were then incubated at 37° C. for 2 hr. The solution was then removed by shaking, and each well was washed three times with wash buffer. 50 ul of 9F10 antibody at 4 ug/ml (purified mouse anti-human CD49d, BD Bioscience Cat #555502) was then added to each well, and the plate was incubated at room temperature for 1 hr with shaking. The solution was again removed by shaking, and each well was washed three times with wash buffer. 50 ul of peroxidase-conjugated AffiniPure Goat anti-mouse IgG (Jackson immune research cat #115-035-003) diluted in 1:5000 in assay buffer was added to each well. The plate was incubated at room temperature for 30 min with shaking. Each well was then washed 3 times with wash buffer. 100 ul of TMB was then added to each well and closely observe during developing time. The reaction was stepped with 2N $H_2SO_4$ and absorbance was read at 450 nm.

α4β7-MAdCAM Cell Adhesion Assay

RPMI 8866 human cells (Sigma #95041316) were cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 µg of streptomycin per ml. The cells were washed two times in DMEM medium (ATCC #30-2002) supplemented with 0.1% BSA, 10 mM HEPES pH 7 and 1 mM $MnCl_2$. The cells were re-suspended in supplemented DMEM medium at a density of 4×10⁶ cells/ml.

A Nunc MaxiSorp plate was coated with rh MAdCAM-1/Fc Chimera (R&D #6065-MC) at 200 ng per well in 50 ul per well in 1×PBS and incubated at 4° C. overnight. The solution was then removed by shaking, blocked with 250 ul per well PBS containing 1% BSA, and incubated at 37° C. for 1 hr. The solution was removed by shaking. Peptides were diluted by serial dilution in a final volume of 50 ul per well (2× concentration). To each well, 50 ul of cells (200,000 cells) were added and the plate was incubated at 37° C., 5% $CO_2$ for 30-45 min to allow cell adhesion. The wells were washed manually three times (100 ul per wash) with supplemented DMEM. After the final wash, 100 ul/well of supplemented DMEM and 10 ul/well of MTT reagent (ATTC cat #30-1010K) were added. The plate was incubated at 37° C., 5% $CO_2$ for 2-3 hrs until a purple precipitate was visible. 100 ul of Detergent Reagent (ATTC cat #30-1010K) was added to each well. The plate was covered from the light, wrapped in Parafilm to prevent evaporation, and left overnight at room temperature in the dark. The plate was shaken for 5 min and the absorbance at 570 nm was measured. To calculate the dose response, the absorbance value of control wells not containing cells was subtracted from each test well.

α4β1-VCAM Cell Adhesion Assay

Jurkat E6.1 human cells (Sigma #88042803) were cultured in RPMI 1640 HEPES medium (Invitrogen #22400-089) supplemented with 10% serum (Fetal Bovine Serum, Invitrogen #16140-071), 1 mM sodium pyruvate (Invitrogen #11360-070), 2 mM L-glutamine (Invitrogen #25030-081) and Penicillin-Streptomycin (Invitrogen #15140-122) at 100 units of penicillin and 100 µg of streptomycin per ml. The cells were washed two times in DMEM medium (ATCC #30-2002) supplemented with 0.1% BSA, 10 mM HEPES pH 7 and 1 mM $MnCl_2$. The cells were re-suspended in supplemented DMEM medium at a density of 4×10⁶ cells/ml.

A Nunc MaxiSorp plate was coated with rh VCAM-1/CD106 Fc chimera (R&D #862-VC) at 400 ng per well in 50 ul per well in 1×PBS at 4° C. overnight. The solution was then removed by shaking, blocked with 250 ul per well PBS containing 1% BSA, and incubated at 37° C. for 1 hr. The solution was removed by shaking. Peptides were diluted by serial dilution in a final volume of 50 ul per well (2× concentration). To each well, 50 ul of cells (200,000 cells) were added and the plate was incubated at 37° C., 5% $CO_2$ for 30-45 min to allow cell adhesion. The wells were washed manually three times (100 ul per wash) with supplemented DMEM. After the final wash, 100 ul/well of supplemented DMEM and 10 ul/well of MTT reagent (ATTC cat #30-1010K) were added. The plate was incubated at 37° C., 5% $CO_2$ for 2-3 hrs until a purple precipitate was visible. 100 ul of Detergent Reagent (ATTC cat #30-1010K) was added to each well. The plate was covered from the light, wrapped in Parafilm to prevent evaporation, and left overnight at room temperature in the dark. The plate was shaken for 5 min and the absorbance at 570 nm was measured. To calculate the dose response, the absorbance value of control wells not containing cells was subtracted from each test well.

α4β7 Cell Adhesion Assay (Mouse)

TK1 cells (ATCC #ATCC-CRL-2396) were cultured in in RPMI 1640 with 2 mM L-glutamine adjusted to contain 1.5 g/L sodium bicarbonate, 4.5 g/L glucose, 10 mM HEPES, and 1.0 mM sodium pyruvate (ATCC #30-2001) and supplemented with 0.1 mM non-essential amino acids, (ATCC #30-2116) 0.05 mM 2-mercaptoethanol (Invitrogen #21985) and 10% serum (Fetal Bovine Serum, Invitrogen #16140-071), and Penicillin-Streptomycin (Invitrogen #15140-122)

at 100 units of penicillin and 100 µg of streptomycin per ml. The cells were washed two times in DMEM medium (ATCC #30-2002) supplemented with 0.1% BSA, 10 mM HEPES pH 7 and 1 mM $MnCl_2$. The cells were re-suspended in supplemented DMEM medium at a density of $4 \times 10^6$ cells/ml.

A Nunc MaxiSorp plate was coated with Recombinant human MAdCAM-1 Fc Chimera (R&D #6065-MC) at 200 ng per well in 100 µl per well in 1×PBS and incubated at 4° C. overnight. The solution was then removed by shaking, blocked with 250 ul per well PBS containing 1% BSA, and incubated at 37° C. for 1 hr. The solution was removed by shaking. DATK 32 (anti-mouse α4β7) and peptides were diluted by serial dilution in a final volume of 50 ul per well (2× concentration). To each well, 50 ul of cells (200,000 cells) are added and the plate is incubated at 37° C., 5% $CO_2$ for 30-45 min to allow cell adhesion. The plate was manually washed three times with supplemented DMEM, 100 ul per wash. After the final wash, 100 ul/well of supplemented DMEM and 10 µL/well of MTT reagent (ATTC cat #30-1010K) was added to each well. Wells were incubated at 37° C. with 5% $CO_2$ for 2-3 hrs until purple precipitate was visible. 100 µl of Detergent Reagent (ATTC cat #30-1010K) was added to each well. The plate was then wrapped with Para film to prevent evaporation, and left overnight at room temperature in the dark. The plate was shaken for 5 min and the absorbance at 570 nm was measured. To calculate the dose response, the absorbance value of control wells not containing cells was subtracted from each test well.

PBMC Memory T Cell Adhesion Assay

Fresh CD4+/CD45RO+ memory T cells were isolated from human peripheral blood mononuclear cell (PBMC) donors by Aragen Bioscience Inc. (Morgan Hill, Calif.). The assay plate was prepared using IgG Fc capture antibody (donkey anti human) immobilized at 500 ng/well in 50 mM sodium bicarbonate buffer, pH 9.5, ON, 4 C onto a Greiner Fluotrac plate (100 ul per well). The plate was rinsed two time with Blocking Buffer (25 mM Tris HCl, pH7.5, 150 mM NaCl, 1.5% BSA, 0.05% Tween), and blocked with Blocking Buffer for 2 hours at 37 C or 5 hours at RT using 200 ul per well. The Blocking Buffer was removed and either MAdCAM-1 or VCAM-1 at 400 ng/well in Blocking Buffer was added and the plate incubated overnight at 4 C (100 ul per well). The plate was washed two times with Blocking Buffer, and rinsed once with 200 ul Binding Media (DMEM phenol red free, 10 mM HEPES, 1×Na pyruvate, 1× Glutamine, and supplemented with 1 mM MnCl2 prior to use). To prepare cells, approximately 25 million CD4+/CD45RO+ memory T cells were counted by trypan blue exclusion using a haemocytometer to determine viability and cell count. The cells were transferred to a 50 ml conical tube, and centrifuged at 1200 rpm for 10 minute. The media was aspirated and the cell pellet resuspended in 15 ml Binding Media. The cells were centrifuged again and resuspended in the appropriate amount of Binding Media to be used for assays (50 ul of cells per well at 2× the final density). To each well, and equal volume (50 ul) of test compound was added and the plate was incubated for 1.5 hours at 37 C, 5% $CO_2$. Each well was rinsed 3× with 150 ul per well of Binding Media. CyQuant NF reagent was prepared as suggested by manufacturer), and 100 ul of CyQuant NF reagent was added per well. The plate was incubated at 37 C, 5% $CO_2$, for 45 minutes. The plate was protected from light by using black adhesive seals. Fluorescence intensity was measured using a Molecular Devices Gemini EM Fluorescent Plate Reader (Ex 485/Em530, Bottom Read, Reading Sensitivity=20). IC50 curves are generated using Graph Pad Prism and the curves analyzed using analyzed using a non-linear regression (four parameters) algorithm. The log (concentration) versus RFU (Ex485/Em530) was plotted to determine IC50 values.

Simulated Intestinal Fluid (SIF) Stability Assay

Studies were carried out in simulated intestinal fluid (SIF) to evaluate intestinal stability of the peptide molecules of the instant invention. To prepare the SIF reagent, blank FASSIF was prepared by dissolving 0.348 g NaOH, 3.954 g sodium phosphate monobasic monohydrate and 6.186 g NaCl in a final volume of 1 liter water (final pH=6.5). To this solution, 24 g porcine pancreatin (Sigma catalog P7545) was added and stirred for 30 minutes (final pancreatin concentration is 2.4%). The solution was filtered through a cheese cloth and a No. 1 Whatman filter, and 10 ml aliquots were stored at −70° C. To run the reaction, a 10 ml aliquot was thawed at 37° C., and 125 µl aliquots were removed and mixed with an equal volume of blank FASSIF. The peptide stock solution (10 mM in 100% DMSO) was diluted 75-fold in blank FASSIF. A 50 µl aliquot of the diluted peptide was combined with 125 µl pancreatin (2.4%) and 125 µl blank FASSIF to yield final concentrations of 1% pancreatin and 2 µM peptide. The reactions were incubated at 37° C., and at various time points 50 µl aliquots were removed and added to 200 µl of quench solution containing 50% acetonitrile, 50% methanol, 5% formic acid, and 1 µg/ml internal standard. The quenched samples were centrifuged at 10,000 rpm for 10 minutes, and the supernatants were analyzed by LCMS/MS. The percent remaining at each time point was calculated based on the peak area response ratio of test to compound to internal standard. Half-lives were calculated by fitting to a first-order exponential decay equation using GraphPad.

Intestinal Wash Assay

Intestinal wash assay solution was prepared from rats fasted for at least 6 hours prior. The animals were euthanized and a midline incision was made from the point of the jaw to the pubis. The abdomen and chest were opened by making 2 incisions through the anterior chest wall on either side. Hemostats were used to clamp off both ends of the animal's stomach—where the esophagus meets the stomach and where the stomach meets the duodenum. A hemostat was also used to clamp 2-3 cm down the intestine from where the stomach meets the duodenum.

Intestinal wash assay solution was prepared by separating 20 cm of the small intestine from the body. Once separated 20 cm, the end was clamped with a hemostat and the section cut from the body, leaving the hemostats in place on the removed section. 1 mL of chilled saline was drawn up with a 1 mL syringe. One end of the intestine was held up and the clamp removed. Approximately 2-2.5 cm of the gavage needle was inserted into the intestine, and the saline was slowly injected. The fluid was massaged down the length of the intestine using gloved fingers. The gavage needle was removed and the clamp was replaced on the end of the intestine. The intestine was sat straight and a q-tip was run firmly up and down the length of the outside of the intestine approximately 3-6 times to mix the enzymes with the saline. One end of the intestine was held up and some of the fluid was carefully moved at the top down. The clamp was removed and that end of the intestine was set into a small weigh boat on ice. The other end of the intestine was carefully picked up and held vertically. Gloved fingers were gently run down it to squeeze the fluid into the container. The previous steps saline injection and fluid procurement steps were repeated twice using only 0.5 mL of chilled saline. The sample was pipetted from the weigh boat into a centrifuge tube and placed on ice. All intestinal wash samples were spun down in a cold centrifuge at 12,000×g for 10 minutes. The supernatant from the top of each centrifuged sample was pipetted into cryotubes, and kept on ice until use.

Intestinal wash assays were performed using intestinal wash assay solution prepared as described above. A sufficient amount of rat intestinal wash was thawed. For each sample, 200 uL of rat intestinal wash fluid was pipetted into 1.5 mL Eppendorf tubes (number of tubes for experiment=number of test peptides×N). The tubes were pre-incubated for about 10 minutes in a water bath at 37° C.

Peptide working solutions (2 mM) were prepared by combining 2 µl of 10 mM DMSO stock with 128 µl 100 mM Tris pH 7.5.

Peptide quench solvent (50% ACN-50% MeOH-5% Formic Acid)+IS (5 ug/ml; 1 ul of 10 mg/mL IS per 2 mL quench solvent) was prepare and a quench plate prepared and placed on ice. 200 ul of quench solution was added to each well of the quench plate for T=0, 10, 20, 30, 60 and 180 min collection.

For each test sample and a positive control, 30 ul of peptide working solution was added to a tube of intestinal wash fluid. The tube was gently vortexed and 30 ul was immediately removed and quenched in T=0 well of quench plate (pipetted directly into the quench solution). This well was covered tightly to prevent evaporation. 30 ul aliquots were removed at T=10 min, T=20 min, T=30 min, T=60 min, and T=180 min, and quenched. When all time points were collected, the quench plate was centrifuged at 10,000 rpm for 10 minutes. 150 uL of each supernatant was transferred to a polypropylene 96-well collection plate. 300 ul Mobile Phase A was added to each collection, and LC/MS/MS analysis was performed to determine the amount or concentration of peptide remaining in each test sample and positive control.

Simulated Gastric Fluid (SGF) Assay

SGF was prepared by adding 20 mg NaCl, 32 mg porcine pepsin (MP Biochemicals, catalog 02102599), and 70 µl HCl to 10 ml water (final pH=2). Aliquots of SGF (0.5 ml each) were pre-warmed at 37° C. For each peptide tested, to start the reaction, 1 µl of peptide stock solution (10 mM in DMSO) was added to 0.5 ml SGF and thoroughly mixed such that the final peptide concentration was 20 µM. The reactions were incubated at 37° C. with gentle shaking. At each time point (0, 15, 30, 60 min), 50 µl aliquots were removed and added to 200 ul acetonitrile containing 0.1% formic acid to quench the reaction. Samples were stored at 4° C. until the end of the experiment and centrifuged at 10,000 rpm for 5 minutes. Aliquots of the supernatant were removed, diluted 1:1 into distilled water containing internal standard, and analyzed by LCMS/MS. Percent remaining at each timepoint was calculated based on the peak area response ratio of test compound to internal standard. Time 0 was set to 100%, and all later timepoints were calculated relative to time 0. Half-lives were calculated by fitting to a first-order exponential decay equation using GraphPad.

Plasma Stability Assay 0.5 mL of rat plasma (one tube per peptide, volume depends on how many time points are to be collected, 50 µL per time point) was added to each well of a 96-well polypropylene plate, and the tubes were incubated in a heated water bath, preset to 37° C. with gentle shaking. 1 µL of 10 mM peptide stock solution was added to each tub, and then 200 L of Acetonitrile w/0.1% Formic Acid was added to each tube (1:4). Samples were collected at the following time points: 0, 10, 30, 45, 60, 120, 180 mins. When all time points were collected, the plate was centrifuged at 5000 rpm for 5 mins. LCM analysis was performed by pipetting 100 µL of each sample to appropriate well of a 96-well deep plate. 100 µL of an internal standard peptide (1 µg/mL) was added in Mobile Phase A to each well. The plate was vortexed and injected Dithiothreitol (DTT) Redox Stability Assay For each peptide tested, the DTT stability assay was conducted by adding 5 µl of a 10 mM peptide stock solution in DMSO to 1 ml of 100 mM Tris-Cl, pH 7.5 (final peptide concentration is 50 µM). At time 0 min, 5 ul of a freshly thawed 100 mM DTT solution was added to the incubation tube containing the peptide, such that the final DTT concentration was 0.5 mM. The reactions were incubated at room temperature. At different time points up to 120 minutes (20 min, 40 min, 80 min, 120 min), 50 µl aliquots were removed, and the reaction was quenched by adding 10 µl of 5M acetic acid. To measure disappearance of the parent peptide, the quenched samples (30 µl) were analyzed by reverse phase HPLC and UV absorbance at 220 nm. The fraction oxidized remaining was graphed versus time, and half-lives were calculated by fitting to a first-order exponential decay equation using Excel.

Cysteine/Cystine Redox Stability Assay

Peptides were diluted to 90 µM by adding 4.545 µl of a 10 mM peptide DMSO stock to 495.45 µl of 100 mM Tris-Cl, pH 7.5. Aliquots of 75 µl were transferred to 8 wells down a column of a 96 well plate. 20 µl of 2.5 mM Cystine in 100 mM Tris-Cl, pH 7.5 was added to each well. Cysteine stock solutions in 100 mM Tris-Cl, pH 7.5 were prepared fresh at the following concentrations: 400 mM, 200 mM, 80 mM, 44 mM, 22 mM, 11 mM, 5.5 mM and blank. At time 0, 25 µl of each cysteine stock solution was added to the 55 µl of cystine/peptide solution, and the mixture was incubated at room temperature for 40 min. The samples were quenched by adding 20 µl of 5M acetic acid and analyzed by reverse phase HPLC. The fraction of oxidized peptide was calculated and plotted against the calculated oxidation reduction potential (ORP) as defined by the Nernst equation. The ORP where half of the oxidized peptide remains is shown below.

| [Cysteine], mM | [Cystine], mM | ORP, mV |
|---|---|---|
| 1.375 | 0.5 | −176 |
| 2.375 | 0.5 | −194 |
| 5.5 | 0.5 | −213 |
| 11 | 0.5 | −231 |
| 20 | 0.5 | −247 |
| 50 | 0.5 | −271 |
| 100 | 0.5 | −290 |

Table 3 provides data demonstrating the potency, selectivity and stability of various peptide monomers and dimers of the present invention. The amino acid sequences of peptide monomers or peptide dimer subunits are provided in Table 3A, shown from N-terminus to C-terminus from left to right, and identified by a sequence identifier number. The accompanying data for each peptide is shown in Tables 3B and 3C. Dimers are indicated by parentheses followed by a subscripted 2. N-terminal and C-terminal groups are indicated, e.g., Ac and $NH_2$, respectively. Dimers are linked at the C-termini of their monomer subunits, and the linker is indicated to the right of the peptide sequence. Each of the peptide sequences shown includes a disulfide linkage between the amino acid residues located at position 4 and position 10, e.g., Pen and Pen. Table 4 provides comparative data demonstrating the greater potency, selectivity and stability of peptide monomer compounds and peptide dimer compounds of the present invention. The amino acid sequences of peptide monomers or peptide dimer subunits are provided in Table 4A, shown from N-terminus to C-terminus from left to right, and identified by a sequence identifier number. The accompanying data for each peptide is shown in Tables 4B and 4C. Dimers are indicated by parentheses followed by a subscripted 2. N-terminal and C-terminal groups are indicated, e.g., Ac and $NH_2$, respectively. Each of the peptide sequences shown includes a disulfide linkage between the amino acid residues located at position 4 and position 10, e.g., Pen and Pen. For the stability assay data, assays were conducted for varying durations of time, so an indication that $t_{1/2}$ was greater than a certain value means that the assay was stopped at that time, before half life could be determined. For DTT assays, where data is not shown for peptides comprising two Pen residues, the predicted DTT assay stability is greater than two hours.

TABLE 3-A

Sequence and Structure of Illustrative Peptide Monomers and Peptide Dimers

| SEQ ID NO. 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| 1 | | (Ac | Pen | N—Me—R | S | D | T | L | Pen | W | Beta-E | k | NH2)2 | DIG | | | |
| 2 | | (Ac | Pen | N—Me—R | S | D | T | L | Pen | f | e | k | NH2)2 | DIG | | | |
| 3 | | (Ac | Pen | N—Me—R | S | D | T | L | Pen | F(4-CF3) | e | k | NH2)2 | DIG | | | |
| 4 | | k | C | N—Me—R | S | D | T | L | C | W | k | NH2)2 | DIG | | | | |
| 5 | DIG | k | C | N—Me—R | S | D | T | L | C | W | k | NH2)2 | DIG | | | | |
| 6 | | (Ac | C | N—Me—R | S | D | T | L | C | W | NH2 | NH2)2 | DIG | | | | |
| 7 | | (Ac | C | N—Me—R | S | D | T | L | C | f | NH2 | NH2)2 | DIG | | | | |
| 8 | | (Ac | Pen | N—Me—R | S | D | T | L | Pen | 1-Nal | e | k | NH2 | | | | |
| 9 | | (Ac | Pen | N—Me—R | S | D | T | L | Pen | 2-Nal | e | k | NH2 | | | | |
| 10 | | (Ac | Pen | N—Me—R | S | D | T | L | Pen | D-1-Nal | E | k | NH2 | | | | |
| 11 | | (Ac | Pen | N—Me—R | S | D | T | L | Pen | D-2-Nal | E | k | NH2 | | | | |
| 12 | | (Ac | Pen | N—Me—R | S | D | T | L | Pen | 1-Nal | e | N—Me-k | NH2 | | | | |
| 13 | | (Ac | Pen | N—Me—R | S | D | T | L | Pen | 2-Nal | e | N—Me-k | NH2 | | | | |
| 14 | | (Ac | Pen | N—Me—R | S | D | T | L | Pen | HPhe | e | k | NH2 | | | | |
| 15 | | (Ac | Pen | N—Me—R | S | D | T | L | Pen | 2-Nal | E | N—Me-k | NH2 | | | | |
| 16 | | (Ac | Pen | N—Me—R | S | D | T | L | Pen | F(2,4-diCl) | E | k | NH2 | | | | |
| 17 | | (Ac | Pen | N—Me—R | S | D | T | L | Pen | F(3,4-diCl) | E | k | NH2 | | | | |
| 18 | | (Ac | Pen | N—Me—R | S | D | T | L | Pen | 1-Nal | E | N—Me-k | NH2 | | | | |
| 19 | | (Ac | Pen | N—Me—R | S | D | T | L | Pen | HPhe | E | k | NH2 | | | | |
| 20 | PEG13 | NH2 | C | N—Me—R | S | D | T | L | Pen | W | NH2 | NH2)2 | | | | | |
| 21 | PEG25 | NH2 | C | N—Me—R | S | D | T | L | Pen | W | NH2 | NH2)2 | | | | | |
| 22 | | (Ac | Pen | N—Me—R | S | D | T | L | Pen | Y | E | k | NH2 | DIG | | | |
| 23 | | (Ac | Pen | N—Me—R | S | D | T | L | Pen | 2-Nal | Y | k | NH2 | DIG | | | |
| 24 | | (Ac | Pen | N—Me—R | S | D | T | L | Pen | 1-Nal | E | k | NH2 | DIG | | | |
| 25 | | (Ac | Pen | N—Me—R | S | D | T | L | Pen | H | E | k | NH2 | DIG | | | |
| 26 | | (Ac | Pen | N—Me—R | S | D | T | L | Pen | H | Y | k | NH2 | DIG | | | |
| 27 | | (Ac | Pen | N—Me—R | S | D | T | L | Pen | 2-Nal | y | k | NH2 | DIG | | | |
| 28 | | (Ac | Pen | N—Me—R | S | D | T | L | Pen | w | E | k | NH2 | DIG | | | |
| 29 | | (Ac | Pen | N—Me—R | S | D | T | L | Pen | 2-Nal | e | k | NH2 | DIG | | | |
| 30 | | (Ac | Pen | N—Me—R | S | D | T | L | Pen | f | E | k | NH2 | DIG | | | |
| 31 | | (Ac | Pen | N—Me—R | S | D | T | L | Pen | W | N—Me-E | k | NH2 | DIG | | | |
| 32 | | (Ac | Pen | N—Me—R | S | D | T | L | Pen | 1-Nal | e | k | NH2 | DIG | | | |
| 33 | | (Ac | Pen | N—Me—R | S | D | T | L | Pen | 2-Nal | e | k | NH2 | DIG | | | |
| 34 | | (Ac | Pen | N—Me—R | S | D | T | L | Pen | D-1-Nal | E | k | NH2 | DIG | | | |
| 35 | | (Ac | Pen | N—Me—R | S | D | T | L | Pen | D-2-Nal | E | k | NH2 | DIG | | | |
| 36 | | (Ac | Pen | N—Me—R | S | D | T | L | Pen | W | E | k | NH2 | DIG | | | |
| 37 | | (Ac | C | N—Me—R | S | D | T | L | Pen | W | k | k | PEG13 | DIG | | | |
| 38 | | (Ac | C | N—Me—R | S | D | T | L | Pen | W | k | NH2)2 | PEG25 | | | | |
| 39 | | (Ac | Pen | N—Me—R | S | D | T | L | Pen | 1-Nal | e | N—Me-k | NH2 | DIG | | | |
| 40 | | (Ac | Pen | N—Me—R | S | D | T | L | Pen | 2-Nal | e | k | NH2 | DIG | | | |
| 41 | | (Ac | Pen | N—Me—R | S | D | T | L | Pen | HPhe | e | N—Me-k | NH2 | DIG | | | |
| 42 | | (Ac | Pen | N—Me—R | S | D | T | L | Pen | 2-Nal | E | k | NH2 | DIG | | | |
| 43 | | (Ac | Pen | N—Me—R | S | D | T | L | Pen | F(2,4-diCl) | E | k | NH2 | DIG | | | |
| 44 | | (Ac | Pen | N—Me—R | S | D | T | L | Pen | F(3,4-diCl) | E | N—Me-k | NH2 | DIG | | | |
| 45 | | (Ac | Pen | N—Me—R | S | D | T | L | Pen | 1-Nal | E | k | NH2 | DIG | | | |
| 46 | | Ac | Pen | N—Me—R | S | D | T | L | Pen | W | E | k | NH2 | | | | |

TABLE 3-A-continued

Sequence and Structure of Illustrative Peptide Monomers and Peptide Dimers

| SEQ ID NO: | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 47 | | | Ac | Pen | N—Me—R | S | Prop acid | T | L | Pen | W | E | k | NH2 | | | | |
| 48 | | | Ac | Pen | N—Me—R | d | D | T | L | Pen | W | E | k | NH2 | | | | |
| 49 | | NH2 | Ac | Pen | N—Me—R | S | D | T | L | Pen | W | E | P | k | NH2 | | | |
| 50 | | NH2 | Ac | Pen | N—Me—R | S | D | T | L | Pen | 2-NaI | Hphe | k | NH2 | | | | |
| 51 | | (NH2 | Ac | Pen | N—Me—R | S | D | T | L | Pen | W | Aic | k | NH2 | | | | |
| 52 | | | Beta-Ala | Pen | N—Me—R | S | D | T | L | Pen | W | E | NH2 | | | | | |
| 53 | | | Beta-Ala | Pen | N—Me—R | S | D | T | L | Pen | W | e | NH2 | | | | | |
| 54 | DIG | | Beta-Ala | Pen | N—Me—R | S | D | T | L | Pen | W | E | NH2)2 | | | | | |
| 55 | | | Ac | Pen | N—Me—R | S | D | T | L | Pen | W | e | Dap | NH2 | | | | |
| 56 | | | Ac | Pen | N—Me—R | S | D | T | L | Pen | W | e | Dab | NH2 | | | | |
| 57 | | | Ac | Pen | N—Me—R | S | D | T | L | Pen | W | E | NH2 | | | | | |
| 58 | | | Ac | Pen | N—Me—R | S | D | T | L | Pen | W | e | Dap | NH2 | | | | |
| 59 | | | Ac | Pen | N—Me—R | S | D | T | L | Pen | W | E | Dap | Ac | | | | |
| 60 | | | Ac | Pen | N—Me—R | S | D | T | L | Pen | W | E | Dab | NH2 | | | | |
| 61 | | | Ac | Pen | N—Me—R | S | D | T | L | Pen | W | e | Dap | Ac | | | | |
| 62 | | | Ac | Pen | N—Me—R | S | D | T | L | Pen | W | e | Dab | Ac | | | | |
| 63 | | | Ac | Pen | N—Me—R | S | D | T | L | Pen | W | E | Dap | Ac | | | | |
| 64 | | | Ac | Pen | N—Me—R | S | D | T | L | Pen | W | E | Dab | Ac | | | | |
| 65 | | | Ac | Pen | N—Me—R | S | D | T | L | Pen | W | e | k | Ac | | | | |
| 66 | | | Ac | Pen | N—Me—R | S | D | T | L | Pen | W | E | k | Ac | | | | |
| 67 | | | (Ac | Pen | N—Me—R | S | D | T | L | Pen | W | e | k | NH2)2 | DIG | | | |
| 68 | | | (Ac | Pen | N—Me—R | S | D | T | L | Pen | W | E | k | NH2)2 | DIG | | | |
| 69 | | | Ac | Pen | N—Me—R | S | D(OMe) | T | L | Pen | W | E | k | NH2 | | | | |
| 70 | | | (Ac | Pen | N—Me—R | S | D | T | L | Pen | W | e | k | NH2)2 | IDA | Biotine | | |
| 71 | | | (Ac | Pen | N—Me—R | S | D | T | L | Pen | W | e | k | NH2)2 | IDA | PEG4 | Biotine | |
| 72 | | | (Ac | Pen | N—Me—R | S | D(OMe) | T | L | Pen | W | e | k | NH2)2 | IDA | | | |
| 73 | | | (Ac | Pen | N—Me—R | S | D | T | L | Pen | W | E | k | DIG | | | | |
| 74 | | | Ac | D-Pen | N—Me—R | S | D | T | L | Pen | W | E | NH2 | DIG | | | | |
| 75 | | | (Ac | Pen | N—Me—R | S | D | T | L | Pen | 2-NaI | E | OH)2 | OH)2 | | | | |
| 76 | | | (Ac | Pen | N—Me—R | S | D | T | L | Pen | W | k | NH2)2 | NH2)2 | | | | |
| 77 | | | (Ac | Pen | N—Me—R | S | D | T | L | Pen | W | N—Me—K | k | NH2 | DIG | | | |
| 78 | | | (Ac | Pen | N—Me—R | S | D | T | L | Pen | E | Bip | k | NH2)2 | DIG | | | |
| 79 | | | (Ac | Pen | N—Me—R | S | D | T | L | Pen | 2-NaI | e | k | OH)2 | DIG | | | |
| 80 | | | (Ac | Pen | N—Me—R | S | D | T | L | Pen | Tic | E | k | NH2)2 | DIG | | | |
| 81 | | | (Ac | Pen | N—Me—R | S | D | T | L | Pen | W | E | k | NH2)2 | IDA | PEG4 | Biotine | |
| 82 | | | (Ac | Pen | N—Me—R | S | D | T | L | Pen | W | Q | k | NH2)2 | DIG | | | |
| 83 | | | (Ac | Pen | N—Me—R | S | D | T | L | Pen | W | N | k | NH2)2 | DIG | | | |
| 84 | | | (Ac | Pen | N—Me—R | S | D | T | L | Pen | W | Cit | k | NH2)2 | DIG | | | |
| 85 | | | (Ac | Pen | N—Me—R | S | D | T | L | Pen | W | F | k | NH2)2 | DIG | | | |
| 86 | | | (Ac | Pen | N—Me—R | S | D | T | L | Pen | W | E(OMe) | k | NH2)2 | DIG | | | |
| 87 | | | Ac | Pen | N—Me—R | S | D | T | L | Pen | W | D | k | NH2)2 | DIG | | | |
| 88 | | | Ac | Pen | N—Me—R | S | D | T | L | Pen | 2-NaI | k | k | NH2 | | | | |
| 89 | | | Ac | Pen | N—Me—R | S | D | T | L | C | Tic | e | k | DIG | | | | |
| 90 | | | Ac | Pen | N—Me—R | S | D | T | L | Pen | 2-NaI | k | k | NH2 | | | | |
| 91 | | | (Ac | Pen | N—Me—R | S | D | T | L | Pen | W | f | k | NH2)2 | DIG | | | |
| 92 | | | (Ac | Pen | N—Me—R | S | D | T | L | C | Tic | y | k | NH2)2 | DIG | | | |
| 93 | | | (Ac | Pen | N—Me—R | S | D | T | L | C | Tic | e | k | NH2)2 | DIG | | | |

TABLE 3-A-continued

Sequence and Structure of Illustrative Peptide Monomers and Peptide Dimers

| SEQ ID NO:1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| 94 |  | (Ac | Pen | N—Me—R | S | D | T | L | Pen | W | P | k | NH2)2 | DIG |  |  |  |
| 95 |  | (Ac | Pen | N—Me—R | S | D | T | L | Pen | W | P | K | NH2)2 | DIG |  |  |  |
| 96 |  | (Ac | Pen | N—Me—R | S | D | T | L | Pen | W | P | K | NH2)2 | DIG |  |  |  |
| 97 |  | (Ac | Pen | N—Me—R | S | D | T | L | Pen | W | E | Dab | NH2)2 | DIG |  |  |  |
| 98 |  | (Ac | Pen | N—Me—R | S | D | T | L | Pen | F(2-carbamoyl) | e | k | NH2)2 | DIG |  |  |  |
| 99 |  | (Ac | Pen | N—Me—R | S | D | T | L | Pen | F(3-carbamoyl) | e | k | NH2)2 | DIG |  |  |  |
| 100 |  | (Ac | Pen | N—Me—R | S | D | T | L | Pen | F(4-COOH) | e | k | NH2)2 | DIG |  |  |  |
| 101 |  | (Ac | Pen | N—Me—R | S | D | T | L | Pen | F(2,4-ci) | e | k | NH2)2 | DIG |  |  |  |
| 102 |  | (Ac | Pen | N—Me—R | S | D | T | L | Pen | F(3,4-ci) | e | k | NH2)2 | DIG |  |  |  |
| 103 |  | (Ac | Pen | N—Me—R | S | D | T | L | Pen | F(4-OMe) | e | k | NH2)2 | DIG |  |  |  |
| 104 |  | (Ac | Pen | N—Me—R | S | D | T | L | Pen | W | h | k | NH2)2 | DIG |  |  |  |
| 105 |  | (Ac | Pen | N—Me—R | S | D | T | L | Pen | W | F(4-COOH) | k | NH2)2 | DIG |  |  |  |
| 106 |  | (Ac | Pen | N—Me—R | S | D | T | L | Pen | F(4Bu) | e | k | NH2)2 | DIG |  |  |  |
| 107 |  | (Ac | Pen | N—Me—R | S | D | T | L | Pen | F(4-F) | e | k | NH2)2 | DIG |  |  |  |
| 108 |  | (Ac | Pen | N—Me—R | S | D | T | L | Pen | Bip | e | k | NH2)2 | DIG |  |  |  |
| 109 |  | (Ac | Pen | N—Me—R | S | D | T | L | Pen | W | Tic | k | NH2)2 | DIG |  |  |  |
| 110 |  | (Ac | Pen | N—Me—R | S | D | T | L | Pen | W | w | k | NH2)2 | DIG |  |  |  |
| 111 |  | (Ac | Pen | N—Me—R | S | D | T | L | Pen | 1-Nal | f | k | NH2)2 | DIG |  |  |  |
| 112 |  | (Ac | Pen | N—Me—R | S | D | T | L | Pen | 1-Nal | h | k | NH2)2 | DIG |  |  |  |
| 113 |  | (Ac | Pen | N—Me—R | S | D | T | L | Pen | 1-Nal | l | k | NH2)2 | DIG |  |  |  |
| 114 |  | (Ac | Pen | N—Me—R | S | D | T | L | Pen | 1-Nal | r | k | NH2)2 | DIG |  |  |  |
| 115 |  | (Ac | Pen | N—Me—R | S | D | T | L | Pen | 1-Nal | Tic | k | NH2)2 | DIG |  |  |  |
| 116 |  | (Ac | Pen | N—Me—R | S | D | T | L | Pen | 2-Nal | t | k | NH2)2 | DIG |  |  |  |
| 117 |  | (Ac | Pen | N—Me—R | S | D | T | L | Pen | 2-Nal | f | k | NH2)2 | DIG |  |  |  |
| 118 |  | (Ac | Pen | N—Me—R | S | D | T | L | Pen | 2-Nal | h | k | NH2)2 | DIG |  |  |  |
| 119 |  | (Ac | Pen | N—Me—R | S | D | T | L | Pen | 2-Nal | l | k | NH2)2 | DIG |  |  |  |
| 120 |  | (Ac | Pen | N—Me—R | S | D | T | L | Pen | 2-Nal | r | k | NH2)2 | DIG |  |  |  |
| 121 |  | (Ac | Pen | N—Me—R | S | D | T | L | Pen | 2-Nal | Tic | k | NH2)2 | DIG |  |  |  |
| 122 |  | (Ac | Pen | N—Me—R | S | D | T | L | Pen | F(4CF3) | e | k | NH2)2 | DIG |  |  |  |
| 123 |  | (Ac | Pen | N—Me—R | S | D | T | L | Pen | Y | e | k | NH2)2 | DIG |  |  |  |
| 124 |  | (Ac | Pen | N—Me—R | S | D | T | L | Pen | H | e | k | NH2)2 | DIG |  |  |  |
| 125 |  | (Ac | Pen | N—Me—R | S | D | T | L | Pen | F(4Bu) | E | N—Me—K | NH2)2 | DIG |  |  |  |
| 126 |  | Ac | Pen | N—Me—R | S | D | T | L | Pen | F(4Bu) | E | OH |  |  |  |  |  |
| 127 |  | Ac | Pen | N—Me—R | S | D | T | L | Pen | W | OH |  |  |  |  |  |  |
| 128 |  | (Ac | Pen | N—Me—R | S | D | T | L | Pen | W | E | k | NH2)2 | DIG |  |  |  |
| 129 |  | (Ac | Pen | N—Me—R | S | D | T | L | Pen | F(4-COOH) | E | k | NH2)2 | DIG |  |  |  |
| 130 |  | (Ac | Pen | N—Me—R | S | D | T | L | Pen | F(4-COOH) | b-H-E | k | NH2)2 | DIG |  |  |  |
| 131 |  | (Ac | Pen | N—Me—R | S | D | T | L | Pen | F(4Bu) | E | k | NH2)2 | DIG |  |  |  |
| 132 |  | (Ac | Pen | N—Me—R | S | D | T | L | Pen | F(4Bu) | b-H-E | k | NH2)2 | DIG |  |  |  |
| 133 |  | (Ac | Pen | N—Me—R | S | D | T | L | Pen | F(4Bu) | E | N—Me—K | NH2)2 | DIG |  |  |  |
| 134 |  | (Ac | Pen | N—Me—R | S | D | T | L | Pen | Bip | E | k | NH2)2 | DIG |  |  |  |
| 135 |  | (Ac | Pen | N—Me—R | S | D | T | L | Pen | Bip | b-H-E | k | NH2)2 | DIG |  |  |  |
| 136 |  | (Ac | Pen | N—Me—R | S | D | T | L | Pen | Bip | E | N—Me—K | NH2)2 | DIG |  |  |  |
| 137 |  | (Ac | Pen | N—Me—R | S | D | T | L | Pen | 2-Nal | E | k | NH2)2 | DIG |  |  |  |
| 138 |  | (Ac | Pen | N—Me—R | S | D | T | L | Pen | 2-Nal | E | N—Me—K | NH2)2 | DIG |  |  |  |
| 139 |  | (Ac | Pen | N—Me—R | S | D | T | L | Pen | F(4-CN) | b-H-E | k | NH2)2 | DIG | Acetate salt |  |  |

TABLE 3-A-continued

Sequence and Structure of Illustrative Peptide Monomers and Peptide Dimers

| SEQ ID NO: 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| 140 | | (Ac | Pen | N—Me—R | S | D | T | L | Pen | 2-NaI | t | k | NH2)2 | DIG | | | |
| 141 | | (Ac | Pen | N—Me—R | S | D | T | L | Pen | W | b-H-E | N—Me—K | NH2)2 | DIG | | | |
| 142 | | (Ac | Pen | N—Me—R | S | D | T | L | Pen | 1-NaI | b-H-E | N—Me—K | NH2)2 | DIG | | | |
| 143 | | (Ac | [Pen | N—Me—R | S | D | T | L | Pen | 2-NaI | E] | | | | | | |
| 144 | | Cyclo | [Pen | N—Me—R | S | D | T | L | Pen | W | E] | | | | | | |
| 145 | | Cyclo | [Pen | N—Me—R | S | D | T | L | Pen | W | e] | | | | | | |
| 146 | | Ac | Pen | N—Me—R | S | D | T | L | Pen | W | b-H-E | OH | | | | | |
| 147 | | (Ac | Pen | N—Me—R | S | D | T | L | Pen | F(4-COOH) | E | N—Me—K | NH2)2 | DIG | | | |
| 148 | | (Ac | Pen | N—Me—R | S | D | T | L | Pen | F(4-COOH) | b-H-E | N—Me—K | NH2)2 | DIG | | | |
| 149 | | (Ac | Pen | N—Me—R | S | D | T | L | Pen | F(4-tBu) | b-H-E | N—Me—K | NH2)2 | DIG | | | |
| 150 | | (Ac | Pen | N—Me—R | S | D | T | L | Pen | Bip | b-H-E | OH | | | | | |
| 151 | | Ac | Pen | N—Me—R | S | D | T | L | Pen | F(4-tBu) | b-H-E | OH | | | | | |
| 152 | | Ac | Pen | N—Me—R | S | D | T | L | Pen | F(4-tBu) | b-H-E | k | NH2 | | | | |
| 153 | | Ac | Pen | N—Me—R | S | D | T | L | Pen | F(4-tBu) | b-H-E | NH2 | | | | | |
| 154 | | Ac | Pen | N—Me—R | S | D | T | L | Pen | Tic | b-H-E | NH2 | | | | | |
| 155 | | Ac | Pen | N—Me—R | S | D | T | V | L | Pen | 2-NaI | e | NH2 | | | | |
| 156 | | Ac | Pen | N—Me—R | S | D | F | L | Pen | 2-NaI | e | NH2 | | | | | |
| 157 | | Ac | Pen | N—Me—R | S | D | Cha | L | Pen | 2-NaI | e | NH2 | | | | | |
| 158 | | Ac | Pen | N—Me—R | S | D | L | L | Pen | 2-NaI | e | NH2 | | | | | |
| 159 | | Ac | Pen | N—Me—R | S | D | I | L | Pen | 2-NaI | e | NH2 | | | | | |
| 160 | | Ac | Pen | N—Me—R | S | D | hLeu | L | Pen | 2-NaI | e | NH2 | | | | | |
| 161 | | Ac | Pen | N—Me—R | S | D | T | F | Pen | 2-NaI | e | NH2 | | | | | |
| 162 | | Ac | Pen | N—Me—R | S | D | T | Q | Pen | 2-NaI | e | NH2 | | | | | |
| 163 | | Ac | Pen | N—Me—R | S | D | T | Y | Pen | 2-NaI | e | NH2 | | | | | |
| 164 | | Ac | Pen | N—Me—R | S | D | T | L | Pen | 2-NaI | b-H-E | NH2 | | | | | |
| 165 | | (Ac | Pen | N—Me—R | S | D | T | L | Pen | F(4-tBu) | b-H-E | k | NH2)2 | IDA | | | |
| 166 | | (Ac | Pen | N—Me—R | S | D | T | L | Pen | F(4-tBu) | b-H-E | k | NH2)2 | IDA | | | |
| 167 | | (Ac | Pen | N—Me—R | S | D | T | L | Pen | F(4tBu) | b-H-E | k | OH)2 | DIG | | | |
| 168 | | Ac | Pen | N—Me—R | S | D | T | L | Pen | F(4-tBu) | b-H-E | k | b-H-E | k | PEG4 | | |
| 169 | | Ac | Pen | N—Me—R | S | D | T | L | Pen | F(4-tBu) | b-H-E | k | b-H-E | k | 4,4,4Triflouro butyric acid | | |
| 170 | | Ac | Pen | N—Me—R | S | D | T | L | Pen | F(4-tBu) | b-H-E | k | b-H-E | k | Hexanoic acid | | |
| 171 | | Ac | Pen | N—Me—R | S | D | T | L | Pen | F(4-tBu) | b-H-E | k | b-H-E | k | Isovalaric acid | | |
| 172 | | Ac | Pen | N—Me—R | S | D | T | L | Pen | F(4-tBu) | b-H-E | k | b-H-E | k | Palmitoyl chloride | | |
| 173 | | Ac | Pen | N—Me—R | S | D | T | L | Pen | F(4-tBu) | b-H-E | k | b-H-E | k | Lauroyl chloride | | |
| 174 | | Ac | Pen | N—Me—R | S | D | T | L | Pen | F(4-tBu) | b-H-E | k | b-H-E | k | Oleoyi chloride | | |
| 175 | | Ac | Pen | N—Me—R | S | D | T | L | Pen | F(4-tBu) | b-H-E | k | b-H-E | k | Myristoy chloride | Biotin | |
| 176 | Hexanoic acid | Pen | N—Me—R | S | D | T | L | Pen | F(4-tBu) | F(4-tBu) | b-H-E | k | NH2 | | | | |
| 177 | Isovalaric acid | Pen | N—Me—R | S | D | T | L | Pen | F(4-tBu) | F(4-tBu) | b-H-E | k | NH2 | | | | |

TABLE 3-A-continued

Sequence and Structure of Illustrative Peptide Monomers and Peptide Dimers

| SEQ ID NO: 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| 178 | Palmitoyl chloride | Pen | N—Me—R | S | D | T | L | Pen | F(4-tBu) | | b-H-E | k | NH2 | | | | |
| 179 | Lauroyl chloride | Pen | N—Me—R | S | D | T | L | Pen | F(4-tBu) | | b-H-E | k | NH2 | | | | |
| 180 | Oleoyl chloride | Pen | N—Me—R | S | D | T | L | Pen | F(4-tBu) | | b-H-E | k | NH2 | | | | |
| 181 | Myrstoyl chloride | Pen | N—Me—R | S | D | T | L | Pen | F(4-tBu) | | b-H-E | k | NH2 | | | | |
| 182 | | (Ac | Pen | N—Me—R | S | D | T | L | Pen | F(4-tBu) | b-H-E | k | NH2)2 | IDA | Alexa-488 | | |
| 182 | | (Ac | Pen | N—Me—R | S | D | T | L | Pen | F(4-tBu) | b-H-E | k | NH2)2 | IDA | Alexa-488 | | |
| 183 | | (Ac | Pen | N—Me—R | S | D | T | L | Pen | F(4-Bu) | b-H-E | k | NH2)2 | IDA | Alexa-647 | | |
| 184 | | (13C(2)-Ac | Pen | N—Me—R | S | D | T | 13C(5)L | Pen | F(4Bu) | b-H-E | k | NH2)2 | DIG | | | |
| 185 | | (Ac | Pen | N—Me—R | S | D | T | L | Pen | F(4Bu) | b-H-E | k | NH2)2 | IDA | | | |
| 186 | | (Ac | Pen | N—Me—R | S | D | I | L | Pen | F(4-tBu) | b-H-E | k | NH2)2 | IDA | | | |
| 187 | | (Ac | Pen | N—Me—R | S | D | T | Q | Pen | F(4-tBu) | b-H-E | k | NH2)2 | IDA | Alexa-647 | | |
| 188 | | (Ac | Pen | N—Me—R | S | Q | I | L | Pen | F(4-tBu) | b-H-E | k | NH2)2 | DIG | | | |
| 189 | | (Ac | Pen | N—Me—R | S | D | T | Q | Pen | F(4-tBu) | b-H-E | k | NH2)2 | DIG | | | |
| 190 | | (Ac | Pen | N—Me—R | S | Q | I | L | Pen | F(4-tBu) | b-H-E | k | NH2)2 | IDA | | | |
| 191 | | (Ac | Pen | N—Me—R | S | D | D | Q | Pen | F(4-tBu) | b-H-E | k | NH2)2 | IDA | | | |
| 192 | | (Ac | Pen | N—Me—R | S | S | I | L | Pen | F(4-tBu) | b-H-E | k | NH2)2 | IDA | Alexa-647 | | |
| 193 | | (Ac | Pen | N—Me—R | S | D | D | L | Pen | F(4-tBu) | b-H-E | k | NH2)2 | IDA | Alexa-647 | | |

TABLE 3-B

Potency, Selectivity, and Stability of Illustrative Peptide Monomers and Dimers

| SEQ ID NO: | α4β7 ELISA IC50 (nM) | α4β7 cell (Hu) IC50 (nM) | α4β7 cell (Mu) IC50 (nM) | α4β1 ELISA IC50 (nM) | α4β1 cell IC50 (nM) | PBMC IC50 (nM) | Stability SIF t½ (min) |
|---|---|---|---|---|---|---|---|
| 1 |  | >50 |  |  |  |  | >180 |
| 2 |  | >100 |  |  |  |  | >180 |
| 3 |  | >25 |  |  |  |  | >180 |
| 4 |  | >10 |  |  |  |  | <20 |
| 5 |  | >50 |  |  |  |  | 6 |
| 6 |  | >50 |  |  |  |  |  |
| 7 |  | >1,000 |  |  |  |  |  |
| 8 | >25 |  |  |  |  |  |  |
| 9 | >10 | >100 |  |  |  |  |  |
| 10 | >10 |  |  |  |  |  |  |
| 11 | >25 |  |  |  |  |  |  |
| 12 | >25 |  |  |  |  |  |  |
| 13 | >10 | >100 |  |  |  |  |  |
| 14 | >25 |  |  |  |  |  |  |
| 15 | ≤10 |  |  |  |  |  |  |
| 16 | >10 |  |  |  |  |  |  |
| 17 | >10 |  |  |  |  |  |  |
| 18 | >10 |  |  | >500 |  |  |  |
| 19 | >10 |  |  |  |  |  |  |
| 20 |  | >50 |  |  |  |  |  |
| 21 |  | >50 |  |  |  |  |  |
| 22 | ≤10 | ≤10 |  | >100 |  |  | <20 |
| 23 |  | ≤10 |  | >100 |  |  | <20 |
| 24 | ≤10 | ≤10 |  | >100 |  |  | 56 |
| 25 |  | >10 |  |  |  |  |  |
| 26 |  | >100 |  |  |  |  |  |
| 27 |  | >25 |  |  |  |  | >180 |
| 28 |  | >50 |  |  |  |  |  |
| 29 | ≤10 | >10 |  |  |  |  | >180 |
| 30 |  | >100 |  |  |  |  |  |
| 31 |  | >50 |  |  |  |  |  |
| 32 | ≤10 | >10 |  | >100 |  |  | >180 |
| 33 | ≤10 | >10 |  | >100 | >100,000 |  | >180 |
| 34 |  | >25 |  |  |  |  |  |
| 35 |  | >100 |  |  |  |  |  |
| 36 |  | >50 |  |  |  |  |  |
| 37 |  | >100 |  |  |  |  |  |
| 38 | ≤10 | ≤10 |  | >100 |  |  | >180 |
| 39 |  | >10 |  |  |  |  | >180 |
| 40 | ≤10 | >100 |  |  |  |  |  |
| 41 | ≤10 | ≤10 |  | >100 |  |  | >180 |
| 42 | ≤10 | ≤10 |  | >100 |  |  | 51, 49 |
| 43 | ≤10 | >10 |  | >100 |  |  | 21 |
| 44 | ≤10 | ≤10 | ≤10 | >100 |  |  | >180 |
| 45 |  | >25 |  |  |  |  | 37 |
| 46 | >1,000 |  |  |  |  |  | >180 |
| 47 | >1,000 |  |  |  |  |  | >180 |
| 48 | >1,000 |  |  |  |  |  | >180 |
| 49 | >10 |  |  |  |  |  | >180 |
| 50 | >10 |  |  |  |  |  | 104 |
| 51 | >25 |  |  |  |  |  | 180 |
| 52 | >10 | >100 |  |  |  |  | 117 |
| 53 | >10 |  |  |  |  |  | >180 |
| 54 |  | >25 |  | >100 |  |  | 32 |
| 55 |  | >100 |  |  |  |  | >180 |
| 56 |  | >500 |  |  |  |  | >180 |
| 57 |  |  |  |  |  |  |  |
| 58 |  |  |  |  |  |  |  |
| 59 |  | >10,000 |  |  |  |  |  |
| 60 |  | >1,000 |  |  |  |  |  |
| 61 |  | >1,000 |  |  |  |  |  |
| 62 |  | >1,000 |  |  |  |  |  |
| 63 |  | >1,000 |  |  |  |  |  |
| 64 |  | >1,000 |  |  |  |  |  |
| 65 |  | >10,000 |  |  |  |  |  |
| 66 |  | >10,000 |  |  |  |  |  |
| 67 | ≤10 | ≤10 | ≤10 | >100 | >100,000 |  | 121 |
| 68 | ≤10 | >25 | ≤10 | >500 | >100,000 | >100 | >300 |
| 69 | >10 | >100 |  |  |  |  |  |
| 70 |  | >25 |  |  |  |  |  |
| 71 |  | >25 |  |  |  |  |  |
| 72 |  | >25 |  |  |  |  |  |

TABLE 3-B-continued

Potency, Selectivity, and Stability of Illustrative Peptide Monomers and Dimers

| | Potency (α4β7) | | | Selectivity (α4β1) | | | |
|---|---|---|---|---|---|---|---|
| SEQ ID NO: | α4β7 ELISA IC50 (nM) | α4β7 cell (Hu) IC50 (nM) | α4β7 cell (Mu) IC50 (nM) | α4β1 ELISA IC50 (nM) | α4β1 cell IC50 (nM) | PBMC IC50 (nM) | Stability SIF t½ (min) |
| 73 | ≤10 | ≤10 | | | | | |
| 74 | | | | | | | |
| 75 | | >50 | | | | | |
| 76 | | >10 | | | | | |
| 77 | | >100 | | | | | >180 |
| 78 | ≤10 | ≤10 | ≤10 | >100 | >100,000 | | |
| 79 | | | | | | | |
| 80 | | >50 | | | | | >180 |
| 81 | | | | | | | |
| 82 | | >50 | | | | | |
| 83 | | >50 | | | | | |
| 84 | | >10 | | | | | <20 |
| 85 | | ≤10 | | | | | |
| 86 | | ≤10 | ≤10 | | | | |
| 87 | | >25 | | | | | |
| 88 | >10 | | | | | | |
| 89 | >25 | | | | | | |
| 90 | | | | | | | |
| 91 | | >100 | | | | | |
| 92 | | >50 | | | | | |
| 93 | | >500 | | | | | |
| 94 | | >100 | | | | | |
| 95 | | >100 | | | | | |
| 96 | | >50 | | | | | |
| 97 | | ≤10 | | | | | |
| 98 | | >50 | | | | | |
| 99 | | >100 | | | | | >180 |
| 100 | | ≤10 | | | | | |
| 101 | | >50 | | | | | |
| 102 | | >100 | | | | | |
| 103 | | >25 | | | | | |
| 104 | | >100 | | | | | 35 |
| 105 | | >50 | | | | | |
| 106 | | ≤10 | | | | | |
| 107 | | >25 | | | | | >180 |
| 108 | | >10 | | | | | |
| 109 | | >100 | | | | | |
| 110 | | >10 | | | | | |
| 111 | | >100 | | | | | |
| 112 | | >50 | | | | | |
| 113 | | >500 | | | | | |
| 114 | | >100 | | | | | |
| 115 | | >100 | | | | | |
| 116 | | >50 | | | | | |
| 117 | | >100 | | | | | |
| 118 | | >25 | | | | | |
| 119 | | >500 | | | | | |
| 120 | | >1,000 | | | | | |
| 121 | | >100 | | | | | |
| 122 | | >50 | | | | | |
| 123 | | >50 | | | | | |
| 124 | | >100 | | | | | |
| 125 | | >100 | | | | | |
| 126 | | >1,000 | | | | | |
| 127 | | >100 | | | | | 35 hr |
| 128 | | >50 | | | | | 180 |
| 129 | ≤10 | ≤10 | | >100 | | ≤10 | >360 (13 hr) |
| 130 | ≤10 | ≤10 | | >100 | | ≤10 | >360 (16 hr) |
| 131 | ≤10 | ≤10 | | >100 | | | >360 (9 hr) |
| 132 | ≤10 | ≤10 | ≤10 | >100 | >100,000 | ≤10 | >360 (10.7 h) |
| 132 | ≤10 | ≤10 | ≤10 | >500 | | ≤10 | 11 hr |
| 133 | ≤10 | ≤10 | | >100 | | ≤10 | >360 (11 hr) |
| 134 | ≤10 | ≤10 | | >100 | | | |
| 135 | | ≤10 | | | | | |
| 136 | | ≤10 | | | | | |
| 137 | ≤10 | ≤10 | | >1,000 | | | |
| 138 | >10 | >10 | | | | | |
| 139 | | ≤10 | | | | | |
| 140 | | >10 | | | | | |
| 141 | ≤10 | ≤10 | | >500 | | | |
| 142 | ≤10 | ≤10 | | >500 | | >50 | |
| 143 | 250 | >10,000 | | | | | |

TABLE 3-B-continued

Potency, Selectivity, and Stability of Illustrative Peptide Monomers and Dimers

| | Potency (α4β7) | | | Selectivity (α4β1) | | | |
|---|---|---|---|---|---|---|---|
| SEQ ID NO: | α4β7 ELISA IC50 (nM) | α4β7 cell (Hu) IC50 (nM) | α4β7 cell (Mu) IC50 (nM) | α4β1 ELISA IC50 (nM) | α4β1 cell IC50 (nM) | PBMC IC50 (nM) | Stability SIF t½ (min) |
| 144 | 364 | >10,000 | | | | | |
| 145 | 504 | >10,000 | | | | | |
| 146 | | >50 | >50 | >1,000 | | | |
| 147 | ≤10 | ≤10 | ≤10 | >100 | | ≤10 | >300 |
| 148 | ≤10 | ≤10 | ≤10 | >100 | | | >300 |
| 149 | ≤10 | ≤10 | ≤10 | >500 | | ≤10 | >300 |
| 150 | ≤10 | ≤10 | ≤10 | >1,000 | | | >300 |
| 151 | >10 | >50 | | | | | 187 |
| 152 | ≤10 | ≤10 | ≤10 | >100 | | >25 | 147 |
| 153 | >10 | >10 | >10 | >1,000 | | | 13.6 hr |
| 154 | | >100 | >1,000 | >1,000 | | | |
| 155 | | >25 | >25 | >1,000 | | | |
| 156 | | >100 | | | | | |
| 157 | | >1,000 | | | | | |
| 158 | | >1,000 | | | | | |
| 159 | | >1,000 | | | | | |
| 160 | | >1,000 | | | | | |
| 161 | | >1,000 | | | | | |
| 162 | | >1,000 | | | | | |
| 163 | | >1,000 | | | | | |
| 164 | | >1,000 | | | | | |
| 165 | | >10 | | | | >100 | >180 |
| 166 | | ≤10 | | | | ≤10 | |
| 167 | | ≤10 | | | | ≤10 | |
| 168 | | ≤10 | | | | ≤10 | |
| 169 | | >10 | | | | | |
| 170 | | >10 | | | | | |
| 171 | | >10 | | | | | |
| 172 | | 965 | | | | | |
| 173 | | >100 | | | | | |
| 174 | | >1,000 | | | | | |
| 175 | | >500 | | | | | |
| 176 | | >50 | | | | | |
| 177 | | >50 | | | | | |
| 178 | | >1,000 | | | | | |
| 179 | | >100 | | | | | |
| 180 | | >1,000 | | | | | |
| 181 | | >1,000 | | | | | |
| 182 | ≤10 | | | | | | >180 |
| 182 | ≤10 | 0 | | | | | >180 |
| 183 | ≤10 | 0 | | | | | >180 (466) |
| 184 | | | | | | | |
| 185 | | | | | | | |
| 186 | | >100 | | | | | |
| 187 | | >100 | | | | | |
| 188 | | ≤10 | | | | | |
| 189 | | >10,000 | | | | | |
| 190 | | >100,000 | | | | | |
| 191 | | >10,000 | | | | | |
| 192 | | >10,000 | | | | | |
| 193 | | >100,000 | | | | | |

For IC50 data: ≤10 is less than or equal to 10 nM; >10 is greater than 10 nM and less than or equal to 25 nM; >25 is greater then 25 nM and less than or equal to 50 nM; >50 is greater than 50 nM and less than or equal to 100 nM; >100 is greater than 100 nM and less than or equal to 500 nM; >500 is greater than 500 nM and less than or equal to 1,000 nM; >1,000 is greater than 1,000 nM and less than or equal to 10,000 nM; >10,000 is greater than >10,000 nM but less than or equal to >100,000 nM; and >100,000 is greater than 100,000 nM.
For stability data: >180 means experiment was stopped after 180 min and half life was not reached; >360 means experiment was stopped after 360 min and half life was not reached.

TABLE 4-A

Comparison of Peptide Monomers and Dimers - Sequences

| peptide | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 194 | | Ac | C | R | S | D | T | L | C | G | | E | NH2 | |
| 195 | | Ac | C | R | S | D | T | L | C | NH2 | | | | |
| 196 | | Ac | C | R | S | D | T | L | C | G | | E | K | NH2 |
| 197 | | (Ac | C | R | S | D | T | L | C | G | | E | K | NH2)2 PEG25 |

TABLE 4-A-continued

Comparison of Peptide Monomers and Dimers - Sequences

| peptide | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 198 | Ac | C | N—Me—R | S | D | T | L | C | G | E | NH2 | | | |
| 199 | Ac | C | N—Me—R | S | D | T | L | C | G | E | K | OH | | |
| 200 | (Ac | C | N—Me—R | S | D | T | L | C | K | OH)2 | PEG25 | | | |
| 201 | (Ac | C | N—Me—R | S | D | T | L | C | G | E | K | OH)2 | DIG | |
| 202 | Ac | C | N—Me—R | S | D | T | L | Pen | k | NH2 | | | | |
| 203 | (Ac | C | N—Me—R | S | D | T | L | Pen | k | NH2)2 | IDA | | | |
| 204 | (Ac | C | N—Me—R | S | D | T | L | Pen | W | k | NH2)2 | DIG | |
| 205 | (Ac | C | N—Me—R | S | D | T | L | Pen | E | k | NH2)2 | DIG | |
| 206 | Ac | Pen | R | S | D | T | L | C | k | NH2 | | | | |
| 207 | (Ac | Pen | R | S | D | T | L | C | k | NH2)2 | DIG | | | |
| 208 | (Ac | Pen | N—Me—R | S | D | T | L | Pen | W | k | NH2 | | | |
| 209 | (Ac | Pen | N—Me—R | S | D | T | L | Pen | W | k | NH2)2 | DIG | |
| 210 | Ac | Pen | N—Me—R | S | D | T | L | Pen | 2-NaI | E | k | NH2 | | |
| 211 | (Ac | Pen | N—Me—R | S | D | T | L | Pen | W | e | k | NH2)2 | DIG |
| 212 | (Ac | Pen | N—Me—R | S | D | T | L | Pen | 2-NaI | E | k | NH2)2 | DIG |
| 213 | (Ac | Pen | N—Me—R | S | D | T | L | Pen | W | b-h-E | k | NH2)2 | DIG |
| 214 | (Ac | Pen | N—Me—R | S | D | T | L | Pen | W | E | N—Me-k | NH2)2 | DIG |
| 215 | (Ac | Pen | N—Me—R | S | D | T | L | Pen | W | E | N—Me—K | NH2)2 | DIG |
| 216 | (Ac | Pen | N—Me—R | S | D | T | L | Pen | W | e | k | OH)2 | DIG |
| 217 | (Ac | Pen | N—Me—R | S | D | T | L | Pen | W | E | k | NH2)2 | DIG |
| 218 | (Ac | Pen | N—Me—R | S | D | T | L | Pen | F(4-tBu) | b-H-E | k | NH2)2 | DIG |

TABLE 4-B

Comparison of Peptide Monomers and Dimers - Potency and Selectivity

| peptide | ELISA α4β7 IC50 (nM) | ELISA_α4β1 IC50 (nM) | Cell Adhesion α4β7 IC50 (nM) | Cell Adhesion α4β1 IC50 (nM) | Cell Adhesion α4β7 Mouse IC50 (nM) | Cell Adhesion PBMC IC50 (nM) |
|---|---|---|---|---|---|---|
| 194 | 97 | 2020 | 590 | | | |
| 195 | 97 | 2880 | 1221 | | | |
| 196 | 87 | 4810 | 6660 | >100,000 | | |
| 197 | 36 | 964 | 301 | >100,000 | | |
| 198 | 20 | 1287 | 1120 | >100,000 | | |
| 199 | 58 | >100,000 | 4691 | | | |
| 200 | 3 | 16667 | 96 | >100,000 | | |
| 201 | 1 | 1244 | 28 | | | |
| 202 | 87 | 1619 | 11049 | >100,000 | | |
| 203 | 7.5 | 700 | 200 | >100,000 | 633 | |
| 204 | 2 | 463 | 22 | >100,000 | | 1277 |
| 205 | 2.4 | 444 | 26 | | | |
| 206 | 97 | | | | | |
| 207 | 26 | | 49 | | | |
| 208 | 30.5 | | 412 | | | |
| 209 | 2.3 | 368 | 24 | >100,000 | 51 | 260 |
| 210 | 11 | 200 | 40 | >100,000 | 60 | 517 |
| 211 | 3 | 302 | 22 | >100,000 | 7.3 | |
| 212 | 2 | 70 | 2.5 | >100,000 | 2.5 | |
| 213 | 4.7 | 539 | 12 | >100,000 | 4.2 | |
| 214 | 4.1 | 436 | 2.5 | | 1.1 | 24.5 |
| 215 | 2.2 | 270 | 3 | | 0.9 | 16.5 |
| 216 | 2.8 | 247 | 4.2 | >100,000 | 1 | 14.5 |
| 217 | 2.3 | 315 | 3.2 | >100,000 | 1.2 | |
| 218 | 2.8 | 490 | 0.78 | >100,000 | 0.5 | 2 |

TABLE 4-C

Comparison of Peptide Monomers and Peptide Dimers - Stability

| peptide | SIF (porcine) Min | Plasma (rat) Min | SGF (porcine) Min | Intestinal Wash (Rat) Min | DTT Min | Cys/CySS (mV) |
|---|---|---|---|---|---|---|
| 194 | <1 | | | | 5.5 | |
| 195 | <1 | | | | 4.7 | |
| 196 | <4 | | | | | |
| 197 | | | | | | |
| 198 | | | | | 30 | 4.5 |
| 199 | 27 | 81 | >360 | | | |
| 200 | 8 | 88 | >360 | | | |
| 201 | 18 | 121 | >360 | | | |

TABLE 4-C-continued

Comparison of Peptide Monomers and Peptide Dimers - Stability

| peptide | SIF (porcine) Min | Plasma (rat) Min | SGF (porcine) Min | Intestinal Wash (Rat) Min | DTT Min | Cys/CySS (mV) |
|---|---|---|---|---|---|---|
| 202 | >360 | >360 | | | 42 | |
| 203 | >293 | >360 | >360 | | 21 | |
| 204 | >360 | >360 | >360 | >180 | 27 | −204 |
| 205 | >360 | >360 | | | 42 | |
| 206 | 26 | | | | 52 | |
| 207 | <20 | | >60 | <10 | 35 | −173 |
| 208 | >360 | | >360 | | >120 | <−300 |
| 209 | >180 | >180 | >180 | >180 | >120 | <−300 |
| 210 | >300 | | | | >120 | <−300 |
| 211 | >300 | | >60 | 179 | >120 | |
| 212 | 90 | | 39 | 98 | >120 | |
| 213 | >180 | | >180 | | | |
| 214 | >810 | >360 | >360 | >360 | >120 | |
| 215 | >360 | >360 | >360 | >360 | >120 | |
| 216 | >180 | >180 | >360 | >360 | | |
| 217 | 121 | >120 | >360 | >180 | >120 | <−300 |
| 218 | 11 hr | >360 | >360 | >360 | >120 | <−300 |

Example 3 Characterization of an Illustrative Peptide Dimer Molecule in Biochemical and Cell Binding Assays Certain embodiments of the invention relate to an α4β7 integrin antagonist peptide dimer of two peptide monomer subunits each having the amino acid sequence shown below:

(SEQ ID NO: 225)
Pen-(N-Me-Arg)-Ser-Asp-Thr-Leu-Pen-[Phe(4-tBu)]-

(β-homoGlu)-(D-Lys).

The two peptide monomer subunits each contain an intramolecular disulfide bond between the two Pen residues present in each peptide monomer subunits.

Each of the two peptide monomer subunits contains an N-terminal acetyl group, and the two peptide monomer subunits are dimerized at each of their C-termini by the DIG linker to produce the peptide dimer referred to herein as Peptide X, which is diagrammed below:

(SEQ ID NO: 302)
[Ac-Pen-(N-Me-Arg)-Ser-Asp-Thr-Leu-Pen-(Phe(4- tBu))-(β-homoGlu)-(D-Lys)]$_2$.

In vitro biochemical and cell binding assays were performed to further characterize Peptide X.

Biochemical and Cell Binding Assays

Biochemical competition ELISA assays were performed for α4β7 and a4(31 integrins. The ELISA assay for α4β7 is based on binding of MAdCAM-1 to immobilized α4β7, whereas the α4β1 ELISA relies on binding of soluble α4β1 to immobilized VCAM-1. These assays are described in Example 2. Under 1 mM Mg$^{2+}$ binding conditions, the IC$_{50}$ for Peptide X was 3 nM and >10,000 nM for α4β7 and α4β1, respectively. In addition, the IC$_{50}$ for Peptide X was >100 uM for both α4β1 and αLβ2. The IC50 of Peptide X for α4β7 T cells was 1 nM.

Peptide X also blocked adhesion of MAdCAM-1 to transformed cell lines expressing α437 integrin. The Peptide X IC$_{50}$ for blocking adhesion of the human B cell lymphoblastoid RPMI8866 or mouse T cell TK1 cell lines to MAdCAM-1 was 0.72 nM and 0.50 nM, respectively.

Peptide X was highly selective in the cell adhesion assays. The human Jurkat cell line expresses both α4β1 and αLβ2 integrins for specific adhesion to VCAM-1 or ICAM-1, respectively. In the Jurkat/VCAM-1 or Jurkat/ICAM-1 cell adhesion assay, Peptide X was inactive at the maximum concentration tested (IC$_{50}$>100,000 nM). Together, these results indicated that Peptide X was specific for α4β7, and did not block the α4β1 and αLβ2 integrins.

Peptide X also blocked adhesion of memory T cells isolated from human PBMC donors. Peptide X blocked adhesion of memory T cells to MAdCAM-1. The Peptide X average IC$_{50}$ was 1.3 nM using cells isolated from 4 different donors. In contrast, Peptide X was inactive at the highest concentration tested in cell adhesion assays specific for α4β1 and αLβ2 (Table 5).

TABLE 5

Potency of Peptide X for memory T cells isolated from human PBMC donors.

| Integrin | α4β7 | α4β1 | αLβ2 |
|---|---|---|---|
| Ligand | MAdCAM-1 | VCAM-1 | ICAM-1 |
| IC$_{50}$ (nM) | 1.3 | >100,000 | >100,000 |

Surface plasmon resonance (SPR) was used to further evaluate the binding properties of Peptide X. An analog of Peptide X (Peptide X-biotin), which contains a biotin group attached to Peptide X via a PEG linker, was synthesized. Another peptide dimer having the following structure, which is closely related to Peptide X, was also synthesized and biotin-labeled:

(Peptide Z)
(SEQ ID NO: 67)
(Ac-Pen-(N-Me-Arg)-S-D-T-L-Pen-W-E-k-NH$_2$)$_2$-DIG.

Vedolizumab was also chemically biotinylated. Peptide X-biotin, Peptide Z-biotin, or biotin-labeled vedolizumab antibody was immobilized to a streptavidin coated SPR chip, and the binding of soluble α4β7 integrin was measured. The sensor grams showed that the calculated half-life for dissociation of Peptide X-biotin from α4β7 integrin was 667 min, or ~11 hours. This half-life is quite long, and may be caused by a tight association between the peptide and the bound Mn$^{2+}$ metal ion on the integrin. These SPR studies also showed that the KD for Peptide X-biotin was 15 nM, which was 3.8-fold lower than that for biotin-labeled vedolizumab (59 nM; Table 6). In addition, the KD for Peptide X-biotin was substantially lower than that for Peptide Z-biotin. In conclusion, these data show that the binding constants for Peptide X are superior to those for the antibody vedolizumab or a closely related peptide dimer. The K$_{on}$/K$_{off}$ of Peptide X-biotin was comparable or superior to that of vedolizumab by SPR.

TABLE 6

Summary of binding rate constants for Peptide X, Peptide Z and vedolizumab.

| | ka ($M^{-1}$ $sec^{-1}$) | kd ($sec^{-1}$) | Half-life for dissociation (min) | $K_D$ (nM) |
|---|---|---|---|---|
| Peptide X-biotin | 1120 | 0.0000173 | 668 | 15.4 |
| Peptide Z-biotin | 1048 | 0.0000546 | 211.54 | 52.10 |
| Vedolizumab-biotin | 4469 | 0.000266 | 43 | 59.5 |

Half-life of dissociation $t_{1/2}$ (sec) = $\ln 2 / k_d$

Schild analysis was used to determine if Peptide X blocked MAdCAM binding to α4β7 integrin by a simple competitive mechanism. Binding of soluble MAdCAM to immobilized α4β7 integrin protein at different Peptide X concentrations was measured by ELISA, and the results showed that antagonism was surmountable by increasing MAdCAM concentration. This result indicated that binding of Peptide X to α4β7 integrin was reversible. Based on the dose-response shifts, global-fit Schild analysis was used to determine the Schild slope and equilibrium dissociation constant (KB). The slope was ~1, which indicated the inhibition is orthosteric antagonism with respect to MAd-CAM, and not allosteric antagonism. This suggests that Peptide X and MAdCAM bind to the same site on α4β7 integrin. The estimated KB value was 1 nM, which was similar to other Peptide X potency values in different assays.

In Vitro FACS Studies

Figure 10A:
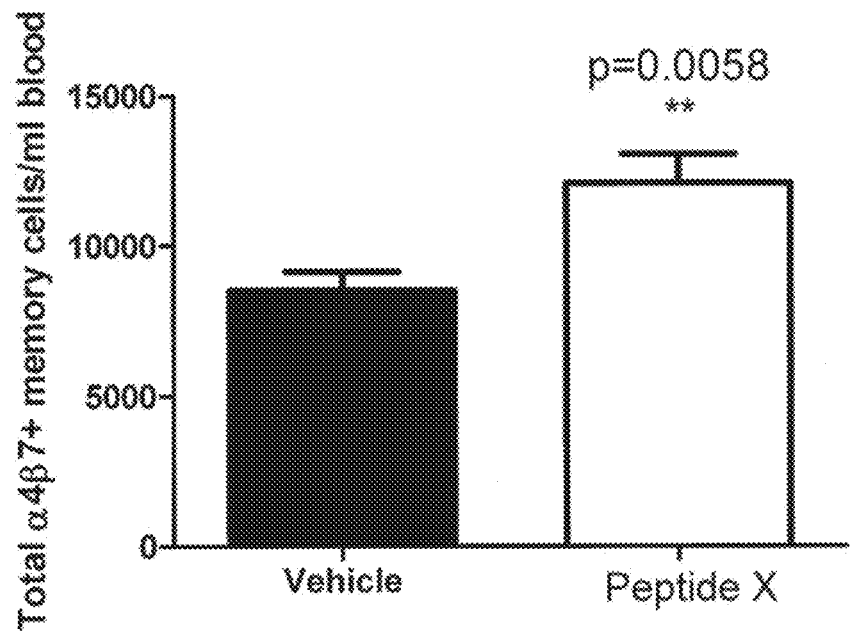
FIGS. 10A and 10B are graphs showing the total α4β7+ memory cells following treatment with vehicle or Peptide X in blood (A) and spleen (B). α4β7+ memory T cells are defined as CD4+, CD45RB$^{low}$, CD44$^{high}$, α4β7$^{+}$. Data are presented as mean±SEM. n=10 mice per group.
Figure 10B:
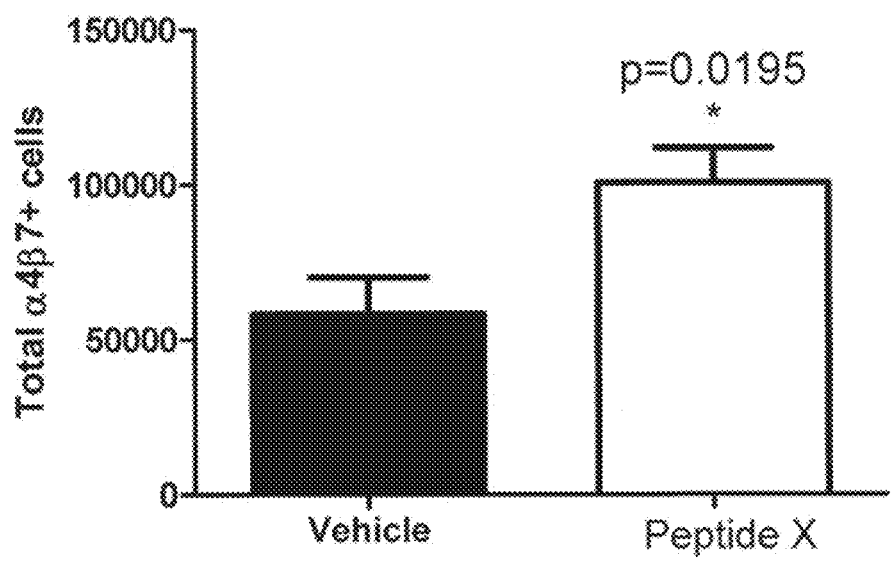

To further evaluate the selectivity of Peptide X in human blood, the fluorescent dye Alexa 647 was conjugated to Peptide X at the same position used for attaching biotin. The Peptide X Alexa 647 conjugate (Peptide X-Alexa647) was active in an RPMI8866/MAdCAM cell adhesion assay ($IC_{50}$=0.15 nM). Heparinized human whole blood was supplemented with 1 mM $MnCl_2$, and stained with the Peptide X-Alexa647 conjugate or biotinylated vedolizumab for 1 hour at room temperature. The samples were fixed (red blood cells lysed) and washed. The vedolizumab samples were stained separately with streptavidin Alexa 647 for stain for 30 minutes at room temperature. FACS analysis was used to assess binding of the peptide or vedolizumab to a broad panel of cell types including NK cells, basophils, monocytes, eosinophils, neutrophils, CD4 naïve T cells, CD4 memory T cells, CD8 naïve T cells, CD8 memory T cells, and B cells. FIG. 10 shows the binding specificities of Peptide X-Alexa647, or vedolizumab conjugated to Alexa Fluor 647, incubated with human whole blood in the presence of 1 mM $MnCl_2$. Table 3 shows that the binding specificities of vedolizumab and Peptide X are nearly identical in whole blood. The binding specificity for vedolizmab shown in Table 7 is also very similar to that reported in the literature (Soler et al, JPET 330:864-875, 2009).

TABLE 7

Binding specificity of vedolizumab or Peptide X-Alexa647 (1 nM) in whole blood.

| | Percent positive staining | |
|---|---|---|
| | Vedolizumab | Peptide X-Alexa 647 |
| CD4 naïve T cells | 55 | 51 |
| CD4 memory T cells | 22 | 20 |
| CD8 naïve T cells | 53 | 52 |
| CD8 memory T cells | 36 | 36 |

TABLE 7-continued

Binding specificity of vedolizumab or Peptide X-Alexa647 (1 nM) in whole blood.

| | Percent positive staining | |
|---|---|---|
| | Vedolizumab | Peptide X-Alexa 647 |
| CD19+ B cells | 85 | 78 |
| NK cells CD16+ 56+ | 42 | 45 |
| Basophils | 86 | 87 |
| Monocytes | 7 | 7 |
| Eosinophils | 91 | 92 |
| Neutrophils | 0.45 | 0.35 |

Blood from cynomolgus monkeys was also analyzed by FACS. These studies showed that cells expressing α4β7 can bind vedolizumab and Peptide X simultaneously. Therefore, Peptide X binds to a site on α4β7 that is distinct from the binding site for vedolizumab.

Binding to αEβ7 integrin in cyno blood was also tested. Cyno blood was incubated with 1 nM Peptide X-Alexa647, and cells expressing α4β7 or αEβ7 were analyzed by FACS. For CD4 memory T cells, Peptide X-Alexa647 bound to α4β7+, but not αEβ7+ cells. Binding to α437 was specific, because it could be blocked in the presence of a large excess (1 uM) of unlabeled Peptide X. Therefore under these conditions, it was concluded that Peptide X binds α4β7, not αEβ7.

Example 4

In Vivo Characterization of an Illustrative Peptide Dimer Molecule

The in vivo pharmacokinetic and efficacy characteristics of Peptide X were also determined in animal studies, including pharmacokinetic studies in Cynomolgus monkeys and efficacy studies in a mouse model of DSS colitis Pharmacokinetic Studies in Cynomolgus Monkey To determine tissue exposure following oral administration of Peptide X, Cynomolgus monkeys were dosed with Peptide X PO QD for 8 days at 12.5 mg/kg, 25 mg/kg or 75 mg/kg. The vehicle was 50 mM phosphate buffer, pH 7. Oral bioavailability in cyno (% F) was about 0.3%. Samples were collected 4 hours after the last dose. Peptide X levels were measured by mass spectrometry and are shown in Table 8 as nM, demonstrating that Peptide X exposure was much greater in intestinal tissues compared to plasma.

TABLE 8

Peptide X exposure in cynomolgus monkey tissues

| Dose (mg/kg) | Plasma | Colon | Small Intestine | Mesenteric Lymph Node |
|---|---|---|---|---|
| 12.5 | 2 | 4157 | 661 | 1501 |
| 25 | 5 | 1549 | 293 | 138 |
| 75 | 21 | 15460 | 7842 | 1980 |

To further evaluate the in vivo properties of Peptide X in a higher species, cynomolgus monkeys were dosed with Peptide X for 7 days. Dosing was oral (nasogastric intubation) once daily. Whole blood (about 3.5 mL) was collected on Day 0 (prior to dosing) and Day 6 (1 hour post the last dose) for PK and PD analysis. On Day 6, blood was also collected from a non-dosed animal. For PD, FACS analysis was used to measure receptor occupancy, down-regulation of α4β7 expression and circulating levels of T cells expressing the integrin α4β7. Table 9 shows the organization of the test groups.

TABLE 9

Organization of test groups for the 7 day cynomolgus monkey study

| Group Number | Test article | Dose (mg/kg/day) | Number of animals Males | Females |
|---|---|---|---|---|
| 1 | Peptide X | 12.5 | 2 | 2 |
| 2 | Peptide X | 25 | 2 | 2 |
| 3 | Peptide X | 75 | 2 | 2 |

For FACS analysis, heparinized whole blood from the cynos was stained with each of two panels of antibodies to evaluate (1) the extent of α4β7 receptor occupancy in Peptide X-treated samples and (2) the abundance of circulating α4β7+, αEβ7+, and α437+αEβ7+ lymphocyte subsets. Receptor occupancy and integrin expression were assessed within memory CD4 T cells, naïve CD4 T cells, and B cells. To evaluate receptor occupancy, whole blood samples were first treated with 1 mM $MnCl_2$ to allow Peptide X binding, and then pre-incubated +/−1 uM unlabeled Peptide X to fully occupy (i.e., block) the α4β7 receptor. Blocked and unblocked samples were stained with 1 nM Alexa 647-labeled Peptide X, followed by staining with antibodies against α4β7, CD45, CD4, CD45RA, and CD19. Samples were processed to lyse erythrocytes and fix leukocytes, followed by staining with a second-step reagent (streptavidin-BV421) and wash steps. To assess integrin expression and cell subset abundance, whole blood samples were stained with antibodies against α4, β7, and αE, in addition to antibodies against CD45, CD4, CD45RA, and CD19. Samples were processed to lyse erythrocytes and fix leukocytes, followed by staining with a second-step reagent (streptavidin-BV421) and wash steps. All stained samples were analyzed by flow cytometry, collecting a constant sample volume to allow calculation of absolute cell counts.

Figure 14:
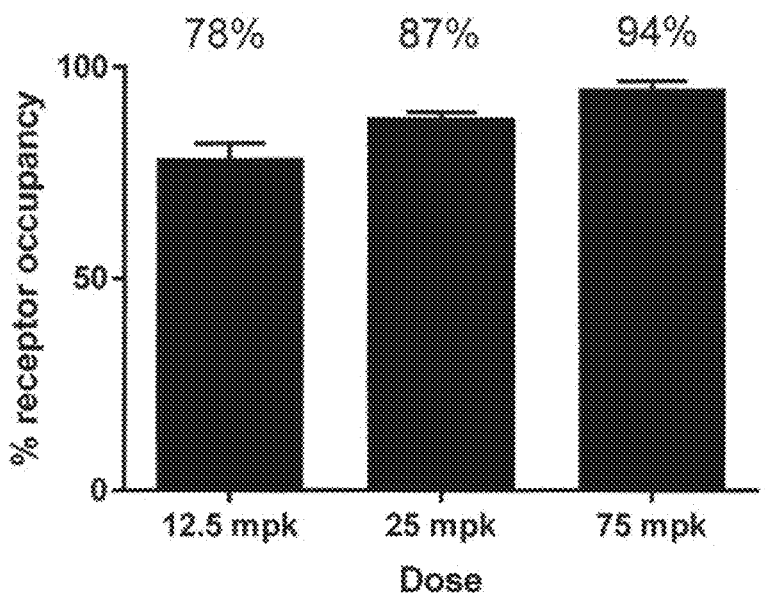
FIG. 14 is a graph showing percent receptor occupancy of CD4 memory α4β7+ T cells by Peptide X after 7 days dosing in cyno monkeys. For each animal, the percent receptor occupancy at Day 6 was normalized to the pre-dose control at Day 0.

FIG. 14 shows that the percent receptor occupancy in blood increases with oral dose, and that receptor occupancy exceeded 90% at the highest dose.

Figure 15:
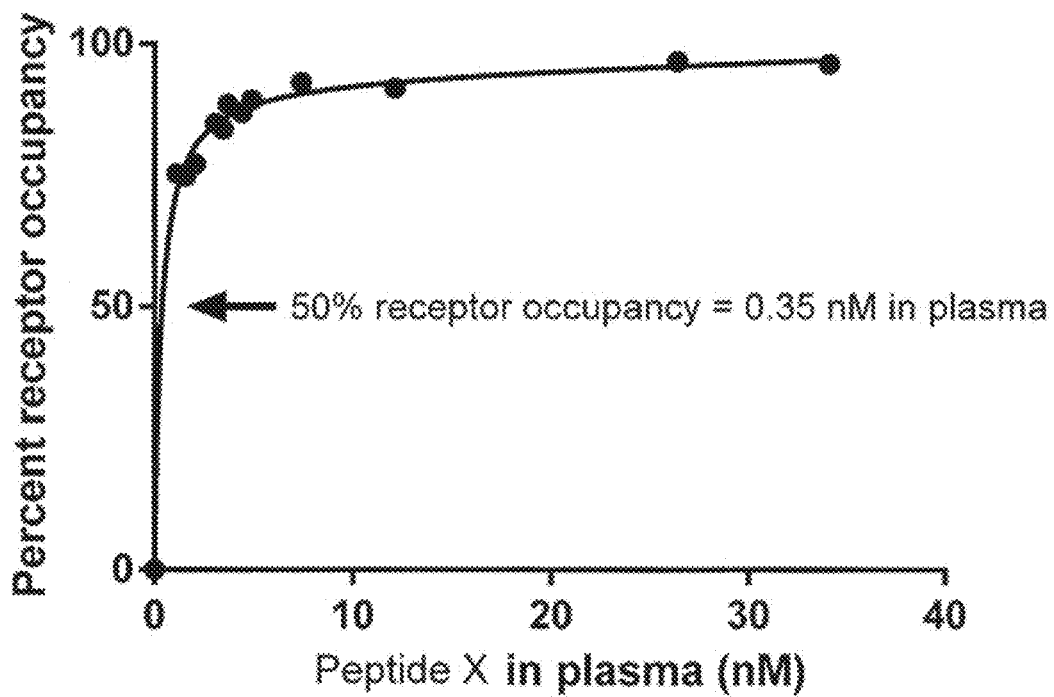
FIG. 15 is a graph showing the percent receptor occupancy versus Peptide X plasma concentration for each animal.

FIG. 15 shows the percent receptor occupancy versus Peptide X plasma concentration for each animal. By extrapolation, it was estimated that a Peptide X plasma concentration of ~0.35 nM is sufficient to occupy 50% of the α4β7 receptors in the blood.

Figure 16:
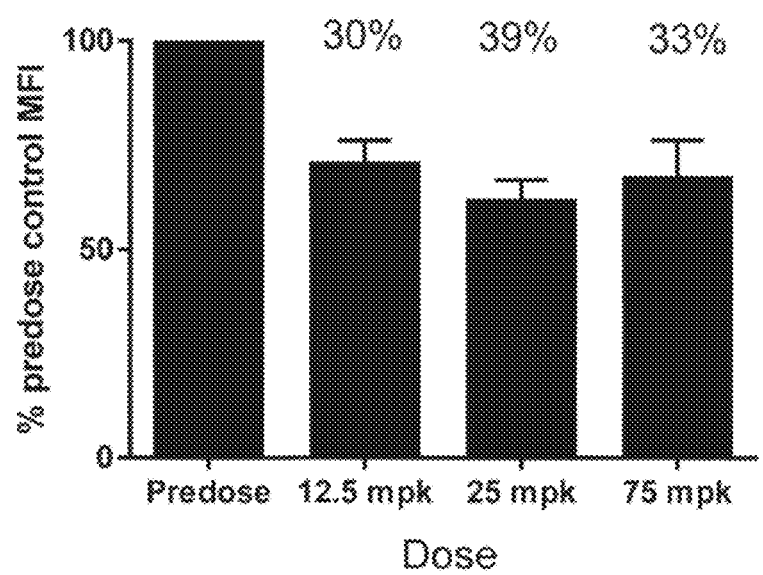
FIG. 16 is graph showing expression of α4β7 on CD4 memory T cells in cyno blood. Shown is the mean fluorescence intensity (MFI) at Day 6 normalized to the pre-dose control at Day 0 for each animal.

FIG. 16 shows that α4β7 expression on CD4 memory T cells decreased at all doses. This is consistent with binding of Peptide X inducing some internalization of α437.

Figure 17A:
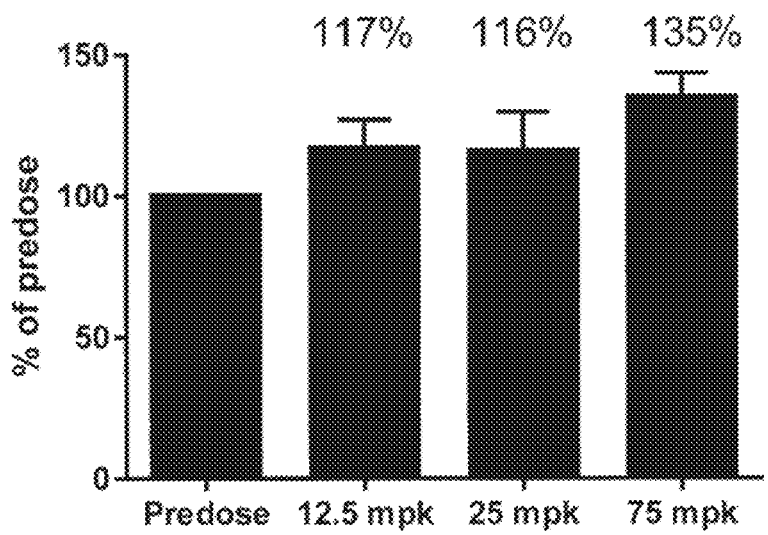
FIGS. 17A and 17B are graphs showing the percent increase in circulating α4β7 memory T cells normalized to total CD4 cells in cyno blood.
Figure 17B:
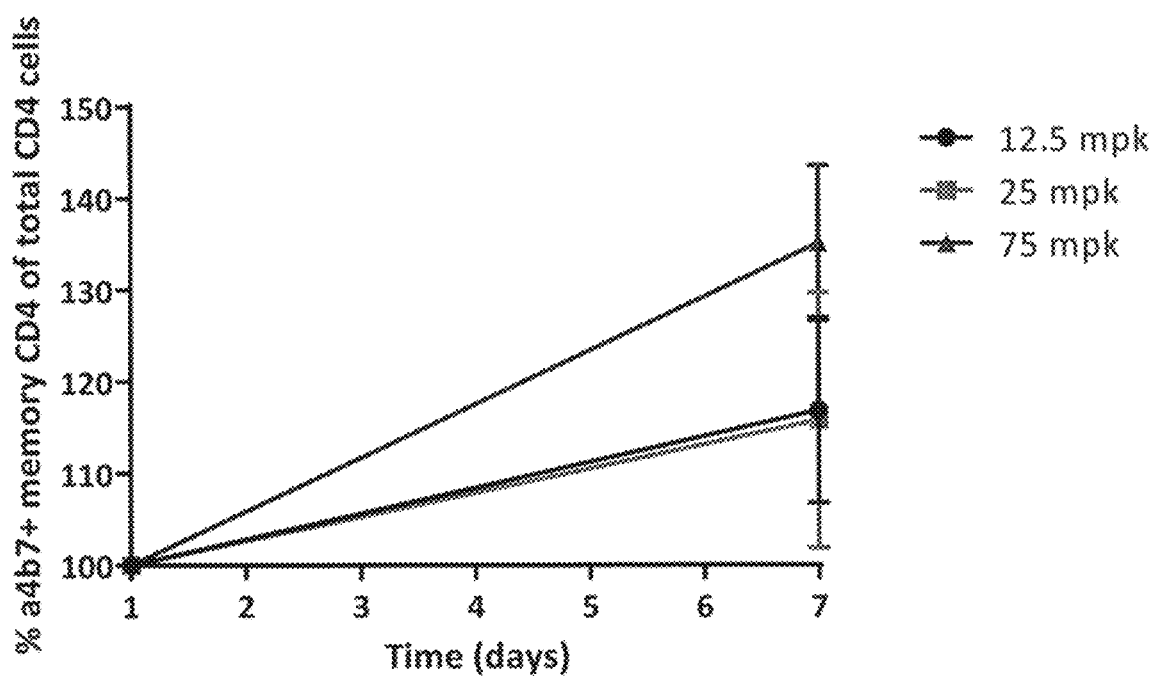
Figure 18A:
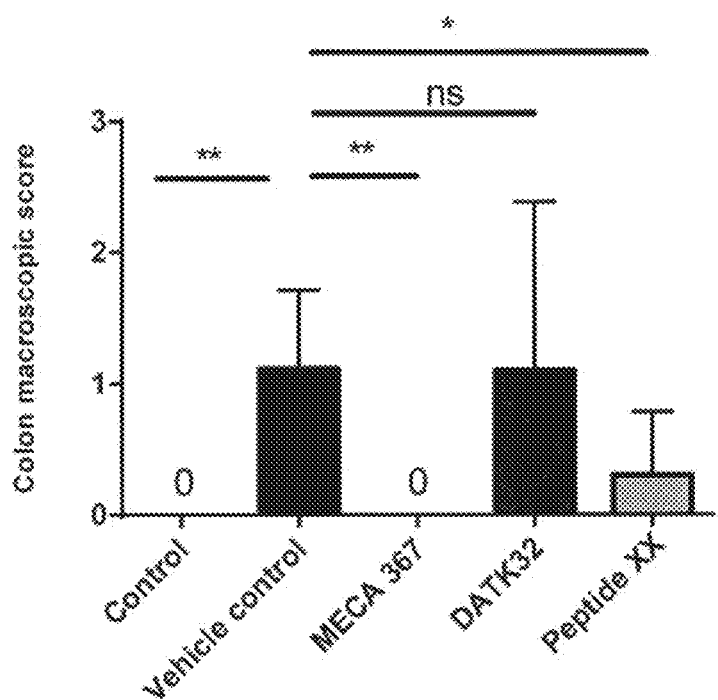
FIGS. 18A-18D provide graphs showing that Peptide XX reduces colon macroscopic histopathology scores comparable to antibodies in a murine 15 day chronic DSS model. *Gross colon score evaluated by a pathologist (0=normal, 1=erythema, 2=erythema, slight edema and small erosions, 3=two or more bleeding ulcers, inflammation, and moderate adhesions, 4=severe ulceration, stenosis with dilation and severe adhesions).
Figure 18B:
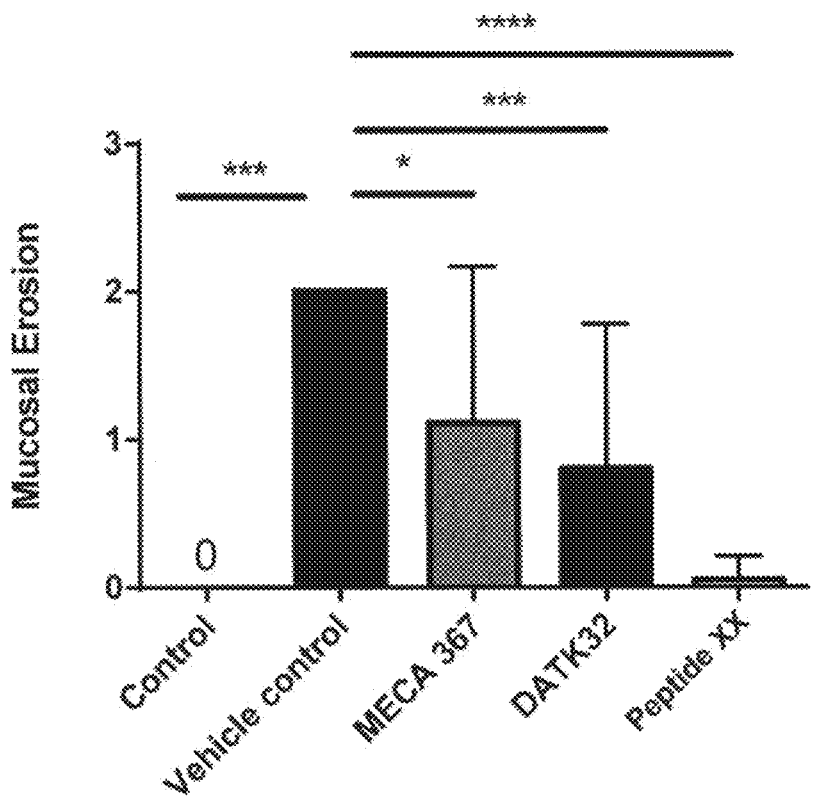
Figure 18C:
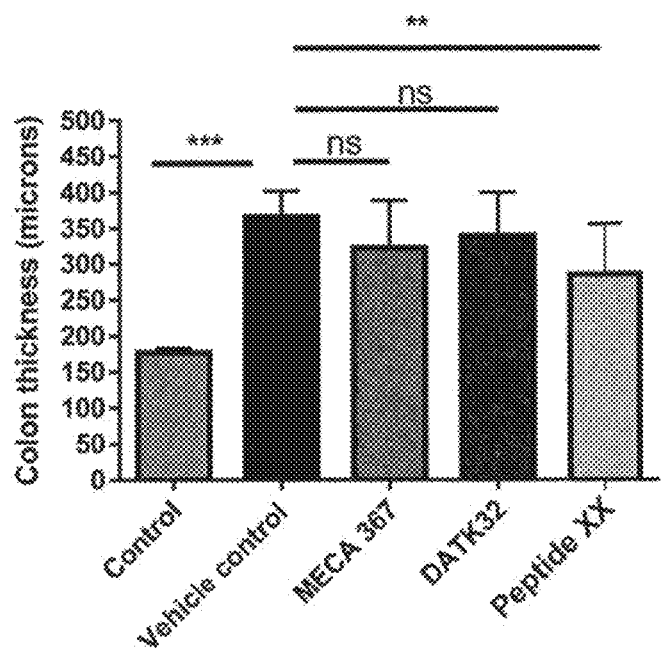
Figure 18D:
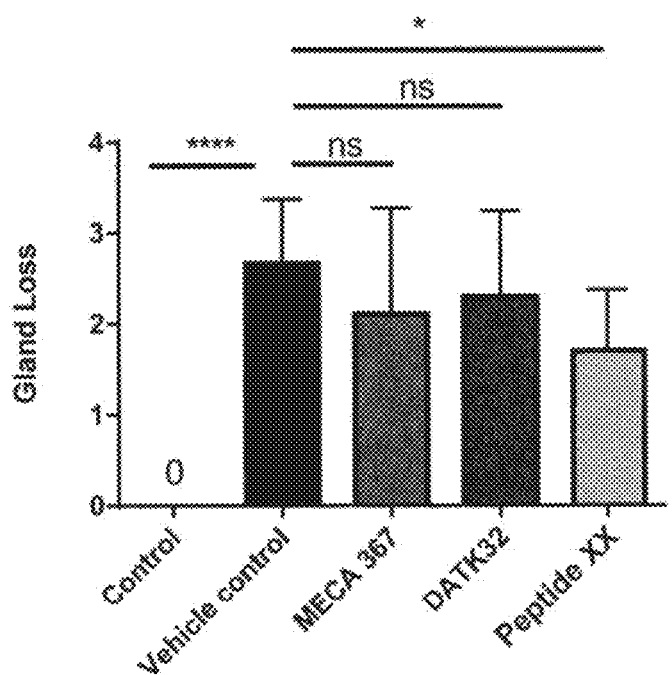

Levels of circulating α4β7+ memory T cells were also measured. FIG. 17 shows that Peptide X dosing caused an increase in the percentage of α4β7+ memory T cells normalized to total CD4 cells. This is similar to the mouse studies. Blocking homing of α4β7+ memory T cells to the gut resulted in their redistribution to the blood.

Effect of Peptide X on Trafficking of a47 Memory T Cells in DSS Mice

The effect of Peptide X on memory T cell trafficking was shown in a mouse DSS colitis model. This study showed that Peptide X affects T cell homing by diverting α4β7 memory T cells from gut lymphoid tissues to the blood and spleen.

Colitis was induced in C57BL/6 male mice (10 animals per group) by exposure to 3% DSS-treated drinking water from day 0 to day 5, when animals were shifted to normal drinking water. Once daily, animal deaths were recorded, and surviving animals were weighed and assessed visually for the presence of diarrhea and/or bloody stool. Immediately prior to sacrifice on day 9, colitis severity was assessed in all animals using video endoscopy, and the resulting images were scored for colitis severity by an observer blinded to group identity.

Starting on day 0, mice were given twice-daily oral doses of either a vehicle/sham control (Group 1) or Peptide X (Group 2: 10 mg/kg, PO, BID). On day 9, only the AM treatment dose was administered. Animals in Group 2 also were administered Peptide X in their drinking water at a concentration of 0.2 mg/mL. The drinking water bottle weights for Groups 1 and 2 were measured, and water consumption was used to estimate the peptide dose ingested via the drinking water. Based on daily water consumption, the average daily Peptide X dose from the combination of oral gavage and drinking water was estimated to be 49 mg/kg.

Mice were sacrificed on day 9, approximately four hours after the final of gavage dose administration. Spleen, Peyer's patches (PP), mesenteric lymph nodes (MLN), and blood were collected from each animal and processed for FACS analysis of α4 and 37 expression on TH memory cells. Takedown and FACS analysis occurred on the same day.

Figure 8:
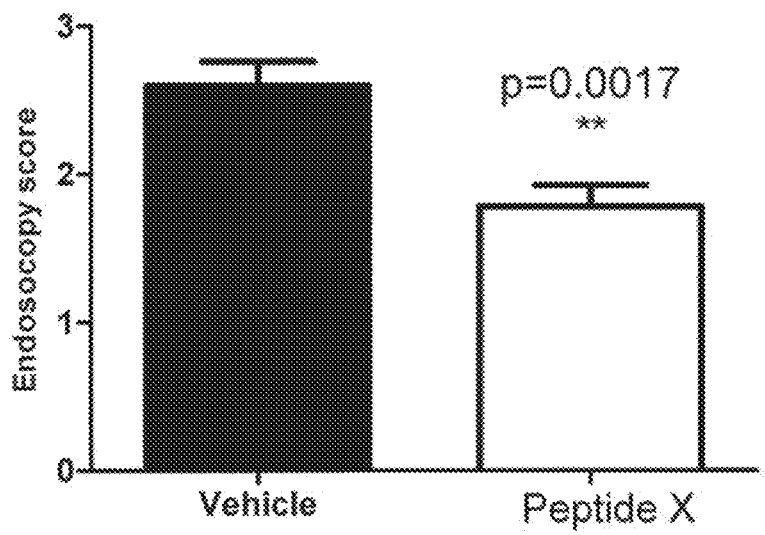
FIG. 8 is a graph showing mean endoscopy score of DSS mice treated with vehicle or Peptide X.
Figure 9:
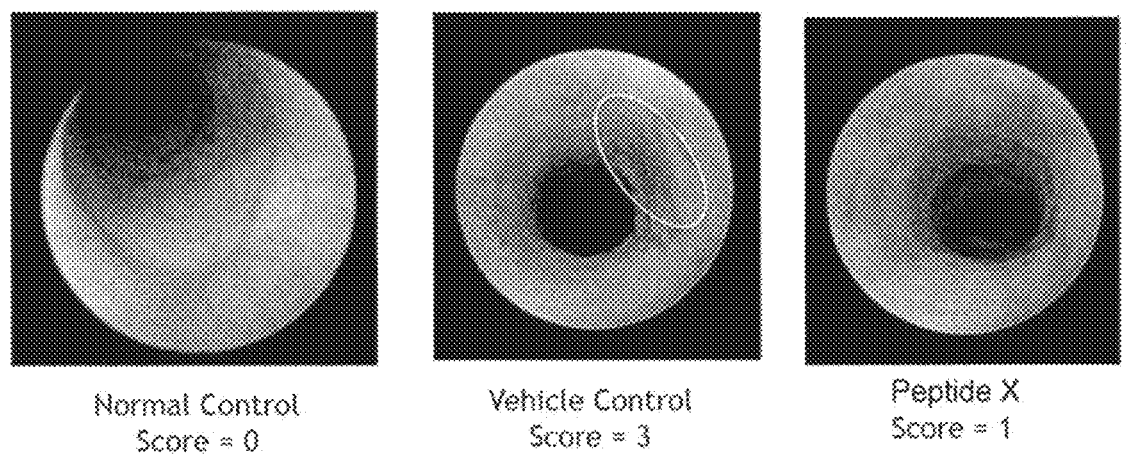
FIG. 9 provides endoscopy images from vehicle control or Peptide X treated DSS mice. A normal control from a different study is also shown. The white circle indicates colonic friability.

These studies showed that treatment with Peptide X had no significant effect on weight loss, fluid intake, colon weight or length, or presence of bloody stool and diarrhea (data not shown). Treatment with Peptide X had a significant effect on the endoscopy scores, reducing the scores by 32% from 2.60±1.6 (vehicle) to 1.78±1.5 (Peptide X) (mean±SD; FIG. 8). Visual assessment of the endoscopy images indicated that Peptide X reduced colonic friability and improved mucosal healing compared to the vehicle control (FIG. 9).

Treatment with Peptide X had significant effects on the memory T cell populations in the blood and spleen (FIG. 10). There was a 42% increase in total α4β7 memory cells per mL blood (10A), and a 73% increase in total α437 memory cells recovered from the spleen (10B). For both blood and spleen, there also were significant increases in the number of memory cells (as a percentage of TH cells), and total memory cells. No significant difference was seen in the total number of cells in either the blood or spleen.

Figure 11A:
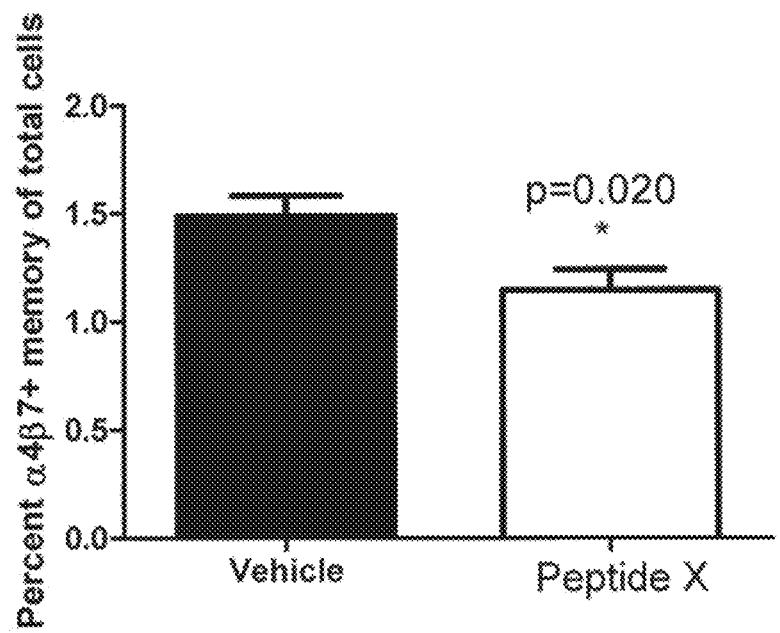
FIGS. 11A and 11B are graphs showing the percent α4β7 memory cells relative to total cells in the MLN (A) and Peyer's Patches (B). α4β7+ memory T cells are defined as CD4+, CD45RB$^{low}$, CD44$^{high}$, α4β7$^{+}$. Data are presented as mean±SEM. N=1-mice per group.
Figure 11B:
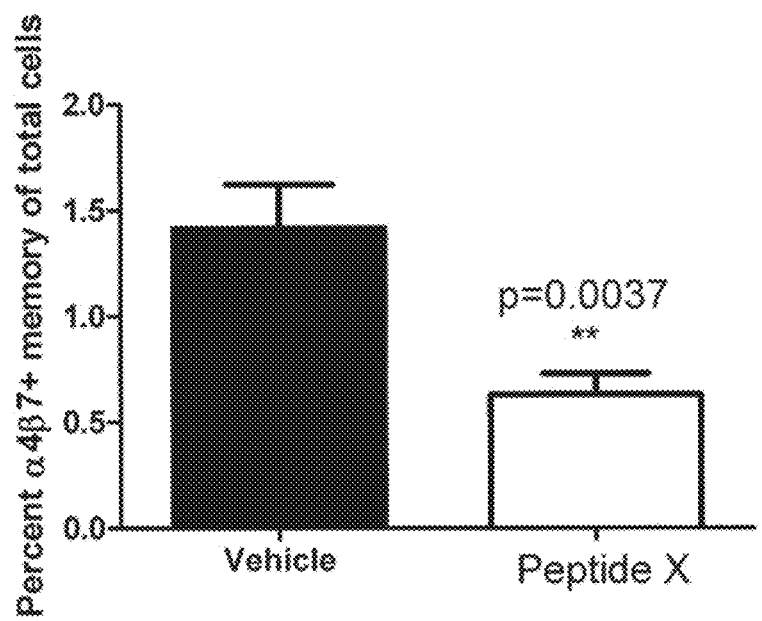

Treatment with Peptide X had significant effects on the α4β7+ memory T cell populations in the MLN and Peyer's patches (FIG. 11). Compared to the vehicle control, there were 23% and 55% decreases in the percentage of α4β7+ memory cells relative to total cells in the MLN (11A) and Peyer's Patches (11B), respectively.

Figure 12:
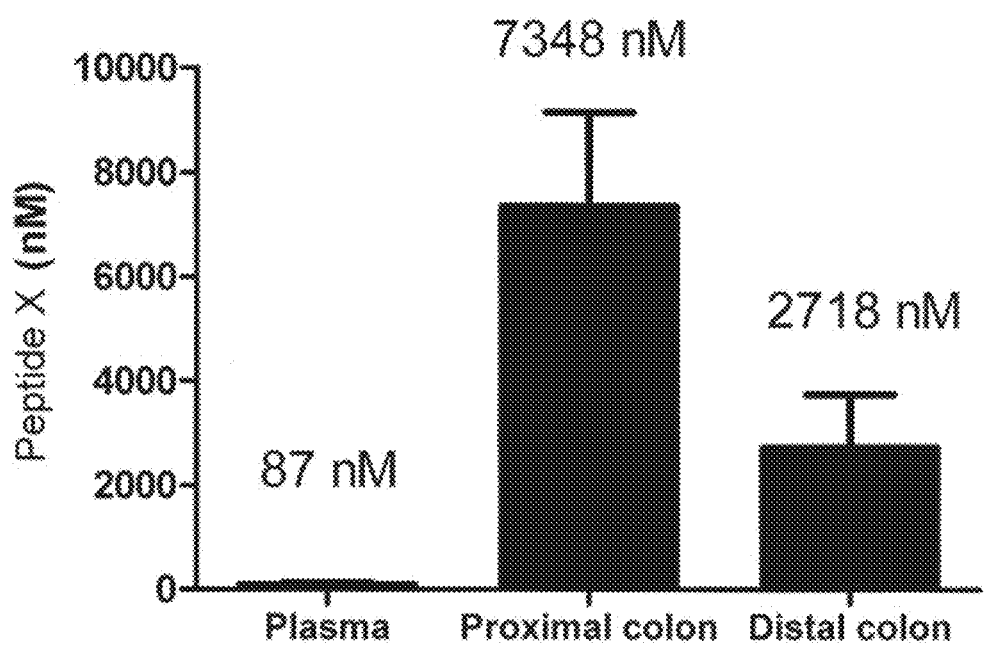
FIG. 12 is a graph showing the exposure of Peptide X in the plasma, proximal colon and distal colon following oral administration.
Figure 13A:
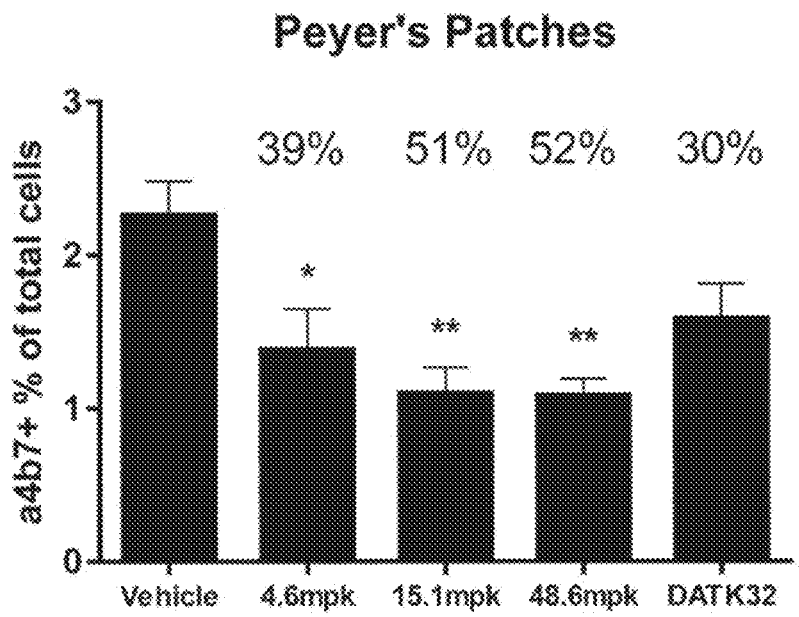
FIGS. 13A-13D provide graphs showing the amount of α4β7+ memory T cells in Peyer's patches (A), blood (B), MLN (C) and spleen (D) in the mouse DSS colitis model. Peyer's patches, MLN, spleen and blood were collected and levels of α4β7+ memory T cells analyzed by FACS. Data is presented as means and SD. N=10 mice per group. Statistical significance was assessed by one-way ANOVA: *:p≤0.05; **:p≤0.01. Percentage values and statistical significance are relative to vehicle control.
Figure 13B:
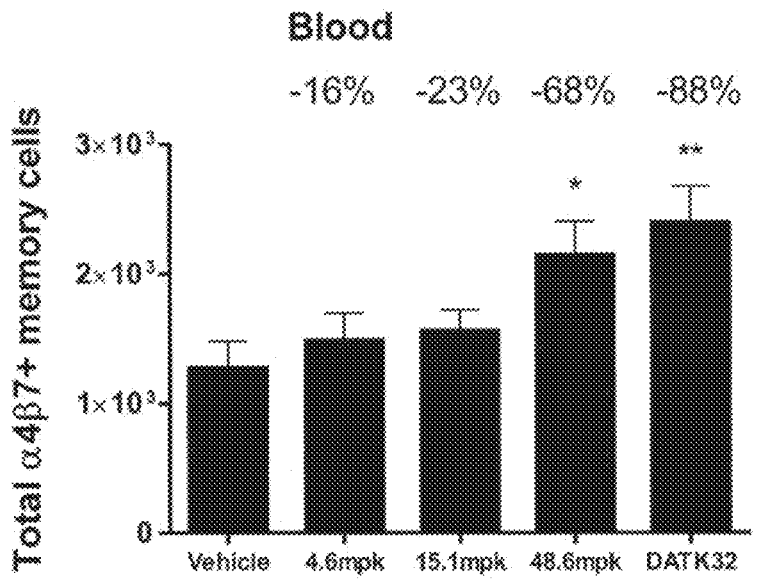
Figure 13C:
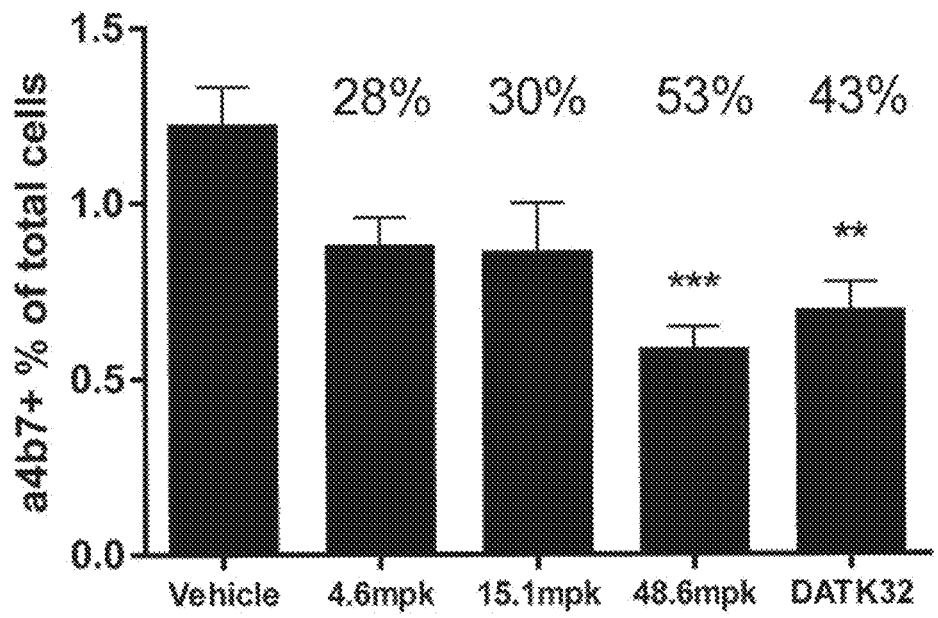
Figure 13D:
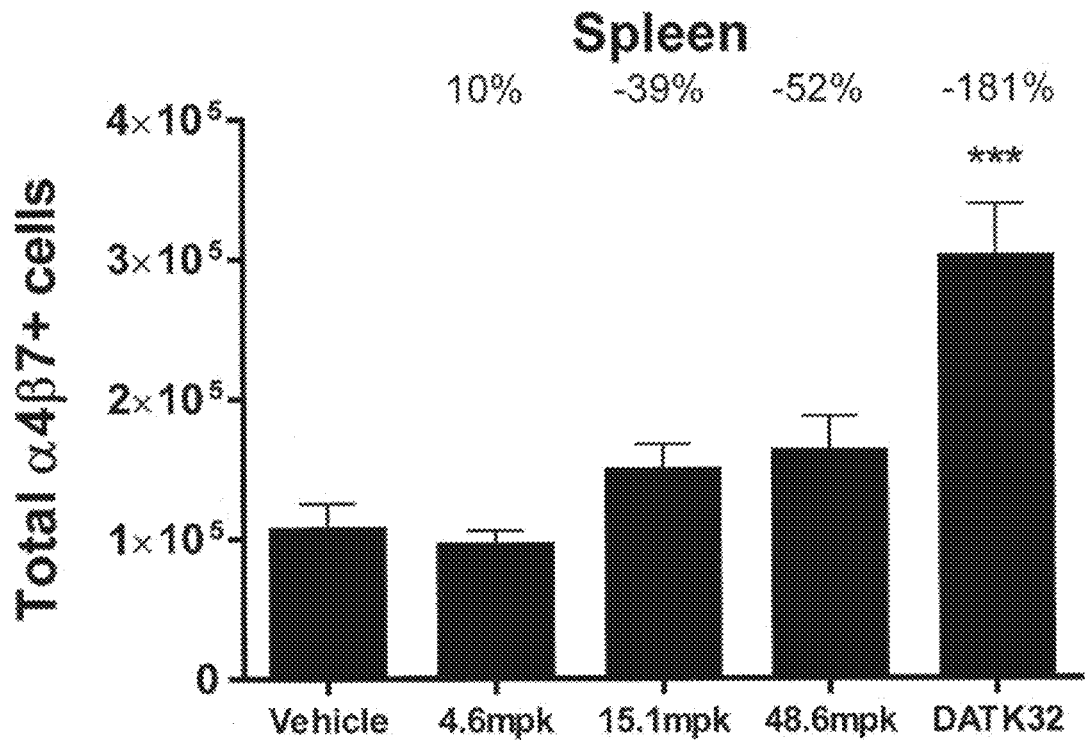

For PK measurements, colon sections from the proximal and distal colon were collected at ~4 hours after the last AM dose and analyzed by mass spectrometry. Exposure in the proximal colon was approximately 3-fold higher than that in the distal colon (FIG. 12). The concentration of Peptide X in the blood was 84-fold and 31-fold lower compared to that in the proximal and distal colon, respectively. Nonetheless at this time point, the plasma concentration was ~80-fold greater than the Peptide $IC_{50}$ value for blocking α4β7 binding to MAdCAM.

Additional DSS colitis studies were performed, which showed that treatment with Peptide X reduced α4β7+ T cells in gut lymphoid tissues and redirected them to blood (FIG. 13). In this 9 day DSS colitis study, C57BL/6 mice were treated with 3% DSS from Day 1 to Day 6, and switched to normal water until Day 10. Daily dosing was PO BID plus drinking water for Peptide X, and 25 mg/kg IP every 3 days for the anti-α4β7 antibody DATK32. PP and blood were collected and levels of α4β7+ memory T cells analyzed by FACS.

Efficacy of Peptide Inhibitors in a Chronic DSS Colitis Mouse Model

To further evaluate the efficacy of peptides of the present invention in treating colitis, a chronic DSS colitis mouse model was used to examine the effects of orally administered Peptide X or another peptide, Peptide XX, as compared to vehicle control or the antibodies, MECA 367 and DATK32. Peptide XX is a dimer having the following structure, where DIG links the two peptide monomers by their C-termini:

(SEQ ID NO: 213)
[Ac-Pen-(N-Me-Arg)-S-D-T-L-Pen-W-(β-HomoGlu)-(D-Lys)-NH$_2$]$_2$.

In this 15 day chronic DSS colitis study, BALB/c mice were treated continuously with 2.5% DSS. Peptide X dosing was 55 mg/kg/day, 17 mg/kg/day or 6 mg/kg/day in drinking water. Peptide XX dosing was 10 mg/kg PO BID plus 0.2 mg/ml in drinking water. The anti-α4β7 Ab DATK32 was dosed 25 mg/kg IP every 3 days, and the anti-MAdCAM Ab MECA 367 was dosed 8 mg/kg IP daily. After takedown, distal colon sections were fixed for histopathology and processed for β7+ cell IH staining using the anti-β7 antibody M293.

FIG. 18 shows that Peptide XX reduced colon macroscopic and histopathology scores comparable to the antibodies in a murine 15 day chronic DSS model.

Figure 19A:
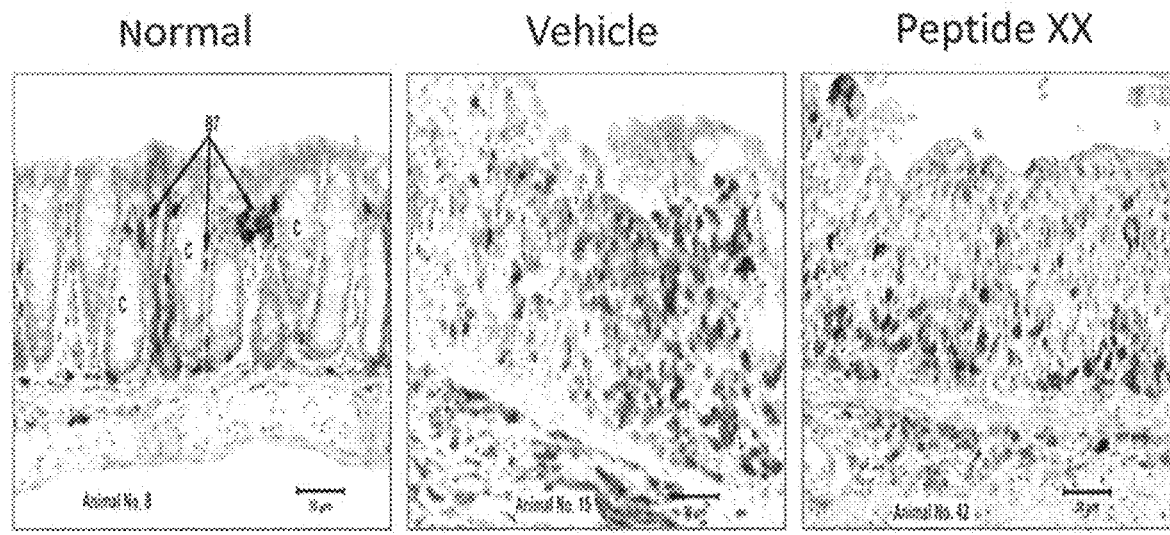
FIGS. 19A and 19B show that Peptide XX reduced infiltration of f37+ cells into the lumina propria of the distal colon in the 15 day chronic DSS colitis model. Data is represented as means and SD. N=10 mice per group. Statistical significance relative to vehicle control assessed by one-way ANOVA: *:p≤0.05; :p≤0.005; *:p≤0.0001; ns: not significant.
Figure 19B:
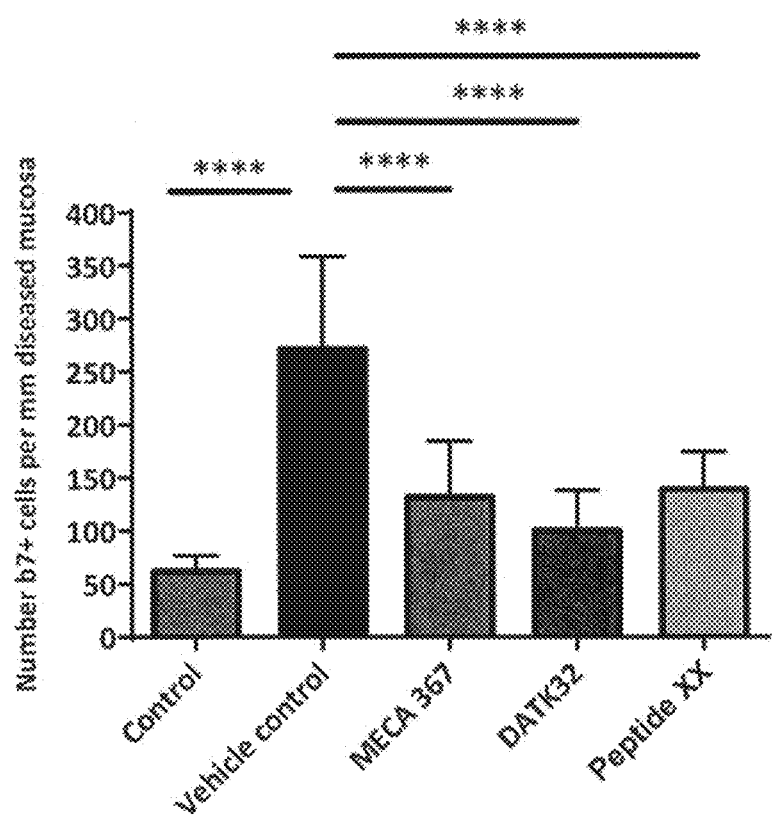
Figure 20:
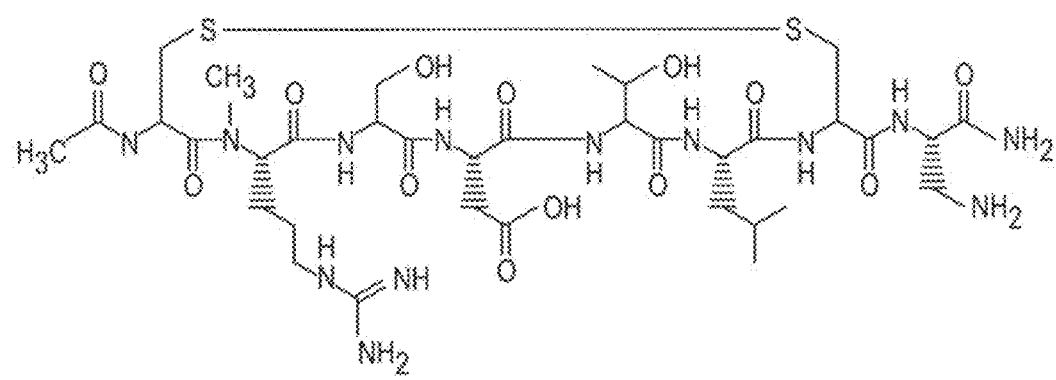
FIG. 20 is a schematic showing an integrin antagonist peptide (SEQ ID NO: 348), wherein Xaa$^4$ and Xaa$^{10}$ are connected by a disulfide bond.

FIG. 19 shows that Peptide XX reduced infiltration of B7+ cells into the lamina propria of the distal colon.

Figure 22:
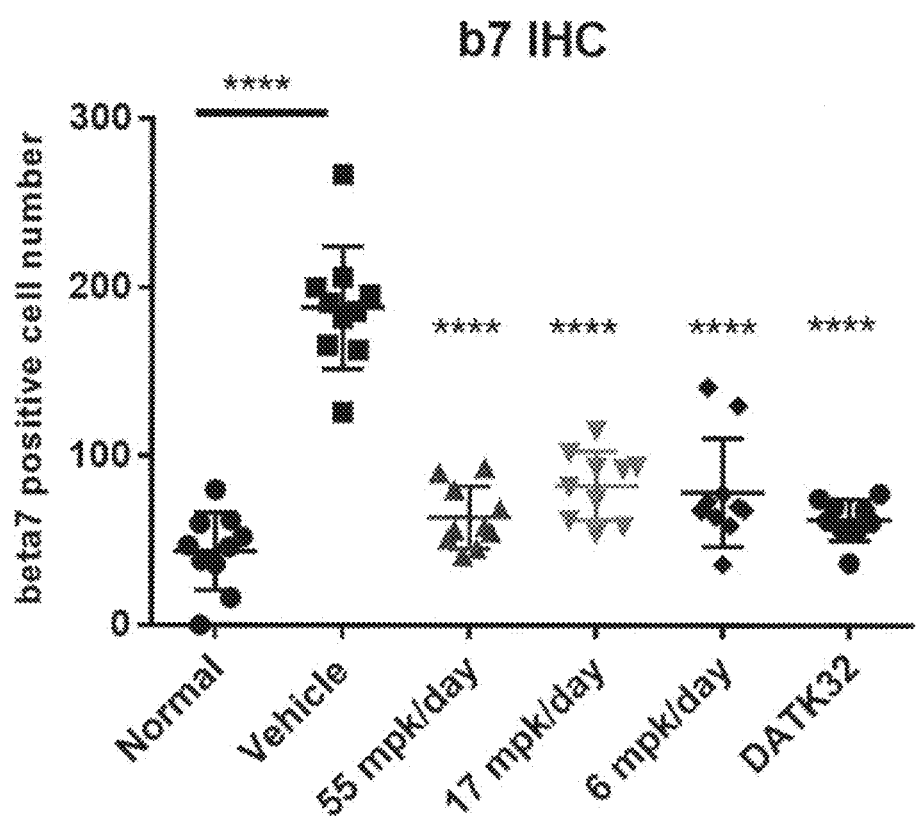
FIG. 22 provides a graph showing that treatment with Peptide X in a chronic model of DSS resulted in reduced infiltration of α4β7+B cells into the lamina propia.

FIG. 22 shows that all doses of Peptide X reduced infiltration of B7+ cells into the lamina propria of the distal colon.

Fluorescence imaging was performed after in oral administration of vehicle or 10 mg/kg or 90 mg/kg of Peptide X conjuaged to Alexa 488 to normal C57BL6 mice (n=2 mice per group). Mice were harvested 3 hours post-dose and the following tissues were collected: 3.8 cm of proximal small intestine and 3.8 cm of distal colong. The samples were fixed in PFA and frozen in OCT, formalin-fixed, and paraffin-embedded. 5 micron slices were DAPI counter-stained to visualize nuclei and subjected to fluorescence microscopy at 40×.

Vehicle-treated animals showed no fluorescence signal in small intestine or colon. The 10 mg/kg PO treated animals showed signal in small intestine with aggregated in crpts (glandular cells). The 90 mg/kg PO treated animals showed weak signal in the epithelial lining, interstitial cells, and glandular cells, and stronger aggregates of signal in crypts and glandular cells in mucosa of the small intestine. A weak signal was present in the epithelial lining of the colon.

Figure 21:
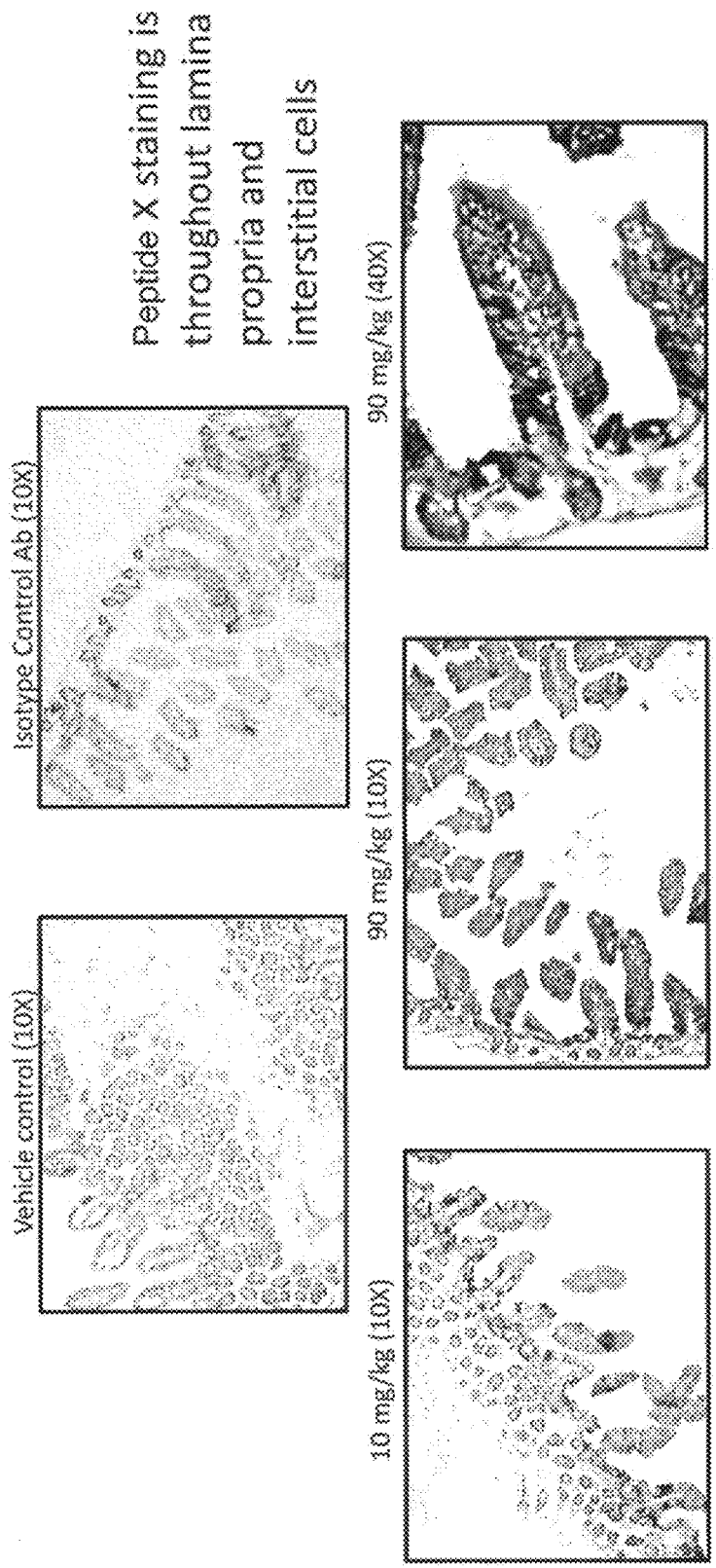
FIG. 21 shows immunohistochemistry of PFA fixed small intestine tissue samples obtained from an animal treated with 10 mg/kg or 90 mg/kg of Peptide X conjugated to Alex 488, stained with an anti-Alex 488 antibody.

Small intestine samples were also examined by immunohistochemistry using an anti-Alexa 488 antibody of PFA fixed tissue. As shown in FIG. 21, Compound X staining was observed throughout the lamino propia and interstitial cells of animals treated with 10 mg/kg or 90 mg/kg of Compound X conjugated to Alexa 488.

These Examples establish that Peptide X and other peptides of the present invention are selective oral peptide antagonists of α4β7 integrin with minimal systemic exposure, and are effective in blocking T cell homing and preventing mucosal damage in murine models of IBD. Peptide X and the clinically validated anti-α4β7 antibody vedolizumab have comparable potency and selectivity in a variety of assays including cell adhesion and binding to human CD4+ memory T cells. PK studies in normal or dextran sodium sulfate (DSS) treated mice and rats show that oral dosing results in marked drug exposure in the small intestine, Peyer's Patches, colon, and mesenteric lymph nodes (MLN), but no significant measurable levels in the blood and urine. To measure the effect of oral dosing on trafficking of endogenous memory T cells, DSS mice were orally dosed daily with Peptide X for 9 days, and harvested tissues were analyzed by FACS. FACS analysis showed a dose dependent reduction of CD4$^+$ CD44$^{high}$ CD45RB$^{low}$ (37$^+$ T cells in the MLN and Peyer's Patches, and a concomitant increase in the spleen and blood. There was also a dose-dependent reduction in body weight loss and mucosal injury as assessed by endoscopy. Peptide X also showed stability to a variety of gastrointestinal (GI) fluids, metabolic enzymes and intestinal bacteria. Peptide X was shown to be an effective oral antagonist selective for α4β7 integrin. In murine colitis models, Peptide X and similar analogs blocked T cell trafficking and reduce histopathology to levels similar to that of pathway specific antibodies. In the blood of cynomolgus monkeys, Peptide X saturated blood receptor occupancy and increased circulating levels of α4β7 CD4 T cells. Peptide X's low blood exposure and high GI exposure suggests that it is locally acting within the gut lymphoid compartment to block memory T cell pathology.

All publications and patent applications described herein are hereby incorporated by reference in their entireties.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for treating Celiac disease in a subject, the method comprising administering to the subject an effective amount of a pharmaceutical composition comprising a peptide dimer compound comprising two monomer subunits, wherein each monomer subunit comprises the amino acid sequence:
Pen-(N-Me-Arg)-Ser-Asp-Thr-Leu-Pen-Phe(4-tBu)-(β-homo-Glu)-(D-Lys) (SEQ ID NO:153)
or a pharmaceutically acceptable salt thereof.

2. The method of claim 1, wherein each monomer subunit comprises a disulfide bond between the two Pen amino acids.

3. The method of claim 1, wherein the peptide dimer compound further comprises a linker moiety.

4. The method of claim 3, wherein the linker moiety is bound to the D-Lys amino acids of the two monomer units.

5. The method of claim 3, wherein the linker moiety is diglycolic acid (DIG).

6. The method of claim 1, wherein the N-terminus of each monomer subunit is acylated.

7. The method of claim 1, wherein each monomer subunit comprises a C-terminal free amide.

8. The method of claim 1, wherein each monomer subunit comprises a disulfide bond between the two Pen amino acids and a linker moiety bound to the D-Lys amino acid, wherein the N-terminus of each monomer subunit is acylated.

9. The method of claim 1, wherein the peptide dimer compound consists of the structure:

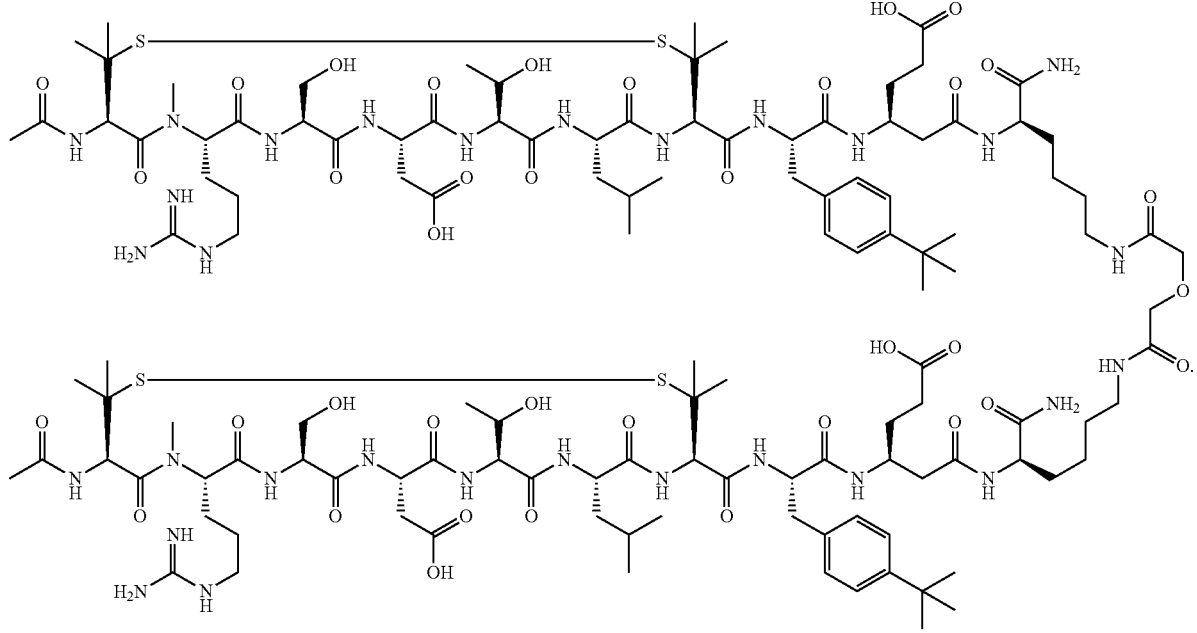 [SMILES: CC(=O)N[C@@H]1C(=O)N(C)[C@@H](CCCNC(=N)N)C(=O)N[C@@H](CO)C(=O)N[C@@H](CC(=O)O)C(=O)N[C@@H](C(C)O)C(=O)N[C@@H](CC(C)C)C(=O)N[C@H](C(=O)N[C@@H](Cc2ccc(C(C)(C)C)cc2)C(=O)N[C@@H](CCC(=O)O)CC(=O)N[C@H](CCCCNC(=O)COCC(=O)NCCCC[C@@H](NC(=O)C[C@H](CCC(=O)O)NC(=O)[C@H](Cc2ccc(C(C)(C)C)cc2)NC(=O)[C@H]2NC(=O)[C@H](CC(C)C)NC(=O)[C@H](C(C)O)NC(=O)[C@H](CC(=O)O)NC(=O)[C@H](CO)NC(=O)[C@H](CCCNC(=N)N)N(C)C(=O)[C@@H](NC(C)=O)C(C)(C)SSC2(C)C)C(N)=O)C(N)=O)C(C)(C)SSC1(C)C]

or a pharmaceutically acceptable salt thereof.

10. The method of claim 1, wherein the pharmaceutically acceptable salt thereof is an acetate salt of the peptide dimer compound.

11. The method of claim 1, wherein the pharmaceutical composition is administered orally.

12. The method of claim 1, wherein the pharmaceutical composition comprises a pharmaceutically acceptable excipient.

13. The method of claim 1, wherein the pharmaceutical composition comprises an enteric coating.

14. The method of claim 1, wherein the peptide dimer compound or pharmaceutically acceptable salt thereof inhibits binding of α4β7 to mucosal addressin cell adhesion molecule (MAdCAM).

* * * * *

UNITED STATES PATENT AND TRADEMARK OFFICE
CERTIFICATE OF CORRECTION

| | | |
|---|---|---|
| PATENT NO. | : 11,111,272 B2 | Page 1 of 1 |
| APPLICATION NO. | : 16/781516 | |
| DATED | : September 7, 2021 | |
| INVENTOR(S) | : Ashok Bhandari et al. | |

It is certified that error appears in the above-identified patent and that said Letters Patent is hereby corrected as shown below:

On the Title Page

Item [54], and in the Specification, Column 1 Line 1:
"$\alpha 4\alpha 7$ PEPTIDE MONOMER AND DIMER ANTAGONISTS"
Should read:
-- $\alpha 4\beta 7$ PEPTIDE MONOMER AND DIMER ANTAGONISTS --

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*